US011554165B2

(12) United States Patent
Kurtis et al.

(10) Patent No.: US 11,554,165 B2

(45) Date of Patent: Jan. 17, 2023

(54) VACCINE FOR FALCIPARUM MALARIA

(71) Applicants: Rhode Island Hospital, Providence, RI (US); Seattle Children's Hospital, Seattle, WA (US)

(72) Inventors: Jonathan Kurtis, Providence, RI (US); Christian Parcher Nixon, Little Compton, RI (US); Dipak Kumar Raj, Pawtucket, RI (US); Jennifer Frances Friedman, Providence, RI (US); Michal Fried, Rockville, MD (US); Patrick Emmet Duffy, Washington, DC (US)

(73) Assignees: Rhode Island Hospital, Providence, RI (US); Seattle Children's Hospital, Seattle, WA (US)

( * ) Notice: Subject to any disclaimer, the term of this patent is extended or adjusted under 35 U.S.C. 154(b) by 0 days.

(21) Appl. No.: 17/178,111

(22) Filed: Feb. 17, 2021

(65) Prior Publication Data

US 2021/0283233 A1 Sep. 16, 2021

Related U.S. Application Data

(60) Continuation of application No. 16/283,472, filed on Feb. 22, 2019, now Pat. No. 10,960,065, which is a division of application No. 15/607,203, filed on May 26, 2017, now Pat. No. 10,213,502, which is a continuation of application No. 14/361,573, filed as application No. PCT/US2012/067404 on Nov. 30, 2012, now Pat. No. 9,662,379.

(60) Provisional application No. 61/641,445, filed on May 2, 2012, provisional application No. 61/566,365, filed on Dec. 2, 2011.

(51) Int. Cl.

| | |
|---|---|
| ***A61K 39/015*** | (2006.01) |
| ***C07K 14/445*** | (2006.01) |
| ***A61K 39/395*** | (2006.01) |
| ***C07K 16/44*** | (2006.01) |
| ***C07K 16/20*** | (2006.01) |
| *A61K 39/00* | (2006.01) |

(52) U.S. Cl.

CPC ...... *A61K 39/015* (2013.01); *A61K 39/39575* (2013.01); *C07K 14/445* (2013.01); *C07K 16/205* (2013.01); *C07K 16/44* (2013.01); *A61K 2039/505* (2013.01); *A61K 2039/522* (2013.01); *A61K 2039/54* (2013.01); *A61K 2039/55* (2013.01); *A61K 2039/575* (2013.01); *C07K 2317/34* (2013.01); *C07K 2317/76* (2013.01); *Y02A 50/30* (2018.01)

(58) Field of Classification Search

None

See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,722,848 | A | 2/1988 | Paoletti et al. |
| 4,837,028 | A | 6/1989 | Allen |
| 4,873,316 | A | 10/1989 | Meade et al. |
| 5,019,369 | A | 5/1991 | Presant et al. |
| 5,204,253 | A | 4/1993 | Sanford et al. |
| 5,279,833 | A | 1/1994 | Rose |
| 5,580,859 | A | 12/1996 | Felgner et al. |
| 5,589,466 | A | 12/1996 | Felgner et al. |
| 5,700,671 | A | 12/1997 | Prieto et al. |
| 5,750,176 | A | 5/1998 | Prieto et al. |
| 5,849,589 | A | 12/1998 | Tedder et al. |
| 9,662,379 | B2 | 5/2017 | Kurtis et al. |
| 10,213,502 | B2 | 2/2019 | Kurtis et al. |
| 10,272,145 | B2 | 4/2019 | Kurtis et al. |
| 2004/0137512 | A1 | 7/2004 | Horii |
| 2005/0136067 | A1 | 6/2005 | Klein et al. |
| 2010/0310602 | A1 | 12/2010 | Reed et al. |
| 2014/0341918 | A1 | 11/2014 | Kurtis et al. |
| 2017/0258884 | A1 | 9/2017 | Kurtis et al. |
| 2017/0326219 | A1 | 11/2017 | Kurtis et al. |
| 2020/0023047 | A1 | 1/2020 | Kurtis et al. |

FOREIGN PATENT DOCUMENTS

| | | | |
|---|---|---|---|
| EP | 0264166 | A1 | 4/1988 |
| WO | 86/06075 | A1 | 10/1986 |
| WO | 91/06309 | A1 | 5/1991 |
| WO | 93/24640 | A2 | 12/1993 |
| WO | 96/18372 | A2 | 6/1996 |
| WO | 2007/140506 | A1 | 12/2007 |
| WO | 2013/082500 | A2 | 6/2013 |

OTHER PUBLICATIONS

Dorvin et al (Science. 2010. 328: 910-912; Genbank Accession No. A0A5K1K8H0).*

(2020) "Human Vaccines & Immunotherapeutics: news", Human Vaccines & Immunotherapeutics, 16(6):1226-1227.

Allison et al. (1998) "The Mode of Action of Immunological Adjuvants", Developments in biological standardization, 92:3-11.

Altschul et al. (1997) "Gapped BLAST and PSI-BLAST: A New Generation of Protein Database Search Programs", Nucleic Acids Research, 25(17):3389-3402.

Amann et al. (Sep. 30, 1988) "Tightly Regulated Tac Promoter Vectors Useful for the Expression of Unfused and Fused Proteins in *Escherichia coli*", Gene, 69(2):301-315.

Aoki et al. (Dec. 6, 2002) "Serine Repeat Antigen (SERA5) is Predominantly Expressed; among the SERA Multigene Family of Plasmodium Falciparum, and the Acquired; Antibody Titers Correlate with Serum Inhibition of the Parasite Growth", The Journal of Biological Chemistry, 277(49):47533-47540.

(Continued)

*Primary Examiner* — Jennifer E Graser

(74) *Attorney, Agent, or Firm* — Adler Pollock & Sheehan P.C.; Michel Morency

(57) ABSTRACT

The invention provides compositions and methods for preventing or reducing the severity of malaria.

12 Claims, 19 Drawing Sheets

Specification includes a Sequence Listing.

(56) References Cited

OTHER PUBLICATIONS

Baldari et al. (Jan. 1987) "A Novel Leader Peptide which Allows Efficient Secretion of a Fragment of Human Interleukin 1 beta in *Saccharomyces cerevisiae*", The EMBO Journal, 6(1):229-234.
Banerji et al. (Jul. 1983) "A Lymphocyte-Specific Cellular Enhancer is Located Downstream of the Joining Region in Immunoglobulin Heavy Chain Genes", Cell, 33(3):729-740.
Blackman Michael J. (Oct. 1, 2008) "Malarial Proteases and Host Cell Egress: an 'Emerging' Cascade", Cellular Microbiology, 10(10):1925-1934.
Brunsvig et al. (Dec. 2006) "Telomerase Peptide Vaccination: a Phase I/II Study in Patients with Non-Small Cell Lung Cancer", Cancer Immunology, Immunotherapy, 55(12):1553-1564.
Bustamante et al. (Aug. 2000) "Differential Ability of Specific Regions of Plasmodium Falciparum Sexual-Stage Antigen, Pfs230, to Induce Malaria Transmission-Blocking Immunity", Parasite Immunology, 22(8):373-380.
Byrne et al. (Jul. 1, 1989) "Multiplex Gene Regulation: A Two-Tiered Approach to Transgene Regulation in Transgenic Mice", Proceedings of the National Academy of Sciences, 86(14):5473-5477.
Calame et al. (1988) "Transcriptional Controlling Elements in the Immunoglobulin and T Cell Receptor Loci", Advances in Immunology, 43:235-275.
Camper et al. (1989) "Postnatal Repression of the α-Fetoprotein Gene is Enhancer Independent", Genes & Development, 3:537-546.
Cebere et al. (Jan. 2006) "Phase I Clinical Trial Safety of DNA- and Modified Virus Ankara-Vectored Human Immunodeficiency Virus Type 1 (HIV-1) Vaccines Administered Alone and in a Prime-Boost Regime to Healthy HIV-1-Uninfected Volunteers", Vaccine, 24(4):417-425.
Cowman et al. (Sep. 17, 2012) "The Cellular and Molecular Basis for Malaria Parasite Invasion of the Human Red Blood Cell", The Journal of Cell Biology, 198(6):961-971.
Database Genbank (May 27, 2010) "GenBank Accession No. XM_001347460", 3 pages.
Database Genbank (May 27, 2010) "GenBank Accession No. XP_001347496", 2 pages.
De Monerri et al. (Mar. 2011) "Global Identification of Multiple Substrates for Plasmodium Falciparum SUB1, an Essential Malarial Processing Protease", Infection and Immunity, 79(3):1086-1097.
Duffy et al. (2020) "Malaria Vaccines since 2000: Progress, Priorities, Products", NPJ Vaccines, Article No. 48, 5:9 pages.
Dupuis et al. (1998) "Dendritic Cells Internalize Vaccine Adjuvant After Intramuscular Injection", Cellular Immunology, 186(1):18-27.
Dvorin et al. (May 14, 2010) "A Plant-Like Kinase in Plasmodium Falciparum Regulates Parasite Egress from Erythrocytes", Science, 323(5980):910-912.
Edlund et al. (Nov. 22, 1985) "Cell-Specific Expression of the Rat Insulin Gene: Evidence for Role of Two Distinct 5' Flanking Elements", Science, 230(4728):912-916.
Felgner et al. (Nov. 1987) "Lipofection: A highly Efficient, Lipid-Mediated DNA-Transfection Procedure", Proceedings of the National Academy of Sciences, 84:7413-7417.
Gabrilovich et al. (Nov. 1996) "IL-12 and Mutant P53 Peptide-Pulsed Dendritic Cells for the Specific Immunotherapy of Cancer", Journal of immunotherapy with emphasis on tumor immunology, 19(6):414-418.
Gardner et al. (Jan. 1, 2002) "Genome Sequence of the Human Malaria Parasite Plasmodium Falciparum", Nature, 419(6906):498-511.
Gottesman et al. (1990) "Gene Expression Technology", Methods in Enzymology, Academic Press, 185:119-128.
Greenland et al. (Mar. 1, 2000) "Problems Due to Small Samples and Sparse Data in Conditional Logistic Regression Analysis", American Journal of Epidemiology, 151(5):531-539.
Hall et al. (Oct. 3, 2002) "Sequence of Plasmodiumfalciparum Chromosomes 1, 3-9 and 13", Nature, 119:527-531.
Hon et al. (Aug. 2020) "Malaria According to GARP: A New Trail towards Anti-disease Vaccination", Trends in Parasitology, 36(8):653-655.
Horii et al. (Sep. 2010) "Evidences of Protection Against Blood-Stage Infection of Plasmodium Falciparum by the Novel Protein Vaccine SE36", Parasitology International, 59(3):380-386.
Hurd Hilary (May 15, 2020) "A Promising New Malaria Vaccine Candidate", BugBitten, 5 pages.
Kabyemela et al. (Jul. 15, 2008) "Decreased Susceptibility to Plasmodium Falciparum Infection in Pregnant Women with Iron Deficiency", The Journal of Infectious Diseases, 198(2):163-166.
Kaslow et al. (Dec. 1994) "*Saccharomyces cerevisiae* Recombinant Pfs25 Adsorbed to Alum Elicits Antibodies that Block Transmission of Plasmodium Falciparum", Infection and Immunity, 62(12):5576-5580.
Kaufman et al. (Jan. 1987) "Translational Efficiency of Polycistronic mRNAs and their Utilization to Express Heterologous Genes in Mammalian Cells", The EMBO Journal, 6(1):187-195.
Kessel et al. (Jul. 27, 1990) "Murine Developmental Control Genes", Science, 249(4967):374-379.
Kurjan et al. (Oct. 1982) "Structure of a Yeast Pheromone Gene (MFα): A Putative a-Factor Precursor Contains Four Tandem Copies of Ma-ture α-Factor", Cell, 30(3):933-943.
Lee et al. (Mar. 2008) "Arresting Malaria Parasite Egress from Infected Red Blood Cells", Nature Chemical Biology, 4(3):161-162.
Luckow et al. (May 1, 1989) "High Level Expression of Nonfused Foreign Genes with Autographa Californica Nuclear Polyhedrosis Virus Expression Vectors", Virology, 170(1):31-39.
Mannino et al. (Jul. 1, 1988) "Liposome Mediated Gene Transfer", BioTechniques, 6(7):682-690.
Moorthy et al. (2003) "Safety of DNA and Modified Vaccinia Virus Ankara Vaccines Against Liver-Stage P. Falciparum Malaria in Non-Immune Volunteers", Vaccine, 21:1995-2002.
Mutabingwa et al. (Dec. 2005) "Maternal Malaria and Gravidity Interact to Modify Infant Susceptibility to Malaria", Public Library of Science, Medicine, 2(12):e407.
Nixon et al. (Sep. 1, 2005) "Antibodies to Rhoptry-Associated Membrane Antigen Predict Resistance to Plasmodium Falciparum", The Journal of Infectious Diseases, 92(5):861-869.
Palacpac et al. (Jun. 14, 2011) "Plasmodium Falciparum Serine Repeat Antigen 5 (SE36) as a Malaria Vaccine Candidate", Vaccine, 29(35):5837-5845.
Petersen et al. (Aug. 2020) "A Thermal Exhaust Port on the Death Star of Plasmodium falciparum-Infected Erythrocytes", Trends in Pharmacological Sciences, 41(8):508-511.
Pinkert et al. (1987) "An Albumin Enhancer Located 10 kb Upstream Functions along with its Promoter to Direct Efficient, Liver-Specific Expression in Transgenic Mice", Genes & Development, 1:268-277.
Putrianti et al. (Jun. 2010) "The Plasmodium Serine-Type SERA Proteases Display Distinct Expression Patterns and Non-Essential in Vivo Roles During Life Cycle Progression of the Malaria Parasite", Microbial Cell, 12(6):725-739.
Queen et al. (Jul. 1983) "Immunoglobulin Gene Transcription is Activated by Downstream Sequence Elements", Cell, 33(3):741-748.
Raj et al. (May 23, 2014) "Antibodies to PfSEA-1 Block Parasite Egress from RBCs and Protect Against Malaria Infection", Science, 344(6186):871-877.
Raj et al. (Apr. 22, 2020) "Anti-PfGARP Activates Programmed Cell Death of Parasites and Reduces Severe Malaria", Nature, 582:104-108(23 pages).
Sabchareon et al. (1991) "Parasitologic and Clinical Human Response to Immunoglobulin Administration in Falciparum Malaria", The American Journal of Tropical Medicine and Hygiene, 45(3):297-308.
Sambrook et al. (1989) "Molecular Cloning, A Laboratory Manual", Cold Spring Harbor Laboratory Press, Ed. 2.
Schnieke et al. (Dec. 19, 1997) "Human Factor IX Transgenic Sheep Produced by Transfer of Nuclei from Transfected Fetal Fibroblasts", Science, 278(5346):2130-2133.

(56) References Cited

OTHER PUBLICATIONS

Schultz et al. (1987) "Expression and Secretion in Yeast of a 400-kda Envelope Glycoprotein Derived from Epstein-Barr Virus", Gene, 54(1):113-123.
Seed B. (Oct. 29, 1987) "An LFA-3 cDNA Encodes a Phospholipid-Linked Membrane Protein Homologous to its Receptor CD2", Nature, 329(6142):840-842.
Singh et al. (Jun. 20, 2007) "Correlation of T-Cell Response, Clinical Activity and Regulatory T-Cell Levels in Renal Cell Carcinoma Patients Treated with IMA901, A Novel Multi-Peptide Vaccine", ASCO Journal, Abstract No. 3017, 2 pages.
Smith et al. (Dec. 1983) "Production of Human Beta Interferon in Insect Cells Infected with a Baculovirus Expression Vector", Molecular and Cellular Biology, 3(12):2156-2165.
Smith et al. (Jul. 15, 1988) "Single-Step Purification of Polypeptides Expressed in *Escherichia coli* as Fusions with Gluthatione S-Transferase", Gene, 67(1):31-40.
Stover et al. (Jun. 6, 1991) "New Use of BCG for Recombinant Vaccines", Nature, 51:456-460.
Studier et al. (1990) "Gene Expression Technology", Methods in Enzymology, 185:60-89.
Szoka et al. (1980) "Comparative Properties and Methods of Preparation of Lipid Vesicles (Liposomes)", Annual Review of Biophysics and Bioengineering, 9:467-508.
Taylor et al. (Nov. 13, 2009) "The Malaria Parasite Cyclic GMP-Dependent Protein Kinase Plays a Central Role in Blood-Stage Schizogony", Eukaryotic Cell, 9(1):37-45.
Triglia et al. (Aug. 8, 1988) "Structure of a Plasmodium Falciparum Gene that Encodes a Glutamic Acid-Rich Protein (GARP)", Molecular and Biochemical Parasitology, 31:199-202.
Trimble et al. (2009) "A Phase I Trial of a Human Papillomavirus DNA Vaccine for HPV16+ Cervical Intraepithelial Neoplasia 2/3", Clinical Cancer Research, 15:361-367.
Wada et al. (1992) "Codon Usage Tabulated from the GenBank Genetic", Nucleic Acids Research, 20:2111-2118.
Weintraub et al. (Dec. 1985) "Antisense RNA as a Molecular Tool for Genetic Analysis", Reviews Trends in Genetics, 1(1):22-25.
Winoto et al. (1989) "A Novel, Inducible and T Cell-Specific Enhancer Located at the 3' End of the T Cell Receptor a Locus", The EMBO Journal, 8(3):729-733.
Wolff et al. (Mar. 23, 1990) "Direct Gene Transfer into Mouse Muscle in Vivo", Science, 247(4949):1465-1468.
Wrighton Katharine H. (Jul. 2020) "A Novel Vaccine Target for Malaria", Nature Reviews Microbiology, 18:361.
Yeoh et al. (Dec. 1, 2007) "Subcellular Discharge of a Serine Protease Mediates Release of Invasive Malaria Parasites from Host Erythrocytes", CELL, 131(6):1072-1083.
Zeger et al. (Mar. 1986) "Longitudinal Data Analysis for Discrete and Continuous Outcomes", Biometrics, 42 (1):121-130.
Raj et al., "Antibodies to Plasmodium Falciparum Glutamic Acid Rich Protein (PfGARP) Inhibit Parasite Growth by Arresting Trophozoite Development", International Journal of Infectious Diseases, vol. 45, Apr. 2016, 377 page.
International Search Report and Written Opinion received in International Application No. PCT/US2012/067404 dated Jul. 10, 2013, 17 pages.
Extended European Search Report dated Mar. 18, 2022; Application No. 21186416.0.

* cited by examiner

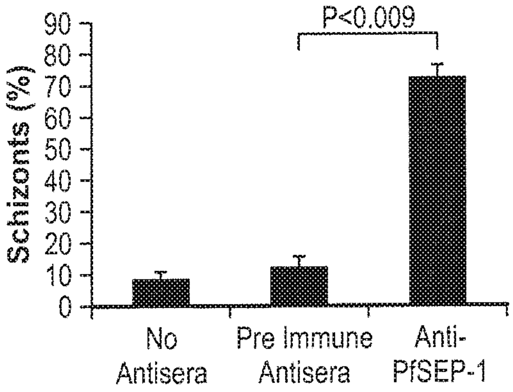
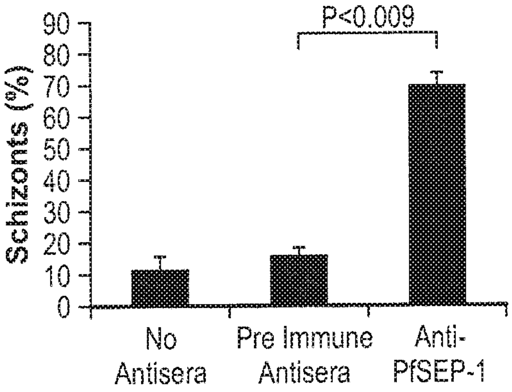
FIG. 14A
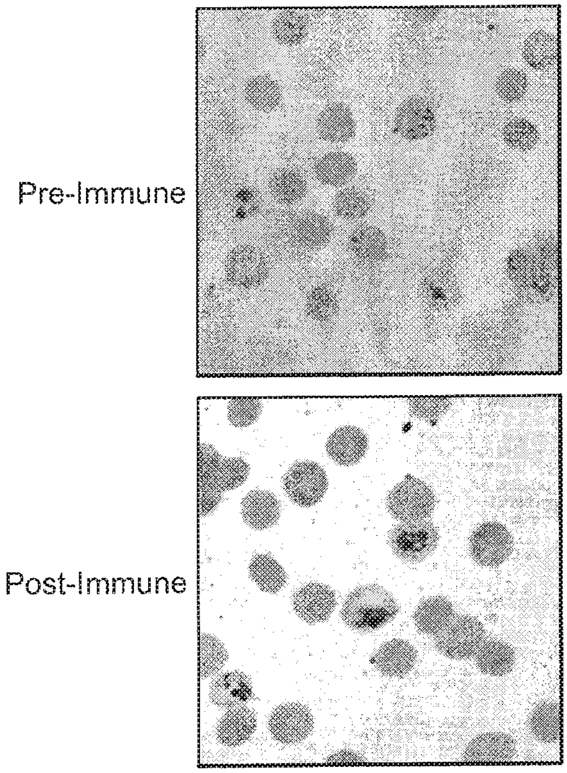
FIG. 14B

Epidemiologic characteristics of resistant and susceptible individuals used in differential screening assays

| Variable | Resistant | Susceptible | P value[a] |
|---|---|---|---|
| Number of Subjects | 12 | 11 | - |
| Hemoglobin phenotype (% AS) | 16.6 | 0 | 0.47 |
| Sex (% female) | 41.6 | 45.4 | 1 |
| Weeks of follow-up (median [IQR]) | 140.5 [44.5] | 152 [44] | 0.31 |
| # of Blood smears from age 2-3.5 yrs (median [IQR]) | 16.5 [21.5] | 21 [24] | 0.31 |
| # of Positive Blood smear from age 2-3.5 yrs (median [IQR]) | 0 [1] | 4 [10] | 0.04 |
| # of anti-malarial treatments before age 2 yrs (median [IQR]) | 2 [1.75] | 8 [8] | 0.01 |
| Pregnancy malaria (%) | 16.6 | 9 | 1 |
| Maternal age (yrs, median [IQR]) | 22.5 [9.5] | 28 [10] | 0.35 |
| Birth Season (% in High Season) | 25 | 9 | 0.59 |
| Children using Bed Net (%) | 33.3 | 0 | 0.09 |
| # of Previous Pregnancies (median [IQR]) | 0 [2] | 1 [2] | 0.19 |
| Parasite density (parasites/200 WBCs) at 2 yr blood draw (median [IQR]) | 0 [0] | 0 [0] | 1 |
| Parasite density (parasites/200 WBCs) from age 2-3.5 yrs (median [IQR]) | 0 [25.6] | 320.3 [944.1] | 0.05 |

[a]Comparisons of catagorical variables by 2 tailed Fisher's exact test.
Comparisons of continuous variables by Mann-Whitney U test

FIG. 16

Epidemiologic characteristics of resistant and susceptible individuals used in confirmatory ELISA assays

| Variable | Resistant | Susceptible | P value[a] |
|---|---|---|---|
| Number of Subjects | 11 | 14 | 1 |
| Hemoglobin phenotype (% AS) | 36 | 21 | 0.66 |
| Sex (% female) | 45 | 43 | 1 |
| Weeks of follow-up (median [IQR]) | 154 [14] | 165 [19] | 0.34 |
| # of Blood smears from age 2-3.5 yrs (median [IQR]) | 14 [5.8] | 20.5 [9.5] | 0.02 |
| # of Positive Blood smear from age 2-3.5 yrs (median [IQR]) | 0 | 7.8 [6] | <0.001 |
| # of anti-malarial treatments before age 2 yrs (median [IQR]) | 2.6 [2.9] | 6.3 [3.1] | 0.008 |
| Pregnancy malaria (%) | 9 | 14 | 1 |
| Maternal age (yrs, median [IQR]) | 27 [8] | 27 [7] | 0.85 |
| Birth Season (% in High Season) | 73 | 50 | 0.41 |
| Children using Bed Net (%) | 0 | 0 | 1 |
| # of Previous Pregnancies (median [IQR]) | 1 [3.0] | 1 [3.0] | 0.89 |
| Parasite density (parasites/200 WBCs) at 2 yr blood draw (median [IQR]) | 0 [0] | 0 [0] | 1 |
| Parasite density (parasites/200 WBCs) from age 2-3.5 yrs (median [IQR]) | 0 [0] | 2106.9 [2700] | <0.001 |

[a] Comparisons of catagorical variables by 2 tailed Fisher's exact test.
Comparisons of continuous variables by Mann-Whitney U test

FIG. 17

FIG. 18A Ring Stage
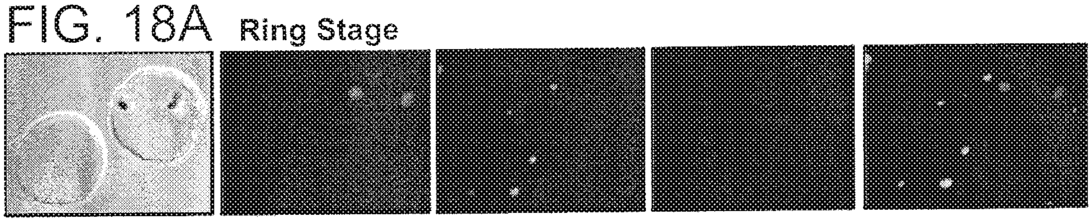
FIG. 18B Mature Trophozoite
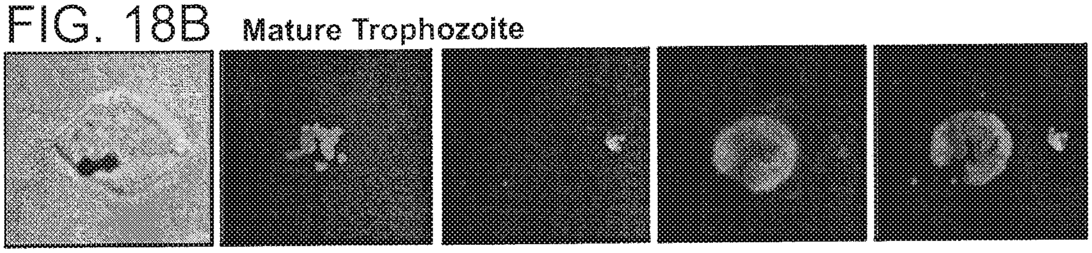
FIG. 18C Mature Schizont
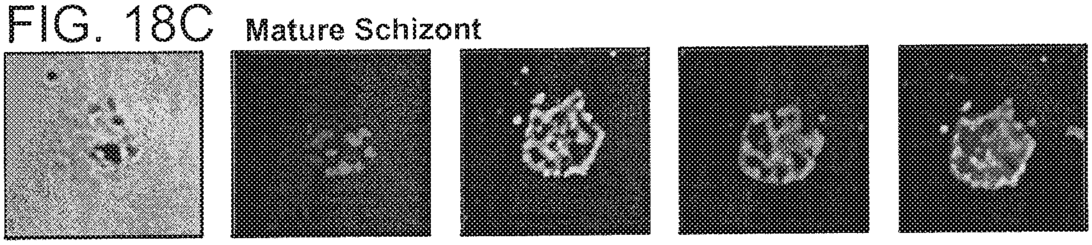
FIG. 18D Free Merozoite
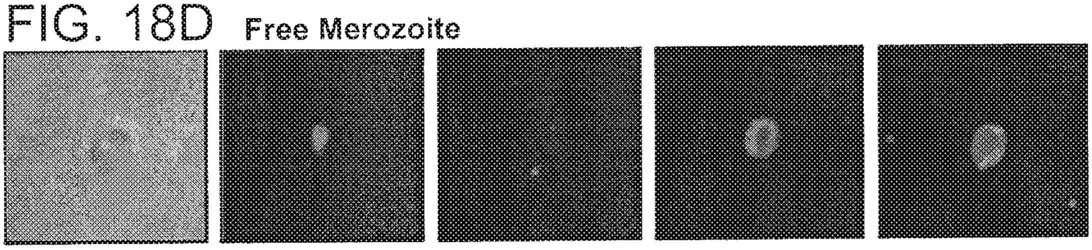
FIG. 18E Stage I gametocyte
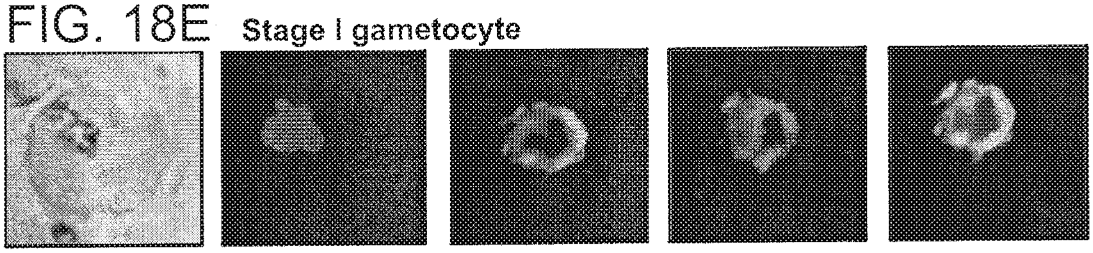
FIG. 18F Stage III gametocyte
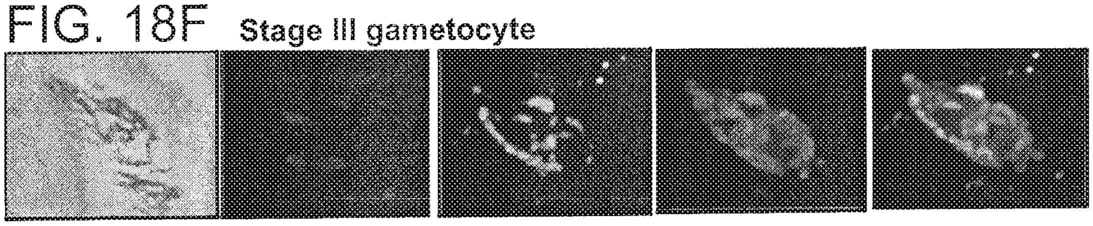
FIG. 18G Mature Schizont
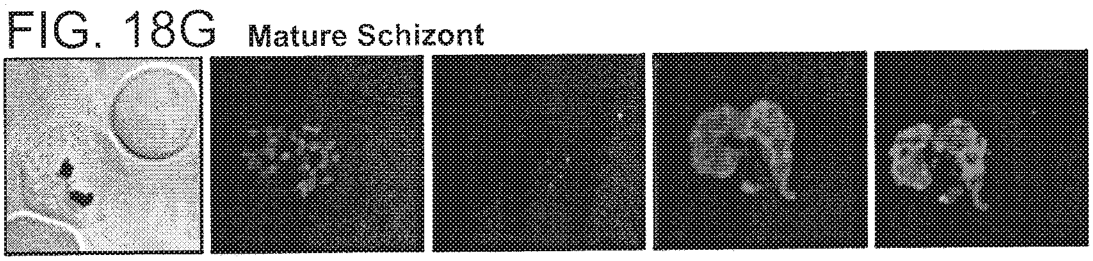

SEQUENCE LISTING

```
<160> NUMBER OF SEQ ID NOS: 77

<210> SEQ ID NO 1
<211> LENGTH: 819
<212> TYPE: DNA
<213> ORGANISM: Artificial Sequence
<220> FEATURE:
<223> OTHER INFORMATION: Fragment of P. falciparum
```

<400> SEQUENCE: 1

```
aacgaggata gaggaatata cgatgaatta ttagaaaatg atatgtgtga tttatacaat      60
ttaaaaatgc atgatttgca taatttaaaa tcctatgatt ttggattatc taaagattta     120
ttaaaaaagg atatttttat atatagtaat aatttgaaaa atgatgatat ggatgatgat     180
gataataata atatgaatga tattgctata ggtgaaaatg taatatatga aaatgatata     240
catgaaaata atatagatga taatgatatg tataataatt acgtgaatgg aaatgattta     300
tatattaaca atatgcagga tgatgccatg gacgatattg tatatgatga ggaagaaatt     360
aaaagcttcc tagataaatt aaaatctgat atatcaaatc aaatgaatgt aaaaaatgga     420
aatgtcgaag ttacaggaaa tggtggtaat gaagaaatgt cttatataaa taatgatgaa     480
aatttacaag cttttgattt gttagataat ttccatatgg atgattatgg taataattat     540
aatgataatg aagaagatgg ggatggggat ggggatgacg atgaacagaa gaaaagaaaa     600
caaaaagagt tacataatgt aaatggaaaa ttaaacttat cagatttaaa tgaattaaat     660
gtagatgata taaataataa tttttatatg tcaactcctc gaaaatctat agatgaacgt     720
aaagatacgg aatgtcaaac agattttccc ttattagatg tatcaaggaa tactaatagg     780
actcctagaa gaaaaagtgt ggaagtaata cttgtagaa                            819
```

<210> SEQ ID NO 2
<211> LENGTH: 273
<212> TYPE: PRT
<213> ORGANISM: Artificial Sequence
<220> FEATURE:
<223> OTHER INFORMATION: Fragment of P. falciparum

<400> SEQUENCE: 2

```
Asn Glu Asp Arg Gly Ile Tyr Asp Glu Leu Leu Glu Asn Asp Met Cys
1               5                   10                  15

Asp Leu Tyr Asn Leu Lys Met His Asp Leu His Asn Leu Lys Ser Tyr
            20                  25                  30

Asp Phe Gly Leu Ser Lys Asp Leu Leu Lys Lys Asp Ile Phe Ile Tyr
        35                  40                  45

Ser Asn Asn Leu Lys Asn Asp Asp Met Asp Asp Asp Asp Asn Asn Asn
    50                  55                  60

Met Asn Asp Ile Ala Ile Gly Glu Asn Val Ile Tyr Glu Asn Asp Ile
65                  70                  75                  80

His Glu Asn Asn Ile Asp Asp Asn Asp Met Tyr Asn Asn Tyr Val Asn
                85                  90                  95

Gly Asn Asp Leu Tyr Ile Asn Asn Met Gln Asp Asp Ala Met Asp Asp
            100                 105                 110

Ile Val Tyr Asp Glu Glu Glu Ile Lys Ser Phe Leu Asp Lys Leu Lys
        115                 120                 125

Ser Asp Ile Ser Asn Gln Met Asn Val Lys Asn Gly Asn Val Glu Val
    130                 135                 140

Thr Gly Asn Gly Gly Asn Glu Glu Met Ser Tyr Ile Asn Asn Asp Glu
145                 150                 155                 160

Asn Leu Gln Ala Phe Asp Leu Leu Asp Asn Phe His Met Asp Asp Tyr
                165                 170                 175

Gly Asn Asn Tyr Asn Asp Asn Glu Glu Asp Gly Asp Gly Asp Gly Asp
            180                 185                 190

Asp Asp Glu Gln Lys Lys Arg Lys Gln Lys Glu Leu His Asn Val Asn
        195                 200                 205
```

```
Gly Lys Leu Asn Leu Ser Asp Leu Asn Glu Leu Asn Val Asp Asp Ile
    210                 215                 220

Asn Asn Asn Phe Tyr Met Ser Thr Pro Arg Lys Ser Ile Asp Glu Arg
225                 230                 235                 240

Lys Asp Thr Glu Cys Gln Thr Asp Phe Pro Leu Leu Asp Val Ser Arg
                245                 250                 255

Asn Thr Asn Arg Thr Pro Arg Arg Lys Ser Val Glu Val Ile Leu Val
            260                 265                 270

Glu


<210> SEQ ID NO 3
<211> LENGTH: 2074
<212> TYPE: PRT
<213> ORGANISM: Artificial Sequence
<220> FEATURE:
<223> OTHER INFORMATION: Fragment of P. falciparum

<400> SEQUENCE: 3

Met Met Glu Asn Lys Tyr Pro Asn Glu Leu Phe Cys Tyr Ile Asn Arg
1               5                   10                  15

Tyr Asn Ile Asn Glu Ile Ile Glu Asn Gly Glu Glu Lys Tyr Val Asn
            20                  25                  30

Glu Tyr Asp Glu Asp Lys Asn Met Ser Ile Asn His Met Asn Glu Asn
        35                  40                  45

Asp Gly Ile Cys Glu Tyr Glu Ile Pro Phe Leu Leu Asp Tyr Val Asp
    50                  55                  60

Asp Ser Asn Lys Glu Asp Ser Glu Lys Asn Ser Leu Lys Ser Tyr Leu
65                  70                  75                  80

Asp Asp Gly Ala Ser Thr Ile Leu Ser Lys Pro Asp Glu Leu Glu Asn
                85                  90                  95

Tyr Asn Lys Gln Asn Glu Asn Glu Phe Asp Glu Asn Asn Asn Asn Lys
            100                 105                 110

Asn Asn Lys Ile Asp Gln Leu Lys Glu Lys Ile Asn Ile Ile Ile Ile
        115                 120                 125

Pro Asn Lys Gly Val Ile Asn Asn Phe Glu Glu Ile Leu Ser Met Ala
    130                 135                 140

Asn Arg Asn Asp Lys Asn Ile Glu Lys Lys Leu Asn Asp Arg Phe Tyr
145                 150                 155                 160

Gln Ile Cys Cys Lys Ser Ile Ala Asp Ile Asn Thr His Asn Leu Asn
                165                 170                 175

Lys Ile Lys Asp Leu Lys Lys Lys Lys Asn Asn Lys Gly Ser Leu Asn
            180                 185                 190

Ile Glu His Ile Asp Tyr Gly Asp Ile Phe Leu Thr Ile His Asp Thr
        195                 200                 205

Leu Lys Ser Asn Asn Lys Ile Lys Gly Asn Asn Lys Thr Asn Leu Leu
    210                 215                 220

His Asp Ser Ser Tyr Glu Ile Lys Lys Lys Thr Arg Arg Gly Thr Asn
225                 230                 235                 240

Ile Tyr Lys Asn Pro Phe His His Arg Gly Ser Tyr Leu Thr Ser Tyr
                245                 250                 255

Glu Asn Gln Lys Asp Ile Ile Tyr Leu Asn Asn Leu Asn Asn Ile Met
            260                 265                 270

Met Asp Lys Tyr Ser Asn Cys Ser Asp Ser Arg Lys Lys Glu Tyr Ser
        275                 280                 285
```

-continued

```
His Phe Asn Ser Gln Glu Phe Ser Tyr Asp Lys Tyr Ser Met Lys Asp
    290                 295                 300

Arg Met Phe Leu Lys Asn Leu Tyr Met Lys Gln Asn Arg Leu Arg Asp
305                 310                 315                 320

Lys Arg Gly Lys Tyr His Lys Leu Gly Asp Tyr Gln Asn Ile Glu Asn
                325                 330                 335

Tyr Arg Lys Thr Gly Glu His Ser Phe Asp Cys Met Asn Met Ser Asp
            340                 345                 350

Ile Met His Ser Asn Lys Met Ser His Val Asn Ile Met Asp His Met
        355                 360                 365

Ile Tyr Lys Asp Asn Asn Asn Met Ser Lys Leu Val Asp Thr Ile Asn
    370                 375                 380

Ser Arg Glu Lys Asp Val Lys Asn Tyr Asp Asp Asn Phe Glu Ser Tyr
385                 390                 395                 400

Asn Asn Phe Phe Lys Asn Asn Asn Asp Glu Gln His Ile Cys Leu Glu
                405                 410                 415

Tyr Asp Asp Thr Tyr Asn Leu Lys Asp Thr Val Lys Asn Ile Ile Val
            420                 425                 430

Glu Glu Glu Gln Cys Gly Lys Gly Val Ala Cys Ile Cys Asp Lys Asn
        435                 440                 445

Glu Asp Val Asp Asp Leu Phe Val Ser Lys Lys Thr Asn Tyr Ser Ser
    450                 455                 460

Asn Lys Lys Arg Glu Asp Tyr Glu Lys Val Phe Leu Glu Asp Asn Leu
465                 470                 475                 480

His Leu Lys Gln Thr Pro Ser Lys Arg Thr Lys Ile Asn Ile Ile Pro
                485                 490                 495

Asp Tyr Tyr Asp Asn Asn Arg Ser Asn Lys Ser Tyr Lys Glu Asn Glu
            500                 505                 510

Glu Asp Ala Leu Phe Glu Val Cys Gly Ser Leu Lys Asn Asp Asp Ile
        515                 520                 525

Leu Tyr Lys Asp Asn Lys Leu Asn Val Ile Asn Glu Asp Asn Ile Lys
    530                 535                 540

Glu Glu Asp Asp Lys Glu Ser Val Val His Leu Asp Asn Asp Glu Asp
545                 550                 555                 560

Lys Lys Glu Glu Met Tyr Lys Asp Val Tyr Pro Asn Val Leu Ser Cys
                565                 570                 575

Glu Lys Glu Thr Ile Arg Arg Asn Glu Lys Tyr Asn Lys Ser Leu Asn
            580                 585                 590

Ser Thr Ser Ser Phe Glu Lys Ile Asp Asn Pro Ser Glu Ile Asn Val
        595                 600                 605

Glu Ser Lys Glu Asp Thr Glu Tyr Phe Asp Leu Leu Ile Lys Lys Tyr
    610                 615                 620

Glu Asp Thr Lys Ile Asn Val Tyr Asp Asn Glu Ser Leu Leu Leu Asp
625                 630                 635                 640

Leu Ser Asn Glu Leu Arg Glu Glu Met Ala Lys Gly Asp Ser Asn Lys
                645                 650                 655

Asn Val Asn Lys Val Glu Asp Asn Asp Asn Lys Lys Glu Asn Ile Cys
            660                 665                 670

His Asp Asn Ile Met Glu Asp Ile Cys His Asn Asn Asn Val Glu Asp
        675                 680                 685

Met Tyr Arg Asn Asn Asn Val Glu Asp Met Tyr Arg Asn Asn Asn Val
    690                 695                 700
```

```
Glu Asp Met Tyr Arg Asn Asn Asn Val Glu Asp Met Tyr Arg Asn Asn
705                 710                 715                 720

Asn Val Glu Asp Val Cys His Asn Asn Asn Val Glu Asp Val Cys His
                725                 730                 735

Asn Asn Asn Val Glu Asp Val Cys His Asn Asn Asn Val Glu Asp Val
            740                 745                 750

Tyr His Asn Asn Asn Val Glu Asp Met Tyr His Asp Asn Asn Ile Glu
        755                 760                 765

Asp Val Cys His Asn Asn Asn Val Glu Asp Val Cys His Asn Asn Asn
    770                 775                 780

Val Glu Asp His Val Asn Tyr Asp Asn Glu Glu Leu Asn Lys Lys Met
785                 790                 795                 800

Asp Glu Met Lys Glu Glu Lys Glu Glu Arg Asn Glu Asp Arg Gly Ile
                805                 810                 815

Tyr Asp Glu Leu Leu Glu Asn Asp Met Cys Asp Leu Tyr Asn Leu Lys
            820                 825                 830

Met His Asp Leu His Asn Leu Lys Ser Tyr Asp Phe Gly Leu Ser Lys
        835                 840                 845

Asp Leu Leu Lys Lys Asp Ile Phe Ile Tyr Ser Asn Asn Leu Lys Asn
    850                 855                 860

Asp Asp Met Asp Asp Asp Asp Asn Asn Asn Met Asn Asp Ile Ala Ile
865                 870                 875                 880

Gly Glu Asn Val Ile Tyr Glu Asn Asp Ile His Glu Asn Asn Ile Asp
                885                 890                 895

Asp Asn Asp Met Tyr Asn Asn Tyr Val Asn Gly Asn Asp Leu Tyr Ile
            900                 905                 910

Asn Asn Met Gln Asp Asp Ala Met Asp Asp Ile Val Tyr Asp Glu Glu
        915                 920                 925

Glu Ile Lys Ser Phe Leu Asp Lys Leu Lys Ser Asp Ile Ser Asn Gln
    930                 935                 940

Met Asn Val Lys Asn Gly Asn Val Glu Val Thr Gly Asn Gly Gly Asn
945                 950                 955                 960

Glu Glu Met Ser Tyr Ile Asn Asn Asp Glu Asn Leu Gln Ala Phe Asp
                965                 970                 975

Leu Leu Asp Asn Phe His Met Asp Asp Tyr Gly Asn Asn Tyr Asn Asp
            980                 985                 990

Asn Glu Glu Asp Gly Asp Gly Asp  Gly Asp Asp Asp Glu  Gln Lys Lys
        995                 1000                1005

Arg Lys  Gln Lys Glu Leu His  Asn Val Asn Gly Lys  Leu Asn Leu
    1010                 1015                 1020

Ser Asp  Leu Asn Glu Leu Asn  Val Asp Asp Ile Asn  Asn Asn Phe
    1025                 1030                 1035

Tyr Met  Ser Thr Pro Arg Lys  Ser Ile Asp Glu Arg  Lys Asp Thr
    1040                 1045                 1050

Glu Cys  Gln Thr Asp Phe Pro  Leu Leu Asp Val Ser  Arg Asn Thr
    1055                 1060                 1065

Asn Arg  Thr Pro Arg Arg Lys  Ser Val Glu Val Ile  Leu Val Glu
    1070                 1075                 1080

Lys Lys  Leu Lys Lys Lys Lys  Gln Lys Cys Met Asp  Lys Tyr Thr
    1085                 1090                 1095

Asp Ala  Asn Glu Asp Ser Asn  Arg Arg Tyr Pro Lys  Arg Asn Arg
    1100                 1105                 1110
```

-continued

```
Ile Lys  Thr Leu Arg Tyr Trp  Ile Gly Glu Arg Glu  Leu Thr Glu
    1115                 1120                 1125

Arg Asn  Pro Tyr Thr Gly Glu  Ile Asp Val Val Gly  Phe Ser Glu
    1130                 1135                 1140

Cys Lys  Asn Leu Gln Asp Leu  Ser Pro His Ile Ile  Gly Pro Ile
    1145                 1150                 1155

Glu Tyr  Lys Lys Ile Tyr Leu  Lys Asn Leu Asn Ser  Asn Glu His
    1160                 1165                 1170

Glu Glu  Asn Glu Asp Asn Asn  Gly Asp Ile Ile Glu  Asn Asn Asn
    1175                 1180                 1185

Gly Asp  Val Ile Glu Asn Asn  Asn Gly Asp Ile Ile  Glu Asp Asn
    1190                 1195                 1200

Asn Ala  Asn Glu Lys Asn His  Asn Asn Leu Glu Ser  Glu Gly Lys
    1205                 1210                 1215

Gly Ile  Val Tyr Asp Asp Val  Asn Asn Leu His Val  His Thr Asn
    1220                 1225                 1230

Ser Asp  Asn Ser Ala His Ser  Lys Lys Ile Lys Gly  Ala Pro Ser
    1235                 1240                 1245

Arg Phe  Ser Asn Thr Asn Asn  Gly Arg Lys Lys Arg  Arg Arg Arg
    1250                 1255                 1260

Lys Phe  Ile Asn Val Val Asn  Tyr Ile Lys Lys Lys  Lys Lys Lys
    1265                 1270                 1275

Lys Leu  Ile Lys Ser Met Asp  Asn Met Glu Val Thr  Asp Asn Phe
    1280                 1285                 1290

Lys Asn  Asp Met Ser Asp Glu  Asn Lys Gln Ser Gly  Asp Glu Asn
    1295                 1300                 1305

Lys Gln  Ser Gly Asp Glu Asn  Lys Gln Ser Gly Asp  Glu Asn Lys
    1310                 1315                 1320

Gln Ser  Gly Asp Glu Asn Lys  Gln Thr Asn Asn Asp  Ile Lys Gln
    1325                 1330                 1335

Ser Asp  Asn Asp Ile Lys Gln  Ser Asp Asp Ile Tyr  Met Asn Glu
    1340                 1345                 1350

Asp Met  Asn Leu Phe Asn Asp  Leu Asn Asp Asn Phe  Asp Asn Asn
    1355                 1360                 1365

Glu Tyr  Phe Ile Asn Asn Gly  Asp Lys Asp Ser His  Ala Glu Glu
    1370                 1375                 1380

Glu Met  Ala Ile Glu Asn Ile  Gln Ser Lys Ser Ile  Glu Lys Asp
    1385                 1390                 1395

Ile Leu  Asn Asn Glu Glu Gln  Asp Asn Asn Asn Ile  Phe Asp Ile
    1400                 1405                 1410

Asp Asn  Glu Leu Ile Asp Met  Lys Asp Gly Asn Val  Asp Glu Met
    1415                 1420                 1425

Glu Ser  Asp Glu Lys Leu Lys  Thr Phe Glu Lys Leu  Glu Ser Leu
    1430                 1435                 1440

Lys Ser  Thr Thr His Leu Asn  Asn Thr Asp Asn Cys  Asp Val Asn
    1445                 1450                 1455

Leu Ser  Glu Gln Thr Asn Glu  Ile Asn Tyr Asp Glu  Glu Lys Lys
    1460                 1465                 1470

Val Asn  Lys Lys Thr Asn His  Glu Lys Met Lys Lys  Lys Lys Lys
    1475                 1480                 1485

Lys Lys  Lys Lys Lys Lys Lys  Lys Lys Lys Lys Glu  Lys Lys Gln
    1490                 1495                 1500
```

```
Ile Asp Ile Met Tyr Lys Asn Leu Ser Arg Leu Asn Leu Asn Leu
    1505                1510                1515

Leu Leu Pro Thr Lys Lys Lys Val Lys Lys Ser Lys Asn Ser Phe
    1520                1525                1530

Lys Lys Glu Glu Glu Lys Gln Lys Lys Lys Asn Lys Lys Val Lys
    1535                1540                1545

Lys Ile Lys Gly Ile Asn Lys Gly Glu Lys Ile Lys Ser Asn Lys
    1550                1555                1560

Lys Glu Asn Lys Asp Asn Asn Asn Asp Ser Ser Thr Glu Cys Val
    1565                1570                1575

Val Glu Gly Glu Lys Gly Lys Asp Leu His Glu Phe Asn Lys Asn
    1580                1585                1590

Gly Asn Leu Glu Asp Glu Gln Met Asp Val Asp Ile Ser Met Asn
    1595                1600                1605

Ile Ser Ser Ile Asn Cys Glu Ser Asp Asn Lys Asn Val Ser Lys
    1610                1615                1620

Glu Gly Glu Glu Glu Lys Lys Asp Ile Ala Glu Asn Lys Glu Glu
    1625                1630                1635

Val Asp Lys Asn Lys Glu Glu Val Tyr Met Asp Lys His Glu Met
    1640                1645                1650

Asp Leu Asn Asn Glu Glu Val Tyr Met Asp Lys Asn Glu Met Asp
    1655                1660                1665

Leu Asn Asn Glu Glu Val Tyr Met Asp Lys His Glu Met Asp Leu
    1670                1675                1680

Asn Asn Glu Glu Val Tyr Met Asp Lys His Glu Met Asp Leu Asn
    1685                1690                1695

Asn Glu Glu Val Tyr Met Asp Lys His Glu Met Asp Leu Asn Lys
    1700                1705                1710

Glu Glu Val Tyr Met Asp Lys His Glu Met Asp Leu Asn Asn Glu
    1715                1720                1725

Glu Val Asp Lys Glu Asn Glu Tyr Asp Glu Asn Ile Leu Ser Asp
    1730                1735                1740

Asn Ile Ile Tyr Asn Glu Asn Asn Ser Phe Gly Asn Asn Lys Asn
    1745                1750                1755

Ser Phe Phe Asn Asn Thr Ser Pro Leu Lys Thr Glu Ile Ile Asn
    1760                1765                1770

Glu Glu Glu Asn Ser Leu Asn Glu Met Lys Glu Asp Ile Asn Glu
    1775                1780                1785

Tyr Val Glu Met Glu Asn Lys Leu Asp Thr Glu Lys Ile Lys Asp
    1790                1795                1800

Ser Glu Lys Ile Gly Gly Lys Ile Glu Val Asp Asn Lys Met Ile
    1805                1810                1815

Ser Pro Ile Asn Arg His Asn Phe Tyr Leu Thr Ile Leu Glu Gly
    1820                1825                1830

Met Asn Lys Asn Phe Pro Arg Gln Trp Asn Lys Asn Asn Ile Thr
    1835                1840                1845

Leu Ser Lys Asn Gln Gly Gln Ile Tyr Lys Gly Arg Lys Glu Lys
    1850                1855                1860

Lys Arg Lys Arg Ser Tyr Arg Asn Asp Glu Lys Leu Leu Asp His
    1865                1870                1875

Ser Ile Leu Asn Asp Ile Asn Ile Ser Asp Lys Met Asp Glu Arg
    1880                1885                1890
```

-continued

```
Asn Glu  Leu Leu Glu Ser Ile  Lys Ser Asn Ser Thr  Ile Asn Asn
    1895                 1900                 1905

Val Leu  Glu Ile Ile Lys Tyr  Asp Asn Arg Lys Lys  Ile Lys Lys
    1910                 1915                 1920

Asn Asp  Thr Asn Lys Glu Ile  Ile Lys Tyr Asp Asn  Phe Thr Ser
    1925                 1930                 1935

Lys Tyr  Asn Asn Lys Ser Asn  Asp Ile Gln Leu Asn  Gly Gly Ile
    1940                 1945                 1950

Tyr Ile  Asn Lys Phe Lys Leu  Ser Leu Asp Met Pro  Ile Asn Lys
    1955                 1960                 1965

Leu Ala  Val Ser Ser Asn Leu  Gly Pro Pro Ser Ser  Ile Gly Ser
    1970                 1975                 1980

Thr Glu  Ile Gln Pro Ile Gln  Lys Asn Phe Asn Asp  Phe Lys Met
    1985                 1990                 1995

Asn Ile  Asn Val Tyr Cys Ile  Arg Met Glu Pro His  Glu Lys Tyr
    2000                 2005                 2010

Ser Ser  Tyr Ser His Lys Asn  Asn Leu Val Val Tyr  Ile Asp Lys
    2015                 2020                 2025

Gly Glu  Lys Ile Asn Ile Ile  Ile Asn Met Ser Lys  Thr Tyr Glu
    2030                 2035                 2040

Lys Gly  Asp Phe Phe Tyr Ile  Pro Arg Phe Ser Asn  Phe Gln Ile
    2045                 2050                 2055

Ile Asn  Asp Ser Arg Cys Asp  Cys Val Leu Tyr Val  Cys Pro Leu
    2060                 2065                 2070

Ile
```

<210> SEQ ID NO 4
<211> LENGTH: 6225
<212> TYPE: DNA
<213> ORGANISM: Artificial Sequence
<220> FEATURE:
<223> OTHER INFORMATION: Fragment of P. falciparum

<400> SEQUENCE: 4

```
atgatggaaa ataaataccc aaatgaatta ttctgttata taaatagata taatataaac     60
gaaataatag aaaatggaga agagaagtat gtaaatgaat atgatgaaga taagaatatg    120
tcaataaatc atatgaatga aaacgatggt atatgtgaat atgaaatacc atttttatta    180
gactatgtgg atgatagtaa taaagaagat tcagagaaaa attcattaaa gagttatctc    240
gatgatggtg catccactat cctttcaaaa ccagatgaac tggaaaatta taataaacaa    300
aatgaaaatg aatttgacga aaataataat aataaaaata ataaaattga ccaattgaag    360
gaaaaaataa atattataat aataccaaat aaaggtgtta taaacaattt tgaagagata    420
ttaagcatgg caaatcgtaa tgataaaaat atagagaaaa agttgaatga tagattttat    480
caaatatgtt gtaaaagtat agctgatata aacacacaca atttaaataa aattaaagat    540
ttgaaaaaaa aaaaaaataa taaaggatcc ttaaatattg aacatataga ttatggagat    600
atttttctta ctatacatga tacattaaaa agtaataata aaataaaagg aaacaataaa    660
actaacttat tacacgattc ttcttatgaa ataaaaaaga aaacaagaag aggaacaaat    720
atatataaaa atccatttca tcatagaggt tcctatttaa cttcgtatga aaatcaaaag    780
gatatcattt accttaataa tttaaacaac attatgatgg ataaatatag taattgtagt    840
gattcacgaa aaaaggaata ttcgcatttc aattcgcagg agttttcata tgataaatat    900
agtatgaaag acagaatgtt tctcaaaaat ttgtatatga aacaaaatag attaagagat    960
```

```
aaaaggggga aatatcacaa attgggagat tatcaaaata ttgaaaacta tcgtaaaacg   1020
ggtgaacata gttttgattg tatgaatatg tcagatatta tgcattcaaa taaaatgagc   1080
catgttaata tcatggatca tatgatatat aaagataata acaatatgag caaactagta   1140
gatacaataa attctcgtga aaaggatgta aaaaattatg acgataactt tgaaagctat   1200
aataattttt ttaagaataa taatgatgaa caacatatat gtttggagta tgacgataca   1260
tataacttaa aagatacagt taaaaatatt attgttgaag aagaacaatg tggtaagggt   1320
gttgcttgta tatgtgataa gaacgaagat gttgacgatt tgtttgtttc aaagaaaacg   1380
aattattctt ctaataaaaa aagagaagat tatgagaaag tatttcttga agataattta   1440
catttaaaac aaactccatc aaaaagaaca aaaattaata taatcccaga ttattatgat   1500
aacaatagaa gtaataagag ttataaggaa aatgaagagg atgctttgtt tgaggtatgt   1560
ggtagtttaa aaaacgatga tatattgtat aaagataata agttgaatgt cataaatgaa   1620
gataatataa aggaagagga tgacaaagaa agtgttgttc atttagataa tgatgaggat   1680
aaaaaagaag aaatgtataa agatgtatat cccaatgtat tgtcttgtga aaaagaaacg   1740
attaggagga atgaaaagta taacaaatca ttgaacagta caagtagctt tgaaaaaatt   1800
gataatccaa gtgaaattaa tgttgaaagt aaggaagata cagaatattt tgatttatta   1860
ataaaaaaat atgaggatac aaaaaataaac gtatatgata atgaatctct tttattggat   1920
cttagtaatg agctacgtga agaaatggcc aaggggggatt ctaataaaaa tgtaaataaa   1980
gtggaagata atgataataa aaaggaaaat atttgtcatg ataatatcat ggaagatatt   2040
tgtcataata ataacgtgga agatatgtat cgtaataata acgtggaaga tatgtatcgt   2100
aataataacg tggaagatat gtatcgtaat aataacgtgg aagatatgta tcgtaataat   2160
aacgtggaag atgtttgtca taataataac gtggaagatg tttgtcataa taataacgtg   2220
gaagatgttt gtcataataa taacgtggaa gatgtttatc ataataataa cgtggaagat   2280
atgtatcatg ataataacat tgaagatgtt tgtcataata ataacgtgga agatgtttgt   2340
cataataata acgtggaaga ccatgttaat tatgataatg aagaattgaa taaaaaaatg   2400
gatgagatga aagaagaaaa ggaagaaaga aacgaggata gaggaatata cgatgaatta   2460
ttagaaaatg atatgtgtga tttatacaat ttaaaaatgc atgatttgca taatttaaaa   2520
tcctatgatt ttggattatc taaagattta ttaaaaaagg atatttttat atatagtaat   2580
aatttgaaaa atgatgatat ggatgatgat gataataata atatgaatga tattgctata   2640
ggtgaaaatg taatatatga aaatgatata catgaaaata atatagatga taatgatatg   2700
tataataatt acgtgaatgg aaatgattta tatattaaca atatgcagga tgatgccatg   2760
gacgatattg tatatgatga ggaagaaatt aaaagcttcc tagataaatt aaaatctgat   2820
atatcaaatc aaatgaatgt aaaaaatgga aatgtcgaag ttacaggaaa tggtggtaat   2880
gaagaaatgt cttatataaa taatgatgaa aatttacaag cttttgattt gttagataat   2940
ttccatatgg atgattatgg taataattat aatgataatg aagaagatgg ggatggggat   3000
ggggatgacg atgaacagaa gaaaagaaaa caaaaagagt tacataatgt aaatggaaaa   3060
ttaaacttat cagatttaaa tgaattaaat gtagatgata taaataataa tttctatatg   3120
tcaactcctc gaaaatctat agatgaacgt aaagatacgg aatgtcaaac agattttcca   3180
ttattagatg tatcaaggaa tactaatagg actcctagaa gaaaaagtgt ggaagtaata   3240
cttgtagaaa aaaaattaaa aaaaaaaaaa cagaaatgta tggataaata tacagatgca   3300
```

aatgaggata gtaatagaag atatcccaaa agaaatcgaa ttaaaacttt gcgttattgg 3360
ataggagaaa gagagttaac tgaaagaaac ccttacacag gagaaataga tgttgtagga 3420
tttagtgagt gtaaaaattt gcaagatttg tcacctcata ttattggtcc gattgaatat 3480
aaaaaaatat atttgaaaaa tcttaatagt aatgaacatg aggaaaatga agataataat 3540
ggagacatta ttgaaaataa taatggggac gttattgaaa ataataatgg agacattatt 3600
gaagataata atgcaaacga aaaaaatcat aataatcttg aatctgaagg taagggtatc 3660
gtatatgatg atgtaaataa tttacatgtt cacacaaaca gtgataatag tgctcattcg 3720
aagaaaataa agggagcccc cagtaggttt agtaatacaa ataatggaag gaagaaacga 3780
agaaggagaa aattcatcaa tgtagttaat tatataaaga agaagaaaaa gaagaaactg 3840
ataaaaagta tggataatat ggaggttaca gataatttta agaatgatat gagtgatgaa 3900
aataaacaaa gtggtgatga aaataaacaa agtggtgatg aaaataaaca aagtggtgat 3960
gaaaataaac aaagtggtga tgaaaataaa caaactaata atgatattaa acagagtgat 4020
aatgatatta aacagagtga tgatatttac atgaatgaag atatgaattt gttcaatgat 4080
ttaaatgata acttcgataa caatgaatat ttcataaaca atggtgataa ggattctcat 4140
gctgaagaag aaatggccat agaaaatatt caaagtaaaa gtatagaaaa ggatatttta 4200
aataatgaag agcaggataa taataacatc tttgatattg ataatgaact tatagatatg 4260
aaggatggaa atgtagatga aatggaaagt gatgaaaaat taaaaacttt tgaaaaattg 4320
gaaagtttga aaagtacaac acatttaaac aataccgata attgtgatgt aaatttgagt 4380
gaacagacca atgaaataaa ttatgatgag gaaaaaaaag ttaataaaaa aacaaatcat 4440
gaaaaaatga agaagaagaa gaagaaaaaa aaaaaaaaaa agaaaaagaa gaagaaagaa 4500
aaaaaacaaa tagatattat gtacaaaaat ttgtccagac ttaatttaaa tttgttactt 4560
ccaaccaaaa aaaaagttaa gaaatcgaaa aactcattta aaaaagagga agaaaaacaa 4620
aagaagaaaa ataaaaaagt taaaaaaatc aaaggtatta acaaggggga aaaaataaaa 4680
agtaataaga aagaaaataa ggacaataat aatgatagta gtacagaatg tgttgtagaa 4740
ggagaaaaag gaaaagattt acatgagttt aataaaaatg gaaatcttga agatgaacaa 4800
atggatgttg atatttctat gaatatttca agtataaatt gtgaaagtga taataaaaat 4860
gtgagtaagg aaggagagga agaaaaaaaa gacatagctg aaaacaaaga agaggtggat 4920
aaaaacaaag aagaggtata tatggacaaa catgagatgg atttgaacaa tgaagaggta 4980
tatatggaca aaaatgagat ggatttgaac aatgaagagg tatatatgga caaacatgag 5040
atggatttga acaatgaaga ggtatatatg gacaaacatg aaatggattt gaacaatgaa 5100
gaggtatata tggacaaaca tgaaatggat ttgaacaaag aagaggtata tatggacaaa 5160
catgagatgg atttgaacaa tgaagaggta gataaagaaa acgaatatga tgaaaatata 5220
cttagtgata acataatata taatgaaaac aattcatttg gaaacaataa gaactctttt 5280
tttaataata caagtccatt aaaaacagaa ataataaatg aagaggaaaa tagtttgaac 5340
gaaatgaaag aagacataaa tgaatacgtt gaaatggaaa acaagttgga tacggaaaaa 5400
ataaaagatt cagaaaaaat aggtggaaaa atagaggtag ataataaaat gatttctcct 5460
attaatagac ataattttta tttaacaatt cttgaaggaa tgaataagaa ttttcctagg 5520
caatggaata aaaataatat aactttatca aaaaatcaag gacaaattta taaaggaagg 5580
aaagaaaaga aaagaaaacg ttcctataga aatgatgaaa aattacttga tcatagtata 5640
ttaaatgata tcaatataag tgacaaaatg gatgaaagaa atgaattatt agagagtata 5700
aaatctaata gtactataaa taatgtatta gaaattataa aatatgataa taggaaaaaa 5760
ataaagaaga atgatacaaa caaggaaata atcaaatatg ataacttcac atctaaatat 5820
aataataaaa gtaatgatat tcaattgaat ggtggaatat atataaataa attcaaactt 5880
tctttagata tgcctataaa taaattagcg gtatcttcaa atcttggacc tccatcatct 5940
ataggatcaa cagaaataca gcctattcaa aagaatttca acgatttcaa aatgaatatt 6000
aacgtgtact gtattaggat ggagccgcat gaaaaataca gctcatatag ccataaaaat 6060
aatttagttg tatatattga taagggagaa aaaattaaca taataatcaa catgtcaaag 6120
acttatgaaa aaggtgattt tttttacata cctagatttt ctaacttcca aataattaat 6180
gatagcagat gtgattgtgt tttatatgtt tgtcctttaa tttaa 6225

<210> SEQ ID NO 5
<211> LENGTH: 852
<212> TYPE: DNA
<213> ORGANISM: Artificial Sequence
<220> FEATURE:
<223> OTHER INFORMATION: Fragment of P. falciparum

<400> SEQUENCE: 5
attaaacaaa aaaattgaag aattacaaaa cagtaaagaa aaaaatgtac atgtattaat 60
taatggaaat tcaattattg atgaaataga aaaaaatgaa gaaaatgatg ataacgaaga 120
aaataatgat gatgacaata catatgaatt agatatgaat gatgacacat tcttaggaca 180
aaataacgat tcacattttg aaaatgttga tgatgacgca gtagaaaatg aacaagaaga 240
tgaaaacaag gaaaaatcag aatcatttcc attattccaa aatttaggat tattcggtaa 300
aaacgtatta tcaaaggtaa aggcacaaag tgaaacagat actcaatcta aaaatgaaca 360
agagatatca acacaaggac aagaagtaca aaaaccagca caaggaggag aatcgacatt 420
tcaaaaagac ctagataaga aattatataa tttaggagat gtttttaatc atgtagttga 480
tatttcaaac aaaaagaaca aaataaatct cgatgaatat ggtaaaaaat atacagattt 540
caaaaaagaa tatgaagact tcgttttaaa ttctaaagaa tatgatataa tcaaaaatct 600
aataattatg tttggtcaag aagataataa gagtaaaaat ggcaaaacgg atattgtaag 660
tgaagctaaa catatgactg atattttcat aaaactattt aaagataagg aataccatga 720
acaatttaaa aattatattt atggtgttta tagttatgca aaacaaaata gtcacttaag 780
tgagaaaaaa ataaaaccag aagaggaata taaaaaattt ttagaatatt catttaattt 840
actaaacaca at 852

<210> SEQ ID NO 6
<211> LENGTH: 284
<212> TYPE: PRT
<213> ORGANISM: Artificial Sequence
<220> FEATURE:
<223> OTHER INFORMATION: Fragment of P. falciparum

<400> SEQUENCE: 6

Leu Asn Lys Lys Ile Glu Glu Leu Gln Asn Ser Lys Glu Lys Asn Val
1 5 10 15

His Val Leu Ile Asn Gly Asn Ser Ile Ile Asp Glu Ile Glu Lys Asn
20 25 30

Glu Glu Asn Asp Asp Asn Glu Glu Asn Asn Asp Asp Asp Asn Thr Tyr
35 40 45

```
Glu Leu Asp Met Asn Asp Asp Thr Phe Leu Gly Gln Asn Asn Asp Ser
    50                  55                  60

His Phe Glu Asn Val Asp Asp Asp Ala Val Glu Asn Glu Gln Glu Asp
65                  70                  75                  80

Glu Asn Lys Glu Lys Ser Glu Ser Phe Pro Leu Phe Gln Asn Leu Gly
                85                  90                  95

Leu Phe Gly Lys Asn Val Leu Ser Lys Val Lys Ala Gln Ser Glu Thr
            100                 105                 110

Asp Thr Gln Ser Lys Asn Glu Gln Glu Ile Ser Thr Gln Gly Gln Glu
        115                 120                 125

Val Gln Lys Pro Ala Gln Gly Gly Glu Ser Thr Phe Gln Lys Asp Leu
    130                 135                 140

Asp Lys Lys Leu Tyr Asn Leu Gly Asp Val Phe Asn His Val Val Asp
145                 150                 155                 160

Ile Ser Asn Lys Lys Asn Lys Ile Asn Leu Asp Glu Tyr Gly Lys Lys
                165                 170                 175

Tyr Thr Asp Phe Lys Lys Glu Tyr Glu Asp Phe Val Leu Asn Ser Lys
            180                 185                 190

Glu Tyr Asp Ile Ile Lys Asn Leu Ile Ile Met Phe Gly Gln Glu Asp
        195                 200                 205

Asn Lys Ser Lys Asn Gly Lys Thr Asp Ile Val Ser Glu Ala Lys His
    210                 215                 220

Met Thr Asp Ile Phe Ile Lys Leu Phe Lys Asp Lys Glu Tyr His Glu
225                 230                 235                 240

Gln Phe Lys Asn Tyr Ile Tyr Gly Val Tyr Ser Tyr Ala Lys Gln Asn
                245                 250                 255

Ser His Leu Ser Glu Lys Lys Ile Lys Pro Glu Glu Glu Tyr Lys Lys
            260                 265                 270

Phe Leu Glu Tyr Ser Phe Asn Leu Leu Asn Thr Met
        275                 280
```

<210> SEQ ID NO 7
<211> LENGTH: 351
<212> TYPE: PRT
<213> ORGANISM: Artificial Sequence
<220> FEATURE:
<223> OTHER INFORMATION: Fragment of P. falciparum

<400> SEQUENCE: 7

```
Met Lys Ser Asn Ile Ile Phe Tyr Phe Ser Phe Phe Phe Val Tyr Leu
1               5                   10                  15

Tyr Tyr Val Ser Cys Asn Gln Ser Thr His Ser Thr Pro Val Asn Asn
            20                  25                  30

Glu Glu Asp Gln Glu Glu Leu Tyr Ile Lys Asn Lys Lys Leu Glu Lys
        35                  40                  45

Leu Lys Asn Ile Val Ser Gly Asp Phe Val Gly Asn Tyr Lys Asn Asn
    50                  55                  60

Glu Glu Leu Leu Asn Lys Lys Ile Glu Glu Leu Gln Asn Ser Lys Glu
65                  70                  75                  80

Lys Asn Val His Val Leu Ile Asn Gly Asn Ser Ile Ile Asp Glu Ile
                85                  90                  95

Glu Lys Asn Glu Glu Asn Asp Asp Asn Glu Glu Asn Asn Asp Asp Asp
            100                 105                 110

Asn Thr Tyr Glu Leu Asp Met Asn Asp Asp Thr Phe Leu Gly Gln Asn
        115                 120                 125
```

-continued

```
Asn Asp Ser His Phe Glu Asn Val Asp Asp Asp Ala Val Glu Asn Glu
    130                 135                 140

Gln Glu Asp Glu Asn Lys Glu Lys Ser Glu Ser Phe Pro Leu Phe Gln
145                 150                 155                 160

Asn Leu Gly Leu Phe Gly Lys Asn Val Leu Ser Lys Val Lys Ala Gln
                165                 170                 175

Ser Glu Thr Asp Thr Gln Ser Lys Asn Glu Gln Glu Ile Ser Thr Gln
            180                 185                 190

Gly Gln Glu Val Gln Lys Pro Ala Gln Gly Gly Glu Ser Thr Phe Gln
        195                 200                 205

Lys Asp Leu Asp Lys Lys Leu Tyr Asn Leu Gly Asp Val Phe Asn His
    210                 215                 220

Val Val Asp Ile Ser Asn Lys Lys Asn Lys Ile Asn Leu Asp Glu Tyr
225                 230                 235                 240

Gly Lys Lys Tyr Thr Asp Phe Lys Lys Glu Tyr Glu Asp Phe Val Leu
                245                 250                 255

Asn Ser Lys Glu Tyr Asp Ile Ile Lys Asn Leu Ile Ile Met Phe Gly
            260                 265                 270

Gln Glu Asp Asn Lys Ser Lys Asn Gly Lys Thr Asp Ile Val Ser Glu
        275                 280                 285

Ala Lys His Met Thr Glu Ile Phe Ile Lys Leu Phe Lys Asp Lys Glu
    290                 295                 300

Tyr His Glu Gln Phe Lys Asn Tyr Ile Tyr Gly Val Tyr Ser Tyr Ala
305                 310                 315                 320

Lys Gln Asn Ser His Leu Ser Glu Lys Lys Ile Lys Pro Glu Glu Glu
                325                 330                 335

Tyr Lys Lys Phe Leu Glu Tyr Ser Phe Asn Leu Leu Asn Thr Met
            340                 345                 350
```

<210> SEQ ID NO 8
<211> LENGTH: 1056
<212> TYPE: DNA
<213> ORGANISM: Artificial Sequence
<220> FEATURE:
<223> OTHER INFORMATION: Fragment of P. falciparum

<400> SEQUENCE: 8

```
atgaagagta atatcatatt ttatttttct tttttttttg tgtacttata ctatgtttcg     60

tgtaatcaat caactcatag tacaccagta aataatgaag aagatcaaga agaattatat    120

attaaaaata aaaaattgga aaaactaaaa aatatagtat caggagattt tgttggaaat    180

tataaaaata atgaagaatt attaaacaaa aaaattgaag aattacaaaa cagtaaagaa    240

aaaaatgtac atgtattaat taatggaaat tcaattattg atgaaataga aaaaaatgaa    300

gaaaatgatg ataacgaaga aaataatgat gatgacaata catatgaatt agatatgaat    360

gatgacacat tcttaggaca aaataacgat tcacattttg aaaatgttga tgatgacgca    420

gtagaaaatg aacaagaaga tgaaaacaag gaaaaatcag aatcatttcc attattccaa    480

aatttaggat tattcggtaa aaacgtatta tcaaaggtaa aggcacaaag tgaaacagat    540

actcaatcta aaaatgaaca agagatatca acacaaggac aagaagtaca aaaaccagca    600

caaggaggag aatcgacatt tcaaaaagac ctagataaga aattatataa tttaggagat    660

gtttttaatc atgtagttga tatttcaaac aaaaagaaca aaataaatct cgatgaatat    720

ggtaaaaaat atacagattt caaaaaagaa tatgaagact tcgttttaaa ttctaaagaa    780
```

-continued

```
tatgatataa tcaaaaatct aataattatg tttggtcaag aagataataa gagtaaaaat    840

ggcaaaacgg atattgtaag tgaagctaaa catatgactg aaattttcat aaaactattt    900

aaagataagg aataccatga acaatttaaa aattatattt atggtgttta tagttatgca    960

aaacaaaata gtcacttaag tgagaaaaaa ataaaaccag aagaggaata taaaaaattc   1020

ttagaatatt catttaattt actaaacaca atgtaa                             1056


<210> SEQ ID NO 9
<211> LENGTH: 1923
<212> TYPE: DNA
<213> ORGANISM: Artificial Sequence
<220> FEATURE:
<223> OTHER INFORMATION: Fragment of P. falciparum

<400> SEQUENCE: 9

gataatgtta ataataataa taataaagaa agttgtgata atattaaaca tatgagaaca     60

aaaagtttaa attttgtaag tagagaatcc tatggcgaac ataaaagtct agatgtttac    120

caggaatgtt atgtaaaaaa taataaactt attaataagg taaatgataa aaaatatgag    180

gacaataata attcctatct taatgaagat gataacgcta gtatgcaatt ttatgaagaa    240

actaatagta atccatatat tgtagaccag gaaaataata tgaaaaaatta tgtcaataat    300

gttttatata acaacaatag caattattat gttgattcaa agaattatga taaatctaaa    360

gagaatgcag aaaataaatc agatgatata ttaaataatg aaaatataca taccttaaaa    420

gatcaaaaaa agaaaaataca aaataataat gaattcatta gtgaacaggc tgatatagaa    480

aatataagaa attctcaaga agaagtatat gagaaagaac acgaaccttt gtgggtaata    540

aatgcatcta atgaagaaaa gaaatcatat gaagaattga tatacagcga tatgtcatct    600

aatcgtgtta cgaaaaataa atatagtgat atgaataatg ttgaggtatt attaaatgaa    660

gataatttat taactactga aaaatacaag gtgcaattag aaaaagaaaa taaaatgatt    720

gatatgtatg aaacggtaga ggagaatata aatacaatta aaacagaaaa tacgaacgac    780

ataaatgaag aagttagaaa cgaacaaaaa agagaaagta tcaatcatat taatgataca    840

aatataaatc atataataga tgaatatccc aatgatacat ataatttcat aaaagatata    900

gaatgtgtac ataacaatga aaataacatg tacaattcta ttgaacaata tacattttat    960

catgatacac gtaataatca tttagttgat aaaaataatc aaaattttat attcgaagag   1020

gaaggtttaa atgaattgaa ctttgaagaa aaaaaggtat atatagaaaa taataccaag   1080

gatgatcaca agggagatag caaaacaagt aacttaacat ctttaaggaa taccatatgt   1140

aaaagtgaaa acgatcataa tgaaaaaaat gaaaacacat atgtggttag aaaaggcgaa   1200

aaaggaatta aacgtaaggt ttccatgaag aaaagaaatg aaaagctaaa tgaagaaaat   1260

tatattaata atatatacga taaaatggat aaccatagac aaaatgatat tacaaaaaaa   1320

gaaaatgacg aagaaaatta tattttgtac aacaacgtaa aggttaatta tgatgaatat   1380

atagaaaatg gaaataaaat aaaaataacg gaagaatcat taaatgtctt ttataaagaa   1440

aatcaaaatg aggaagattc ttctacaaaa aagttgaata gtacaagtaa aataaaacgt   1500

gcaaacaaag ggaaaacaaa aaaaaagaat gttatcacaa gggtacataa aacaaaacaa   1560

aaaattgaat atgttacaaa tagttttaat aaatcttcca aaggtgaaaa ttcagaaata   1620

ggaaaaattg gaggtaggag taaatcatta ttaacacaca gcaagaaagt tagtgaacga   1680

aataaaaata aaatagaaaa aattaatgat acaaattcaa agataataaa aggaaaaaag   1740

agtaatagcc aaagcaaact tgggaaggat acaaaaatta gagggaaatc aaaaactggg   1800
```

gaatatataa aaaataaaga tttaagaaaa aaatctaacg aaaaaaacaa aacagtgatg 1860
gataatataa atactataaa taattcttca gtatctaacc taaaaagcaa aaaacataaa 1920
ttg 1923

<210> SEQ ID NO 10
<211> LENGTH: 641
<212> TYPE: PRT
<213> ORGANISM: Artificial Sequence
<220> FEATURE:
<223> OTHER INFORMATION: Fragment of P. falciparum

<400> SEQUENCE: 10

Asp Asn Val Asn Asn Asn Asn Asn Lys Glu Ser Cys Asp Asn Ile Lys
1 5 10 15

His Met Arg Thr Lys Ser Leu Asn Phe Val Ser Arg Glu Ser Tyr Gly
20 25 30

Glu His Lys Ser Leu Asp Val Tyr Gln Glu Cys Tyr Val Lys Asn Asn
35 40 45

Lys Leu Ile Asn Lys Val Asn Asp Lys Lys Tyr Glu Asp Asn Asn Asn
50 55 60

Ser Tyr Leu Asn Glu Asp Asp Asn Ala Ser Met Gln Phe Tyr Glu Glu
65 70 75 80

Thr Asn Ser Asn Pro Tyr Ile Val Asp Gln Glu Asn Asn Met Lys Asn
85 90 95

Tyr Val Asn Asn Val Leu Tyr Asn Asn Asn Ser Asn Tyr Tyr Val Asp
100 105 110

Ser Lys Asn Tyr Asp Lys Ser Lys Glu Asn Ala Glu Asn Lys Ser Asp
115 120 125

Asp Ile Leu Asn Asn Glu Asn Ile His Thr Leu Lys Asp Gln Lys Lys
130 135 140

Lys Ile Gln Asn Asn Asn Glu Phe Ile Ser Glu Gln Ala Asp Ile Glu
145 150 155 160

Asn Ile Arg Asn Ser Gln Glu Glu Val Tyr Glu Lys Glu His Glu Pro
165 170 175

Leu Trp Val Ile Asn Ala Ser Asn Glu Glu Lys Lys Ser Tyr Glu Glu
180 185 190

Leu Ile Tyr Ser Asp Met Ser Ser Asn Arg Val Thr Lys Asn Lys Tyr
195 200 205

Ser Asp Met Asn Asn Val Glu Val Leu Leu Asn Glu Asp Asn Leu Leu
210 215 220

Thr Thr Glu Lys Tyr Lys Val Gln Leu Glu Lys Glu Asn Lys Met Ile
225 230 235 240

Asp Met Tyr Glu Thr Val Glu Glu Asn Ile Asn Thr Ile Lys Thr Glu
245 250 255

Asn Thr Asn Asp Ile Asn Glu Glu Val Arg Asn Glu Gln Lys Arg Glu
260 265 270

Ser Ile Asn His Ile Asn Asp Thr Asn Ile Asn His Ile Ile Asp Glu
275 280 285

Tyr Pro Asn Asp Thr Tyr Asn Phe Ile Lys Asp Ile Glu Cys Val His
290 295 300

Asn Asn Glu Asn Asn Met Tyr Asn Ser Ile Glu Gln Tyr Thr Phe Tyr
305 310 315 320

His Asp Thr Arg Asn Asn His Leu Val Asp Lys Asn Asn Gln Asn Phe
325 330 335

```
Ile Phe Glu Glu Glu Gly Leu Asn Glu Leu Asn Phe Glu Glu Lys Lys
            340                 345                 350

Val Tyr Ile Glu Asn Asn Thr Lys Asp Asp His Lys Gly Asp Ser Lys
        355                 360                 365

Thr Ser Asn Leu Thr Ser Leu Arg Asn Thr Ile Cys Lys Ser Glu Asn
    370                 375                 380

Asp His Asn Glu Lys Asn Glu Asn Thr Tyr Val Val Arg Lys Gly Glu
385                 390                 395                 400

Lys Gly Ile Lys Arg Lys Val Ser Met Lys Lys Arg Asn Glu Lys Leu
                405                 410                 415

Asn Glu Glu Asn Tyr Ile Asn Asn Ile Tyr Asp Lys Met Asp Asn His
            420                 425                 430

Arg Gln Asn Asp Ile Thr Lys Lys Glu Asn Asp Glu Glu Asn Tyr Ile
        435                 440                 445

Leu Tyr Asn Asn Val Lys Val Asn Tyr Asp Glu Tyr Ile Glu Asn Gly
    450                 455                 460

Asn Lys Ile Lys Ile Thr Glu Glu Ser Leu Asn Val Phe Tyr Lys Glu
465                 470                 475                 480

Asn Gln Asn Glu Glu Asp Ser Ser Thr Lys Lys Leu Asn Ser Thr Ser
                485                 490                 495

Lys Ile Lys Arg Ala Asn Lys Gly Lys Thr Lys Lys Lys Asn Val Ile
            500                 505                 510

Thr Arg Val His Lys Thr Lys Gln Lys Ile Glu Tyr Val Thr Asn Ser
        515                 520                 525

Phe Asn Lys Ser Ser Lys Gly Glu Asn Ser Glu Ile Gly Lys Ile Gly
    530                 535                 540

Gly Arg Ser Lys Ser Leu Leu Thr His Ser Lys Lys Val Ser Glu Arg
545                 550                 555                 560

Asn Lys Asn Lys Ile Glu Lys Ile Asn Asp Thr Asn Ser Lys Ile Ile
                565                 570                 575

Lys Gly Lys Lys Ser Asn Ser Gln Ser Lys Leu Gly Lys Asp Thr Lys
            580                 585                 590

Ile Arg Gly Lys Ser Lys Thr Gly Glu Tyr Ile Lys Asn Lys Asp Leu
        595                 600                 605

Arg Lys Lys Ser Asn Glu Lys Asn Lys Thr Val Met Asp Asn Ile Asn
    610                 615                 620

Thr Ile Asn Asn Ser Ser Val Ser Asn Leu Lys Ser Lys Lys His Lys
625                 630                 635                 640

Leu


<210> SEQ ID NO 11
<211> LENGTH: 2227
<212> TYPE: PRT
<213> ORGANISM: Artificial Sequence
<220> FEATURE:
<223> OTHER INFORMATION: Fragment of P. falciparum

<400> SEQUENCE: 11

Met Arg Ser Lys Ser Ile Ser Tyr Phe Leu Phe Phe Lys Lys Asn Lys
1               5                   10                  15

Lys Lys Asn Asp Ser Cys Asp Ser Val Ile Ile Ser Ser Asn Lys Asn
            20                  25                  30

Leu Ser Ile Gln Leu Ser Lys Gly Glu Asp Asp Glu Lys Asn Glu Ile
        35                  40                  45
```

-continued

```
Asn Glu Glu Lys Ser Tyr Ile Lys Asn Glu Asp Val Tyr Lys Lys Glu
    50                  55                  60

Lys Leu Lys Lys Lys Lys Glu Asn Lys Glu Asn Asn Lys Lys Lys Asp
65                  70                  75                  80

Lys Asn Glu Val Val Tyr Asp Tyr His Asp Ile Ser Asn Asp Ala Thr
                85                  90                  95

Ser Asp Tyr Val Asn Asn Tyr Lys Val Tyr Glu Met Asn Thr Cys Asn
            100                 105                 110

Ile Lys Lys Lys Arg Glu Ser Phe Phe Lys Lys Ile Asn Ile Leu Gln
        115                 120                 125

Lys Tyr Lys Asn Tyr Lys Ile Arg Lys Ala Ala Ser Thr Phe His Thr
    130                 135                 140

Ile Gly His Lys Thr Ser Phe Ser Gly Thr Asp Asp Glu Ile Glu Asn
145                 150                 155                 160

Asn Gln Lys Lys Gln Lys Lys Tyr Lys Ile Lys Ile Ser Glu Trp Lys
                165                 170                 175

Asp Asp Lys Ser His Thr Phe His Lys Lys Asn Asp Ile Leu Val Phe
            180                 185                 190

Asp Lys Met Asp Lys Asn Lys Lys Phe Lys Ile Asp Asn Asn Lys Asn
        195                 200                 205

Asn Gln Ile Asn Ile Asp Asn Glu Glu Arg Val Asn Lys Asn Tyr Pro
    210                 215                 220

Met Ala Thr Asn Val Gln Asn Phe Asn Ile Lys Tyr Thr Ser Ile Asp
225                 230                 235                 240

Val Thr Asn Asp Glu Tyr Ile Ile Asp Ser Asn Lys Pro Glu Gly Ser
                245                 250                 255

Ile Met Ser Thr Asp Lys Lys Asn Asn Lys Leu Asn Tyr Asn Asn Asp
            260                 265                 270

Thr Tyr Asp Val Asp Lys Ser Ser Asp Ile Asn Lys Leu Gly Asn Ile
        275                 280                 285

Lys Lys Asn Lys Phe Asp Ile Ile Thr Lys Thr Thr His Asn Ile Asn
    290                 295                 300

Asn Asn Val Asn Asn Ile His Asn Tyr Met Met Tyr Thr Asn Lys Glu
305                 310                 315                 320

Asn Ile Lys Ile Asn Ile Asn His Gly Asn Leu Asn Gly Arg Glu Gln
                325                 330                 335

Asn Asn Tyr Asp Glu Glu Arg Lys Ala Asn Val Tyr Glu Ile Phe Glu
            340                 345                 350

Asn Ala Lys Lys Leu Glu Pro Asn Asn Ile Asn Ile Asn Thr Glu Glu
        355                 360                 365

His Ile His Ile Ser Glu Pro Ser Ile Pro Phe Asp Met Lys Asp His
    370                 375                 380

Lys Asn Asp Ile Asn Glu Lys Asp Ile Ile Leu Lys Leu Met Tyr Asn
385                 390                 395                 400

Asn Asn Gly Ile Tyr Phe Asp Asp Asp Asp Glu Asn His Lys Asn Leu
                405                 410                 415

Leu Tyr Lys Asn Lys Asp Thr His Val Lys His Leu Asn Asn Lys Phe
            420                 425                 430

Asn His Asn Phe Ile Ile Tyr Asn Asp Arg Glu Glu Gly Val Asn Gln
        435                 440                 445

Lys His Ala Gln Lys Lys Leu Lys Lys Lys Asn Thr Ile Leu Asn Lys
    450                 455                 460
```

```
Asn Glu Asn Glu Asp Ile Asn His Asn Ser Phe Lys Arg Pro Leu Ser
465                 470                 475                 480

Asn Thr Asn Ile Cys Tyr Lys Asp Lys Asp Asp Lys Ile Lys Asn Gly
                485                 490                 495

Ser Asn Lys Tyr Asp Ile Leu Asn Asn Asp Tyr Ser Asn Glu His Glu
            500                 505                 510

Lys Asn Lys Tyr Asn Asp His Ile Thr Lys Asn Lys Arg Asn Gln Ser
        515                 520                 525

Ala Asn Glu Val Lys Ser Asn Asn Asn Asp Asn His Asn Asn Lys Lys
    530                 535                 540

Asn Asn Asn Phe Asn Ile Asn Ile Asn Asp Ser Tyr Ser Thr Asn Ile
545                 550                 555                 560

Asn Arg Asn Gln Asn Val Met Ile Asn Asp Val Asn Asp Val Ile Lys
                565                 570                 575

Asp Pro Asn Met Gln Glu Asn Thr Gln Gly Asp Asp Glu Gly Gly Ile
            580                 585                 590

Ile Asn Lys Tyr Leu Ile Asn Pro Ile Tyr Asn Leu Phe Leu Arg Ala
        595                 600                 605

Asn Glu Glu Ile Gln Asn Ser Asn Ser Thr Asn Asn Lys Leu Lys Met
    610                 615                 620

Asn Asn Ile Thr Lys Ser Tyr Thr Asn Glu Leu Gln Lys Thr Tyr Lys
625                 630                 635                 640

Ser Met Tyr Asp Ile Asn Asp Ile Ser Asn Lys Arg Lys Ile Asn Asn
                645                 650                 655

Lys Asp Ile Arg Gly Thr Asn Leu Tyr Asn Thr Lys Leu Cys Asn Asn
            660                 665                 670

Lys Leu Tyr Asn Ser Asn Pro Tyr Asn Met Ile Pro Tyr Asn Ile Asn
        675                 680                 685

Thr Tyr Asn Asn Asn Asn Asn Asn Lys Glu Thr Cys Thr Ser Ile Asn
    690                 695                 700

Ile Lys His Ser Glu Asn Lys Tyr Pro Phe Asn Lys Ser His Val Asn
705                 710                 715                 720

Ser Tyr Met Lys Asn Thr Asn His Leu Pro His Arg Asn Ala Ile Thr
                725                 730                 735

Ser Asn Asn Arg Asn Asn Glu Glu Tyr Glu Lys Glu Lys Glu Lys Asp
            740                 745                 750

Arg Asn Ile Thr Asn Gly Asn Asn Asn Tyr Leu Val Glu Tyr Asn Asn
        755                 760                 765

Ser Cys Ile Pro Pro Pro Leu Lys Lys Met Ile Pro Ile Asp Gly Val
    770                 775                 780

Arg Asn Lys Ser Ile Asn Lys Leu Asn Asn Val Thr Asn Thr Gln Arg
785                 790                 795                 800

Thr Ser Ser Val Ser Tyr Thr Asn Lys Asn Ile Asp Glu Asn Ser Phe
                805                 810                 815

Asp Met Pro Ile Ile Asn Gly Ile Arg Glu Ser Lys Tyr Ile Ser Asn
            820                 825                 830

Asn Asn Asn Ile Asn Gly Asn Ser Ile Gly Phe Asn Ser Ser Lys Leu
        835                 840                 845

Asp Asn Tyr His His Gln Ser Met Asn Val Asn Glu Ser Tyr Pro Leu
    850                 855                 860

Lys Asn Met Met Lys Asn Asn Tyr Ile Glu His Asn Tyr Asp Asp Lys
865                 870                 875                 880
```

-continued

```
Asn Asn Ile Phe Leu Val Lys Asn Tyr Glu Asp Thr Tyr Ser Asn Ile
                885                 890                 895

His Asn Gly Ile His Glu Asn Ser Met Leu Lys Asn Tyr Asn Leu Lys
            900                 905                 910

Lys Ala Cys Thr Phe His Gly Tyr Ser Arg Asn His Gln Lys Asn Met
        915                 920                 925

Tyr Thr Glu Glu Asn Leu Asn Ile Asn Gln Lys Lys Asn Tyr Ser His
    930                 935                 940

Tyr His Asn Asn Gly Thr Val Leu Lys Pro Leu Val Asn Thr Asn Asn
945                 950                 955                 960

Val Ala Val Asn Glu Phe Ala Asp Ile Asn Leu Ser Ala Gln Lys Arg
                965                 970                 975

Leu His Ser Leu Lys Ser Met Gly Tyr Glu Asp Lys Ser Met Glu Asn
            980                 985                 990

Tyr Arg Asn Lys Ile Tyr Asn Asn  Ile Asn Asn Asn Asn  Asn Asn Asn
        995                 1000                1005

Asn Asp  Asn Asn Ile Tyr Asn  Asp Asn Glu Tyr Cys  Gln Tyr Asn
    1010                 1015                 1020

Asn Ser  Tyr Cys Phe Asp His  Ser Asp Leu Lys Asn  Met Phe Pro
    1025                 1030                 1035

Leu Asn  His Gln Asn Ser Lys  Leu Leu Thr His Ser  Asn Asn Lys
    1040                 1045                 1050

Asn Ser  Phe Phe Asn Gly Ile  Asn Val Glu Ser Lys  His His Leu
    1055                 1060                 1065

Ala Asn  Pro Glu Ile Lys Thr  Phe Ala His Asn Ser  Tyr Pro Ile
    1070                 1075                 1080

Leu Asn  Gln Gly Leu Ile Asn  Cys Asn Pro Leu Gln  Cys Leu Gly
    1085                 1090                 1095

Tyr Asp  Ser Asn Gln Arg Asn  Lys His Asn Val Val  Tyr Ile Lys
    1100                 1105                 1110

Lys Asn  Glu Tyr Leu Asn Lys  Asn Ile Gly Ser Ile  Ile Asn Val
    1115                 1120                 1125

Leu Lys  Arg Glu Gly Leu Arg  Lys Ile Ser Thr His  Asn Gly Lys
    1130                 1135                 1140

Phe Glu  Ser Phe Ser Asn Met  Asp Asn Lys Asn Val  Tyr Met Glu
    1145                 1150                 1155

Gly Leu  Asn Ile Gln Asp Asn  Val Asn Asn Asn Asn  Asn Lys Glu
    1160                 1165                 1170

Ser Cys  Asp Asn Ile Lys His  Met Arg Thr Lys Ser  Leu Asn Phe
    1175                 1180                 1185

Val Ser  Arg Glu Ser Tyr Gly  Glu His Lys Ser Leu  Asp Val Tyr
    1190                 1195                 1200

Gln Glu  Cys Tyr Val Lys Asn  Asn Lys Leu Ile Asn  Lys Val Asn
    1205                 1210                 1215

Asp Lys  Lys Tyr Glu Asp Asn  Asn Asn Ser Tyr Leu  Asn Glu Asp
    1220                 1225                 1230

Asp Asn  Ala Ser Met Gln Phe  Tyr Glu Glu Thr Asn  Ser Asn Pro
    1235                 1240                 1245

Tyr Ile  Val Asp Gln Glu Asn  Asn Met Lys Asn Tyr  Val Asn Asn
    1250                 1255                 1260

Val Leu  Tyr Asn Asn Asn Ser  Asn Tyr Tyr Val Asp  Ser Lys Asn
    1265                 1270                 1275
```

Tyr Asp Lys Ser Lys Glu Asn Ala Glu Asn Lys Ser Asp Asp Ile
1280 1285 1290

Leu Asn Asn Glu Asn Ile His Thr Leu Lys Asp Gln Lys Lys Lys
1295 1300 1305

Ile Gln Asn Asn Asn Glu Phe Ile Ser Glu Gln Ala Asp Ile Glu
1310 1315 1320

Asn Ile Arg Asn Ser Gln Glu Glu Val Tyr Glu Lys Glu His Glu
1325 1330 1335

Pro Leu Trp Val Ile Asn Ala Ser Asn Glu Glu Lys Lys Ser Tyr
1340 1345 1350

Glu Glu Leu Ile Tyr Ser Asp Met Ser Ser Asn Arg Val Thr Lys
1355 1360 1365

Asn Lys Tyr Ser Asp Met Asn Asn Val Glu Val Leu Leu Asn Glu
1370 1375 1380

Asp Asn Leu Leu Thr Thr Glu Lys Tyr Lys Val Gln Leu Glu Lys
1385 1390 1395

Glu Asn Lys Met Ile Asp Met Tyr Glu Thr Val Glu Glu Asn Ile
1400 1405 1410

Asn Thr Ile Lys Thr Glu Asn Thr Asn Asp Ile Asn Glu Glu Val
1415 1420 1425

Arg Asn Glu Gln Lys Arg Glu Ser Ile Asn His Ile Asn Asp Thr
1430 1435 1440

Asn Ile Asn His Ile Ile Asp Glu Tyr Pro Asn Asp Thr Tyr Asn
1445 1450 1455

Phe Ile Lys Asp Ile Glu Cys Val His Asn Asn Glu Asn Asn Met
1460 1465 1470

Tyr Asn Ser Ile Glu Gln Tyr Thr Phe Tyr His Asp Thr Arg Asn
1475 1480 1485

Asn His Leu Val Asp Lys Asn Asn Gln Asn Phe Ile Phe Glu Glu
1490 1495 1500

Glu Gly Leu Asn Glu Leu Asn Phe Glu Glu Lys Lys Val Tyr Ile
1505 1510 1515

Glu Asn Asn Thr Lys Asp Asp His Lys Gly Asp Ser Lys Thr Ser
1520 1525 1530

Asn Leu Thr Ser Leu Arg Asn Thr Ile Cys Lys Ser Glu Asn Asp
1535 1540 1545

His Asn Glu Lys Asn Glu Asn Thr Tyr Val Val Arg Lys Gly Glu
1550 1555 1560

Lys Gly Ile Lys Arg Lys Val Ser Met Lys Lys Arg Asn Glu Lys
1565 1570 1575

Leu Asn Glu Glu Asn Tyr Ile Asn Asn Ile Tyr Asp Lys Met Asp
1580 1585 1590

Asn His Arg Gln Asn Asp Ile Thr Lys Lys Glu Asn Asp Glu Glu
1595 1600 1605

Asn Tyr Ile Leu Tyr Asn Asn Val Lys Val Asn Tyr Asp Glu Tyr
1610 1615 1620

Ile Glu Asn Gly Asn Lys Ile Lys Ile Thr Glu Glu Ser Leu Asn
1625 1630 1635

Val Phe Tyr Lys Glu Asn Gln Asn Glu Glu Asp Ser Ser Thr Lys
1640 1645 1650

Lys Leu Asn Ser Thr Ser Lys Ile Lys Arg Ala Asn Lys Gly Lys
1655 1660 1665

```
Thr Lys Lys Lys Asn Val Ile Thr Arg Val His Lys Thr Lys Gln
    1670                1675                1680

Lys Ile Glu Tyr Val Thr Asn Ser Phe Asn Lys Ser Ser Lys Gly
    1685                1690                1695

Glu Asn Ser Glu Ile Gly Lys Ile Gly Gly Arg Ser Lys Ser Leu
    1700                1705                1710

Leu Thr His Ser Lys Lys Val Ser Glu Arg Asn Lys Asn Lys Ile
    1715                1720                1725

Glu Lys Ile Asn Asp Thr Asn Ser Lys Ile Ile Lys Gly Lys Lys
    1730                1735                1740

Ser Asn Ser Gln Ser Lys Leu Gly Lys Asp Thr Lys Ile Arg Gly
    1745                1750                1755

Lys Ser Lys Thr Gly Glu Tyr Ile Lys Asn Lys Asp Leu Arg Lys
    1760                1765                1770

Lys Ser Asn Glu Lys Asn Lys Thr Val Met Asp Asn Ile Asn Thr
    1775                1780                1785

Ile Asn Asn Ser Ser Val Ser Asn Leu Lys Ser Lys Lys His Lys
    1790                1795                1800

Leu Lys Lys Lys Lys Lys Lys Asn Ile Ser Met Glu Asn Ile Asn
    1805                1810                1815

Lys Asn Ile Thr Asn Glu Phe Cys Ser Met Glu Arg Lys Gly Thr
    1820                1825                1830

Val Leu Leu Ser Asn Met Ser Ile Lys Lys Ile Asp Asn Ala Asn
    1835                1840                1845

Ser Cys Thr Leu Asn Glu Pro Leu Glu Glu Asn Thr Leu Asn Tyr
    1850                1855                1860

Glu Ser Asn Asn Asn Cys Ser Asn Ser Asn Leu Ser Lys Asp Lys
    1865                1870                1875

Glu Lys Asp Arg Asn Ile Leu Cys Asn Lys Tyr Tyr Ser Asp Glu
    1880                1885                1890

Glu Thr Asn Ser Leu Asn Lys Met Tyr Thr Ser Asn Ile Pro Glu
    1895                1900                1905

Ile Ser Asn Tyr Tyr Lys Glu Ile Gln Ala Ile Asn Tyr Ile Leu
    1910                1915                1920

Ser Asn Ile Asn Asn Pro Asn Phe Leu Asn Ser Leu Glu Leu Asn
    1925                1930                1935

Asp Leu Ile Asn Ile Glu Lys Lys Phe Ile Asn Glu Asn Ile Tyr
    1940                1945                1950

Ile Asn Lys Gln Ile Ile Ala Cys Asn Val Lys Asn Glu Lys Ser
    1955                1960                1965

Asn Asp Glu Met Val Glu Lys Asn Glu Arg Lys Val Asp Glu Glu
    1970                1975                1980

Lys Gly Glu Asp Glu Gln Glu Ile Lys Ala Lys Glu Asn Asn Asn
    1985                1990                1995

Lys Glu Glu Asn Gln Asp Asn Glu Asn Asn Asn Lys Glu Glu Asn
    2000                2005                2010

His Asp Asn Glu Asn Asn Asn Lys Glu Glu Asn Gln Asp Asn Glu
    2015                2020                2025

Asn Asn Asn Lys Glu Glu Asn Gln Asp Asn Glu Asn Asn Asn Lys
    2030                2035                2040

Glu Glu Asn Gln Asp Asn Glu Asn Asn Asn Lys Glu Glu Asn Gln
    2045                2050                2055
```

```
Lys Asn  Glu Asn Gly Ile Ile  Tyr Asp Ser Arg Phe  Ser Ile Ile
    2060                 2065                 2070

Tyr Leu  Glu His Asp Leu Ile  Tyr Leu Lys Lys Asn  Asn Leu Lys
    2075                 2080                 2085

Val Ile  Leu Asn Val Leu Leu  Ser Asn Val Tyr Cys  Phe Phe Glu
    2090                 2095                 2100

Ile Lys  Leu Thr Ile Ile Leu  Leu Asn Phe Phe Ile  Ser Asn Asn
    2105                 2110                 2115

Cys Gln  Trp Ser Phe Ser Leu  Phe Pro Leu Ser Leu  Ile Asn Lys
    2120                 2125                 2130

Leu Ile  His Lys Phe Ser Leu  Lys Ile Asn Lys Lys  Val Pro Lys
    2135                 2140                 2145

Tyr Lys  Leu Glu Asn Met Asn  Ile Asn Ser Pro Asn  Ile Pro Tyr
    2150                 2155                 2160

Thr Tyr  Leu Phe Ile Cys Asp  Gly Ser Asn Tyr Leu  Cys Ile Asn
    2165                 2170                 2175

Asp Asn  Ser Leu Asn Asn Glu  Val Tyr Glu Asn Lys  Met Lys Leu
    2180                 2185                 2190

Asn Asn  Ile Ile Gly Tyr Tyr  His Tyr Ile Asn Leu  Asn Arg Leu
    2195                 2200                 2205

Thr Tyr  Tyr Leu Glu Lys Val  Asn Ala Asn Phe Val  Tyr Asn His
    2210                 2215                 2220

His Ile  Tyr Glu
    2225
```

<210> SEQ ID NO 12
<211> LENGTH: 6684
<212> TYPE: DNA
<213> ORGANISM: Artificial Sequence
<220> FEATURE:
<223> OTHER INFORMATION: Fragment of P. falciparum

<400> SEQUENCE: 12

```
atgagatcga aatccatttc gtatttctta ttttttaaaa aaaacaaaaa gaaaaatgat     60

tcttgtgata gtgtcataat atctagcaat aagaatttat ccattcaatt atcgaaaggt    120

gaggatgatg aaaaaaatga aataaatgag gaaaagagtt atataaaaaa tgaagatgta    180

tataaaaagg aaaaattaaa aaagaagaaa gaaaacaagg aaaataataa aaagaaagat    240

aaaaatgaag tagtatatga ttatcatgac atttcaaatg atgctactag tgattatgtt    300

aataattata aagtatatga aatgaatact tgtaatataa aaaagaagag agaaagtttt    360

tttaaaaaaa ttaatatttt acaaaaatat aaaaattaca aaattagaaa ggcagctagt    420

acctttcata ccataggaca taaaacatct ttttctggta cagatgatga aatagaaaat    480

aatcaaaaga aacaaaaaaa atataaaata aaaatttctg aatggaagga tgataaatca    540

catacttttc ataaaaaaaa tgacatattg gtatttgata agatggataa aaataaaaaa    600

tttaaaattg ataacaacaa aaacaatcaa attaatatag ataatgaaga aagagttaat    660

aaaaattatc ctatggctac taatgtacaa aattttaata taaaatatac atcaatagat    720

gtaacaaatg acgaatatat tatagattct aataaacctg aaggttctat tatgtctaca    780

gataaaaaga ataataaact taattataat aatgatacat atgatgtaga caaaagctct    840

gatataaata agttaggtaa tataaaaaag aataaatttg atattattac taaaacaaca    900

cataatatta ataataatgt aaataatata cataattata tgatgtatac aaataaagaa    960
```

-continued

```
aatataaaaa taaatataaa tcatggaaat ctaaatggaa gagaacaaaa caattatgat   1020
gaagaaagga aagcaaatgt ttatgaaata tttgaaaatg caaaaaaatt agaacctaat   1080
aatattaata tcaacacaga agaacatatt catattagtg aacccagcat accatttgat   1140
atgaaggatc ataaaaatga tataaatgaa aaagatataa tattaaaatt gatgtataac   1200
aataacggta tttattttga tgatgatgat gaaaatcaca agaatttatt atacaaaaat   1260
aaagatacac atgtaaaaca tttaaataat aaatttaacc ataattttat tatatataat   1320
gatcgcgaag aaggggtaaa tcagaaacac gcacaaaaaa aattaaaaaa aaaaaatact   1380
attcttaaca aaaacgaaaa tgaagatatt aatcataata gtttcaaaag acctttatct   1440
aatacgaata tatgttataa ggacaaagat gataaaatta aaaatggttc taataagtat   1500
gatatattaa ataatgacta ttctaatgaa cacgaaaaaa ataaatataa tgatcatata   1560
acaaaaaata aaagaaatca atcagcaaat gaagtaaaat ctaataataa tgataaccac   1620
aataataaaa aaaataataa ttttaatatt aatattaatg attcatattc tacaaatata   1680
aatagaaacc aaaatgtgat gataaatgat gtaaacgatg ttattaagga tccaaatatg   1740
caggaaaata cacaaggtga tgacgaaggt ggtattataa acaaatattt aattaaccct   1800
atttacaatt tatttctacg tgctaatgaa gaaatacaaa attcaaatag tacaaacaat   1860
aaattaaaaa tgaataatat aacaaaaagt tatacaaacg aactacaaaa gacatataaa   1920
agtatgtacg atataaatga tatatcaaat aagagaaaaa ttaataataa agatatacgt   1980
ggaactaatt tgtataacac caaattatgt aataataaat tatataattc gaatccatat   2040
aatatgattc catataatat aaacacatat aataataata ataataataa ggaaacttgt   2100
accagcataa atatcaaaca ttccgaaaat aaatatccct tcaataaatc tcatgtaaac   2160
tcatatatga aaaatacaaa tcatcttcct catagaaatg cgattacatc aaataataga   2220
aacaatgaag aatatgagaa agaaaaagaa aaagatcgta acattactaa tgggaacaat   2280
aattatttgg ttgaatataa taattcttgt atacctccac cactcaaaaa aatgatacca   2340
atagatggtg tgagaaataa aagtataaat aaattaaata atgtaactaa tacgcaacgt   2400
acatcaagtg tttcatatac gaataagaat attgatgaga attcgtttga tatgcctata   2460
ataaatggaa taagagaatc taaatatata agtaataata ataatattaa tggtaattcc   2520
attggtttta attcatctaa gttagataat tatcatcacc aatctatgaa tgtgaatgaa   2580
tcttatcctc taaaaaatat gatgaaaaat aattatattg aacataatta tgatgataaa   2640
aataatattt tccttgttaa aaattatgaa gatacatatt caaatattca taatggcata   2700
catgaaaata gcatgctaaa aaattataat ttaaaaaaag cgtgcacttt tcatgggtac   2760
tctagaaatc accaaaaaaa tatgtatacg gaagaaaatt taaatattaa tcaaaaaaag   2820
aattatagtc attatcataa taatggaacg gtattaaaac ctttggtaaa tactaataat   2880
gttgcagtga acgaatttgc agatattaat ttatcggctc aaaaaagatt acatagttta   2940
aaaagtatgg ggtacgagga taagagtatg gaaaattaca gaaacaaaat atacaacaac   3000
atcaataata ataataataa taataatgat aataatatat ataatgataa tgaatattgt   3060
cagtataata atagttattg tttcgatcat agtgatttaa aaaatatgtt tccattaaat   3120
catcagaata gcaagttatt aacacatagt aataataaaa attcattttt taacggaata   3180
aatgtagaat cgaaacatca tttagcaaat cctgaaataa aaacatttgc acacaatagt   3240
tatcctatat taaatcaagg tttaataaat tgtaacccct tacaatgctt gggttatgat   3300
tcaaatcaaa ggaataagca taatgtagta tacataaaaa aaaatgaata ccttaataaa   3360
```

```
aacattggct ctattataaa tgttcttaaa agagaaggac taagaaaaat ttctacacat   3420
aatggaaaat tcgaatcatt tagtaatatg gataataaaa atgtatatat ggaaggacta   3480
aacatacaag ataatgttaa taataataat aataaagaaa gttgtgataa tattaaacat   3540
atgagaacaa aaagtttaaa ttttgtaagt agagaatcct atggcgaaca taaaagtcta   3600
gatgtttacc aggaatgtta tgtaaaaaat aataaactta ttaataaggt aaatgataaa   3660
aaatatgagg acaataataa ttcctatctt aatgaagatg ataacgctag tatgcaattt   3720
tatgaagaaa ctaatagtaa tccatatatt gtagaccagg aaaataatat gaaaaattat   3780
gtcaataatg ttttatataa caacaatagc aattattatg ttgattcaaa gaattatgat   3840
aaatctaaag agaatgcaga aaataaatca gatgatatat taaataatga aaatatacat   3900
accttaaaag atcaaaaaaa gaaaatacaa aataataatg aattcattag tgaacaggct   3960
gatatagaaa atataagaaa ttctcaagaa gaagtatatg agaaagaaca cgaacctttg   4020
tgggtaataa atgcatctaa tgaagaaaag aaatcatatg aagaattgat atacagcgat   4080
atgtcatcta atcgtgttac gaaaaataaa tatagtgata tgaataatgt tgaggtatta   4140
ttaaatgaag ataatttatt aactactgaa aaatacaagg tgcaattaga aaaagaaaat   4200
aaaatgattg atatgtatga aacggtagag gagaatataa atacaattaa aacagaaaat   4260
acgaacgaca taaatgaaga agttagaaac gaacaaaaaa gagaaagtat caatcatatt   4320
aatgatacaa atataaatca tataatagat gaatatccca atgatacata taatttcata   4380
aaagatatag aatgtgtaca taacaatgaa aataacatgt acaattctat tgaacaatat   4440
acattttatc atgatacacg taataatcat ttagttgata aaaataatca aaattttata   4500
ttcgaagagg aaggtttaaa tgaattgaac tttgaagaaa aaaaggtata tatagaaaat   4560
aataccaagg atgatcacaa gggagatagc aaaacaagta acttaacatc tttaaggaat   4620
accatatgta aaagtgaaaa cgatcataat gaaaaaaatg aaaacacata tgtggttaga   4680
aaaggcgaaa aaggaattaa acgtaaggtt tccatgaaga aaagaaatga aaagctaaat   4740
gaagaaaatt atattaataa tatatacgat aaaatggata accatagaca aaatgatatt   4800
acaaaaaaag aaaatgacga agaaaattat attttgtaca acaacgtaaa ggttaattat   4860
gatgaatata tagaaaatgg aaataaaata aaaataacgg aagaatcatt aaatgtcttt   4920
tataaagaaa atcaaaatga ggaagattct tctacaaaaa agttgaatag tacaagtaaa   4980
ataaaacgtg caaacaaagg gaaaacaaaa aaaaagaatg ttatcacaag ggtacataaa   5040
acaaaacaaa aaattgaata tgttacaaat agttttaata aatcttccaa aggtgaaaat   5100
tcagaaatag gaaaaattgg aggtaggagt aaatcattat taacacacag caagaaagtt   5160
agtgaacgaa ataaaaataa aatagaaaaa attaatgata caaattcaaa gataataaaa   5220
ggaaaaaaga gtaatagcca aagcaaactt gggaaggata caaaaaattag agggaaatca   5280
aaaactgggg aatatataaa aaataaagat ttaagaaaaa aatctaacga aaaaaacaaa   5340
acagtgatgg ataatataaa tactataaat aattcttcag tatctaacct aaaaagcaaa   5400
aaacataaat tgaaaaaaaa aaaaaaaaaa aatatatcta tggaaaatat aaataaaaat   5460
ataacaaatg aattttgttc tatggaaaga aaaggaaccg ttctattatc taatatgagt   5520
attaagaaga ttgataatgc aaatagttgt acattaaatg aaccattaga ggaaaatacc   5580
ttaaattatg aaagtaataa taactgtagt aatagtaatt tatctaagga taaagaaaaa   5640
gatagaaata tattgtgtaa taaatattat agtgatgagg aaacaaactc tttaaacaaa   5700
```

-continued

```
atgtatacat cgaatatacc agaaataagt aattattata aggaaattca agcaattaat   5760

tacatattaa gtaatattaa taatccaaat tttttaaatt ccctcgaact gaatgattta   5820

ataaatattg aaaaaaaatt tattaacgaa aatatatata ttaataagca gataatagcc   5880

tgtaatgtaa aaaatgaaaa atcaaatgat gagatggtcg agaaaaatga acgcaaagtg   5940

gatgaagaaa aaggagaaga cgaacaagaa ataaaagcaa aggaaaataa taataaagaa   6000

gaaaaccaag ataatgaaaa taataataaa gaagaaaacc atgataatga aaataataat   6060

aaagaagaaa atcaagataa tgaaaataat aataaagaag aaaaccaaga taatgaaaat   6120

aataataaag aagaaaatca agataatgaa aataataata aagaagaaaa ccaaaaaaat   6180

gaaaatggta ttatttatga tagcaggttt agtattatct atttagaaca cgatttaata   6240

tatttaaaaa aaaataattt aaaagtgata cttaatgttt tgctgtcaaa tgtgtattgc   6300

ttttttgaaa ttaaattaac cataatattg ttaaatttct ttatatctaa taattgtcaa   6360

tggagtttca gtttatttcc cctttcatta attaataaat taatacataa attcagttta   6420

aagataaata agaaagttcc taaatataaa ttggaaaata tgaatattaa ctcaccaaat   6480

attccatata catatctttt tatatgtgat ggaagtaact atttatgtat taatgacaat   6540

tcattaaata acgaggtata tgaaaacaag atgaaattga acaatatcat tggatattac   6600

cattatatta atttgaatag attaacatat tatttagaaa aggtaaatgc taattttgtt   6660

tataaccatc atatatatga ataa                                          6684
```

```
<210> SEQ ID NO 13
<211> LENGTH: 238
<212> TYPE: DNA
<213> ORGANISM: Artificial Sequence
<220> FEATURE:
<223> OTHER INFORMATION: Fragment of P. falciparum

<400> SEQUENCE: 13

agaattctag gggaagaaaa accaaatgtg gacggagtaa gtactagtaa tactcctgga     60

ggaaatgaat cttcaagtgc ttcccccaat ttatctgacg cagcagaaaa aaaggatgaa    120

aaagaagctt ctgaacaagg agaagaaagt cataaaaaag aaaattccca agaaagcgcg    180

aatggtaagg atgatgttaa agaagaaaaa aaaactaatg aaaaaaaaga tgatggaa      238
```

```
<210> SEQ ID NO 14
<211> LENGTH: 79
<212> TYPE: PRT
<213> ORGANISM: Artificial Sequence
<220> FEATURE:
<223> OTHER INFORMATION: Fragment of P. falciparum

<400> SEQUENCE: 14

Arg Ile Leu Gly Glu Glu Lys Pro Asn Val Asp Gly Val Ser Thr Ser
1               5                   10                  15

Asn Thr Pro Gly Gly Asn Glu Ser Ser Ser Ala Ser Pro Asn Leu Ser
            20                  25                  30

Asp Ala Ala Glu Lys Lys Asp Glu Lys Glu Ala Ser Glu Gln Gly Glu
        35                  40                  45

Glu Ser His Lys Lys Glu Asn Ser Gln Glu Ser Ala Asn Gly Lys Asp
    50                  55                  60

Asp Val Lys Glu Glu Lys Lys Thr Asn Glu Lys Lys Asp Asp Gly
65                  70                  75


<210> SEQ ID NO 15
```

<211> LENGTH: 272
<212> TYPE: PRT
<213> ORGANISM: Artificial Sequence
<220> FEATURE:
<223> OTHER INFORMATION: Fragment of P. falciparum

<400> SEQUENCE: 15

Met Trp Ile Val Lys Phe Leu Ile Val Val His Phe Phe Ile Ile Cys
1 5 10 15

Thr Ile Asn Phe Asp Lys Leu Tyr Ile Ser Tyr Ser Tyr Asn Ile Val
20 25 30

Pro Glu Asn Gly Arg Met Leu Asn Met Arg Ile Leu Gly Glu Glu Lys
35 40 45

Pro Asn Val Asp Gly Val Ser Thr Ser Asn Thr Pro Gly Gly Asn Glu
50 55 60

Ser Ser Ser Ala Ser Pro Asn Leu Ser Asp Ala Ala Glu Lys Lys Asp
65 70 75 80

Glu Lys Glu Ala Ser Glu Gln Gly Glu Glu Ser His Lys Lys Glu Asn
85 90 95

Ser Gln Glu Ser Ala Asn Gly Lys Asp Asp Val Lys Glu Glu Lys Lys
100 105 110

Thr Asn Glu Lys Lys Asp Asp Gly Lys Thr Asp Lys Val Gln Glu Lys
115 120 125

Val Leu Glu Lys Ser Pro Lys Glu Ser Gln Met Val Asp Asp Lys Lys
130 135 140

Lys Thr Glu Ala Ile Pro Lys Lys Val Val Gln Pro Ser Ser Ser Asn
145 150 155 160

Ser Gly Gly His Val Gly Glu Glu Glu Asp His Asn Glu Gly Glu Gly
165 170 175

Glu His Glu Glu Glu Glu Glu His Glu Glu Asp Asp Asp Asp Glu Asp
180 185 190

Asp Asp Thr Tyr Asn Lys Asp Asp Leu Glu Asp Glu Asp Leu Cys Lys
195 200 205

His Asn Asn Gly Gly Cys Gly Asp Asp Lys Leu Cys Glu Tyr Val Gly
210 215 220

Asn Arg Arg Val Lys Cys Lys Cys Lys Glu Gly Tyr Lys Leu Glu Gly
225 230 235 240

Ile Glu Cys Val Glu Leu Leu Ser Leu Ala Ser Ser Ser Leu Asn Leu
245 250 255

Ile Phe Asn Ser Phe Ile Thr Ile Phe Val Val Ile Leu Leu Ile Asn
260 265 270

<210> SEQ ID NO 16
<211> LENGTH: 819
<212> TYPE: DNA
<213> ORGANISM: Artificial Sequence
<220> FEATURE:
<223> OTHER INFORMATION: Fragment of P. falciparum

<400> SEQUENCE: 16
atgtggatag ttaaattttt aatagtagtt catttttta taatttgtac cataaacttt 60
gataaattgt atatcagtta ttcttataat atagtaccag aaaatggaag aatgttaaat 120
atgagaattc taggggaaga aaaaccaaat gtggacggag taagtactag taatactcct 180
ggaggaaatg aatcttcaag tgcttccccc aatttatctg acgcagcaga aaaaaaggat 240
gaaaaagaag cttctgaaca aggagaagaa agtcataaaa aagaaaattc ccaagaaagc 300

-continued

```
gcgaatggta aggatgatgt taaagaagaa aaaaaaacta atgaaaaaaa agatgatgga    360

aaaacagaca aggttcaaga aaaggttcta gaaaagtctc caaaagaatc ccaaatggtt    420

gatgataaaa aaaaaactga agctatccct aaaaaggtag ttcaaccaag ttcatcaaat    480

tcaggtggcc atgttggaga ggaggaagac cacaacgaag gagaaggaga acatgaagag    540

gaggaagaac atgaagaaga tgacgatgac gaagatgatg atacttataa taaggacgat    600

ttggaagatg aagatttatg taaacataat aatgggggtt gtggagatga taaattatgt    660

gaatatgttg ggaatagaag agtaaaatgt aaatgtaaag aaggatataa attagaaggt    720

attgaatgtg ttgaattatt atccttagca tcttcttctt taaatttaat ttttaattca    780

tttataacaa tatttgttgt tatattgtta ataaattaa                           819
```

<210> SEQ ID NO 17
<211> LENGTH: 300
<212> TYPE: DNA
<213> ORGANISM: Artificial Sequence
<220> FEATURE:
<223> OTHER INFORMATION: Fragment of P. falciparum

<400> SEQUENCE: 17

```
ttcttttatc ctttatttga aaaaaataaa agcattttag tacttgaact ttccttgcag     60

tgtggatttt ccatacctcc aatatatgat gaaacagata tgttagaaaa cttattaaaa    120

aatatcgaaa aatatgatca aagcttagtt atttcttcgg gatatttaaa cttcccaatg    180

aattttctta aattaattag aaatatatat atcaacgtta tgcaaaaaaa aaatggtatt    240

ttacaattaa tcacagcgtc cccatgcgct aatatttttt ataaatctaa agggatatct    300
```

<210> SEQ ID NO 18
<211> LENGTH: 100
<212> TYPE: PRT
<213> ORGANISM: Artificial Sequence
<220> FEATURE:
<223> OTHER INFORMATION: Fragment of P. falciparum

<400> SEQUENCE: 18

```
Phe Phe Tyr Pro Leu Phe Glu Lys Asn Lys Ser Ile Leu Val Leu Glu
1               5                   10                  15

Leu Ser Leu Gln Cys Gly Phe Ser Ile Pro Pro Ile Tyr Asp Glu Thr
            20                  25                  30

Asp Met Leu Glu Asn Leu Leu Lys Asn Ile Glu Lys Tyr Asp Gln Ser
        35                  40                  45

Leu Val Ile Ser Ser Gly Tyr Leu Asn Phe Pro Met Asn Phe Leu Lys
    50                  55                  60

Leu Ile Arg Asn Ile Tyr Ile Asn Val Met Gln Lys Lys Asn Gly Ile
65                  70                  75                  80

Leu Gln Leu Ile Thr Ala Ser Pro Cys Ala Asn Ser Phe Tyr Lys Ser
                85                  90                  95

Lys Gly Ile Ser
            100
```

<210> SEQ ID NO 19
<211> LENGTH: 661
<212> TYPE: PRT
<213> ORGANISM: Artificial Sequence
<220> FEATURE:
<223> OTHER INFORMATION: Fragment of P. falciparum -continued

<400> SEQUENCE: 19

```
Met Ala Leu Lys Phe Val Ile His Glu Pro Lys Ala Lys Leu Leu Phe
1               5                   10                  15

Thr Pro Lys Glu Phe Phe Asn Thr Leu Asn Asp Ile Phe Lys Asn Ser
            20                  25                  30

Gln Asn Arg Ile Val Ile Ser Cys Leu Tyr Met Gly Ile Gly Glu Leu
        35                  40                  45

Glu Lys Glu Leu Ile Asp Ser Ile Lys Lys Asn Val Asn Ile Lys Asp
    50                  55                  60

Leu Lys Val Asp Ile Leu Leu Asp Arg Gln Arg Gly Thr Arg Leu Glu
65                  70                  75                  80

Gly Lys Phe Asn Glu Ser Ser Val Ser Ile Leu Ser Glu Leu Phe Lys
                85                  90                  95

Cys Ser Asp Asn Ile Asn Ile Ser Leu Phe His Asn Pro Leu Leu Gly
            100                 105                 110

Pro Ile Leu Tyr Asn Ile Leu Pro Pro Arg Ala Asn Glu Ala Ile Gly
        115                 120                 125

Val Met His Met Lys Ile Tyr Ile Gly Asp Asn Ile Leu Met Leu Ser
    130                 135                 140

Gly Ala Asn Leu Ser Asp Ser Tyr Leu Arg Asn Arg Gln Asp Arg Tyr
145                 150                 155                 160

Phe Val Ile Glu Asn Lys Phe Leu Ala Asp Ser Ile His Asn Ile Ile
                165                 170                 175

Asn Thr Ile Gln Gly Met Ser Phe Thr Leu Asn Arg Asp Leu Thr Ile
            180                 185                 190

Lys Trp Glu Asn Asp Leu Met Asn Pro Leu Ile Asp Ala Tyr Val Phe
        195                 200                 205

Arg Glu Gln Tyr Tyr Arg Arg Ile Arg Phe Met Leu Gln Gly Ile Gln
    210                 215                 220

Lys His Ile Ser Gln Tyr Asn Lys Asn Tyr Ser Tyr Asn Asn Tyr Tyr
225                 230                 235                 240

Lys Asn Ile Lys Asn Asp Pro Ile Asn Asp Lys Thr Tyr Ile Tyr Asn
                245                 250                 255

Asn Gln Asn Asn Asn Lys Tyr Ser Tyr Thr Ser Asn Glu Phe Arg Met
            260                 265                 270

Leu Asn Ser Phe Ser Thr Asp Ile Phe Asp Lys Asp Thr Tyr Asn Asn
        275                 280                 285

Lys Asn Gln Lys Asn Asn His Lys Lys Glu Asn Met Glu Thr His Thr
    290                 295                 300

Leu Leu Asp Thr Asn His Gly Thr Cys Asp Ser Thr Ile Asn Leu Leu
305                 310                 315                 320

Asn Asn Asn Gln Asn Glu Asn His Thr Asn Asn Leu Phe Thr Tyr Leu
                325                 330                 335

Asn Glu Lys Asp Glu Phe Phe Tyr Pro Leu Phe Glu Lys Asn Lys Ser
            340                 345                 350

Ile Leu Val Leu Glu Leu Ser Leu Gln Cys Gly Phe Ser Ile Pro Pro
        355                 360                 365

Ile Tyr Asp Glu Thr Asp Met Leu Glu Asn Leu Leu Lys Asn Ile Glu
    370                 375                 380

Lys Tyr Asp Gln Ser Leu Val Ile Ser Ser Gly Tyr Leu Asn Phe Pro
385                 390                 395                 400
```

```
Met Asn Phe Leu Lys Leu Ile Arg Asn Ile Tyr Ile Asn Val Met Gln
                405                 410                 415

Lys Lys Asn Gly Ile Leu Gln Leu Ile Thr Ala Ser Pro Cys Ala Asn
            420                 425                 430

Ser Phe Tyr Lys Ser Lys Gly Ile Ser Tyr Tyr Ile Pro Ser Ser Tyr
        435                 440                 445

Ser Ala Met Ala Asn Val Cys Ile Glu Tyr Ile Thr Lys Asn Leu Thr
    450                 455                 460

Asn Phe Leu Lys Lys Val Asn Gly Gln Asn Val Ser Glu Gln Asn Asp
465                 470                 475                 480

Ile Ser Asn Gln Lys Ile Tyr Ile Glu Tyr Tyr Lys Pro Ser Trp Thr
                485                 490                 495

Phe His Ser Lys Gly Ile Trp Ile Met Asp Asn Met Lys Ser Met Lys
            500                 505                 510

Asn Val Ser Asn Asp Asn Asp Asn Asp Asn Asp Asn Asn Asn Asn Asp
        515                 520                 525

Asn Asn Asn Asn Asn Asn Ile Asn Asn Asn Glu Phe His Ser Ala Lys
    530                 535                 540

Lys Tyr Glu Gln Asn Val Asn Asn Ser Pro Asn Val Lys Asn Asn Leu
545                 550                 555                 560

Asn Lys Ser Glu Tyr Phe Asn Asn Glu Asn Phe Asp Lys Asn Ile Asp
                565                 570                 575

Glu Glu Asn Asp Tyr Tyr Asp Asn Leu Pro Trp Cys Thr Val Ile Gly
            580                 585                 590

Ser Ser Asn Tyr Gly Tyr Arg Ala Lys Tyr Arg Asp Leu Glu Met Ser
        595                 600                 605

Phe Ile Ile Lys Thr Asn Asp Tyr Asn Leu Arg Cys Gln Leu Lys Lys
    610                 615                 620

Glu Leu Asn Ile Ile Tyr Glu Ser Ser His Phe Val Gln Val Asp Glu
625                 630                 635                 640

Leu Lys Leu Arg Tyr Ala Phe Trp Leu Lys Phe Leu Val Lys Tyr Ile
                645                 650                 655

Phe Lys Trp Leu Leu
            660
```

<210> SEQ ID NO 20
<211> LENGTH: 1986
<212> TYPE: DNA
<213> ORGANISM: Artificial Sequence
<220> FEATURE:
<223> OTHER INFORMATION: Fragment of P. falciparum

<400> SEQUENCE: 20

```
atggctctga agtttgtcat tcatgaacct aaagcaaaat tattatttac tcctaaagaa      60

tttttttaata ccttaaatga catttttaag aactcacaaa atcgtattgt gattagctgt    120

ttatatatgg gaataggaga attagaaaaa gaattaatag atagtataaa aaagaatgtg     180

aatataaaag atttaaaagt tgatatatta ttagatagac aaagaggtac aagactagaa     240

gggaaattta atgaaagttc agttagtatt ttatcagaac tttttaaatg ttcagataat     300

attaatataa gcttatttca taatccttta ttaggtccta tactttataa tatcttacct     360

cctagagcaa atgaagctat aggtgtaatg catatgaaaa tttatattgg ggataatatt     420

ctaatgttat caggagccaa tttaagtgat agctatttac gaaatagaca agatagatat     480

tttgttattg aaaataaatt cttagctgat tctattcata atattattaa taccatacaa     540
```

```
ggtatgtcat ttactctaaa tcgagattta accataaagt gggaaaatga tttaatgaac    600

ccacttatag atgcttacgt atttcgtgaa caatattata gaagaatacg ttttatgtta    660

caaggaattc aaaaacatat ttcacaatat aataaaaatt attcatataa taattattat    720

aaaaatataa aaaatgatcc aataaatgat aagacatata tttataataa tcaaaataac    780

aataaatata gttatacatc aaacgaattt cgcatgttaa attctttcag tacagatata    840

ttcgataaag atacttataa taataaaaac caaaaaaata atcataaaaa agaaaatatg    900

gaaacacata ctttattaga tactaatcat ggaacatgtg attcaacaat taatcttcta    960

aataataatc aaaatgaaaa ccatacaaat aatttattta catatctaaa tgaaaaagat   1020

gaattctttt atccattatt tgaaaaaaat aaaagcattt tagtacttga actttccttg   1080

cagtgtggat tttccatacc tccaatatat gatgaaacag atatgttaga aaacttatta   1140

aaaaatatcg aaaaatatga tcaaagctta gttatttctt cgggatattt aaacttccca   1200

atgaattttc ttaaattaat tagaaatata tatatcaacg ttatgcaaaa aaaaaatggt   1260

attttacaat taatcacagc gtcaccatgc gctaatagtt tttataaatc taaagggata   1320

tcttattata taccaagttc atattcagct atggctaatg tgtgtattga atatattacc   1380

aaaaatttaa ccaatttttct aaaaaaagta aatggacaaa atgtttctga acaaaatgat   1440

atttcaaatc aaaaaatata tattgaatat tacaaacctt catggacatt tcattcgaaa   1500

ggtatatgga taatggacaa tatgaaaagt atgaaaaatg tgagtaatga taatgataat   1560

gataatgata ataataataa tgataataat aataataata atattaataa taatgaattt   1620

cattcagcta aaaaatatga acaaaatgtt aataactcac caaatgtaaa aaataacctg   1680

aacaagtcag aatattttaa caacgaaaat tttgataaga atattgatga agagaatgat   1740

tattatgata atttaccctg gtgtacagtg attggaagtt ctaattatgg gtatagagca   1800

aaatatagag atttggagat gagttttata ataaaaacaa atgattataa tttgaggtgt   1860

cagttaaaga aagaattaaa tataatatat gagtcatctc attttgtaca agtggatgaa   1920

ttgaaattac gatatgcttt ttggttaaaa tttttagtga aatatatatt caaatggctt   1980

ttataa                                                               1986
```

```
<210> SEQ ID NO 21
<211> LENGTH: 459
<212> TYPE: DNA
<213> ORGANISM: Artificial Sequence
<220> FEATURE:
<223> OTHER INFORMATION: Fragment of P. falciparum

<400> SEQUENCE: 21

gtaaaagaag gaattaaaga aaatgatact gaaaataaag ataaagtgat aggacaagaa     60

ataataactg aagaagtaaa agaaggaatt aaagaaaatg atactgaaaa taaagataaa    120

gtgataggac aagaaataat aactgaagaa gtaaaaaaag aaattgaaaa acaagaagaa    180

aaaggaaata aagaaaatat tcttgaaatt aaagatatag taattggaca agaagtaata    240

atagaagaag taaaaaaagt aattaaaaaa aaagtagaaa aaggaattaa agaaaatcat    300

actgaaagta aagataaagt gataggacaa gaaataatag ttgaagaagt aaaagaagaa    360

attgaaaaac aagtagaaga aggaattaaa gaaaatgata ctgaaagtaa agataaagtg    420

ataggacaag aagtgataaa aggagatgtt aatgaagaa                           459


<210> SEQ ID NO 22
```

<211> LENGTH: 153
<212> TYPE: PRT
<213> ORGANISM: Artificial Sequence
<220> FEATURE:
<223> OTHER INFORMATION: Fragment of P. falciparum

<400> SEQUENCE: 22

Val Lys Glu Gly Ile Lys Glu Asn Asp Thr Glu Asn Lys Asp Lys Val
1 5 10 15

Ile Gly Gln Glu Ile Ile Thr Glu Glu Val Lys Glu Gly Ile Lys Glu
20 25 30

Asn Asp Thr Glu Asn Lys Asp Lys Val Ile Gly Gln Glu Ile Ile Thr
35 40 45

Glu Glu Val Lys Lys Glu Ile Glu Lys Gln Glu Glu Lys Gly Asn Lys
50 55 60

Glu Asn Ile Leu Glu Ile Lys Asp Ile Val Ile Gly Gln Glu Val Ile
65 70 75 80

Ile Glu Glu Val Lys Lys Val Ile Lys Lys Lys Val Glu Lys Gly Ile
85 90 95

Lys Glu Asn His Thr Glu Ser Lys Asp Lys Val Ile Gly Gln Glu Ile
100 105 110

Ile Val Glu Glu Val Lys Glu Glu Ile Glu Lys Gln Val Glu Glu Gly
115 120 125

Ile Lys Glu Asn Asp Thr Glu Ser Lys Asp Lys Val Ile Gly Gln Glu
130 135 140

Val Ile Lys Gly Asp Val Asn Glu Glu
145 150

<210> SEQ ID NO 23
<211> LENGTH: 1434
<212> TYPE: PRT
<213> ORGANISM: Artificial Sequence
<220> FEATURE:
<223> OTHER INFORMATION: Fragment of P. falciparum

<400> SEQUENCE: 23

Met Glu Val Ile Cys Arg Asn Leu Cys Tyr Asp Lys Lys Asn Asn Met
1 5 10 15

Met Glu Asn Glu Gly Asn Lys Val Lys Lys Val Tyr Asn Asn Ser Ser
20 25 30

Leu Lys Lys Tyr Met Lys Phe Cys Leu Cys Thr Ile Ile Cys Val Phe
35 40 45

Leu Leu Asp Ile Tyr Thr Asn Cys Glu Ser Pro Thr Tyr Ser Tyr Ser
50 55 60

Ser Ile Lys Asn Asn Asn Asp Arg Tyr Val Arg Ile Leu Ser Glu Thr
65 70 75 80

Glu Pro Pro Met Ser Leu Glu Glu Ile Met Arg Thr Phe Asp Glu Asp
85 90 95

His Leu Tyr Ser Ile Arg Asn Tyr Ile Glu Cys Leu Arg Asn Ala Pro
100 105 110

Tyr Ile Asp Asp Pro Leu Trp Gly Ser Val Val Thr Asp Lys Arg Asn
115 120 125

Asn Cys Leu Gln His Ile Lys Leu Leu Glu Met Gln Glu Ser Glu Arg
130 135 140

Arg Lys Gln Gln Glu Glu Glu Asn Ala Lys Asp Ile Glu Glu Ile Arg
145 150 155 160

```
Lys Lys Glu Lys Glu Tyr Leu Met Lys Glu Leu Glu Glu Met Asp Glu
                165                 170                 175

Ser Asp Val Glu Lys Ala Phe Arg Glu Leu Gln Phe Ile Lys Leu Arg
            180                 185                 190

Asp Arg Thr Arg Pro Arg Lys His Val Asn Val Met Gly Glu Ser Lys
        195                 200                 205

Glu Thr Asp Glu Ser Lys Glu Thr Asp Glu Ser Lys Glu Thr Gly Glu
    210                 215                 220

Ser Lys Glu Thr Gly Glu Ser Lys Glu Thr Gly Glu Ser Lys Glu Thr
225                 230                 235                 240

Gly Glu Ser Lys Glu Thr Gly Glu Ser Lys Glu Thr Gly Glu Ser Lys
                245                 250                 255

Glu Thr Gly Glu Ser Lys Glu Thr Gly Glu Ser Lys Glu Thr Gly Glu
            260                 265                 270

Ser Lys Glu Thr Gly Glu Ser Lys Glu Thr Gly Glu Ser Lys Glu Thr
        275                 280                 285

Gly Glu Ser Lys Glu Thr Gly Glu Ser Lys Glu Thr Gly Glu Ser Lys
    290                 295                 300

Glu Thr Arg Ile Tyr Glu Glu Thr Lys Tyr Asn Lys Ile Thr Ser Glu
305                 310                 315                 320

Phe Arg Glu Thr Glu Asn Val Lys Ile Thr Glu Glu Ser Lys Asp Arg
                325                 330                 335

Glu Gly Asn Lys Val Ser Gly Pro Tyr Glu Asn Ser Glu Asn Ser Asn
            340                 345                 350

Val Thr Ser Glu Ser Glu Glu Thr Lys Lys Leu Ala Glu Lys Glu Glu
        355                 360                 365

Asn Glu Gly Glu Lys Leu Gly Glu Asn Val Asn Asp Gly Ala Ser Glu
    370                 375                 380

Asn Ser Glu Asp Pro Lys Lys Leu Thr Glu Gln Glu Glu Asn Gly Thr
385                 390                 395                 400

Lys Glu Ser Ser Glu Glu Thr Lys Asp Asp Lys Pro Glu Glu Asn Glu
                405                 410                 415

Lys Lys Ala Asp Asn Lys Lys Lys Ser Lys Lys Lys Lys Lys Ser Phe
            420                 425                 430

Phe Gln Met Leu Gly Cys Asn Phe Leu Cys Asn Lys Asn Ile Glu Thr
        435                 440                 445

Asp Asp Glu Glu Glu Thr Leu Val Val Lys Asp Asp Ala Lys Lys Lys
    450                 455                 460

His Lys Phe Leu Arg Glu Ala Asn Thr Glu Lys Asn Asp Asn Glu Lys
465                 470                 475                 480

Lys Asp Lys Leu Leu Gly Glu Gly Asp Lys Glu Asp Val Lys Glu Lys
                485                 490                 495

Asn Asp Glu Gln Lys Asp Lys Val Leu Gly Glu Gly Asp Lys Glu Asp
            500                 505                 510

Val Lys Glu Lys Asn Asp Glu Gln Lys Asp Lys Val Leu Gly Glu Gly
        515                 520                 525

Asp Lys Glu Asp Val Lys Glu Lys Asn Asp Gly Lys Lys Asp Lys Val
    530                 535                 540

Ile Gly Ser Glu Lys Thr Gln Lys Glu Ile Lys Glu Lys Val Glu Lys
545                 550                 555                 560

Arg Val Lys Lys Lys Cys Lys Lys Lys Val Lys Lys Gly Ile Lys Glu
                565                 570                 575
```

-continued

```
Asn Asp Thr Glu Gly Asn Asp Lys Val Lys Gly Pro Glu Ile Ile Ile
            580                 585                 590

Glu Glu Val Lys Glu Glu Ile Lys Lys Gln Val Glu Asp Gly Ile Lys
        595                 600                 605

Glu Asn Asp Thr Glu Gly Asn Asp Lys Val Lys Gly Pro Glu Ile Ile
    610                 615                 620

Thr Glu Glu Val Lys Glu Glu Ile Lys Lys Gln Val Glu Glu Gly Ile
625                 630                 635                 640

Lys Glu Asn Asp Thr Glu Gly Asn Asp Lys Val Lys Gly Pro Glu Ile
                645                 650                 655

Ile Thr Glu Glu Val Lys Glu Glu Ile Lys Lys Gln Val Glu Glu Gly
            660                 665                 670

Ile Lys Glu Asn Asp Thr Glu Ser Lys Asp Lys Leu Ile Gly Gln Glu
        675                 680                 685

Ile Ile Thr Glu Glu Val Lys Glu Gly Ile Lys Glu Asn Asp Thr Glu
    690                 695                 700

Asn Lys Asp Lys Val Ile Gly Gln Glu Ile Ile Thr Glu Glu Val Lys
705                 710                 715                 720

Glu Gly Ile Lys Glu Asn Asp Thr Glu Asn Lys Asp Lys Val Ile Gly
                725                 730                 735

Gln Glu Ile Ile Thr Glu Glu Val Lys Lys Glu Ile Glu Lys Gln Glu
            740                 745                 750

Glu Lys Gly Asn Lys Glu Asn Ile Leu Glu Ile Lys Asp Ile Val Ile
        755                 760                 765

Gly Gln Glu Val Ile Ile Glu Glu Val Lys Lys Val Ile Lys Lys Lys
    770                 775                 780

Val Glu Lys Gly Ile Lys Glu Asn His Thr Glu Ser Lys Asp Lys Val
785                 790                 795                 800

Ile Gly Gln Glu Ile Ile Val Glu Glu Val Lys Glu Glu Ile Glu Lys
                805                 810                 815

Gln Val Glu Glu Gly Ile Lys Glu Asn Asp Thr Glu Ser Lys Asp Lys
            820                 825                 830

Val Ile Gly Gln Glu Val Ile Lys Gly Asp Val Asn Glu Glu Gly Pro
        835                 840                 845

Glu Asn Lys Asp Lys Val Thr Lys Gln Glu Lys Val Lys Glu Val Lys
    850                 855                 860

Lys Glu Val Lys Lys Lys Val Lys Lys Arg Val Lys Lys Arg Asn Asn
865                 870                 875                 880

Lys Asn Glu Arg Lys Asp Asn Val Ile Gly Lys Glu Ile Met Lys Glu
                885                 890                 895

Asp Val Asn Glu Lys Asp Thr Ala Asn Lys Asp Lys Glu Ile Glu Gln
            900                 905                 910

Glu Lys Glu Lys Glu Glu Val Lys Glu Lys Glu Glu Val Lys Glu Lys
        915                 920                 925

Glu Glu Val Lys Glu Lys Glu Glu Val Lys Glu Lys Glu Glu Val Lys
    930                 935                 940

Glu Lys Glu Glu Val Lys Glu Lys Glu Glu Val Lys Glu Lys Glu Glu
945                 950                 955                 960

Val Lys Glu Lys Asp Thr Glu Ser Lys Asp Lys Glu Ile Glu Gln Glu
                965                 970                 975

Lys Glu Lys Glu Glu Val Lys Glu Val Lys Glu Lys Asp Thr Glu Asn
            980                 985                 990
```

```
Lys Asp Lys Val Ile Gly Gln Glu  Ile Ile Ile Glu Glu  Ile Lys Lys
        995                 1000                 1005

Glu Val  Lys Lys Arg Val Lys  Lys Arg Asn Asn Lys  Asn Glu Asn
    1010                 1015                 1020

Lys Asp  Asn Val Ile Val Gln  Glu Ile Met Asn Glu  Asp Val Asn
    1025                 1030                 1035

Glu Lys  Asp Thr Ala Asn Lys  Asp Lys Val Ile Glu  Gln Glu Lys
    1040                 1045                 1050

Glu Lys  Glu Glu Val Lys Glu  Lys Glu Glu Val Lys  Glu Lys Glu
    1055                 1060                 1065

Glu Val  Lys Glu Lys Glu Glu  Val Lys Glu Lys Glu  Glu Val Lys
    1070                 1075                 1080

Glu Lys  Glu Glu Val Lys Glu  Lys Asp Thr Glu Ser  Lys Asp Asn
    1085                 1090                 1095

Val Ile  Val Gln Glu Ile Met  Asn Glu Asp Val Asn  Glu Lys Asp
    1100                 1105                 1110

Thr Glu  Ser Lys Asp Lys Met  Ile Gly Lys Glu Val  Ile Ile Glu
    1115                 1120                 1125

Glu Val  Lys Glu Glu Val Lys  Lys Arg Val Asn Lys  Glu Val Asn
    1130                 1135                 1140

Lys Arg  Val Asn Arg Arg Asn  Arg Lys Asn Glu Arg  Lys Asp Val
    1145                 1150                 1155

Ile Glu  Gln Glu Ile Val Ser  Glu Glu Val Asn Glu  Lys Asp Thr
    1160                 1165                 1170

Lys Asn  Asn Asp Lys Lys Ile  Gly Lys Arg Val Lys  Lys Pro Ile
    1175                 1180                 1185

Asp Asp  Cys Lys Lys Glu Arg  Glu Val Gln Glu Glu  Ser Glu Glu
    1190                 1195                 1200

Glu Ser  Glu Glu Glu Ser Glu  Glu Glu Ser Glu Glu  Glu Ser Glu
    1205                 1210                 1215

Glu Glu  Ser Glu Glu Glu Ser  Glu Glu Glu Ser Glu  Glu Glu Ser
    1220                 1225                 1230

Glu Glu  Glu Ser Glu Glu Glu  Ser Glu Glu Glu Ser  Glu Glu Glu
    1235                 1240                 1245

Ser Glu  Glu Glu Ser Glu Glu  Glu Ser Glu Glu Glu  Ser Glu Glu
    1250                 1255                 1260

Glu Ser  Glu Glu Glu Ser Asp  Glu Glu Lys Asn Thr  Ser Gly Leu
    1265                 1270                 1275

Val His  Arg Arg Asn Cys Lys  Lys Glu Lys Lys Tyr  Asn Asn Gly
    1280                 1285                 1290

Glu Leu  Glu Glu Tyr Tyr Lys  Glu Lys Gln Asn Glu  Glu Tyr Phe
    1295                 1300                 1305

Asp Glu  Glu Tyr Ile Ile Gln  Ser Lys Glu His Asn  Thr Leu Asn
    1310                 1315                 1320

Thr Phe  Pro Asn Met Ala Leu  Asn Glu Asp Phe Arg  Arg Glu Phe
    1325                 1330                 1335

His Asn  Ile Leu Ser Ile His  Glu Asp Thr Asp Leu  Met Glu Leu
    1340                 1345                 1350

Lys Arg  Ile Leu Tyr Asn Leu  Phe Leu Glu Tyr Asn  Pro His Met
    1355                 1360                 1365

Asn Asn  Lys Gln Lys Ala Glu  Leu Asp Lys Lys Phe  Ser Glu Met
    1370                 1375                 1380
```

-continued

```
Asn Val  Val His Gln Ile Leu  Asn Tyr Glu Glu Arg  Ile Arg Met
    1385                 1390                 1395

Tyr Glu  Glu Asn Ala Ala Arg  Gly Arg Leu Asn Thr  Val Ile Leu
    1400                 1405                 1410

Asp Pro  Ile Ile Thr Phe Asn  Val Ile Phe Gly Asp  Asp Thr Met
    1415                 1420                 1425

Phe Lys  Phe Ile Asp Glu
    1430


<210> SEQ ID NO 24
<211> LENGTH: 4304
<212> TYPE: DNA
<213> ORGANISM: Artificial Sequence
<220> FEATURE:
<223> OTHER INFORMATION: Fragment of P. falciparum

<400> SEQUENCE: 24

tggaggtaat ttgtagaaat ttatgctacg ataagaaaaa taatatgatg gaaaatgaag     60

ggaacaaagt gaaaaaagtg tataataatt cttctttaaa gaaatatatg aagttttgtt    120

tatgcactat aatatgtgtt tttttattag atatctatac gaattgtgaa tcacccacct    180

attcatacag ttcaataaag aataataatg acagatatgt aagaatttta agtgaaactg    240

aaccaccgat gagtttagag gaaataatga gaacatttga tgaagatcat ctatattcta    300

taagaaacta tattgaatgt ttaagaaacg ctccatatat cgatgatcct ttgtggggtt    360

cggttgttac agataaacgt aataattgtc ttcagcatat taaattattg gaaatgcaag    420

aatccgaaag aagaaaacaa caagaagagg agaatgctaa ggatattgaa gaaataagaa    480

agaaagaaaa agaatacctt atgaaagaat tagaagaaat ggatgaatcc gatgtagaaa    540

aggcatttag agaattacaa tttattaagt taagagatag aactagacct agaaaacatg    600

tgaatgtaat gggagaatct aaggaaacag atgaatctaa ggaaacagat gaatctaagg    660

aaactggtga atctaaggaa actggtgaat ctaaggaaac tggtgaatct aaggaaactg    720

gtgaatctaa ggaaactggt gaatctaagg aaactggtga atctaaggaa actggtgaat    780

ctaaggaaac tggtgaatct aaggaaactg gtgaatctaa ggaaactggt gaatctaagg    840

aaactggtga atctaaggaa actggtgaat ctaaggaaac tggtgaatct aaggaaactg    900

gtgaatctaa ggaaacaaga atatatgagg aaacaaaata taacaaaata acgagtgaat    960

ttagagaaac agaaaacgtg aagataacag aggaatctaa ggatagagaa ggtaacaaag   1020

tatcaggtcc atatgaaaac tcagaaaatt ccaatgtaac aagtgaatct gaagagacca   1080

aaaaattagc cgaaaaagag gagaatgagg gagaaaaatt aggagaaaat gttaatgatg   1140

gggcatcaga aaattcagaa gatcccaaaa aattaacaga acaagaagaa aatggtacaa   1200

aggaaagttc tgaagaaaca aaagatgata aaccggaaga aaatgagaaa aaggcagata   1260

ataaaaaaaa aagtaaaaaa aagaaaaaat catttttttca aatgttagga tgtaatttcc   1320

tatgtaataa aaatattgaa actgatgatg aagaagaaac gttggtagta aaagatgatg   1380

ctaaaaagaa acataaattt ttaagagaag ctaatactga aaaaaatgat aatgaaaaga   1440

aagataaatt attaggagaa ggagataaag aagatgttaa agaaaagaat gatgaacaga   1500

aagataaagt attaggagaa ggagataaag aagatgttaa agaaaagaat gatgaacaga   1560

aagataaagt attaggagaa ggagataaag aagatgttaa agaaaagaat gatggaaaga   1620

aagataaagt gataggatca gaaaaaacac aaaaggaaat taaagaaaaa gtagaaaaaa   1680

gagttaaaaa aaagtgtaaa aaaaaagtaa aaaaaggaat taaagaaaat gatactgaag   1740
```

```
gtaacgataa agtgaaagga ccagaaataa taattgaaga agtaaaagaa gaaattaaaa   1800
aacaagtaga agatggaatt aaagaaaatg atactgaagg taacgataaa gtgaaagggc   1860
cagaaataat aactgaagaa gtaaaagaag aaattaaaaa acaagtagaa gaaggaatta   1920
aagaaaatga tactgaaggt aacgataaag tgaaagggcc agaaataata actgaagaag   1980
taaaagaaga aattaaaaaa caagtagaag aaggaattaa agaaaatgat actgaaagta   2040
aggataaatt gataggacaa gaaataataa ctgaagaagt aaaagaagga attaaagaaa   2100
atgatactga aaataaagat aaagtgatag gacaagaaat aataactgaa gaagtaaaag   2160
aaggaattaa agaaaatgat actgaaaata aagataaagt gataggacaa gaaataataa   2220
ctgaagaagt aaaaaaagaa attgaaaaac aagaagaaaa aggaaataaa gaaaatattc   2280
ttgaaattaa agatatagta attggacaag aagtaataat agaagaagta aaaaaagtaa   2340
ttaaaaaaaa agtagaaaaa ggaattaaag aaaatcatac tgaaagtaaa gataaagtga   2400
taggacaaga aataatagtt gaagaagtaa aagaagaaat tgaaaaacaa gtagaagaag   2460
gaattaaaga aaatgatact gaaagtaaag ataaagtgat aggacaagaa gtgataaaag   2520
gagatgttaa tgaagaaggt cccgaaaaca aagataaagt gacaaaacag gaaaaagtaa   2580
aagaagttaa aaaagaagta aaaaaaaaag ttaaaaaaag agtaaaaaaa agaaataata   2640
agaatgaaag aaaagataat gtgataggaa aagaaataat gaaagaagat gttaatgaaa   2700
aagataccgc aaacaaagat aaagagatag aacaagaaaa agaaaaagaa gaagttaaag   2760
aaaaagaaga agttaaagaa aaagaagaag ttaaagaaaa agaagaagta aaagaaaaag   2820
aagaagtaaa agaaaaagaa gaagtaaaag aaaaagaaga agtaaaagaa aaagaagaag   2880
taaaagaaaa agataccgaa agcaaagata aagagataga acaagaaaaa gaaaaagaag   2940
aagtaaaaga agttaaagaa aaagataccg aaaacaaaga taaagtgata ggacaagaaa   3000
taataataga agaaataaaa aaagaagtta aaaaaagagt aaaaaaaaga aataataaaa   3060
atgaaaacaa agataatgtg atagtacaag aaataatgaa cgaagatgtt aacgaaaaag   3120
ataccgcaaa caaagataag gtgatagaac aagaaaaaga aaaagaagaa gttaaagaaa   3180
aagaagaagt taaagaaaaa gaagaagtaa aagaaaaaga agaagtaaaa gaaaaagaag   3240
aagtaaaaga aaaagaagaa gtaaaagaaa aagataccga aagcaaagat aatgtgatag   3300
tacaagaaat aatgaacgaa gatgttaacg aaaaagatac cgaaagcaaa gataaaatga   3360
taggaaaaga agtaataata gaagaagtaa aagaagaagt taaaaaaaga gtaaacaaag   3420
aagttaacaa aagagtaaac agaagaaata gaaaaaatga aagaaaagat gtgatagaac   3480
aagaaatagt aagcgaagaa gttaacgaaa aagataccaa aaacaacgat aaaaagatag   3540
gaaaaagagt caaaaaacca atagatgatt gtaaaaaaga aagagaagta caagaagaat   3600
ctgaagaaga gtctgaagaa gagtctgaag aagaatctga agaagagtct gaagaagaat   3660
ctgaagaaga gtctgaagaa gaatctgaag aagagtctga agaagaatct gaagaagaat   3720
ctgaagaaga gtctgaagaa gaatctgaag aagagtctga agaagagtct gaagaagagt   3780
ctgaagaaga atctgaagaa gaatctgatg aagaaaaaaa tacatcaggt ttggtacata   3840
gaagaaattg taaaaaagaa aagaaatata ataatggaga attagaagaa tattataaag   3900
agaaacagaa tgaagaatat tttgatgaag aatatattat tcaatcaaaa gaacataata   3960
ctttgaatac attcccaaat atggcattaa atgaagattt cagaagagaa tttcacaata   4020
tattaagtat tcatgaagat acagatttga tggaactaaa aagaatctta tataatttat   4080
```

-continued

```
ttttagaata taatccacat atgaataata aacagaaagc agaattggat aagaaattta   4140

gtgaaatgaa tgtggtacat caaatattaa attatgaaga gagaatacgc atgtatgaag   4200

aaaatgcagc acgaggaaga ctaaatacag ttattctgga tccaattatt acatttaatg   4260

taatattcgg agatgataca atgtttaagt ttattgatga ataa                    4304
```

<210> SEQ ID NO 25
<211> LENGTH: 792
<212> TYPE: DNA
<213> ORGANISM: Artificial Sequence
<220> FEATURE:
<223> OTHER INFORMATION: Fragment of P. falciparum

<400> SEQUENCE: 25

```
tcaaaagaac acaaatcaaa aggaaagaaa gataaaggaa agaaagataa aggaaaacat     60

aaaaaagcaa aaaaagaaaa agtaaaaaaa cacgtagtta aaaatgttat agaagatgaa    120

gacaaagatg gtgtagaaat aataaactta gaagataaag aggcatgtga agaacaacac    180

ataacagtag aaagtagacc actaagccaa ccacaatgta aactaataga tgaaccagaa    240

caattaacat taatggataa atcaaaagtt gaagaaaaaa acttatccat acaagagcaa    300

ttaataggta ccataggacg tgttaatgta gtacccagaa gagataatca taagaaaaaa    360

atggcgaaga tagaggaagc tgaacttcaa aaacagaaac atgttgataa ggaagaagac    420

aaaaaagaag aatccaaaga agtagaagaa gaatctaaag aggtacaaga agatgaagaa    480

gaagtagaag aagatgaaga agaagaagaa gaagaagagg aagaagaaga agaagaagaa    540

gaagaagagg aagaagaaga agatgaagta gaagaagatg aagatgatgc tgaagaagat    600

gaagatgatg ctgaagaaga tgaagatgat gctgaagaag atgatgatga tgctgaagaa    660

gatgatgatg atgctgaaga agatgatgat gaagatgaag atgaagatga agaagaagaa    720

gaagatgaag aagaagaaga agaatcagaa aaaaaaataa aaagaaattt gagaaaaaat    780

gccaaaattt aa                                                        792
```

<210> SEQ ID NO 26
<211> LENGTH: 263
<212> TYPE: PRT
<213> ORGANISM: Artificial Sequence
<220> FEATURE:
<223> OTHER INFORMATION: Fragment of P. falciparum

<400> SEQUENCE: 26

```
Ser Lys Glu His Lys Ser Lys Gly Lys Lys Asp Lys Gly Lys Lys Asp
1               5                   10                  15

Lys Gly Lys His Lys Lys Ala Lys Lys Glu Lys Val Lys Lys His Val
            20                  25                  30

Val Lys Asn Val Ile Glu Asp Glu Asp Lys Asp Gly Val Glu Ile Ile
        35                  40                  45

Asn Leu Glu Asp Lys Glu Ala Cys Glu Glu Gln His Ile Thr Val Glu
    50                  55                  60

Ser Arg Pro Leu Ser Gln Pro Gln Cys Lys Leu Ile Asp Glu Pro Glu
65                  70                  75                  80

Gln Leu Thr Leu Met Asp Lys Ser Lys Val Glu Glu Lys Asn Leu Ser
                85                  90                  95

Ile Gln Glu Gln Leu Ile Gly Thr Ile Gly Arg Val Asn Val Val Pro
            100                 105                 110

Arg Arg Asp Asn His Lys Lys Lys Met Ala Lys Ile Glu Glu Ala Glu
        115                 120                 125
```

-continued

```
Leu Gln Lys Gln Lys His Val Asp Lys Glu Glu Asp Lys Lys Glu Glu
    130                 135                 140

Ser Lys Glu Val Glu Glu Glu Ser Lys Glu Val Gln Glu Asp Glu Glu
145                 150                 155                 160

Glu Val Glu Glu Asp Glu Glu Glu Glu Glu Glu Glu Glu Glu Glu Glu
                165                 170                 175

Glu Glu Glu Glu Glu Glu Glu Glu Glu Glu Glu Asp Glu Val Glu Glu
            180                 185                 190

Asp Glu Asp Asp Ala Glu Glu Asp Glu Asp Asp Ala Glu Glu Asp Glu
        195                 200                 205

Asp Asp Ala Glu Glu Asp Asp Asp Asp Ala Glu Glu Asp Asp Asp Asp
    210                 215                 220

Ala Glu Glu Asp Asp Asp Glu Asp Glu Asp Glu Asp Glu Glu Glu Glu
225                 230                 235                 240

Glu Asp Glu Glu Glu Glu Glu Glu Ser Glu Lys Lys Ile Lys Arg Asn
                245                 250                 255

Leu Arg Lys Asn Ala Lys Ile
            260
```

<210> SEQ ID NO 27
<211> LENGTH: 673
<212> TYPE: PRT
<213> ORGANISM: Artificial Sequence
<220> FEATURE:
<223> OTHER INFORMATION: Fragment of P. falciparum

<400> SEQUENCE: 27

```
Met Asn Val Leu Phe Leu Ser Tyr Asn Ile Cys Ile Leu Phe Phe Val
1               5                   10                  15

Val Cys Thr Leu Asn Phe Ser Thr Lys Cys Phe Ser Asn Gly Leu Leu
            20                  25                  30

Lys Asn Gln Asn Ile Leu Asn Lys Ser Phe Asp Ser Ile Thr Gly Arg
        35                  40                  45

Leu Leu Asn Glu Thr Glu Leu Glu Lys Asn Lys Asp Asp Asn Ser Lys
    50                  55                  60

Ser Glu Thr Leu Leu Lys Glu Glu Lys Asp Glu Lys Asp Asp Val Pro
65                  70                  75                  80

Thr Thr Ser Asn Asp Asn Leu Lys Asn Ala His Asn Asn Asn Glu Ile
                85                  90                  95

Ser Ser Ser Thr Asp Pro Thr Asn Ile Ile Asn Val Asn Asp Lys Asp
            100                 105                 110

Asn Glu Asn Ser Val Asp Lys Lys Lys Asp Lys Lys Glu Lys Lys His
        115                 120                 125

Lys Lys Asp Lys Lys Glu Lys Lys Glu Lys Lys Asp Lys Lys Glu Lys
    130                 135                 140

Lys Asp Lys Lys Glu Lys Lys His Lys Lys Glu Lys Lys His Lys Lys
145                 150                 155                 160

Asp Lys Lys Lys Glu Glu Asn Ser Glu Val Met Ser Leu Tyr Lys Thr
                165                 170                 175

Gly Gln His Lys Pro Lys Asn Ala Thr Glu His Gly Glu Glu Asn Leu
            180                 185                 190

Tyr Glu Glu Met Val Ser Glu Ile Asn Asn Asn Ala Gln Gly Gly Leu
        195                 200                 205

Leu Leu Ser Ser Pro Tyr Gln Tyr Arg Glu Gln Gly Gly Cys Gly Ile
    210                 215                 220
```

```
Ile Ser Ser Val His Glu Thr Ser Asn Asp Thr Lys Asp Asn Asp Lys
225                 230                 235                 240

Glu Asn Ile Ser Glu Asp Lys Lys Glu Asp His Gln Gln Glu Glu Met
                245                 250                 255

Leu Lys Thr Leu Asp Lys Lys Glu Arg Lys Gln Lys Glu Lys Glu Met
            260                 265                 270

Lys Glu Gln Glu Lys Ile Glu Lys Lys Lys Lys Lys Gln Glu Glu Lys
        275                 280                 285

Glu Lys Lys Lys Gln Glu Lys Glu Arg Lys Lys Gln Glu Lys Lys Glu
    290                 295                 300

Arg Lys Gln Lys Glu Lys Glu Met Lys Lys Gln Lys Lys Ile Glu Lys
305                 310                 315                 320

Glu Arg Lys Lys Lys Glu Glu Lys Glu Lys Lys Lys Lys Lys His Asp
                325                 330                 335

Lys Glu Asn Glu Glu Thr Met Gln Gln Pro Asp Gln Thr Ser Glu Glu
            340                 345                 350

Thr Asn Asn Glu Ile Met Val Pro Leu Pro Ser Pro Leu Thr Asp Val
        355                 360                 365

Thr Thr Pro Glu Glu His Lys Glu Gly Glu His Lys Glu Glu Glu His
    370                 375                 380

Lys Glu Gly Glu His Lys Glu Gly Glu His Lys Glu Glu Glu His Lys
385                 390                 395                 400

Glu Glu Glu His Lys Lys Glu Glu His Lys Ser Lys Glu His Lys Ser
                405                 410                 415

Lys Gly Lys Lys Asp Lys Gly Lys Lys Asp Lys Gly Lys His Lys Lys
            420                 425                 430

Ala Lys Lys Glu Lys Val Lys Lys His Val Val Lys Asn Val Ile Glu
        435                 440                 445

Asp Glu Asp Lys Asp Gly Val Glu Ile Ile Asn Leu Glu Asp Lys Glu
    450                 455                 460

Ala Cys Glu Glu Gln His Ile Thr Val Glu Ser Arg Pro Leu Ser Gln
465                 470                 475                 480

Pro Gln Cys Lys Leu Ile Asp Glu Pro Glu Gln Leu Thr Leu Met Asp
                485                 490                 495

Lys Ser Lys Val Glu Glu Lys Asn Leu Ser Ile Gln Glu Gln Leu Ile
            500                 505                 510

Gly Thr Ile Gly Arg Val Asn Val Val Pro Arg Arg Asp Asn His Lys
        515                 520                 525

Lys Lys Met Ala Lys Ile Glu Glu Ala Glu Leu Gln Lys Gln Lys His
    530                 535                 540

Val Asp Lys Glu Glu Asp Lys Lys Glu Glu Ser Lys Glu Val Glu Glu
545                 550                 555                 560

Glu Ser Lys Glu Val Gln Glu Asp Glu Glu Glu Val Glu Glu Asp Glu
                565                 570                 575

Glu Glu Glu Glu Glu Glu Glu Glu Glu Glu Glu Glu Glu Glu Glu Glu
            580                 585                 590

Glu Glu Glu Glu Glu Asp Glu Val Glu Glu Asp Glu Asp Asp Ala Glu
        595                 600                 605

Glu Asp Glu Asp Asp Ala Glu Glu Asp Glu Asp Asp Ala Glu Glu Asp
    610                 615                 620

Asp Asp Asp Ala Glu Glu Asp Asp Asp Asp Ala Glu Glu Asp Asp Asp
625                 630                 635                 640
```

```
Glu Asp Glu Asp Glu Asp Glu Glu Glu Glu Glu Asp Glu Glu Glu Glu
                645                 650                 655

Glu Glu Ser Glu Lys Lys Ile Lys Arg Asn Leu Arg Lys Asn Ala Lys
            660                 665                 670

Ile


<210> SEQ ID NO 28
<211> LENGTH: 2022
<212> TYPE: DNA
<213> ORGANISM: Artificial Sequence
<220> FEATURE:
<223> OTHER INFORMATION: Fragment of P. falciparum

<400> SEQUENCE: 28

atgaatgtgc tatttctttc gtataatatt tgtattcttt tttttgttgt atgcacatta     60

aatttttcta ctaagtgctt ttccaatggt ttattgaaga atcaaaatat cctaaacaaa    120

agttttgatt ccataacggg aagattatta aacgaaaccg aattagaaaa aaataaagat    180

gataattcaa aatctgaaac gttgttaaaa gaggaaaaag atgaaaagga tgatgtacct    240

acaacgagta atgacaacct taagaatgct cataataata atgaaatttc aagttcaact    300

gatccaacga atattattaa tgttaatgat aaagataatg aaaactctgt agataaaaaa    360

aaagataaaa aagaaaaaaa gcataaaaaa gataaaaaag aaaaaaaaga aaaaaaagat    420

aaaaaagaaa aaaaagataa aaaagaaaaa aaacataaaa aagaaaaaaa acataaaaaa    480

gataaaaaaa aagaagaaaa cagtgaagtg atgtctttat ataaaacggg tcaacataaa    540

ccaaaaaacg caacagaaca tggtgaagaa aatttatatg aagaaatggt aagtgaaata    600

aataataatg cacaaggtgg actcctttta tcaagcccat atcaatatag agaacaagga    660

ggatgtggaa tcatatctag tgttcatgag acgtctaatg atacaaaaga taatgataaa    720

gaaaatatat ccgaagacaa aaaggaggac catcaacaag aagaaatgtt gaaaacactt    780

gataaaaaag aacgtaaaca aaaagaaaaa gaaatgaaag aacaagaaaa aatcgaaaaa    840

aaaaaaaaaa agcaagaaga aaaggaaaag aaaaaacaag aaaaagaaag aaaaaaacaa    900

gaaaagaaag aacgtaaaca aaaagaaaaa gaaatgaaaa aacaaaaaaa aatagaaaaa    960

gaaagaaaaa agaaagaaga aaaggaaaag aaaaagaaaa aacatgataa ggaaaatgaa   1020

gaaacaatgc aacaaccaga tcaaacaagt gaagaaacca acaatgaaat tatggtacca   1080

ttaccaagtc cattgacaga cgtaactaca ccagaagaac acaaagaagg agaacacaaa   1140

gaagaagaac acaaagaagg agaacacaaa gaaggagaac acaaagaaga agaacacaaa   1200

gaagaagaac acaaaaaaga agaacacaaa tcaaaagaac acaaatcaaa aggaaagaaa   1260

gataaaggaa agaaagataa aggaaaacat aaaaaagcaa aaaaagaaaa agtaaaaaaa   1320

cacgtagtta aaaatgttat agaagatgaa gacaaagatg gtgtagaaat aataaactta   1380

gaagataaag aggcatgtga agaacaacac ataacagtag aaagtagacc actaagccaa   1440

ccacaatgta aactaataga tgaaccagaa caattaacat taatggataa atcaaaagtt   1500

gaagaaaaaa acttatccat acaagagcaa ttaataggta ccataggacg tgttaatgta   1560

gtacccagaa gagataatca taagaaaaaa atggcgaaga tagaggaagc tgaacttcaa   1620

aaacagaaac atgttgataa ggaagaagac aaaaaagaag aatccaaaga agtagaagaa   1680

gaatctaaag aggtacaaga agatgaagaa gaagtagaag aagatgaaga agaagaagaa   1740

gaagaagagg aagaagaaga agaagaagaa gaagaagagg aagaagaaga agatgaagta   1800

gaagaagatg aagatgatgc tgaagaagat gaagatgatg ctgaagaaga tgaagatgat   1860
```

```
gctgaagaag atgatgatga tgctgaagaa gatgatgatg atgctgaaga agatgatgat   1920

gaagatgaag atgaagatga agaagaagaa gaagatgaag aagaagaaga agaatcagaa   1980

aaaaaaataa aaagaaattt gagaaaaaat gccaaaattt aa                      2022


<210> SEQ ID NO 29
<211> LENGTH: 303
<212> TYPE: DNA
<213> ORGANISM: Artificial Sequence
<220> FEATURE:
<223> OTHER INFORMATION: Fragment of P. falciparum

<400> SEQUENCE: 29

gaacatggtg aaatgctaaa tcaaaaaaga aaacttaaac aacatgaact tgatagaaga     60

gcacaaaggg aaaaaatgtt agaagaacat agtagaggaa tatttgctaa aggatatttg    120

ggagaagtag aatcagaaac tataaaaaag aaaacggaac accatgaaaa tgtaaatgaa    180

gataatgtag aaaaaccaaa attgcaacaa cataaagttc aaccaccaaa agtccaacaa    240

caaaaagttc aaccaccaaa atcacaacaa caaaaagttc aaccaccaaa atcacaacaa    300

caa                                                                  303


<210> SEQ ID NO 30
<211> LENGTH: 101
<212> TYPE: PRT
<213> ORGANISM: Artificial Sequence
<220> FEATURE:
<223> OTHER INFORMATION: Fragment of P. falciparum

<400> SEQUENCE: 30

Glu His Gly Glu Met Leu Asn Gln Lys Arg Lys Leu Lys Gln His Glu
1               5                   10                  15

Leu Asp Arg Arg Ala Gln Arg Glu Lys Met Leu Glu Glu His Ser Arg
            20                  25                  30

Gly Ile Phe Ala Lys Gly Tyr Leu Gly Glu Val Glu Ser Glu Thr Ile
        35                  40                  45

Lys Lys Lys Thr Glu His His Glu Asn Val Asn Glu Asp Asn Val Glu
    50                  55                  60

Lys Pro Lys Leu Gln Gln His Lys Val Gln Pro Pro Lys Val Gln Gln
65                  70                  75                  80

Gln Lys Val Gln Pro Pro Lys Ser Gln Gln Gln Lys Val Gln Pro Pro
                85                  90                  95

Lys Ser Gln Gln Gln
            100


<210> SEQ ID NO 31
<211> LENGTH: 383
<212> TYPE: PRT
<213> ORGANISM: Artificial Sequence
<220> FEATURE:
<223> OTHER INFORMATION: Fragment of P. falciparum

<400> SEQUENCE: 31

Met Ala Val Ser Thr Tyr Asn Asn Thr Arg Arg Asn Gly Leu Arg Tyr
1               5                   10                  15

Val Leu Lys Arg Arg Thr Ile Leu Ser Val Phe Ala Val Ile Cys Met
            20                  25                  30

Leu Ser Leu Asn Leu Ser Ile Phe Glu Asn Asn Asn Asn Asn Tyr Gly
        35                  40                  45
```

```
Phe His Cys Asn Lys Arg His Phe Lys Ser Leu Ala Glu Ala Ser Pro
    50                  55                  60

Glu Glu His Asn Asn Leu Arg Ser His Ser Thr Ser Asp Pro Lys Lys
65                  70                  75                  80

Asn Glu Glu Lys Ser Leu Ser Asp Glu Ile Asn Lys Cys Asp Met Lys
                85                  90                  95

Lys Tyr Thr Ala Glu Glu Ile Asn Glu Met Ile Asn Ser Ser Asn Glu
            100                 105                 110

Phe Ile Asn Arg Asn Asp Met Asn Ile Ile Phe Ser Tyr Val His Glu
        115                 120                 125

Ser Glu Arg Glu Lys Phe Lys Lys Val Glu Glu Asn Ile Phe Lys Phe
    130                 135                 140

Ile Gln Ser Ile Val Glu Thr Tyr Lys Ile Pro Asp Glu Tyr Lys Met
145                 150                 155                 160

Arg Lys Phe Lys Phe Ala His Phe Glu Met Gln Gly Tyr Ala Leu Lys
                165                 170                 175

Gln Glu Lys Phe Leu Leu Glu Tyr Ala Phe Leu Ser Leu Asn Gly Lys
            180                 185                 190

Leu Cys Glu Arg Lys Lys Phe Lys Glu Val Leu Glu Tyr Val Lys Arg
        195                 200                 205

Glu Trp Ile Glu Phe Arg Lys Ser Met Phe Asp Val Trp Lys Glu Lys
    210                 215                 220

Leu Ala Ser Glu Phe Arg Glu His Gly Glu Met Leu Asn Gln Lys Arg
225                 230                 235                 240

Lys Leu Lys Gln His Glu Leu Asp Arg Arg Ala Gln Arg Glu Lys Met
                245                 250                 255

Leu Glu Glu His Ser Arg Gly Ile Phe Ala Lys Gly Tyr Leu Gly Glu
            260                 265                 270

Val Glu Ser Glu Thr Ile Lys Lys Lys Thr Glu His His Glu Asn Val
        275                 280                 285

Asn Glu Asp Asn Val Glu Lys Pro Lys Leu Gln Gln His Lys Val Gln
    290                 295                 300

Pro Pro Lys Val Gln Gln Gln Lys Val Gln Pro Pro Lys Ser Gln Gln
305                 310                 315                 320

Gln Lys Val Gln Pro Pro Lys Ser Gln Gln Gln Lys Val Gln Pro Pro
                325                 330                 335

Lys Val Gln Gln Gln Lys Val Gln Pro Pro Lys Val Gln Lys Pro Lys
            340                 345                 350

Leu Gln Asn Gln Lys Gly Gln Lys Gln Val Ser Pro Lys Ala Lys Gly
        355                 360                 365

Asn Asn Gln Ala Lys Pro Thr Lys Gly Asn Lys Leu Lys Lys Asn
    370                 375                 380
```

<210> SEQ ID NO 32
<211> LENGTH: 1152
<212> TYPE: DNA
<213> ORGANISM: Artificial Sequence
<220> FEATURE:
<223> OTHER INFORMATION: Fragment of P. falciparum

<400> SEQUENCE: 32

```
atggctgtta gtacatataa taatactcga aggaatggtc taagatatgt ccttaaaaga      60

cgtaccattc tatctgtttt tgctgtcatt tgtatgttat cattgaattt atcaatattt     120

gaaaataata ataataatta tggattccat tgcaataaaa gacattttaa aagtttagct     180
```

-continued

```
gaagcaagtc cagaagaaca taacaattta agaagtcatt caacaagtga tccaaagaag    240

aatgaagaga aatcattaag tgacgaaata aataaatgtg atatgaaaaa atacactgct    300

gaagaaataa atgaaatgat taacagttct aatgaattta taaatagaaa tgatatgaat    360

ataatattta gttatgtaca tgaatctgag agagaaaaat ttaaaaaggt agaagaaaat    420

atatttaaat ttattcaaag tatagtagaa acatataaaa taccagatga atataaaatg    480

agaaaattca aatttgcaca ctttgaaatg caaggatatg cattaaaaca agaaaagttc    540

cttttagaat atgcttttct ttccttaaat ggtaaattat gtgaacgtaa aaaatttaaa    600

gaagttttag aatatgtaaa aagggaatgg attgagttta gaaaatcaat gtttgacgta    660

tggaaggaaa aattagcttc tgaattcaga gaacatggtg aaatgctaaa tcaaaaaaga    720

aaacttaaac aacatgaact tgatagaaga gcacaaaggg aaaaaatgtt agaagaacat    780

agtagaggaa tatttgctaa aggatatttg ggagaagtag aatcagaaac tataaaaaag    840

aaaacggaac accatgaaaa tgtaaatgaa gataatgtag aaaaaccaaa attgcaacaa    900

cataaagttc aaccaccaaa agtccaacaa caaaaagttc aaccaccaaa atcacaacaa    960

caaaaagttc aaccaccaaa atcacaacaa caaaaagttc aaccaccaaa agtacaacaa   1020

caaaaagttc aaccaccaaa agtgcaaaaa ccaaaacttc aaaatcaaaa aggacaaaag   1080

caagtatctc ccaaagcaaa gggtaataat caagcgaaac caaccaaagg aaacaagtta   1140

aagaaaaatt aa                                                        1152
```

```
<210> SEQ ID NO 33
<211> LENGTH: 242
<212> TYPE: DNA
<213> ORGANISM: Artificial Sequence
<220> FEATURE:
<223> OTHER INFORMATION: Fragment of P. falciparum

<400> SEQUENCE: 33

gttaaagaaa agggagaaaa gcataatgga aaaaaaccat gcagcaaaaa aactaacgaa     60

gaaaataaaa ataaagaaaa aaccaataat tcaaaatcag atggatcaaa agctcatgaa    120

aaaaaagaaa atgaaacaaa aaacaccgct ggagaaaata aaaaagtaga ttctacttca    180

gctgataata aatcaacaaa tgctgctaca ccaggcgcaa aagataaaac tcaaggagga    240

aa                                                                   242
```

```
<210> SEQ ID NO 34
<211> LENGTH: 80
<212> TYPE: PRT
<213> ORGANISM: Artificial Sequence
<220> FEATURE:
<223> OTHER INFORMATION: Fragment of P. falciparum

<400> SEQUENCE: 34

Val Lys Glu Lys Gly Glu Lys His Asn Gly Lys Lys Pro Cys Ser Lys
1               5                   10                  15

Lys Thr Asn Glu Glu Asn Lys Asn Lys Glu Lys Thr Asn Asn Ser Lys
            20                  25                  30

Ser Asp Gly Ser Lys Ala His Glu Lys Lys Glu Asn Glu Thr Lys Asn
        35                  40                  45

Thr Ala Gly Glu Asn Lys Lys Val Asp Ser Thr Ser Ala Asp Asn Lys
    50                  55                  60

Ser Thr Asn Ala Ala Thr Pro Gly Ala Lys Asp Lys Thr Gln Gly Gly
65                  70                  75                  80
```

<210> SEQ ID NO 35
<211> LENGTH: 654
<212> TYPE: PRT
<213> ORGANISM: Artificial Sequence
<220> FEATURE:
<223> OTHER INFORMATION: Fragment of P. falciparum

<400> SEQUENCE: 35

```
Met Lys Ser Phe Lys Asn Lys Asn Thr Leu Arg Arg Lys Lys Ala Phe
1               5                   10                  15

Pro Val Phe Thr Lys Ile Leu Leu Val Ser Phe Leu Val Trp Val Leu
            20                  25                  30

Lys Cys Ser Asn Asn Cys Asn Asn Gly Asn Gly Ser Gly Asp Ser Phe
        35                  40                  45

Asp Phe Arg Asn Lys Arg Thr Leu Ala Gln Lys Gln His Glu His His
    50                  55                  60

His His His His His Gln His Gln His Gln His Gln Ala Pro His Gln
65                  70                  75                  80

Ala His His His His His His Gly Glu Val Asn His Gln Ala Pro Gln
                85                  90                  95

Val His Gln Gln Val His Gly Gln Asp Gln Ala His His His His His
            100                 105                 110

His His His His Gln Leu Gln Pro Gln Gln Pro Gln Gly Thr Val Ala
        115                 120                 125

Asn Pro Pro Ser Asn Glu Pro Val Val Lys Thr Gln Val Phe Arg Glu
    130                 135                 140

Ala Arg Pro Gly Gly Gly Phe Lys Ala Tyr Glu Glu Lys Tyr Glu Ser
145                 150                 155                 160

Lys His Tyr Lys Leu Lys Glu Asn Val Val Asp Gly Lys Lys Asp Cys
                165                 170                 175

Asp Glu Lys Tyr Glu Ala Ala Asn Tyr Ala Phe Ser Glu Glu Cys Pro
            180                 185                 190

Tyr Thr Val Asn Asp Tyr Ser Gln Glu Asn Gly Pro Asn Ile Phe Ala
        195                 200                 205

Leu Arg Lys Arg Phe Pro Leu Gly Met Asn Asp Glu Asp Glu Glu Gly
    210                 215                 220

Lys Glu Ala Leu Ala Ile Lys Asp Lys Leu Pro Gly Gly Leu Asp Glu
225                 230                 235                 240

Tyr Gln Asn Gln Leu Tyr Gly Ile Cys Asn Glu Thr Cys Thr Thr Cys
                245                 250                 255

Gly Pro Ala Ala Ile Asp Tyr Val Pro Ala Asp Ala Pro Asn Gly Tyr
            260                 265                 270

Ala Tyr Gly Gly Ser Ala His Asp Gly Ser His Gly Asn Leu Arg Gly
        275                 280                 285

His Asp Asn Lys Gly Ser Glu Gly Tyr Gly Tyr Glu Ala Pro Tyr Asn
    290                 295                 300

Pro Gly Phe Asn Gly Ala Pro Gly Ser Asn Gly Met Gln Asn Tyr Val
305                 310                 315                 320

Pro Pro His Gly Ala Gly Tyr Ser Ala Pro Tyr Gly Val Pro His Gly
                325                 330                 335

Ala Ala His Gly Ser Arg Tyr Ser Ser Phe Ser Ser Val Asn Lys Tyr
            340                 345                 350

Gly Lys His Gly Asp Glu Lys His His Ser Ser Lys Lys His Glu Gly
        355                 360                 365
```

```
Asn Asp Gly Glu Gly Glu Lys Lys Lys Lys Ser Lys Lys His Lys Asp
    370                 375                 380

His Asp Gly Glu Lys Lys Lys Ser Lys Lys His Lys Asp Asn Glu Asp
385                 390                 395                 400

Ala Glu Ser Val Lys Ser Lys Lys His Lys Ser His Asp Cys Glu Lys
                405                 410                 415

Lys Lys Ser Lys Lys His Lys Asp Asn Glu Asp Ala Glu Ser Val Lys
            420                 425                 430

Ser Lys Lys Ser Val Lys Glu Lys Gly Glu Lys His Asn Gly Lys Lys
        435                 440                 445

Pro Cys Ser Lys Lys Thr Asn Glu Glu Asn Lys Asn Lys Glu Lys Thr
    450                 455                 460

Asn Asn Ser Lys Ser Asp Gly Ser Lys Ala His Glu Lys Lys Glu Asn
465                 470                 475                 480

Glu Thr Lys Asn Thr Ala Gly Glu Asn Lys Lys Val Asp Ser Thr Ser
                485                 490                 495

Ala Asp Asn Lys Ser Thr Asn Ala Ala Thr Pro Gly Ala Lys Asp Lys
            500                 505                 510

Thr Gln Gly Gly Lys Thr Asp Lys Thr Gly Ala Ser Thr Asn Ala Ala
        515                 520                 525

Thr Asn Lys Gly Gln Cys Ala Ala Glu Gly Ala Thr Lys Gly Ala Thr
    530                 535                 540

Lys Glu Ala Ser Thr Ser Lys Glu Ala Thr Lys Glu Ala Ser Thr Ser
545                 550                 555                 560

Lys Glu Ala Thr Lys Glu Ala Ser Thr Ser Lys Glu Ala Thr Lys Glu
                565                 570                 575

Ala Ser Thr Ser Lys Gly Ala Thr Lys Glu Ala Ser Thr Thr Glu Gly
            580                 585                 590

Ala Thr Lys Gly Ala Ser Thr Thr Ala Gly Ser Thr Thr Gly Ala Thr
        595                 600                 605

Thr Gly Ala Asn Ala Val Gln Ser Lys Asp Glu Thr Ala Asp Lys Asn
    610                 615                 620

Ala Ala Asn Asn Gly Glu Gln Val Met Ser Arg Gly Gln Ala Gln Leu
625                 630                 635                 640

Gln Glu Ala Gly Lys Lys Lys Lys Lys Arg Gly Cys Cys Gly
                645                 650
```

<210> SEQ ID NO 36
<211> LENGTH: 1965
<212> TYPE: DNA
<213> ORGANISM: Artificial Sequence
<220> FEATURE:
<223> OTHER INFORMATION: Fragment of P. falciparum

<400> SEQUENCE: 36

```
atgaaaagtt ttaagaacaa aaatactttg aggagaaaga aggctttccc tgtttttact      60

aaaattcttt tagtctcttt tttagtatgg gttttgaagt gctctaataa ctgcaataat     120

ggaaacggat ccggtgactc cttcgatttc agaaataaga gaactttagc acaaaagcaa     180

catgaacacc atcaccacca tcaccatcaa catcaacacc aacaccaagc tccacaccaa     240

gcacaccacc atcatcatca tggagaagta aatcaccaag caccacaggt tcaccaacaa     300

gtacatggtc aagaccaagc acaccatcac catcatcacc accatcatca attacaacct     360

caacaacccc agggaacagt tgctaatcct cctagtaatg aaccagttgt aaaaacccaa     420

gtattcaggg aagcaagacc aggtggaggt ttcaaagcat atgaagaaaa atacgaatca     480
```

aaacactata aattaaagga aaatgttgtc gatggtaaaa aagattgtga tgaaaaatac 540
gaagctgcca attatgcttt ctccgaagag tgcccataca ccgtaaacga ttatagccaa 600
gaaaatggtc caaatatatt tgccttaaga aaaagattcc ctcttggaat gaatgatgaa 660
gatgaagaag gtaaagaagc attagcaata aaagataaat taccaggtgg tttagatgaa 720
taccaaaacc aattatatgg aatatgtaat gagacatgta ccacatgtgg acctgccgct 780
atagattatg ttccagcaga tgcaccaaat ggctatgctt atggaggaag tgcacacgat 840
ggttctcacg gtaatttaag aggacacgat aataaaggtt cagaaggtta tggatatgaa 900
gctccatata acccaggatt taatggtgct cctggaagta atggtatgca aaattatgtc 960
ccaccccatg gtgcaggcta ttcagctcca tacggagttc cacatggtgc agcccatggt 1020
tcaagatata gttcattcag ttccgtaaat aaatatggaa aacacggtga tgaaaaacac 1080
cattcctcta aaaagcatga aggaaatgac ggtgaaggag aaaaaaagaa aaaatcaaaa 1140
aaacacaaag accacgatgg agaaaagaaa aaatcaaaaa aacacaaaga caatgaagat 1200
gcagaaagcg taaaatcaaa aaaacacaaa agccacgatt gtgaaaagaa aaaatcaaaa 1260
aaacacaaag acaatgaaga tgcagaaagc gtaaaatcaa aaaaaagtgt taaagaaaag 1320
ggagaaaagc ataatggaaa aaaaccatgc agcaaaaaaa ctaacgaaga aaataaaaat 1380
aaagaaaaaa ccaataattc aaaatcagat ggatcaaaag ctcatgaaaa aaaagaaaat 1440
gaaacaaaaa acaccgctgg agaaaataaa aaagtagatt ctacttcagc tgataataaa 1500
tcaacaaatg ctgctacacc aggcgcaaaa gataaaactc aaggaggaaa aactgacaaa 1560
acaggagcaa gtactaatgc cgcaacaaat aaaggacaat gtgctgctga aggagcaact 1620
aagggagcaa ctaaagaagc aagtacttct aaagaagcaa caaaagaagc aagtacttct 1680
aaagaagcaa caaaagaagc aagtacttct aaagaagcaa caaaagaagc aagtacttct 1740
aaaggagcaa ctaaagaagc aagtactact gaaggagcaa ctaaaggagc aagtactact 1800
gcaggttcaa ctacaggagc aactacagga gctaatgcag tacaatctaa agatgaaact 1860
gccgataaaa atgctgcaaa taatggtgaa caagtaatgt caagaggaca agcacaatta 1920
caagaagcag gaaagaaaaa gaagaaaaga ggatgctgtg gttaa 1965

<210> SEQ ID NO 37
<211> LENGTH: 432
<212> TYPE: DNA
<213> ORGANISM: Artificial Sequence
<220> FEATURE:
<223> OTHER INFORMATION: Fragment of P. falciparum

<400> SEQUENCE: 37
gaagaatcca aaaatgaaga atttaaaaat gaagaattca aaaatgtaga taaagaaaat 60
tatgatgata aaaatatttt ctatggttat agtgataatg atgatgaaag ctttttagaa 120
actgattctt atgaagaata tgaagacgaa gataaagatg ttgaagatga gtatgaagaa 180
agtttcttac aaaatgatga gaaaaaaatg gtcttttatg atttatacaa gccagaagaa 240
aatgaatctt attatgaaaa gaaacaaaag aaagaagaaa aagaagagaa agaagagaaa 300
gaacaaagtt tgaacaaaca aaacgatatg gaagaccaag aagataatga agaatataaa 360
tttgaagaag aaaataaaga agaccttcta gatgtccaac aagatgaaga attaccaagt 420
gaaggaaaac aa 432

<210> SEQ ID NO 38

<211> LENGTH: 144
<212> TYPE: PRT
<213> ORGANISM: Artificial Sequence
<220> FEATURE:
<223> OTHER INFORMATION: Fragment of P. falciparum

<400> SEQUENCE: 38

Glu Glu Ser Lys Asn Glu Glu Phe Lys Asn Glu Glu Phe Lys Asn Val
1               5                   10                  15

Asp Lys Glu Asn Tyr Asp Asp Lys Asn Ile Phe Tyr Gly Tyr Ser Asp
            20                  25                  30

Asn Asp Asp Glu Ser Phe Leu Glu Thr Asp Ser Tyr Glu Glu Tyr Glu
        35                  40                  45

Asp Glu Asp Lys Asp Val Glu Asp Glu Tyr Glu Glu Ser Phe Leu Gln
    50                  55                  60

Asn Asp Glu Lys Lys Met Val Phe Tyr Asp Leu Tyr Lys Pro Glu Glu
65                  70                  75                  80

Asn Glu Ser Tyr Tyr Glu Lys Lys Gln Lys Lys Glu Glu Lys Glu Glu
                85                  90                  95

Lys Glu Glu Lys Glu Gln Ser Leu Asn Lys Gln Asn Asp Met Glu Asp
            100                 105                 110

Gln Glu Asp Asn Glu Glu Tyr Lys Phe Glu Glu Glu Asn Lys Glu Asp
        115                 120                 125

Leu Leu Asp Val Gln Gln Asp Glu Glu Leu Pro Ser Glu Gly Lys Gln
    130                 135                 140

<210> SEQ ID NO 39
<211> LENGTH: 704
<212> TYPE: PRT
<213> ORGANISM: Artificial Sequence
<220> FEATURE:
<223> OTHER INFORMATION: Fragment of P. falciparum

<400> SEQUENCE: 39

Ile Ser Phe Ser Asp Tyr Glu Arg Ser Ile Lys Asn Phe Ser Ile Ser
1               5                   10                  15

Ser His Ala Glu Asn Asn Tyr Asp Asn Ile Ile Asn Glu Tyr Lys Lys
            20                  25                  30

Ile Lys Asp Ile Asn Asn Asn Ile Asn Ile Leu Ser Ser Val His Arg
        35                  40                  45

Lys Gly Arg Ile Leu Tyr Asp Ser Phe Leu Glu Ile Asn Lys Leu Glu
    50                  55                  60

Asn Asp Lys Lys Glu Lys His Glu Lys Glu Asp Glu Tyr Glu Asp Asn
65                  70                  75                  80

Asp Glu Ser Phe Leu Glu Thr Glu Glu Tyr Glu Asp Asn Glu Asp Glu
                85                  90                  95

Lys Tyr Asn Lys Asp Glu Asp Asp Tyr Ala Glu Ser Phe Ile Glu Thr
            100                 105                 110

Asp Glu Tyr Glu Asp Asn Glu Asp Asp Lys Tyr Asn Lys Asp Glu Asp
        115                 120                 125

Asp Tyr Ser Glu Ser Phe Ile Glu Thr Asp Glu Tyr Asp Asp Asn Glu
    130                 135                 140

Glu Glu Gln Tyr Asn Lys Asp Glu Asp Asp Tyr Ala Asp Ser Phe Ile
145                 150                 155                 160

Glu Thr Asp His Tyr Glu Asn Asn Asp Asp Lys Asn Glu Glu Glu Glu
                165                 170                 175

```
Glu Tyr Asn Asp Gln Asp Asn Asp Tyr Gly Tyr Asn Phe Leu Glu Thr
            180                 185                 190

Asp Glu Tyr Asp Asp Ser Glu Glu Tyr Asp Tyr Asp Asp Lys Glu Tyr
        195                 200                 205

Gly Glu Ser Phe Leu Glu Lys Glu Glu Gly Glu Glu Met Lys Asp Glu
    210                 215                 220

Glu Met Lys Asp Glu Glu Met Lys Asp Val Glu Met Lys Asp Glu Glu
225                 230                 235                 240

Met Lys Asp Glu Glu Ile Lys Tyr Asp Glu Met Lys Asn Glu Glu Met
                245                 250                 255

Lys Tyr Asp Glu Met Lys Asp Glu Val Met Lys Asp Glu Glu Met Lys
            260                 265                 270

Asp Glu Val Met Lys Asp Glu Glu Met Lys Asp Glu Gln Met Lys Tyr
        275                 280                 285

Glu Glu Phe Lys Asn Glu Glu Ser Lys Asn Glu Glu Ser Lys Asn Glu
    290                 295                 300

Glu Ser Lys Asn Glu Glu Ser Lys Asn Glu Glu Phe Lys Asn Glu Glu
305                 310                 315                 320

Ser Lys Asn Glu Glu Phe Lys Asn Glu Glu Phe Lys Asn Val Asp Lys
                325                 330                 335

Glu Asn Tyr Asp Asp Lys Asn Ile Phe Tyr Gly Tyr Ser Asp Asn Asp
            340                 345                 350

Asp Glu Ser Phe Leu Glu Thr Asp Ser Tyr Glu Glu Tyr Glu Asp Glu
        355                 360                 365

Asp Lys Asp Val Glu Asp Glu Tyr Glu Glu Ser Phe Leu Gln Asn Asp
    370                 375                 380

Glu Lys Lys Met Val Phe Tyr Asp Leu Tyr Lys Pro Glu Glu Asn Glu
385                 390                 395                 400

Ser Tyr Tyr Glu Lys Lys Gln Lys Lys Glu Glu Lys Glu Glu Lys Glu
                405                 410                 415

Glu Lys Glu Gln Ser Leu Asn Lys Gln Asn Asp Met Glu Asp Gln Glu
            420                 425                 430

Asp Asn Glu Glu Tyr Lys Phe Glu Glu Glu Asn Lys Glu Asp Leu Leu
        435                 440                 445

Asp Val Gln Gln Asp Glu Glu Leu Pro Ser Glu Gly Lys Gln Lys Val
    450                 455                 460

Lys Gly Lys Ser Phe Asp Asn Glu His Leu Asn Glu Ile Gln Asn Val
465                 470                 475                 480

Ser Asp Val His Ala Phe Ile Gln Lys Asp Met Lys Tyr Leu Asp Asp
                485                 490                 495

Leu Ile Asp Glu Glu Gln Thr Ile Lys Asp Ala Val Lys Lys Ser Ala
            500                 505                 510

Tyr Lys Gly Asn Lys Lys Leu Gly Asn Asn Lys Lys Ser Gln Met Ile
        515                 520                 525

Leu Glu Glu Glu Pro Glu Glu Asn Phe Glu Glu Asp Ala Asp Glu Glu
    530                 535                 540

Leu Asn Lys Leu Met Glu Gln Glu Lys Asn Ile Val Asp Lys Glu Ile
545                 550                 555                 560

Lys Asn Ser Lys Ala Asn Lys Ser Asn Lys Lys Leu Gln Phe Asn Asn
                565                 570                 575

Thr Asn Lys Gln Asn Lys Met Tyr Met Lys Asn Glu Tyr Asn Asn Lys
            580                 585                 590
```

```
Thr Lys Asn Asn Lys Asn Asn Lys Phe Glu Gln Gln Asn Tyr Asp Glu
        595                 600                 605

Ser Tyr Met Asp Asp Asp Tyr Glu Gln Asn Glu Glu Phe Asn Asp Asn
    610                 615                 620

Asn Gln Ser Glu Asp Met Lys Glu Thr Asn Glu Leu Asp Lys Ile Asn
625                 630                 635                 640

Asp Glu Leu Leu Thr Asp Gln Gly Pro Asn Glu Asp Thr Leu Leu Glu
                645                 650                 655

Asn Asn Asn Lys Ile Phe Asp Asn Lys Phe Val Ala His Lys Lys Arg
            660                 665                 670

Glu Lys Ser Ile Ser Pro His Ser Tyr Gln Lys Val Ser Thr Lys Val
        675                 680                 685

Gln Asn Lys Glu Asp Met Glu Asn Lys Glu Glu Lys Gln Leu Ile Ser
    690                 695                 700


<210> SEQ ID NO 40
<211> LENGTH: 2114
<212> TYPE: DNA
<213> ORGANISM: Artificial Sequence
<220> FEATURE:
<223> OTHER INFORMATION: Fragment of P. falciparum

<400> SEQUENCE: 40

attagctttt ctgattatga gagatcaata aaaaactttt ctatttcttc tcatgcagaa     60

aataattatg ataatataat aaatgaatat aaaaaaataa aagatattaa caacaatata    120

aacatattat catcagtaca tagaaaagga agaatattgt acgacagctt tttagaaata    180

aataagttgg aaaatgacaa aaaagagaaa catgaaaaag aagatgaata tgaagataat    240

gatgaaagct ttttagaaac tgaagaatat gaagataatg aagatgaaaa atataacaaa    300

gatgaagatg attatgcaga aagttttatt gagactgatg aatatgaaga taatgaagat    360

gataaatata ataaagatga agatgattat tcagaaagct ttattgagac tgatgaatat    420

gatgataatg aagaagaaca atataataaa gatgaagatg attatgcaga tagttttatt    480

gagacagacc attatgaaaa taacgatgat aaaaatgaag aagaagaaga atataatgat    540

caagataatg attatggata taacttttta gaaactgacg aatacgatga tagcgaagaa    600

tatgattacg acgataagga atacggagag agtttcctcg aaaaagaaga aggtgaagaa    660

atgaaagatg aagagatgaa agatgaagaa atgaaagatg tagaaatgaa agatgaagag    720

atgaaagatg aagagataaa atatgacgag atgaaaaatg aagagatgaa atatgacgag    780

atgaaagatg aagtgatgaa agatgaagag atgaaagatg aagtgatgaa agatgaagag    840

atgaaagacg aacaaatgaa atatgaagaa ttcaaaaatg aagaatccaa aaatgaagaa    900

tccaaaaatg aagaatccaa aaatgaagaa tccaaaaatg aagaattcaa aaatgaagaa    960

tccaaaaatg aagaatttaa aaatgaagaa ttcaaaaatg tagataaaga aaattatgat   1020

gataaaaata ttttctatgg ttatagtgat aatgatgatg aaagcttttt agaaactgat   1080

tcttatgaag aatatgaaga cgaagataaa gatgttgaag atgagtatga agaaagtttc   1140

ttacaaaatg atgagaaaaa aatggtcttt tatgatttat acaagccaga agaaaatgaa   1200

tcttattatg aaaagaaaca aaagaaagaa gaaaaagaag agaaagaaga gaaagaacaa   1260

agtttgaaca aacaaaacga tatggaagac caagaagata atgaagaata taaatttgaa   1320

gaagaaaata aagaagacct tctagatgtc caacaagatg aagaattacc aagtgaagga   1380

aaacaaaaag taaaaggaaa atcattcgat aatgaacatt tgaatgaaat acaaaatgtt   1440
```

-continued

```
agcgacgtac atgcatttat acaaaaagat atgaaatatt tagatgatct catagatgaa   1500

gagcaaacta ttaaagatgc cgtcaaaaaa agtgcttata aaggaaataa gaaattagga   1560

aataataaaa aatcacaaat gatactggaa gaagaaccag aagaaaattt tgaagaagat   1620

gctgatgaag aattaaataa actaatggaa caagaaaaaa atattgtaga taaagaaatc   1680

aaaaatagta aagcaaataa aagcaacaaa aaattacaat tcaataacac taataaacaa   1740

aacaaaatgt atatgaaaaa cgaatataat aataagacaa aaaataataa aaacaataaa   1800

tttgaacaac aaaattatga tgaatcatat atggatgatg attatgaaca aaatgaagaa   1860

tttaatgata ataatcaaag cgaagatatg aaagaaacaa atgaactcga taaaattaat   1920

gatgaactat taactgatca aggaccaaac gaagatacat tattagaaaa taataataaa   1980

attttcgata ataaatttgt agcacataaa aaaagagaaa aaagtatatc cccacacagt   2040

taccaaaagg tatctaccaa agtacaaaat aaggaagaca tggaaaataa ggaagagaaa   2100

caattgataa gtaa                                                     2114
```

```
<210> SEQ ID NO 41
<211> LENGTH: 650
<212> TYPE: DNA
<213> ORGANISM: Artificial Sequence
<220> FEATURE:
<223> OTHER INFORMATION: Fragment of P. falciparum

<400> SEQUENCE: 41

tcaccaaata aaacagaatt aaaaaaagga gaagaaggaa aagtacaaac atgttataca     60

acaataccta ttgaaacatt attagctcaa ggatcttata gttctaaaga tatattcaat    120

tttagtgaac aggaaattaa tatgcaacat agtgatatat tagaaggaga acgattaaaa    180

catcttaatg aactagaaac tattatatat gaaagtagaa gtagacttaa tggtatatat    240

aaaaattttg ttatggatga tgaaagagat cgtattttac tttccttaga tgattatgaa    300

aattggttat atgataatat agaagaaaat aaaaatatgt ttattaaaaa aaaagaagaa    360

attagagatc ttataaaaaa tattgtacaa aaatttgatg tatataattc aaaacaacaa    420

aatctaggaa atataattaa tcatcttaat aatatcataa cacaatgttc aaataaacca    480

tcggatgaaa gtcaaaatat aattaataga acaacgaaat tcttaaataa tattaattct    540

ttacaagaac aagaaaaaaa taaaccacta tacgaaccac ctgtatatac acttaacgat    600

attgaagcag aatttaatga agtcacacaa ctcgctcaaa aattcttttc               650
```

```
<210> SEQ ID NO 42
<211> LENGTH: 216
<212> TYPE: PRT
<213> ORGANISM: Artificial Sequence
<220> FEATURE:
<223> OTHER INFORMATION: Fragment of P. falciparum

<400> SEQUENCE: 42

Ser Pro Asn Lys Thr Glu Leu Lys Lys Gly Glu Glu Gly Lys Val Gln
1               5                   10                  15

Thr Cys Tyr Thr Thr Ile Pro Ile Glu Thr Leu Leu Ala Gln Gly Ser
            20                  25                  30

Tyr Ser Ser Lys Asp Ile Phe Asn Phe Ser Glu Gln Glu Ile Asn Met
        35                  40                  45

Gln His Ser Asp Ile Leu Glu Gly Glu Arg Leu Lys His Leu Asn Glu
    50                  55                  60
```

```
Leu Glu Thr Ile Ile Tyr Glu Ser Arg Ser Arg Leu Asn Gly Ile Tyr
65                  70                  75                  80

Lys Asn Phe Val Met Asp Asp Glu Arg Asp Arg Ile Leu Leu Ser Leu
                85                  90                  95

Asp Asp Tyr Glu Asn Trp Leu Tyr Asp Asn Ile Glu Glu Asn Lys Asn
            100                 105                 110

Met Phe Ile Lys Lys Lys Glu Glu Ile Arg Asp Leu Ile Lys Asn Ile
        115                 120                 125

Val Gln Lys Phe Asp Val Tyr Asn Ser Lys Gln Gln Asn Leu Gly Asn
    130                 135                 140

Ile Ile Asn His Leu Asn Asn Ile Ile Thr Gln Cys Ser Asn Lys Pro
145                 150                 155                 160

Ser Asp Glu Ser Gln Asn Ile Ile Asn Arg Thr Thr Lys Phe Leu Asn
                165                 170                 175

Asn Ile Asn Ser Leu Gln Glu Gln Glu Lys Asn Lys Pro Leu Tyr Glu
            180                 185                 190

Pro Pro Val Tyr Thr Leu Asn Asp Ile Glu Ala Glu Phe Asn Glu Val
        195                 200                 205

Thr Gln Leu Ala Gln Lys Phe Phe
    210                 215


<210> SEQ ID NO 43
<211> LENGTH: 873
<212> TYPE: PRT
<213> ORGANISM: Artificial Sequence
<220> FEATURE:
<223> OTHER INFORMATION: Fragment of P. falciparum

<400> SEQUENCE: 43

Met Ser Val Leu Gly Ile Asp Ile Gly Asn Asp Asn Ser Val Val Ala
1               5                   10                  15

Thr Ile Asn Lys Gly Ala Ile Asn Val Val Arg Asn Asp Ile Ser Glu
            20                  25                  30

Arg Leu Thr Pro Thr Leu Val Gly Phe Thr Glu Lys Glu Arg Leu Ile
        35                  40                  45

Gly Asp Ser Ala Leu Ser Lys Leu Lys Ser Asn Tyr Lys Asn Thr Cys
    50                  55                  60

Arg Asn Ile Lys Asn Leu Ile Gly Lys Ile Gly Thr Asp Val Lys Asp
65                  70                  75                  80

Asp Ile Glu Ile His Glu Ala Tyr Gly Asp Leu Ile Pro Cys Glu Tyr
                85                  90                  95

Asn Tyr Leu Gly Tyr Glu Val Glu Tyr Lys Asn Glu Lys Val Val Phe
            100                 105                 110

Ser Ala Val Arg Val Leu Ser Ala Leu Leu Ser His Leu Ile Lys Met
        115                 120                 125

Ala Glu Lys Tyr Ile Gly Lys Glu Cys Lys Glu Ile Val Leu Ser Tyr
    130                 135                 140

Pro Pro Thr Phe Thr Asn Cys Gln Lys Glu Cys Leu Leu Ala Ala Thr
145                 150                 155                 160

Lys Ile Ile Asn Ala Asn Val Leu Arg Ile Ile Ser Asp Asn Thr Ala
                165                 170                 175

Val Ala Leu Asp Tyr Gly Met Tyr Arg Met Lys Glu Phe Lys Glu Asp
            180                 185                 190

Asn Gly Ser Leu Leu Val Phe Val Asn Ile Gly Tyr Ala Asn Thr Cys
        195                 200                 205
```

-continued

```
Val Cys Val Ala Arg Phe Phe Ser Asn Lys Cys Glu Ile Leu Cys Asp
    210                 215                 220

Ile Ala Asp Ser Asn Leu Gly Gly Arg Asn Leu Asp Asn Glu Leu Ile
225                 230                 235                 240

Lys Tyr Ile Thr Asn Ile Phe Val Asn Asn Tyr Lys Met Asn Pro Leu
                245                 250                 255

Tyr Lys Asn Asn Thr Pro Glu Leu Cys Pro Met Gly Thr Gly Arg Leu
            260                 265                 270

Asn Lys Phe Leu Val Thr Ser Thr Ala Ser Asp Gln Gln Asn Gly Ile
        275                 280                 285

Asn Asn Lys Val Arg Ile Lys Leu Gln Glu Val Ala Ile Lys Thr Lys
    290                 295                 300

Lys Val Leu Ser Ala Asn Asn Glu Ala Ser Ile His Val Glu Cys Leu
305                 310                 315                 320

Tyr Glu Asp Leu Asp Cys Gln Gly Ser Ile Asn Arg Glu Thr Phe Glu
                325                 330                 335

Glu Leu Cys Ser Asn Phe Phe Leu Thr Lys Leu Lys His Leu Leu Asp
            340                 345                 350

Thr Ala Leu Cys Ile Ser Lys Val Asn Ile Gln Asp Ile His Ser Ile
        355                 360                 365

Glu Val Leu Gly Gly Ser Thr Arg Val Pro Phe Ile Gln Asn Phe Leu
    370                 375                 380

Gln Gln Tyr Phe Gln Lys Pro Leu Ser Lys Thr Leu Ile Ala Asp Glu
385                 390                 395                 400

Ser Ile Ala Arg Gly Cys Val Leu Ser Ala Ala Met Val Ser Lys His
                405                 410                 415

Tyr Lys Val Lys Glu Tyr Glu Cys Val Glu Lys Val Thr His Pro Ile
            420                 425                 430

Asn Val Glu Trp His Asn Ile Asn Asp Ala Ser Lys Ser Asn Val Glu
        435                 440                 445

Lys Leu Tyr Thr Arg Asp Ser Leu Lys Lys Lys Val Lys Lys Ile Val
    450                 455                 460

Ile Pro Glu Lys Gly His Ile Lys Leu Thr Ala Tyr Tyr Glu Asn Thr
465                 470                 475                 480

Pro Asp Leu Pro Ser Asn Cys Ile Lys Glu Leu Gly Ser Cys Ile Val
                485                 490                 495

Lys Ile Asn Glu Lys Asn Asp Lys Ile Val Glu Ser His Val Met Thr
            500                 505                 510

Thr Phe Ser Asn Tyr Asp Thr Phe Thr Phe Leu Gly Ala Gln Thr Val
        515                 520                 525

Thr Lys Ser Val Ile Lys Ser Lys Asp Glu Lys Lys Lys Ala Asp Asp
    530                 535                 540

Lys Thr Glu Asp Lys Gly Glu Lys Lys Asp Ala Lys Asp Gln Glu Gln
545                 550                 555                 560

Asn Asp Asp Lys Asp Gln Thr Asn Asp Asn Asn Met Asn Glu Lys Asp
                565                 570                 575

Thr Asn Asp Lys Lys Glu Lys Asn Asn Glu Thr Asn Ser Pro Asn Lys
            580                 585                 590

Thr Glu Leu Lys Lys Gly Glu Glu Gly Lys Val Gln Thr Cys Tyr Thr
        595                 600                 605

Thr Ile Pro Ile Glu Thr Leu Leu Ala Gln Gly Ser Tyr Ser Ser Lys
    610                 615                 620
```

```
Asp Ile Phe Asn Phe Ser Glu Gln Glu Ile Asn Met Gln His Ser Asp
625                 630                 635                 640

Ile Leu Glu Gly Glu Arg Leu Lys His Leu Asn Glu Leu Glu Thr Ile
                645                 650                 655

Ile Tyr Glu Ser Arg Ser Arg Leu Asn Gly Ile Tyr Lys Asn Phe Val
            660                 665                 670

Met Asp Asp Glu Arg Asp Arg Ile Leu Leu Ser Leu Asp Asp Tyr Glu
        675                 680                 685

Asn Trp Leu Tyr Asp Asn Ile Glu Glu Asn Lys Asn Met Phe Ile Lys
    690                 695                 700

Lys Lys Glu Glu Ile Arg Asp Leu Ile Lys Asn Ile Val Gln Lys Phe
705                 710                 715                 720

Asp Val Tyr Asn Ser Lys Gln Gln Asn Leu Gly Asn Ile Ile Asn His
                725                 730                 735

Leu Asn Asn Ile Ile Thr Gln Cys Ser Asn Lys Pro Ser Asp Glu Ser
            740                 745                 750

Gln Asn Ile Ile Asn Arg Thr Thr Lys Phe Leu Asn Asn Ile Asn Ser
        755                 760                 765

Leu Gln Glu Gln Glu Lys Asn Lys Pro Leu Tyr Glu Pro Pro Val Tyr
    770                 775                 780

Thr Leu Asn Asp Ile Glu Ala Glu Phe Asn Glu Val Thr Gln Leu Ala
785                 790                 795                 800

Gln Lys Phe Phe Ser Lys Leu Glu Val Glu Glu Leu Ala Lys Gln Lys
                805                 810                 815

Ala Lys Gln Glu Lys Glu Lys Glu Lys Glu Lys Glu Lys Glu Lys Glu
            820                 825                 830

Lys Glu Lys Glu Lys Asn Glu Glu Thr Asn Leu Asp Ala Asn Glu Glu
        835                 840                 845

Gln Asn Asn Glu Ala Lys Asn Asn Glu Glu Lys Glu Asn Ser Thr Lys
    850                 855                 860

Asn Glu Asn Ser Ala Asn Pro Glu Glu
865                 870


<210> SEQ ID NO 44
<211> LENGTH: 2622
<212> TYPE: DNA
<213> ORGANISM: Artificial Sequence
<220> FEATURE:
<223> OTHER INFORMATION: Fragment of P. falciparum

<400> SEQUENCE: 44

atgtcggttt taggtataga tataggaaat gacaattctg ttgtagctac tattaataaa      60

ggtgctataa atgttgtgag gaatgacata tccgaaaggt taacccccgac attagttggt    120

ttcaccgaaa aagaaagatt aataggtgat agtgctttat ctaaattgaa atctaattat    180

aagaatacat gtaggaatat aaagaatttg ataggtaaaa taggtaccga tgtaaaagat    240

gatatagaaa tacatgaagc atatggggat ttaataccat gtgaatataa ttatttaggt    300

tatgaagttg aatataaaaa tgaaaaagtt gtatttagtg ctgttcgtgt tttatcagcc    360

ttattatcac atttgattaa aatggctgaa aaatatattg gaaaggaatg taaagaaatt    420

gtcttatcat atcctccaac atttacaaat tgtcaaaaag aatgtttatt agctgcaact    480

aaaattatta atgctaatgt tttgagaatt attagtgata atacagctgt tgctctagat    540

tatggaatgt acagaatgaa agaattcaaa gaagataatg gatccttact agtttttgtt    600

aacattggtt atgcaaatac ttgtgtatgt gttgcgcgtt ttttttctaa taaatgtgaa    660
```

```
atcttatgtg atattgctga ttcaaattta ggtggtagaa atttagataa tgaacttatt    720
aaatatatta caaatatatt tgttaataat tataaaatga atccattata taaaaacaat    780
actccggaat tatgccccat gggtactggt agattaaata agtttttagt aacatctaca    840
gcatctgatc aacaaaatgg tattaataat aaagtacgta ttaaattaca agaagttgct    900
ataaaaacaa agaaagtact ttcagcaaat aatgaagcgt ccatacatgt tgaatgttta    960
tatgaagatt tagattgtca aggttccatt aatagagaaa cctttgaaga attgtgttca   1020
aacttcttct taacaaaatt aaaacatctt ctagatactg ctctatgtat tagtaaagta   1080
aacatacaag atatacattc tattgaagtt ttgggtggat ccacaagagt tccatttatt   1140
caaaattttt tacaacaata ttttcagaaa ccattatcta agacccttat agcagatgaa   1200
tctatagcaa gaggttgtgt actatcagct gctatggtta gtaaacatta taaagtaaaa   1260
gaatatgaat gtgtagaaaa agttacacat ccaattaatg ttgaatggca taatattaat   1320
gacgcatcta aaagtaatgt agaaaaatta tatacaagag attccttaaa aaagaaagtt   1380
aagaaaattg ttatcccaga aaaaggacac attaaactta cagcttatta tgaaaataca   1440
ccagatttac catccaattg tataaaagaa ttgggatcat gtattgttaa aataaatgaa   1500
aagaatgata aaattgttga atcccacgtt atgaccacct tttcaaatta tgatacattt   1560
acatttttag gtgcacagac agtaaccaag tctgttatta agtccaagga tgaaaaaaaa   1620
aaagcagatg acaaaacgga ggataaggga gaaaaaaaag atgcaaaaga tcaagaacaa   1680
aatgatgata aagatcaaac aaatgataat aacatgaatg agaaagatac taatgataaa   1740
aaagaaaaaa ataatgaaac aaactcacca aataaaacag aattaaaaaa aggagaagaa   1800
ggaaaagtac aaacatgtta tacaacaata cctattgaaa cattattagc tcaaggatct   1860
tatagttcta aagatatatt caattttagt gaacaggaaa ttaatatgca acatagtgat   1920
atattagaag gagaacgatt aaaacatctt aatgaactag aaactattat atatgaaagt   1980
agaagtagac ttaatggtat atataaaaat tttgttatgg atgatgaaag agatcgtatt   2040
ttactttcct tagatgatta tgaaaattgg ttatatgata atatagaaga aaataaaaat   2100
atgtttatta aaaaaaaaga agaaattaga gatcttataa aaaatattgt acaaaaattt   2160
gatgtatata attcaaaaca acaaaatcta ggaaatataa ttaatcatct taataatatc   2220
ataacacaat gttcaaataa accatcggat gaaagtcaaa atataattaa tagaacaacg   2280
aaattcttaa ataatattaa ttctttacaa gaacaagaaa aaaataaacc actatacgaa   2340
ccacctgtat atacacttaa cgatattgaa gcagaattta atgaagtcac acaactcgct   2400
caaaaattct tttcaaagct tgaagtagaa gaactagcca aacaaaaagc aaagcaagaa   2460
aaggaaaagg aaaaggaaaa agaaaaagag aaagaaaaag aaaaggaaaa aaatgaagag   2520
acaaacttgg atgcaaatga ggaacaaaat aatgaagcaa aaaataatga agaaaaggag   2580
aactcaacaa aaaatgaaaa ttcagctaat ccagaggaat aa                      2622
```

<210> SEQ ID NO 45
<211> LENGTH: 255
<212> TYPE: DNA
<213> ORGANISM: Artificial Sequence
<220> FEATURE:
<223> OTHER INFORMATION: Fragment of P. falciparum

<400> SEQUENCE: 45
ttcttagcag cttgtttaga tcatagtata tttcaacaag atgttatctg tagaaatgct 60
ttcaatgttt ttgatttaga tggtgatggt gttataacaa aggatgaatt atttaaaatt 120
ctatccttta gtgctgtaca agtatccttt agtaaagaaa ttattgaaaa tcttattaaa 180
gaagtcgatt ctaataatga tggatttata gattatgatg aattttataa gatgatgacg 240
ggagttaaag aatga 255

<210> SEQ ID NO 46
<211> LENGTH: 84
<212> TYPE: PRT
<213> ORGANISM: Artificial Sequence
<220> FEATURE:
<223> OTHER INFORMATION: Fragment of P. falciparum

<400> SEQUENCE: 46

Phe Leu Ala Ala Cys Leu Asp His Ser Ile Phe Gln Gln Asp Val Ile
1 5 10 15

Cys Arg Asn Ala Phe Asn Val Phe Asp Leu Asp Gly Asp Gly Val Ile
20 25 30

Thr Lys Asp Glu Leu Phe Lys Ile Leu Ser Phe Ser Ala Val Gln Val
35 40 45

Ser Phe Ser Lys Glu Ile Ile Glu Asn Leu Ile Lys Glu Val Asp Ser
50 55 60

Asn Asn Asp Gly Phe Ile Asp Tyr Asp Glu Phe Tyr Lys Met Met Thr
65 70 75 80

Gly Val Lys Glu

<210> SEQ ID NO 47
<211> LENGTH: 568
<212> TYPE: PRT
<213> ORGANISM: Artificial Sequence
<220> FEATURE:
<223> OTHER INFORMATION: Pf-CDPK5

<400> SEQUENCE: 47

Met Lys Glu Thr Glu Val Glu Asp Met Asp Thr Asn Arg Lys Asp Gly
1 5 10 15

Lys Ile Lys Lys Lys Glu Lys Ile Val Asn Met Lys Asn Glu Glu Val
20 25 30

Lys Ser Thr Thr Lys Ser Thr Leu Ala Asp Ser Asp Glu Asp Tyr Ser
35 40 45

Ile Ile Thr Leu Cys Thr Lys Cys Leu Ser Lys Lys Leu Glu Asp Asn
50 55 60

Lys Asn Arg Ile Ile Leu Asp Ser Lys Ala Phe Lys Asp Asn Arg Leu
65 70 75 80

Lys Gly Arg Cys Ser Val Ser Ser Asn Glu Asp Pro Leu Asp Asn Lys
85 90 95

Leu Asn Leu Ser Pro Tyr Phe Asp Arg Ser Gln Ile Ile Gln Glu Ile
100 105 110

Ile Leu Met Asn Asn Asp Glu Leu Ser Asp Val Tyr Glu Ile Asp Arg
115 120 125

Tyr Lys Leu Gly Lys Gly Ser Tyr Gly Asn Val Val Lys Ala Val Ser
130 135 140

Lys Arg Thr Gly Gln Gln Arg Ala Ile Lys Ile Ile Glu Lys Lys Lys
145 150 155 160

-continued

```
Ile His Asn Ile Glu Arg Leu Lys Arg Glu Ile Leu Ile Met Lys Gln
                165                 170                 175

Met Asp His Pro Asn Ile Ile Lys Leu Tyr Glu Val Tyr Glu Asp Asn
            180                 185                 190

Glu Lys Leu Tyr Leu Val Leu Glu Leu Cys Asp Gly Gly Glu Leu Phe
        195                 200                 205

Asp Lys Ile Val Lys Tyr Gly Ser Phe Ser Glu Tyr Glu Ala Tyr Lys
    210                 215                 220

Ile Met Lys Gln Ile Phe Ser Ala Leu Tyr Tyr Cys His Ser Lys Asn
225                 230                 235                 240

Ile Met His Arg Asp Leu Lys Pro Glu Asn Ile Leu Tyr Val Asp Asn
                245                 250                 255

Thr Glu Asp Ser Pro Ile Gln Ile Ile Asp Trp Gly Phe Ala Ser Lys
            260                 265                 270

Cys Met Asn Asn His Asn Leu Lys Ser Val Val Gly Thr Pro Tyr Tyr
        275                 280                 285

Ile Ala Pro Glu Ile Leu Arg Gly Lys Tyr Asp Lys Arg Cys Asp Ile
    290                 295                 300

Trp Ser Ser Gly Val Ile Met Tyr Ile Leu Leu Cys Gly Tyr Pro Pro
305                 310                 315                 320

Phe Asn Gly Lys Asn Asn Asp Glu Ile Leu Lys Lys Val Glu Lys Gly
                325                 330                 335

Glu Phe Val Phe Asp Ser Asn Tyr Trp Ala Arg Val Ser Asp Asp Ala
            340                 345                 350

Lys Asp Leu Ile Cys Gln Cys Leu Asn Tyr Asn Tyr Lys Glu Arg Ile
        355                 360                 365

Asp Val Glu Gln Val Leu Lys His Arg Trp Phe Lys Lys Phe Lys Ser
    370                 375                 380

Asn Asn Leu Ile Ile Asn Lys Thr Leu Asn Lys Thr Leu Ile Glu Lys
385                 390                 395                 400

Phe Lys Glu Phe His Lys Leu Cys Lys Ile Lys Lys Leu Ala Val Thr
                405                 410                 415

Cys Ile Ala Tyr Gln Leu Asn Glu Lys Asp Ile Gly Lys Leu Lys Lys
            420                 425                 430

Thr Phe Glu Ala Phe Asp His Asn Gly Asp Gly Val Leu Thr Ile Ser
        435                 440                 445

Glu Ile Phe Gln Cys Leu Lys Val Asn Asp Asn Glu Phe Asp Arg Glu
    450                 455                 460

Leu Tyr Phe Leu Leu Lys Gln Leu Asp Thr Asp Gly Asn Gly Leu Ile
465                 470                 475                 480

Asp Tyr Thr Glu Phe Leu Ala Ala Cys Leu Asp His Ser Ile Phe Gln
                485                 490                 495

Gln Asp Val Ile Cys Arg Asn Ala Phe Asn Val Phe Asp Leu Asp Gly
            500                 505                 510

Asp Gly Val Ile Thr Lys Asp Glu Leu Phe Lys Ile Leu Ser Phe Ser
        515                 520                 525

Ala Val Gln Val Ser Phe Ser Lys Glu Ile Ile Glu Asn Leu Ile Lys
    530                 535                 540

Glu Val Asp Ser Asn Asn Asp Gly Phe Ile Asp Tyr Asp Glu Phe Tyr
545                 550                 555                 560

Lys Met Met Thr Gly Val Lys Glu
                565
```

-continued

<210> SEQ ID NO 48
<211> LENGTH: 1707
<212> TYPE: DNA
<213> ORGANISM: Artificial Sequence
<220> FEATURE:
<223> OTHER INFORMATION: Pf-CDPK5

<400> SEQUENCE: 48
atgaaagaga cggaggtcga agatatggat acgaatagaa aagatggtaa aattaaaaag 60
aaagaaaaaa tagtaaatat gaaaaatgaa gaagtgaaaa gtacgacaaa gagtacgtta 120
gccgatagtg atgaagacta ttcgattata actttatgta cgaaatgttt atctaaaaaa 180
cttgaagata ataagaatcg aataattctt gatagtaaag cttttaaaga taatagatta 240
aaaggtagat gtagtgttag ttccaatgaa gatcctttag ataacaaatt aaatttatca 300
ccatattttg atagatccca aataattcaa gaaataattt tgatgaataa tgatgaatta 360
agtgatgtat atgaaataga tagatacaag ttaggcaaag gatcttatgg aaatgttgtt 420
aaagccgtaa gtaaaagaac tggtcaacag agagctataa aaattataga gaaaaagaaa 480
attcataata ttgaaagatt aaaaagagaa atattaataa tgaaacagat ggatcatcct 540
aatattataa aattatatga agtttatgaa gacaatgaaa aattatattt agtattagaa 600
ttatgtgacg gtggagaatt atttgataaa attgtaaaat atggtagctt ctctgaatat 660
gaagcatata aaattatgaa acaaatattt tcagctttat attattgtca tagtaaaaat 720
attatgcata gagatttaaa accagaaaat attttatatg tagataatac agaagattct 780
cctatacaaa taattgattg gggattcgct agtaaatgta tgaataatca taatttgaaa 840
tcagttgttg ggacacctta ttatatagca cccgaaatat taagaggtaa atatgacaaa 900
agatgtgata tatggagtag tggtgtaatt atgtatattt tattatgtgg atatccacca 960
tttaatggaa aaaataatga tgaaatctta aaaaaagtgg aaaaaggaga atttgttttc 1020
gattccaatt attgggcaag agttagtgat gatgctaaag atttaatttg tcaatgttta 1080
aattataatt ataaagaaag aatagatgtt gagcaagttc taaaacatag atggttcaaa 1140
aaatttaaat caaataatct tattataaat aaaacattaa ataaaacttt aatcgaaaaa 1200
tttaaagaat tccataaatt atgtaaaatt aaaaagctag ctgtaacatg tatagcatac 1260
caattaaatg aaaaagatat agggaaatta aaaaaaacat ttgaagcttt tgatcataat 1320
ggagatggag tattaaccat atcagaaatt tttcaatgtt taaaagttaa tgacaatgaa 1380
tttgatagag aattatactt tttattaaaa caacttgata cagatggaaa tggattaatt 1440
gattatactg aattcttagc agcttgttta gatcatagta tatttcaaca agatgttatc 1500
tgtagaaatg ctttcaatgt ttttgattta gatggtgatg gtgttataac aaaggatgaa 1560
ttatttaaaa ttctatcctt tagtgctgta caagtatcct ttagtaaaga aattattgaa 1620
aatcttatta aagaagtcga ttctaataat gatggattta tagattatga tgaattttat 1680
aagatgatga cgggagttaa agaatga 1707

<210> SEQ ID NO 49
<211> LENGTH: 34
<212> TYPE: DNA
<213> ORGANISM: Artificial Sequence
<220> FEATURE:
<223> OTHER INFORMATION: Primer

<400> SEQUENCE: 49
gaagatgttt gtcataataa taacgtggaa gacc 34

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
tcctacaaca tctatttctc ctgtgtaagg 30

<210> SEQ ID NO 51
<211> LENGTH: 26
<212> TYPE: DNA
<213> ORGANISM: Artificial Sequence
<220> FEATURE:
<223> OTHER INFORMATION: Primer

<400> SEQUENCE: 51
gaataaaaaa atggatgaga tgaaag 26

<210> SEQ ID NO 52
<211> LENGTH: 36
<212> TYPE: DNA
<213> ORGANISM: Artificial Sequence
<220> FEATURE:
<223> OTHER INFORMATION: Primer

<400> SEQUENCE: 52
ctattactat cctcatttgc atctgtatat ttatcc 36

<210> SEQ ID NO 53
<211> LENGTH: 29
<212> TYPE: DNA
<213> ORGANISM: Artificial Sequence
<220> FEATURE:
<223> OTHER INFORMATION: Primer

<400> SEQUENCE: 53
gcactgcaga gcactgaata aatgaaatg 29

<210> SEQ ID NO 54
<211> LENGTH: 31
<212> TYPE: DNA
<213> ORGANISM: Artificial Sequence
<220> FEATURE:
<223> OTHER INFORMATION: Primer

<400> SEQUENCE: 54
gcagcggccg cgtggatgca ccatcatcga g 31

<210> SEQ ID NO 55
<211> LENGTH: 29
<212> TYPE: DNA
<213> ORGANISM: Artificial Sequence
<220> FEATURE:
<223> OTHER INFORMATION: Primer

<400> SEQUENCE: 55
gcactgcagg agttatctcg atgatggtg 29

<210> SEQ ID NO 56
<211> LENGTH: 34
<212> TYPE: DNA
<213> ORGANISM: Artificial Sequence
<220> FEATURE:

<223> OTHER INFORMATION: Primer

<400> SEQUENCE: 56
gcagcggccg cgatccatga tattaacatg gctc 34

<210> SEQ ID NO 57
<211> LENGTH: 26
<212> TYPE: DNA
<213> ORGANISM: Artificial Sequence
<220> FEATURE:
<223> OTHER INFORMATION: Primer

<400> SEQUENCE: 57
catgttttgt aatttatggg atagcg 26

<210> SEQ ID NO 58
<211> LENGTH: 25
<212> TYPE: DNA
<213> ORGANISM: Artificial Sequence
<220> FEATURE:
<223> OTHER INFORMATION: Primer

<400> SEQUENCE: 58
cgccaagctc gaaattaacc ctcac 25

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
gccacatata attcttgtac ttgtc 25

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
cgaaattaac cctcactaaa gg 22

<210> SEQ ID NO 61
<211> LENGTH: 25
<212> TYPE: DNA
<213> ORGANISM: Artificial Sequence
<220> FEATURE:
<223> OTHER INFORMATION: Primer

<400> SEQUENCE: 61
gacaagtaca agaattatat gtggc 25

<210> SEQ ID NO 62
<211> LENGTH: 27
<212> TYPE: DNA
<213> ORGANISM: Artificial Sequence
<220> FEATURE:
<223> OTHER INFORMATION: Primer

<400> SEQUENCE: 62
gtatgatgga aaataaatac ccaaatg 27

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
cgaaattaac cctcactaaa gg 22

<210> SEQ ID NO 64
<211> LENGTH: 25
<212> TYPE: DNA
<213> ORGANISM: Artificial Sequence
<220> FEATURE:
<223> OTHER INFORMATION: Primer

<400> SEQUENCE: 64
gacaagtaca agaattatat gtggc 25

<210> SEQ ID NO 65
<211> LENGTH: 828
<212> TYPE: DNA
<213> ORGANISM: Artificial Sequence
<220> FEATURE:
<223> OTHER INFORMATION: PbSEP-1A

<400> SEQUENCE: 65
ttaaaagata gtgatggata tgagaaatta ttaaaaaatg acatgtacga tttatataat 60
attaagatgc atgatttaaa taacttaaaa tcatatgatt ttgaattttc aaaaaattta 120
ttaaaaaacg agattttttt ttgtggtgat aatataaaaa gtgatgaaat aaatttaaat 180
gataatgaca taaatgaaaa gattgattca ctaatgaaca attacaatat tatgaaaaac 240
aaacgtgaca aatttaatga agaagaaaac gaaattcaaa actttttagc agaattaaaa 300
gctgatgtaa ctaatcaact caatctaaat aacggggaag atgaacaggc ttttgatttg 360
cttaattcgt ttgatataaa caataacttt gacgattttg ttggcaactt tgatgataca 420
aatgataaca tagctcaaaa taaatcagac atagacaata ataaagagtt cgaacacgaa 480
aatgatataa atcatgatta taacgattgt ggtacatata tggatgatat atataataac 540
aataatggtg atgatatttc gagaaaggga tcacgtctga aattgtctga tttaaatgac 600
gaaaagaatt tatttccaga tgtcaactcc tcttttaata ctcctataaa atcttctgaa 660
ctaaagagag attcagaatg ccaaacaaat tcaccactta tattttctag aagtaataga 720
actcctagga aaaaaagtgt agaagtaata ttagtaaaga aaaaattaaa aaaaagaaaa 780
gaaaaagaat caaatatatc atttgaaaat acaacacatg atgattat 828

<210> SEQ ID NO 66
<211> LENGTH: 276
<212> TYPE: PRT
<213> ORGANISM: Artificial Sequence
<220> FEATURE:
<223> OTHER INFORMATION: PbSEP-1A

<400> SEQUENCE: 66

Leu Lys Asp Ser Asp Gly Tyr Glu Lys Leu Leu Lys Asn Asp Met Tyr
1 5 10 15

Asp Leu Tyr Asn Ile Lys Met His Asp Leu Asn Asn Leu Lys Ser Tyr
20 25 30

Asp Phe Glu Phe Ser Lys Asn Leu Leu Lys Asn Glu Ile Phe Phe Cys
35 40 45

Gly Asp Asn Ile Lys Ser Asp Glu Ile Asn Leu Asn Asp Asn Asp Ile
50 55 60

Asn Glu Lys Ile Asp Ser Leu Met Asn Asn Tyr Asn Ile Met Lys Asn
65 70 75 80

Lys Arg Asp Lys Phe Asn Glu Glu Glu Asn Glu Ile Gln Asn Phe Leu
85 90 95

Ala Glu Leu Lys Ala Asp Val Thr Asn Gln Leu Asn Leu Asn Asn Gly
100 105 110

Glu Asp Glu Gln Ala Phe Asp Leu Leu Asn Ser Phe Asp Ile Asn Asn
115 120 125

Asn Phe Asp Asp Phe Val Gly Asn Phe Asp Asp Thr Asn Asp Asn Ile
130 135 140

Ala Gln Asn Lys Ser Asp Ile Asp Asn Asn Lys Glu Phe Glu His Glu
145 150 155 160

Asn Asp Ile Asn His Asp Tyr Asn Asp Cys Gly Thr Tyr Met Asp Asp
165 170 175

Ile Tyr Asn Asn Asn Asn Gly Asp Asp Ile Ser Arg Lys Gly Ser Arg
180 185 190

Leu Lys Leu Ser Asp Leu Asn Asp Glu Lys Asn Leu Phe Pro Asp Val
195 200 205

Asn Ser Ser Phe Asn Thr Pro Ile Lys Ser Ser Glu Leu Lys Arg Asp
210 215 220

Ser Glu Cys Gln Thr Asn Ser Pro Leu Ile Phe Ser Arg Ser Asn Arg
225 230 235 240

Thr Pro Arg Lys Lys Ser Val Glu Val Ile Leu Val Lys Lys Lys Leu
245 250 255

Lys Lys Arg Lys Glu Lys Glu Ser Asn Ile Ser Phe Glu Asn Thr Thr
260 265 270

His Asp Asp Tyr
275

<210> SEQ ID NO 67
<211> LENGTH: 1810
<212> TYPE: PRT
<213> ORGANISM: Artificial Sequence
<220> FEATURE:
<223> OTHER INFORMATION: PBANKA_050600

<400> SEQUENCE: 67

Met Thr Asp Asn Glu Asp Gln Asn Lys Glu Asp Leu Ile Tyr Tyr Ile
1 5 10 15

Asn Arg Tyr Ser Val Asn Asp Ile Leu Gly Asn Leu Glu Glu Asn Asp
20 25 30

Lys Leu Thr Asn Tyr Asp Glu Asn Ser Gly Ile Cys Glu Tyr Glu Ile
35 40 45

Pro Phe Leu Leu Glu Asn Val Asp Asn Asn Asn Asn Asn Asn Thr Lys
50 55 60

Glu His Ser Asp Arg Asn Ser Val Ser Ser Tyr Phe Asp Asp Gly Thr
65 70 75 80

Cys Ser Ile Ile Ser Lys Asn Asp Glu Lys His Tyr Ile Asp Lys Cys
85 90 95

Glu Lys Asp Lys Met Pro Lys Glu Lys Ile Asn Ile Ile Phe Ile Gln
100 105 110

Asn Lys Gly Glu Met Asn Ser Phe Glu Asp Ile Leu Ser Met Asn Asn
115 120 125

-continued

```
Ala Ser Ser Glu Asn Leu Glu Asn Lys Leu Asn Asp Arg Phe Tyr Gln
    130                 135                 140

Leu Cys Cys Lys Ser Ile Ala Asp Val Asn Thr His Asn Leu Asn Lys
145                 150                 155                 160

Thr Lys Asn Ile Val Lys Asp Lys Lys Gly Thr Leu Asn Ile Glu His
                165                 170                 175

Ile Asp Tyr Gly Asp Ile Phe Leu Thr Ile Arg His Arg Leu Arg Gly
            180                 185                 190

Arg Glu Glu Lys Thr Asn Asn Met Leu Asn Asn Asn Asn Asn Asn Asp
        195                 200                 205

Asn Asn Asn Asn His Leu Tyr Ser Asp Met Ala Asp Ser Val Ile Ser
    210                 215                 220

Asn Trp Arg Glu Ile Lys Asn His Glu Asn Phe Ile Lys Tyr Glu Asn
225                 230                 235                 240

Tyr Lys Glu His Glu Lys Glu Phe Ile Arg Arg Lys Leu Lys Lys Lys
                245                 250                 255

Cys Val Asn Ser Leu Asn Gly Asp Lys Tyr Phe Met Ala Asn Arg Lys
            260                 265                 270

Val Phe Asp Tyr Tyr Arg Asn Asn Leu Asp Ser Tyr Met Thr Asn Gly
        275                 280                 285

Asn Glu Lys Asp Ile Cys Lys Gln Glu Asn Met Ser Leu His Phe Leu
    290                 295                 300

Pro Lys Lys Arg Lys Ser Met Asn Asn Ser Ser Leu Tyr Asn Ser Gln
305                 310                 315                 320

Ile Ile Gly Gln Asn Glu Tyr Ile Leu Lys Asn Arg Thr Phe Leu Lys
                325                 330                 335

Lys Phe Tyr Ile Lys Lys Asn Phe Lys Gln Gln Glu His Ile His Asn
            340                 345                 350

Asp Asp Tyr Tyr Cys Asp Asp Asn His Ser Glu Asn Leu Tyr Asn Asp
        355                 360                 365

Asp Ile Tyr Asn Tyr Asn Lys Asn Leu Ser Asn Arg Gln Gly Asn Leu
    370                 375                 380

Pro Ser Asn Asp Phe Ile Tyr Ser Cys Glu Ile Gln Asn Lys Lys Asn
385                 390                 395                 400

Ser Ile Pro His Asn Ile Cys Val Asp Arg Asn Val Ile Thr Pro Arg
                405                 410                 415

Asn Ser Thr Trp Asn Asn Glu Asn Glu Ile His Glu Glu Asp Met Val
            420                 425                 430

Tyr Tyr His Ser Gln Asn Lys Gly Lys Asn Ser His Tyr Val Glu Ala
        435                 440                 445

Glu Asn Glu Ile Gln Ser Asn His Tyr Cys Glu Asp Lys Asn Thr Asn
    450                 455                 460

Ser Phe Asn Glu Tyr Val Asn Glu Ile Asp Lys Leu Asp Glu Asn Tyr
465                 470                 475                 480

Asn Met Phe Asn Lys Val Glu Glu Asp Asp Asn Asn Asn Asn Lys Glu
                485                 490                 495

Asn Phe Asn Ile Tyr Asp Gly Asp Glu Ile Asp Asn Asn Glu Ala Phe
            500                 505                 510

Asp Ile Lys Ile Glu Glu Asn Asp Asp Tyr Glu Thr Tyr Asn Asn Glu
        515                 520                 525

Leu Glu Leu Glu Val Glu Val Asp Asp Gly Ile Gly Asn Asn Ile Pro
    530                 535                 540
```

-continued

```
Phe Asn Asn Asn Asp Asn Phe Val Asn Ser Asn Lys Asn Glu Asp Leu
545                 550                 555                 560

Asp Asn Ile Asn Asn Cys Glu His Val Ser Asn Ser Asn His Thr Lys
                565                 570                 575

Tyr Gly Glu Glu Asp Asn Glu Gln Lys Ala Pro Ser Ile Thr Ser Lys
            580                 585                 590

Asp Asp Lys Asp Tyr Phe Asp Leu Leu Ile Lys Lys Tyr Glu Gln Thr
        595                 600                 605

Arg Met Ser Ile Asn Glu Ser Ser Thr Ala Ser Leu Ser Glu Ser Ile
    610                 615                 620

Tyr Leu Ser Lys Glu Gly Thr Lys Glu Pro Ser Leu Asn Ala His Glu
625                 630                 635                 640

Met Leu Lys Ile Ala Ser Asn Thr Lys Asn Asp Val Asn Asn Lys Ile
                645                 650                 655

Glu Cys Leu Asn Glu Asn Leu Ile Asp Leu Lys Asn Asn Lys Glu Ile
            660                 665                 670

Ile Asn Glu Gly Glu Cys Phe Ser Asn Gly Phe Ser Ile Glu Lys Asn
        675                 680                 685

Asp Ile Glu Lys Glu Asn Asp Asn Ile Val Lys Leu Gly Ser Val Tyr
    690                 695                 700

Asn Asn Asp Lys Thr Glu Gly Glu Arg Gly Asn Ile Gly Asn Lys Asn
705                 710                 715                 720

Glu Lys Val Asp Leu Lys Asp Ser Asp Gly Tyr Glu Lys Leu Leu Lys
                725                 730                 735

Asn Asp Met Tyr Asp Leu Tyr Asn Ile Lys Met His Asp Leu Asn Asn
            740                 745                 750

Leu Lys Ser Tyr Asp Phe Glu Phe Ser Lys Asn Leu Leu Lys Asn Glu
        755                 760                 765

Ile Phe Phe Cys Gly Asp Asn Ile Lys Ser Asp Glu Ile Asn Leu Asn
    770                 775                 780

Asp Asn Asp Ile Asn Glu Lys Ile Asp Ser Leu Met Asn Asn Tyr Asn
785                 790                 795                 800

Ile Met Lys Asn Lys Arg Asp Lys Phe Asn Glu Glu Glu Asn Glu Ile
                805                 810                 815

Gln Asn Phe Leu Ala Glu Leu Lys Ala Asp Val Thr Asn Gln Leu Asn
            820                 825                 830

Leu Asn Asn Gly Glu Asp Glu Gln Ala Phe Asp Leu Leu Asn Ser Phe
        835                 840                 845

Asp Ile Asn Asn Asn Phe Asp Asp Phe Val Gly Asn Phe Asp Asp Thr
    850                 855                 860

Asn Asp Asn Ile Ala Gln Asn Lys Ser Asp Ile Asp Asn Asn Lys Glu
865                 870                 875                 880

Phe Glu His Glu Asn Asp Ile Asn His Asp Tyr Asn Asp Cys Gly Thr
                885                 890                 895

Tyr Met Asp Asp Ile Tyr Asn Asn Asn Asn Gly Asp Asp Ile Ser Arg
            900                 905                 910

Lys Gly Ser Arg Leu Lys Leu Ser Asp Leu Asn Asp Glu Lys Asn Leu
        915                 920                 925

Phe Pro Asp Val Asn Ser Ser Phe Asn Thr Pro Ile Lys Ser Ser Glu
    930                 935                 940

Leu Lys Arg Asp Ser Glu Cys Gln Thr Asn Ser Pro Leu Ile Phe Ser
945                 950                 955                 960
```

-continued

```
Arg Ser Asn Arg Thr Pro Arg Lys Lys Ser Val Glu Val Ile Leu Val
                965                 970                 975

Lys Lys Lys Leu Lys Lys Arg Lys Glu Lys Glu Ser Asn Ile Ser Phe
            980                 985                 990

Glu Asn Thr Thr His Asp Asp Tyr  Thr Val Gly Thr Thr  Thr Ala Thr
        995                 1000                1005

Ser Ser  Ile Asn Ser Lys Arg  Arg Tyr Pro Lys Arg  Asn Arg Ile
    1010                 1015                1020

Lys Thr  Leu Arg Tyr Trp Ile  Gly Glu Arg Glu Leu  Thr Arg Arg
    1025                 1030                1035

Asn Pro  Glu Thr Gly Glu Ile  Asp Val Val Gly Phe  Ser Glu Cys
    1040                 1045                1050

Lys Asn  Leu Glu Glu Leu Ser  Pro His Ile Ile Gly  Pro Val Tyr
    1055                 1060                1065

Tyr Lys  Lys Met Tyr Leu Arg  Asp Val Asn Asn Leu  His Gly Lys
    1070                 1075                1080

Gly Asn  Glu Asp Ala Asn Asn  Asn Ile Asp Arg Asn  Asp Asn Thr
    1085                 1090                1095

Asp Glu  Glu Asn Glu Ile Thr  Ile Glu Ile Asn Asn  Gly Met Tyr
    1100                 1105                1110

Glu Asn  Glu Val Tyr Asn Lys  Ile Gln Asn Lys Glu  Asn Ser Val
    1115                 1120                1125

Asn Lys  Asn Asp Asn Val Ser  Asn Ile Leu Lys Lys  Ser Ile Asn
    1130                 1135                1140

Gly Ser  Ile His Asn Arg Ser  Asp Asn Asp Ala Ile  Thr Arg Asn
    1145                 1150                1155

Gly Lys  Lys Lys Arg Lys Lys  Phe Ile Asn Val Val  Asn Tyr Ile
    1160                 1165                1170

Lys Lys  Lys Thr Lys Lys Lys  Leu Val Lys Val Ile  Asp Lys Glu
    1175                 1180                1185

Val Glu  Gln Glu Asn Glu Asn  Val Asp Asn Arg Asn  Thr Phe Ser
    1190                 1195                1200

Asn Asn  Asp Asn Ile Ile Asn  Asp Ile Thr Asn Val  Asn His Asn
    1205                 1210                1215

Ser Gln  Asn Asn Leu Asp Gln  Asn Phe Ile Ala Ile  Ser Asn Asp
    1220                 1225                1230

Phe Ile  Glu Asn Asp Asp Asn  Ile Phe Phe Asp Ala  Ile Ser Leu
    1235                 1240                1245

Gly Asp  Asn Ala His Ile Asn  Asp Ile Pro Glu Lys  Ser Glu Glu
    1250                 1255                1260

Ile Ile  Glu Ala Pro Gly Val  Asp Ala Ile Glu Thr  Thr Lys Val
    1265                 1270                1275

Asn Gly  Asn Glu Lys Glu Ile  Asn Leu Glu Lys Glu  Ile Asn Leu
    1280                 1285                1290

Glu Lys  Glu Ile Asn Leu Glu  Lys Asn Lys Asp Val  His Val Lys
    1295                 1300                1305

Lys Lys  Leu Leu Asp Lys Lys  Lys Lys Lys Lys Lys  Lys Lys Asn
    1310                 1315                1320

Lys Gly  Lys Glu Lys Glu Ile  Asp Glu Met Tyr Lys  Gln Leu Ser
    1325                 1330                1335

Phe Leu  Asn Phe Asn Ser Phe  Tyr Ser Lys Gly Asn  Glu Asp Lys
    1340                 1345                1350
```

```
Ser Lys  Ile Glu Ile Leu Lys  Lys Thr Ser Thr Lys  Lys Lys Gly
    1355                 1360                 1365

Ser Lys  Ile Asp Lys Glu Lys  Val Asp Glu Glu Asn  Asp Lys His
    1370                 1375                 1380

Asn Lys  Asn Ser Gly Lys Glu  Ala Lys Glu Leu Ile  Thr Lys Lys
    1385                 1390                 1395

Lys Lys  Ala Lys Asn Met Lys  Lys Asn Lys Lys Arg  Asn Met Gln
    1400                 1405                 1410

Asn Lys  Glu Met Lys Asn Tyr  Tyr Glu Tyr Thr Asn  Asn Glu Ile
    1415                 1420                 1425

Glu Lys  Phe Tyr Asn Asn Pro  Asn Asp Arg Ile Glu  Asn Glu Tyr
    1430                 1435                 1440

Asn Met  Gly Val Asp Leu Glu  Ala Ser Ile Lys Thr  Glu Glu Glu
    1445                 1450                 1455

Lys Thr  Glu Lys Ile Gly Glu  Leu Pro Ile Leu Asn  Ser Tyr Thr
    1460                 1465                 1470

Asn Glu  Gln Tyr Glu His Ile  Thr Asn Thr Asn Asp  Ile Thr Asn
    1475                 1480                 1485

Ser Lys  Ser Glu Asn Phe Glu  Leu His Lys Asn Glu  Asp Glu Glu
    1490                 1495                 1500

Val Glu  Lys Leu Gln Thr Ser  Thr Arg Arg Lys Lys  Lys Lys Lys
    1505                 1510                 1515

Ser Glu  Ser Leu Ile His Asp  Thr Asn Glu Leu Asn  Lys Lys Arg
    1520                 1525                 1530

Arg Lys  Thr Asp Gly Asn Asn  Ser Gly Glu Leu Ile  Ser Ile Asn
    1535                 1540                 1545

Glu Asn  Asp Glu Ile Lys Asn  Val Asp Ala Asp Lys  Lys Ile Asn
    1550                 1555                 1560

Asp Lys  Glu Gly Lys Tyr Ile  Lys Lys Val Asp Lys  Asp Thr Ile
    1565                 1570                 1575

Met Gly  Ser Asn Gly Asn Asn  Ile Asp Glu Leu Asn  Lys Asp Phe
    1580                 1585                 1590

Glu Asp  Asn Asp Gln Ile Lys  Asn Ile Lys Lys Asp  Glu Lys Lys
    1595                 1600                 1605

Lys Glu  Thr Asn Thr Asp Gly  Ser Asn Asn Met Arg  Asn Ile Asn
    1610                 1615                 1620

Leu Leu  Glu Glu Ile Asp Ala  Asn Glu Lys Asn Ser  Thr Leu Cys
    1625                 1630                 1635

Leu Val  Thr His Asn Lys Lys  Asn Asn Thr Asn Ser  Gln Ser Phe
    1640                 1645                 1650

Ile Ile  Asp Lys Leu Lys Ser  Tyr Phe Asn Ile Lys  Glu Leu Ile
    1655                 1660                 1665

Asn Val  Lys Lys Gln Lys Thr  Asn Asn Val Ile Leu  Asn Thr Phe
    1670                 1675                 1680

Glu Asn  Lys Gln Ile Ile Asn  Asn Asn Pro Ile Arg  Ile Ser Leu
    1685                 1690                 1695

Ser Tyr  Pro Ser Ser Val Glu  Leu Ser Val Glu Asn  Arg Cys Asn
    1700                 1705                 1710

Gln Thr  Arg Asn Gly Gln Phe  Pro Leu Ile Gln Lys  Asn Leu Ser
    1715                 1720                 1725

Asn Phe  Lys Val Asp Ile Asn  Leu Phe Cys Val Gln  Ile Phe Pro
    1730                 1735                 1740
```

```
Asn Lys  Ala His Ser Ser Asn  Ser Tyr Asp Lys Ile  Leu Ile Gly
    1745                 1750                 1755

Tyr Ile  Tyr Gln Gly Lys Lys  Val Lys Ile Tyr Phe  Lys Asn Gln
    1760                 1765                 1770

Glu Arg  Tyr Phe Glu Lys Asp  Glu Phe Phe Tyr Ile  Pro Lys Tyr
    1775                 1780                 1785

Ser Pro  Phe Lys Ile Val Asn  Ile Ser Arg Asp Asn  Cys Ile Leu
    1790                 1795                 1800

Tyr Val  Tyr Pro Ile Asn Lys
    1805                 1810
```

<210> SEQ ID NO 68
<211> LENGTH: 5434
<212> TYPE: DNA
<213> ORGANISM: Artificial Sequence
<220> FEATURE:
<223> OTHER INFORMATION: PBANKA_050600

<400> SEQUENCE: 68

```
atgacagaca acgaggatca aaataaagaa gatctgatat attacataaa tagatacagt     60

gtcaatgata tattgggaaa tttagaagaa aatgataagt taacaaatta tgatgaaaat    120

agcggaatat gtgaatatga aattccattt cttttggaaa atgtcgataa taataataat    180

aataatacta aagaacattc cgatagaaat tctgtatcta gttatttcga tgatggaaca    240

tgttcgatta tttctaaaaa tgatgaaaaa cattatatag acaaatgtga aaaagacaaa    300

atgccaaagg aaaaaataaa tattatattt attcagaata aaggtgaaat gaatagcttt    360

gaagatattt tatccatgaa taatgcaagc agtgaaaatt tagaaaacaa gttaaatgat    420

agattttatc aactatgttg taaaagtatt gctgatgtga acacccacaa tttaaataaa    480

actaaaaata ttgtaaaaga taaaaaaggg acattgaata ttgagcatat agattatggt    540

gatatatttt taaccattcg tcatcgtcta agagggcgtg aagaaaaaac gaataacatg    600

ctaaataata ataataataa tgataataat aataatcatt tatatagtga catggctgat    660

agtgttatta gtaattggag ggaaataaaa aatcatgaaa attttataaa atatgaaaac    720

tataaagagc atgaaaagga gtttataagg aggaaattga aaaagaaatg cgtcaatagt    780

ttaaatggag ataaatattt tatggccaat agaaaagtat ttgattatta tcgtaataat    840

ttagatagtt acatgactaa tgggaatgaa aaagatatat gcaagcaaga aaatatgtct    900

ctacattttt taccaaaaaa gagaaaatca atgaataata gttctttata caattctcaa    960

ataattggac aaaatgaata tattttaaag aatagaacat tttaaaaaaa attttatata   1020

aaaaaaaatt ttaagcaaca agaacatatc cataatgatg attattattg tgatgataat   1080

catagtgaaa atttatataa tgatgatata tataattata ataaaaactt gagtaataga   1140

caaggtaatc tacccagcaa tgattttatt tattcatgtg aaattcaaaa taagaaaaat   1200

tcaataccac ataatatatg tgtcgataga aatgtaataa ccccacggaa cagtacatgg   1260

aataatgaaa acgaaattca cgaagaggat atggtttatt atcattctca aaataaggga   1320

aaaaattcac attatgtaga agcagaaaat gaaatacaat caaatcatta ttgtgaagat   1380

aaaaatacaa acagttttaa cgaatatgtt aatgaaattg ataaactcga tgaaaattat   1440

aatatgttta acaaagttga agaggacgat aataataata acaaagaaaa ttttaacatt   1500

tatgatggtg atgaaataga taataacgaa gcatttgata tcaaaatcga agaaaatgat   1560

gattatgaaa catataacaa cgaattagaa ttagaggtag aggtagatga tggaataggt   1620
```

```
aataatattc catttaataa taatgataat tttgtaaatt caaataagaa tgaagatttg   1680
gataatataa ataattgtga acatgtttca aattcaaatc atacaaaata tggggaagaa   1740
gacaatgagc aaaaagctcc atcaataacc agtaaagatg ataaagatta ttttgattta   1800
ctaataaaaa aatatgaaca aactagaatg tcaattaatg aatctagtac agcctcactt   1860
agtgaaagta tttatttatc aaaagaagga acaaaagaac cttctttaaa tgctcacgaa   1920
atgttaaaaa tcgcatctaa cacaaagaat gatgtaaata ataaaattga atgtttgaat   1980
gaaaacttaa tagatttaaa aaataacaag gaaattatta atgaagggga atgttttagt   2040
aatggttttt ctatcgaaaa aaatgacata gaaaaggaaa atgataatat agtaaaatta   2100
ggaagtgtat ataataatga caaaacagag ggggaaagag ggaatattgg aaacaaaaat   2160
gaaaaagtag accttaaaag atagtgatgg atatgagaaa ttattaaaaa atgacatgta   2220
cgatttatat aatattaaga tgcatgattt aaataactta aaatcatatg attttgaatt   2280
ttcaaaaaat ttattaaaaa acgagatttt tttttgtggt gataatataa aaagtgatga   2340
aataaattta aatgataatg acataaatga aaagattgat tcactaatga acaattacaa   2400
tattatgaaa aacaaacgtg acaaatttaa tgaagaagaa aacgaaattc aaaacttttt   2460
agcagaatta aaagctgatg taactaatca actcaatcta aataacgggg aagatgaaca   2520
ggcttttgat ttgcttaatt cgtttgatat aaacaataac tttgacgatt ttgttggcaa   2580
ctttgatgat acaaatgata acatagctca aaataaatca gacatagaca ataataaaga   2640
gttcgaacac gaaaatgata taaatcatga ttataacgat tgtggtacat atatggatga   2700
tatatataat aacaataatg gtgatgatat ttcgagaaag ggatcacgtc tgaaattgtc   2760
tgatttaaat gacgaaaaga atttatttcc agatgtcaac tcctctttta atactcctat   2820
aaaatcttct gaactaaaga gagattcaga atgccaaaca aattcaccac ttatattttc   2880
tagaagtaat agaactccta ggaaaaaaag tgtagaagta atattagtaa agaaaaaatt   2940
aaaaaaaaga aaagaaaaag aatcaaatat atcatttgaa aatacaacac atgatgatta   3000
tactgttggt acaactactg ctactagtag catcaattcg aaaagaagat atcctaaaag   3060
aaatagaata aaaacgttgc gatactggat aggtgaaagg gaacttacta gaagaaatcc   3120
tgaaacaggc gaaatagatg ttgtaggttt tagtgaatgc aaaaatttag aagaattatc   3180
tcctcatatt attggtccag tttattataa aaaaatgtat ttacgagatg tgaataattt   3240
acatggaaaa ggaaacgaag atgctaacaa caatatagat agaaatgata atactgatga   3300
agaaaatgaa ataacgatag aaatcaataa tggaatgtat gaaaatgaag tgtataataa   3360
aattcagaat aaagagaatt ctgtgaataa aaatgataat gttagtaaca tattgaaaaa   3420
aagtataaat ggtagcattc ataatagaag tgataatgat gcaataacta gaaatgggaa   3480
aaagaaaaga aaaaagttta ttaatgttgt taattatatt aaaaaaaaaa caaaaaaaaa   3540
attagtcaaa gttatagata aagaagtaga gcaggaaaat gaaaatgtag ataatcgtaa   3600
cactttttca aataatgata atataattaa tgacataaca aatgtcaatc acaattctca   3660
aaataatttg gatcaaaatt ttattgcaat tagtaatgat tttattgaaa atgatgacaa   3720
tatttttttc gatgcgatta gtcttggcga taatgctcac ataaatgata ttccagaaaa   3780
aagcgaagaa attattgaag caccaggagt agatgcaatt gaaacgacta aagttaatgg   3840
aaacgaaaag gaaatcaatt tagaaaagga aatcaattta gaaaaggaaa tcaatttaga   3900
aaagaataaa gatgtacatg tgaaaaagaa attattagat aaaaagaaaa agaaaaaaaa   3960
```

-continued

```
aaagaaaaac aagggaaaag aaaaggaaat agacgaaatg tacaagcaat tatcattttt   4020
gaattttaat tcgttttatt ctaaaggaaa tgaagataaa tcaaaaatag aaattttgaa   4080
aaaaacaagt accaaaaaaa aagggagtaa aattgataaa gaaaaggtag atgaggaaaa   4140
tgataaacat aataaaaatt cgggaaagga agccaaagaa ttaattacaa aaaaaaagaa   4200
agccaagaat atgaagaaaa ataaaaagag aaatatgcag aataaagaaa tgaaaaatta   4260
ttatgaatat acaaataatg aaatcgaaaa gttctacaac aatccaaatg atagaataga   4320
gaatgaatac aatatgggag tcgatttaga agcatcaata aaaactgaag aagaaaaaac   4380
agaaaaaatt ggagagttgc ccattttaaa ttcatatact aatgagcaat atgagcacat   4440
aacgaataca aatgatataa caaattcgaa aagtgaaaat tttgaactcc acaaaaatga   4500
agacgaagaa gtggaaaagc tacaaacttc tacacgtcga aaaaagaaaa aaaaaagtga   4560
aagtttaatt catgatacaa atgaattgaa taaaaagcga agaaaaacag atggaaataa   4620
ttcaggggaa ttaatttcta ttaatgaaaa tgatgagata aaaaatgtag atgctgataa   4680
aaaaataaat gacaaagaag gtaaatatat aaagaaagtt gacaaggata caattatggg   4740
atcaaatgga aataatattg atgaattaaa taaggatttt gaagataatg atcaaattaa   4800
aaatataaaa aaagatgaaa aaaaaaaaga gacaaataca gatggttcta ataatatgag   4860
aaatataaat ttattagaag aaatagatgc aaatgaaaaa aatagtacat tatgtttggt   4920
aactcacaat aaaaaaaata atacgaatag tcaaagtttt attatagata aattaaaatc   4980
gtatttcaat ataaaagagt taataaatgt caaaaaacaa aaaacaaata atgtaatatt   5040
aaatactttt gaaaataaac aaataataaa taataatcct atacgtattt ctctttccta   5100
tccttctagt gtagaattat cagttgaaaa tagatgcaac caaacaagaa atggacaatt   5160
tccacttata caaaagaact taagcaactt caaggtagac ataaatttat tttgtgttca   5220
aattttccca aacaaagcac atagctcgaa tagttatgat aaaattttga ttgggtatat   5280
atatcaggga aaaaaggtaa agatttattt taagaaccaa gaaagatatt ttgaaaagga   5340
tgagtttttt tacataccca aatactctcc tttcaaaatt gtcaacataa gcagggacaa   5400
ttgtatttta tatgtttatc caataaataa ataa                               5434
```

<210> SEQ ID NO 69
<211> LENGTH: 2994
<212> TYPE: DNA
<213> ORGANISM: Artificial Sequence
<220> FEATURE:
<223> OTHER INFORMATION: SERA5

<400> SEQUENCE: 69

```
atgaagtcat atatttcctt gtttttcata ttgtgtgtta tatttaacaa aaatgttata     60
aaatgtacag gagaaagtca aacaggtaat acaggaggag gtcaagcagg taatacagga    120
ggagatcaag caggtagtac aggaggaagt ccacaaggta gtacgggagc aagtccacaa    180
ggtagtacgg gagcaagtcc acaaggtagt acgggagcaa gtcaacccgg aagttccgaa    240
ccaagcaatc ctgtaagttc cggacattct gtaagtactg tatcagtatc acaaacttca    300
acttcttcag aaaaacagga tacaattcaa gtaaaatcag ctttattaaa agattatatg    360
ggtttaaaag ttactggtcc atgtaacgaa aatttcataa tgttcttagt tcctcatata    420
tatattgatg ttgatacaga agatactaat atcgaattaa gaacaacatt gaaaaaaaca    480
aataatgcaa tatcatttga atcaaacagt ggttcattag aaaaaaaaaa atatgtaaaa    540
ctaccatcaa atggtacaac tggtgaacaa ggttcaagta cgggaacagt tagaggagat    600
```

```
acagaaccaa tttcagattc aagctcaagt tcaagttcaa gctctagttc aagttcaagt    660
tcaagttcaa gttctagttc aagttctagt tcaagttcag aaagtcttcc tgctaatgga    720
cctgattccc ctactgttaa accgccaaga aatttacaaa atatatgtga aactggaaaa    780
aacttcaagt tggtagtata tattaaggag aatacattaa tacttaaatg gaaagtatac    840
ggagaaacaa aagatactac tgaaaataac aaagttgatg taagaaagta tttgataaat    900
gaaaaggaaa ccccatttac taatatacta atacatgcgt ataaagaaca taatggaaca    960
aacttaatag aaagtaaaaa ctacgcaata ggatcagaca ttccagaaaa atgtgatacc   1020
ttagcttcca attgcttttt aagtggtaat tttaacattg aaaaatgctt tcaatgtgct   1080
cttttagtag aaaaagaaaa taaaaatgac gtatgttaca aatacctatc tgaagatatt   1140
gtaagtaaat tcaaagaaat aaaagctgag acagaagatg atgatgaaga tgattatact   1200
gaatataaat taacagaatc tattgataat atattagtaa aaatgtttaa aacaaatgaa   1260
aataatgata aatcagaatt aataaaatta gaagaagtag atgatagttt gaaattagaa   1320
ttaatgaatt actgtagttt acttaaagac gtagatacaa caggtacctt agataattat   1380
gggatgggaa atgaaatgga tatatttaat aacttaaaga gattattaat ttatcattca   1440
gaagaaaata ttaatacttt aaaaaataaa ttccgtaatg cagctgtatg tcttaaaaat   1500
gttgatgatt ggattgtaaa taagagaggt ttagtattac ctgaattaaa ttatgattta   1560
gaatatttca atgaacattt atataatgat aaaaattctc cagaagataa agataataaa   1620
ggaaaaggtg tcgtacatgt tgatacaact ttagaaaaag aagatacttt atcatatgat   1680
aactcagata atatgttttg taataaagaa tattgtaaca gattaaaaga tgaaaataat   1740
tgtatatcta atcttcaagt tgaagatcaa ggtaattgtg atacttcatg gatttttgct   1800
tcaaaatatc atttagaaac tattagatgt atgaaaggat atgaacctac caaaatttct   1860
gctctttatg tagctaattg ttataaaggt gaacataaag atagatgtga tgaaggttct   1920
agtccaatgg aattcttaca aattattgaa gattatggat tcttaccagc agaatcaaat   1980
tatccatata actatgtgaa agttggagaa caatgtccaa aggtagaaga tcactggatg   2040
aatctatggg ataatggaaa aatcttacat aacaaaaatg aacctaatag tttagatggt   2100
aagggatata ctgcatatga aagtgaaaga tttcatgata atatggatgc atttgttaaa   2160
attattaaaa ctgaagtaat gaataaaggt tcagttattg catatattaa agctgaaaat   2220
gttatgggat atgaatttag tggaaagaaa gtacagaact tatgtggtga tgatacagct   2280
gatcatgcag ttaatattgt tggttatggt aattatgtga atagcgaagg agaaaaaaaa   2340
tcctattgga ttgtaagaaa cagttggggt ccatattggg gagatgaagg ttattttaaa   2400
gtagatatgt atggaccaac tcattgtcat tttaacttta ttcacagtgt tgttatattc   2460
aatgttgatt tacctatgaa taataaaaca actaaaaaag aatcaaaaat atatgattat   2520
tatttaaagg cctctccaga attttatcat aacctttact ttaagaattt taatgttggt   2580
aagaaaaatt tattctctga aaaggaagat aatgaaaaca acaaaaaatt aggtaacaac   2640
tatattatat tcggtcaaga tacggcagga tcaggacaaa gtggaaagga aagcaatact   2700
gcattagaat ctgcaggaac ttcaaatgaa gtctcagaac gtgttcatgt ttatcacata   2760
ttaaaacata taaaggatgg caaaataaga atgggtatgc gtaaatatat agatacacaa   2820
```

gatgtaaata agaaacattc ttgtacaaga tcctatgcat ttaatccaga gaattatgaa 2880
aaatgtgtaa atttatgtaa tgtgaactgg aaaacatgcg aggaaaaaac atcaccagga 2940
ctttgtttat ccaaattgga tacaaataac gaatgttatt tctgttatgt ataa 2994

<210> SEQ ID NO 70
<211> LENGTH: 997
<212> TYPE: PRT
<213> ORGANISM: Artificial Sequence
<220> FEATURE:
<223> OTHER INFORMATION: SERA5

<400> SEQUENCE: 70

```
Met Lys Ser Tyr Ile Ser Leu Phe Phe Ile Leu Cys Val Ile Phe Asn
1               5                   10                  15

Lys Asn Val Ile Lys Cys Thr Gly Glu Ser Gln Thr Gly Asn Thr Gly
            20                  25                  30

Gly Gly Gln Ala Gly Asn Thr Gly Gly Asp Gln Ala Gly Ser Thr Gly
        35                  40                  45

Gly Ser Pro Gln Gly Ser Thr Gly Ala Ser Pro Gln Gly Ser Thr Gly
    50                  55                  60

Ala Ser Pro Gln Gly Ser Thr Gly Ala Ser Gln Pro Gly Ser Ser Glu
65                  70                  75                  80

Pro Ser Asn Pro Val Ser Ser Gly His Ser Val Ser Thr Val Ser Val
                85                  90                  95

Ser Gln Thr Ser Thr Ser Ser Glu Lys Gln Asp Thr Ile Gln Val Lys
            100                 105                 110

Ser Ala Leu Leu Lys Asp Tyr Met Gly Leu Lys Val Thr Gly Pro Cys
        115                 120                 125

Asn Glu Asn Phe Ile Met Phe Leu Val Pro His Ile Tyr Ile Asp Val
    130                 135                 140

Asp Thr Glu Asp Thr Asn Ile Glu Leu Arg Thr Thr Leu Lys Lys Thr
145                 150                 155                 160

Asn Asn Ala Ile Ser Phe Glu Ser Asn Ser Gly Ser Leu Glu Lys Lys
                165                 170                 175

Lys Tyr Val Lys Leu Pro Ser Asn Gly Thr Thr Gly Glu Gln Gly Ser
            180                 185                 190

Ser Thr Gly Thr Val Arg Gly Asp Thr Glu Pro Ile Ser Asp Ser Ser
        195                 200                 205

Ser Ser Ser Ser Ser Ser Ser Ser Ser Ser Ser Ser Ser Ser Ser Ser
    210                 215                 220

Ser Ser Ser Ser Ser Ser Ser Ser Ser Glu Ser Leu Pro Ala Asn Gly
225                 230                 235                 240

Pro Asp Ser Pro Thr Val Lys Pro Pro Arg Asn Leu Gln Asn Ile Cys
                245                 250                 255

Glu Thr Gly Lys Asn Phe Lys Leu Val Val Tyr Ile Lys Glu Asn Thr
            260                 265                 270

Leu Ile Leu Lys Trp Lys Val Tyr Gly Glu Thr Lys Asp Thr Thr Glu
        275                 280                 285

Asn Asn Lys Val Asp Val Arg Lys Tyr Leu Ile Asn Glu Lys Glu Thr
    290                 295                 300

Pro Phe Thr Asn Ile Leu Ile His Ala Tyr Lys Glu His Asn Gly Thr
305                 310                 315                 320

Asn Leu Ile Glu Ser Lys Asn Tyr Ala Ile Gly Ser Asp Ile Pro Glu
                325                 330                 335
```

```
Lys Cys Asp Thr Leu Ala Ser Asn Cys Phe Leu Ser Gly Asn Phe Asn
            340                 345                 350

Ile Glu Lys Cys Phe Gln Cys Ala Leu Leu Val Glu Lys Glu Asn Lys
        355                 360                 365

Asn Asp Val Cys Tyr Lys Tyr Leu Ser Glu Asp Ile Val Ser Lys Phe
    370                 375                 380

Lys Glu Ile Lys Ala Glu Thr Glu Asp Asp Asp Glu Asp Asp Tyr Thr
385                 390                 395                 400

Glu Tyr Lys Leu Thr Glu Ser Ile Asp Asn Ile Leu Val Lys Met Phe
                405                 410                 415

Lys Thr Asn Glu Asn Asn Asp Lys Ser Glu Leu Ile Lys Leu Glu Glu
            420                 425                 430

Val Asp Asp Ser Leu Lys Leu Glu Leu Met Asn Tyr Cys Ser Leu Leu
        435                 440                 445

Lys Asp Val Asp Thr Thr Gly Thr Leu Asp Asn Tyr Gly Met Gly Asn
    450                 455                 460

Glu Met Asp Ile Phe Asn Asn Leu Lys Arg Leu Leu Ile Tyr His Ser
465                 470                 475                 480

Glu Glu Asn Ile Asn Thr Leu Lys Asn Lys Phe Arg Asn Ala Ala Val
                485                 490                 495

Cys Leu Lys Asn Val Asp Asp Trp Ile Val Asn Lys Arg Gly Leu Val
            500                 505                 510

Leu Pro Glu Leu Asn Tyr Asp Leu Glu Tyr Phe Asn Glu His Leu Tyr
        515                 520                 525

Asn Asp Lys Asn Ser Pro Glu Asp Lys Asp Asn Lys Gly Lys Gly Val
    530                 535                 540

Val His Val Asp Thr Thr Leu Glu Lys Glu Asp Thr Leu Ser Tyr Asp
545                 550                 555                 560

Asn Ser Asp Asn Met Phe Cys Asn Lys Glu Tyr Cys Asn Arg Leu Lys
                565                 570                 575

Asp Glu Asn Asn Cys Ile Ser Asn Leu Gln Val Glu Asp Gln Gly Asn
            580                 585                 590

Cys Asp Thr Ser Trp Ile Phe Ala Ser Lys Tyr His Leu Glu Thr Ile
        595                 600                 605

Arg Cys Met Lys Gly Tyr Glu Pro Thr Lys Ile Ser Ala Leu Tyr Val
    610                 615                 620

Ala Asn Cys Tyr Lys Gly Glu His Lys Asp Arg Cys Asp Glu Gly Ser
625                 630                 635                 640

Ser Pro Met Glu Phe Leu Gln Ile Ile Glu Asp Tyr Gly Phe Leu Pro
                645                 650                 655

Ala Glu Ser Asn Tyr Pro Tyr Asn Tyr Val Lys Val Gly Glu Gln Cys
            660                 665                 670

Pro Lys Val Glu Asp His Trp Met Asn Leu Trp Asp Asn Gly Lys Ile
        675                 680                 685

Leu His Asn Lys Asn Glu Pro Asn Ser Leu Asp Gly Lys Gly Tyr Thr
    690                 695                 700

Ala Tyr Glu Ser Glu Arg Phe His Asp Asn Met Asp Ala Phe Val Lys
705                 710                 715                 720

Ile Ile Lys Thr Glu Val Met Asn Lys Gly Ser Val Ile Ala Tyr Ile
                725                 730                 735

Lys Ala Glu Asn Val Met Gly Tyr Glu Phe Ser Gly Lys Lys Val Gln
            740                 745                 750
```

-continued

```
Asn Leu Cys Gly Asp Asp Thr Ala Asp His Ala Val Asn Ile Val Gly
        755                 760                 765

Tyr Gly Asn Tyr Val Asn Ser Glu Gly Glu Lys Lys Ser Tyr Trp Ile
    770                 775                 780

Val Arg Asn Ser Trp Gly Pro Tyr Trp Gly Asp Glu Gly Tyr Phe Lys
785                 790                 795                 800

Val Asp Met Tyr Gly Pro Thr His Cys His Phe Asn Phe Ile His Ser
                805                 810                 815

Val Val Ile Phe Asn Val Asp Leu Pro Met Asn Asn Lys Thr Thr Lys
            820                 825                 830

Lys Glu Ser Lys Ile Tyr Asp Tyr Tyr Leu Lys Ala Ser Pro Glu Phe
        835                 840                 845

Tyr His Asn Leu Tyr Phe Lys Asn Phe Asn Val Gly Lys Lys Asn Leu
    850                 855                 860

Phe Ser Glu Lys Glu Asp Asn Glu Asn Asn Lys Lys Leu Gly Asn Asn
865                 870                 875                 880

Tyr Ile Ile Phe Gly Gln Asp Thr Ala Gly Ser Gly Gln Ser Gly Lys
                885                 890                 895

Glu Ser Asn Thr Ala Leu Glu Ser Ala Gly Thr Ser Asn Glu Val Ser
            900                 905                 910

Glu Arg Val His Val Tyr His Ile Leu Lys His Ile Lys Asp Gly Lys
        915                 920                 925

Ile Arg Met Gly Met Arg Lys Tyr Ile Asp Thr Gln Asp Val Asn Lys
    930                 935                 940

Lys His Ser Cys Thr Arg Ser Tyr Ala Phe Asn Pro Glu Asn Tyr Glu
945                 950                 955                 960

Lys Cys Val Asn Leu Cys Asn Val Asn Trp Lys Thr Cys Glu Glu Lys
                965                 970                 975

Thr Ser Pro Gly Leu Cys Leu Ser Lys Leu Asp Thr Asn Asn Glu Cys
            980                 985                 990

Tyr Phe Cys Tyr Val
        995
```

<210> SEQ ID NO 71
<211> LENGTH: 561
<212> TYPE: DNA
<213> ORGANISM: Artificial Sequence
<220> FEATURE:
<223> OTHER INFORMATION: Y2H Clone name: 1 7-1

<400> SEQUENCE: 71

```
aactttattc acagtgttgt tatattcaat gttgatttac ctatgaataa taaaacaact      60

aaaaaagaat caaaaatata tgattattat ttaaaggcct ctccagaatt ttatcataac     120

ctttacttta agaattttaa tgttggtaag aaaaatttat tctctgaaaa ggaagataat     180

gaaaacaaca aaaaattagg taacaactat attatattcg gtcaagatac ggcaggatca     240

ggacaaagtg gaaaggaaag caatactgca ttagaatctg caggaacttc aaatgaagtc     300

tcagaacgtg ttcatgttta tcacatatta aaacatataa aggatggcaa aataagaatg     360

ggtatgcgta aatatataga tacacaagat gtaaataaga aacattcttg tacaagatcc     420

tatgcattta atccagagaa ttatgaaaaa tgtgtaaatt tatgtaatgt gaactggaaa     480

acatgcgagg aaaaaacatc accaggactt tgtttatcca aattggatac aaataacgaa     540

tgttatttct gttatgtata a                                               561
```

<210> SEQ ID NO 72
<211> LENGTH: 186
<212> TYPE: PRT
<213> ORGANISM: Artificial Sequence
<220> FEATURE:
<223> OTHER INFORMATION: Y2H Clone name: 1 7-1

<400> SEQUENCE: 72

```
Asn Phe Ile His Ser Val Val Ile Phe Asn Val Asp Leu Pro Met Asn
1               5                   10                  15

Asn Lys Thr Thr Lys Lys Glu Ser Lys Ile Tyr Asp Tyr Tyr Leu Lys
            20                  25                  30

Ala Ser Pro Glu Phe Tyr His Asn Leu Tyr Phe Lys Asn Phe Asn Val
        35                  40                  45

Gly Lys Lys Asn Leu Phe Ser Glu Lys Glu Asp Asn Glu Asn Asn Lys
    50                  55                  60

Lys Leu Gly Asn Asn Tyr Ile Ile Phe Gly Gln Asp Thr Ala Gly Ser
65                  70                  75                  80

Gly Gln Ser Gly Lys Glu Ser Asn Thr Ala Leu Glu Ser Ala Gly Thr
                85                  90                  95

Ser Asn Glu Val Ser Glu Arg Val His Val Tyr His Ile Leu Lys His
            100                 105                 110

Ile Lys Asp Gly Lys Ile Arg Met Gly Met Arg Lys Tyr Ile Asp Thr
        115                 120                 125

Gln Asp Val Asn Lys Lys His Ser Cys Thr Arg Ser Tyr Ala Phe Asn
    130                 135                 140

Pro Glu Asn Tyr Glu Lys Cys Val Asn Leu Cys Asn Val Asn Trp Lys
145                 150                 155                 160

Thr Cys Glu Glu Lys Thr Ser Pro Gly Leu Cys Leu Ser Lys Leu Asp
                165                 170                 175

Thr Asn Asn Glu Cys Tyr Phe Cys Tyr Val
            180                 185
```

<210> SEQ ID NO 73
<211> LENGTH: 2067
<212> TYPE: DNA
<213> ORGANISM: Artificial Sequence
<220> FEATURE:
<223> OTHER INFORMATION: SUB1

<400> SEQUENCE: 73

```
atgatgctca ataaaaaagt tgttgctttg tgcacactta ccttacatct tttttgtata     60

tttctatgtc taggaaagga agtaaggtct gaagaaaatg ggaaaataca agatgatgct    120

aaaaagattg ttagcgaatt acgattccta gaaaaagtag aagatgttat tgaaaagagt    180

aacataggag ggaatgaggt agatgccgat gaaaattcat ttaatccgga tactgaggtt    240

cccatagaag agatagaaga aataaaaatg agggaactga aagatgtaaa ggaagaaaaa    300

aataaaaatg acaaccataa taataataat aataatatta gtagtagtag tagtagtagt    360

agtaatactt ttggtgaaga aaaagaagaa gtatctaaga aaaaaaaaaa gttaagactt    420

atagttagcg agaatcatgc aactaccccc tcgtttttcc aagaatccct tttagaacct    480

gatgttttat cctttttaga aagtaaaggg aatttgtcca acttgaaaaa tatcaattct    540

atgattatag aactaaagga agatacaacg gatgatgaat taatatctta tattaaaatt    600

cttgaggaga agggagcttt gattgaatca gataaattag tgagtgcaga taatattgat    660

ataagtggta taaaagatgc tataagaaga ggtgaagaaa atattgatgt taatgattat    720
```

-continued

```
aaaagtatgt tagaagtcga aaatgatgct gaagattatg ataaaatgtt tggtatgttt    780

aatgaatcac atgctgcaac atctaaaagg aaacgccatt caacaaatga gcgtggatat    840

gatacatttt catcaccttc atataagaca tattcaaaaa gtgattattt atatgatgat    900

gataataata ataataatta ttattatagt catagtagta atggtcataa tagtagtagt    960

cgtaatagta gtagtagtcg tagtagacca ggtaaatatc atttcaatga tgaatttcgt   1020

aatttgcaat ggggtttaga tttatccaga ttagatgaaa cacaagaatt aattaacgaa   1080

catcaagtga tgagtactcg tatatgtgtt atagatagtg gtattgatta taatcatccc   1140

gatttaaaag ataatattga attaaattta aaagaattac atggaaggaa aggttttgat   1200

gatgataata atggtatagt tgatgatata tatggtgcta attttgtaaa taattcagga   1260

aacccgatgg atgataatta tcatggtact catgtatcag gaattatatc tgccatagga   1320

aataataata taggtgttgt aggtgttgat gtaaattcaa aattaattat ttgtaaagca   1380

ttagatgaac ataaattagg aagattagga gatatgttca aatgtttaga ttattgtata   1440

agtagaaatg cacatatgat aaatggaagc ttttcatttg atgaatatag tggtattttt   1500

aattcttctg tagaatattt acaaagaaaa ggtatcctct tttttgtatc tgcaagtaat   1560

tgtagtcatc ctaaatcgtc aacaccagat attagaaaat gtgatttatc cataaatgca   1620

aaatatcccc ctatcttatc tactgtttat gataatgtta tatctgttgc taatttaaaa   1680

aaaaatgata ataataatca ttattcatta tccattaatt ctttttatag caataaatat   1740

tgtcaactag ctgcaccagg aactaatata tattctactg ctccacataa ttcatatcga   1800

aaattaaatg gtacatctat ggctgctcca catgtagctg caatagcatc actcatattt   1860

tctattaatc ctgacttatc atataaaaaa gttatacaaa tattaaaaga ttctattgta   1920

tatctccctt ccttaaaaaa tatggttgca tgggcaggat atgcagatat aaataaggca   1980

gtcaatttag ccataaaatc aaaaaaaaca tatatcaatt ctaatatatc taacaagtgg   2040

aaaaaaaaaa gtagatattt gcattaa                                        2067
```

```
<210> SEQ ID NO 74
<211> LENGTH: 688
<212> TYPE: PRT
<213> ORGANISM: Artificial Sequence
<220> FEATURE:
<223> OTHER INFORMATION: SUB1

<400> SEQUENCE: 74

Met Met Leu Asn Lys Lys Val Val Ala Leu Cys Thr Leu Thr Leu His
1               5                   10                  15

Leu Phe Cys Ile Phe Leu Cys Leu Gly Lys Glu Val Arg Ser Glu Glu
            20                  25                  30

Asn Gly Lys Ile Gln Asp Asp Ala Lys Lys Ile Val Ser Glu Leu Arg
        35                  40                  45

Phe Leu Glu Lys Val Glu Asp Val Ile Glu Lys Ser Asn Ile Gly Gly
    50                  55                  60

Asn Glu Val Asp Ala Asp Glu Asn Ser Phe Asn Pro Asp Thr Glu Val
65                  70                  75                  80

Pro Ile Glu Glu Ile Glu Glu Ile Lys Met Arg Glu Leu Lys Asp Val
                85                  90                  95

Lys Glu Glu Lys Asn Lys Asn Asp Asn His Asn Asn Asn Asn Asn Asn
            100                 105                 110

Ile Ser Ser Ser Ser Ser Ser Ser Ser Asn Thr Phe Gly Glu Glu Lys
        115                 120                 125
```

```
Glu Glu Val Ser Lys Lys Lys Lys Lys Leu Arg Leu Ile Val Ser Glu
    130                 135                 140

Asn His Ala Thr Thr Pro Ser Phe Phe Gln Glu Ser Leu Leu Glu Pro
145                 150                 155                 160

Asp Val Leu Ser Phe Leu Glu Ser Lys Gly Asn Leu Ser Asn Leu Lys
                165                 170                 175

Asn Ile Asn Ser Met Ile Ile Glu Leu Lys Glu Asp Thr Thr Asp Asp
            180                 185                 190

Glu Leu Ile Ser Tyr Ile Lys Ile Leu Glu Glu Lys Gly Ala Leu Ile
        195                 200                 205

Glu Ser Asp Lys Leu Val Ser Ala Asp Asn Ile Asp Ile Ser Gly Ile
    210                 215                 220

Lys Asp Ala Ile Arg Arg Gly Glu Glu Asn Ile Asp Val Asn Asp Tyr
225                 230                 235                 240

Lys Ser Met Leu Glu Val Glu Asn Asp Ala Glu Asp Tyr Asp Lys Met
                245                 250                 255

Phe Gly Met Phe Asn Glu Ser His Ala Ala Thr Ser Lys Arg Lys Arg
            260                 265                 270

His Ser Thr Asn Glu Arg Gly Tyr Asp Thr Phe Ser Ser Pro Ser Tyr
        275                 280                 285

Lys Thr Tyr Ser Lys Ser Asp Tyr Leu Tyr Asp Asp Asp Asn Asn Asn
    290                 295                 300

Asn Asn Tyr Tyr Tyr Ser His Ser Ser Asn Gly His Asn Ser Ser Ser
305                 310                 315                 320

Arg Asn Ser Ser Ser Ser Arg Ser Arg Pro Gly Lys Tyr His Phe Asn
                325                 330                 335

Asp Glu Phe Arg Asn Leu Gln Trp Gly Leu Asp Leu Ser Arg Leu Asp
            340                 345                 350

Glu Thr Gln Glu Leu Ile Asn Glu His Gln Val Met Ser Thr Arg Ile
        355                 360                 365

Cys Val Ile Asp Ser Gly Ile Asp Tyr Asn His Pro Asp Leu Lys Asp
    370                 375                 380

Asn Ile Glu Leu Asn Leu Lys Glu Leu His Gly Arg Lys Gly Phe Asp
385                 390                 395                 400

Asp Asp Asn Asn Gly Ile Val Asp Asp Ile Tyr Gly Ala Asn Phe Val
                405                 410                 415

Asn Asn Ser Gly Asn Pro Met Asp Asp Asn Tyr His Gly Thr His Val
            420                 425                 430

Ser Gly Ile Ile Ser Ala Ile Gly Asn Asn Asn Ile Gly Val Val Gly
        435                 440                 445

Val Asp Val Asn Ser Lys Leu Ile Ile Cys Lys Ala Leu Asp Glu His
    450                 455                 460

Lys Leu Gly Arg Leu Gly Asp Met Phe Lys Cys Leu Asp Tyr Cys Ile
465                 470                 475                 480

Ser Arg Asn Ala His Met Ile Asn Gly Ser Phe Ser Phe Asp Glu Tyr
                485                 490                 495

Ser Gly Ile Phe Asn Ser Ser Val Glu Tyr Leu Gln Arg Lys Gly Ile
            500                 505                 510

Leu Phe Phe Val Ser Ala Ser Asn Cys Ser His Pro Lys Ser Ser Thr
        515                 520                 525

Pro Asp Ile Arg Lys Cys Asp Leu Ser Ile Asn Ala Lys Tyr Pro Pro
    530                 535                 540
```

```
Ile Leu Ser Thr Val Tyr Asp Asn Val Ile Ser Val Ala Asn Leu Lys
545                 550                 555                 560

Lys Asn Asp Asn Asn Asn His Tyr Ser Leu Ser Ile Asn Ser Phe Tyr
                565                 570                 575

Ser Asn Lys Tyr Cys Gln Leu Ala Ala Pro Gly Thr Asn Ile Tyr Ser
            580                 585                 590

Thr Ala Pro His Asn Ser Tyr Arg Lys Leu Asn Gly Thr Ser Met Ala
        595                 600                 605

Ala Pro His Val Ala Ala Ile Ala Ser Leu Ile Phe Ser Ile Asn Pro
    610                 615                 620

Asp Leu Ser Tyr Lys Lys Val Ile Gln Ile Leu Lys Asp Ser Ile Val
625                 630                 635                 640

Tyr Leu Pro Ser Leu Lys Asn Met Val Ala Trp Ala Gly Tyr Ala Asp
                645                 650                 655

Ile Asn Lys Ala Val Asn Leu Ala Ile Lys Ser Lys Lys Thr Tyr Ile
            660                 665                 670

Asn Ser Asn Ile Ser Asn Lys Trp Lys Lys Lys Ser Arg Tyr Leu His
        675                 680                 685


<210> SEQ ID NO 75
<211> LENGTH: 2562
<212> TYPE: DNA
<213> ORGANISM: Artificial Sequence
<220> FEATURE:
<223> OTHER INFORMATION: PKG (cGMP-dependent protein kinase)

<400> SEQUENCE: 75

atggaagaag atgataatct aaaaaaaggg aatgaaagaa ataaaaagaa ggctatattt     60

tcaaatgatg attttacagg agaagatagt ttaatggagg atcatttaga acttcgggaa    120

aagctttcag aagatattga tatgataaag acttccttaa aaaataatct agtttgtagt    180

acattaaacg ataatgaaat attgactctg tctaattata tgcaattctt tgtttttaaa    240

agtggaaatt tagtaataaa acaaggggaa aaagggtcat actttttcat tattaatagt    300

ggcaaatttg acgtttatgt aaatgataaa aaagtaaaga ctatgggaaa aggtagttct    360

ttcggtgaag ctgctttaat tcataatacc caaagaagtg caactattat tgcagaaact    420

gatggaactc tatggggagt tcaaagaagt acatttagag ctaccctaaa acaattatct    480

aatagaaatt ttaacgaaaa cagaacattt atcgattccg tttcagtttt tgatatgtta    540

actgaagcac aaaaaaacat gattactaat gcttgtgtaa tacaaaactt taaatctggt    600

gaaaccattg ttaaacaagg agattatgga gatgtcttat acattttgaa agaaggaaag    660

gctacagtat atattaacga tgaagagata agggttttag agaaaggttc ctattttggg    720

gaaagagctc tactgtatga tgaaccaaga agtgcaacaa tcattgcaaa agaaccaacc    780

gcttgtgcat ccatttgtag gaaattatta aatattgttc taggaaactt acaagtagtt    840

ttatttcgta atattatgac tgaagcttta caacagagtg aaatttttaa acaatttagt    900

ggggatcaat taaacgattt agcagatacc gccattgttc gagattatcc agctaattat    960

aatatattac ataaggataa ggtaaaatcc gttaaatata ttattgtatt ggaaggtaaa   1020

gtagaattat ttcttgatga tacttctatt ggtatattat ccagaggaat gtcttttgga   1080

gatcaatatg tattaaatca gaaacaacca tttaagcata ctattaaatc attagaagtt   1140

tgtaaaatcg cattaataac ggaaacttgt ttagctgatt gtctaggaaa taataatatt   1200

gatgcatcta ttgattataa taataaaaaa agtattataa agaaaatgta tatctttaga   1260
```

```
tacttaactg ataaacaatg taatttatta attgaagctt ttagaaccac aagatatgaa   1320

gaaggtgatt atataataca agaaggagaa gtaggatcta gattttatat aataaaaaat   1380

ggagaagtag aaatagtaaa aaataaaaaa aggttacgta ccttaggaaa gaatgattac   1440

tttggtgaaa gagctttatt atatgatgaa ccaagaacag cttctgttat aagtaaagta   1500

aataatgttg aatgttggtt tgttgataaa agtgtgtttt tacaaattat acaaggacct   1560

atgttagcac atttggaaga aagaataaaa atgcaagata ctaaagtaga aatggatgaa   1620

ctagaaacag aacgaattat tggaagaggt actttcggaa cagttaaatt agttcatcat   1680

aaaccaacaa aaataagata tgctttaaaa tgtgttagta aaagaagtat tattaattta   1740

aatcaacaaa acaatataaa attagaaaga gaaataacag cagaaaatga tcatccattt   1800

attataagat tagtaagaac atttaaagat tctaaatatt tctattttct aacagaatta   1860

gtaacaggtg gagaattata tgatgctatt agaaaattag gtttattatc taaatcacaa   1920

gctcaatttt atttaggttc tatcatttta gctattgaat atttacatga aagaaatatt   1980

gtatatagag atttaaaacc agaaaacatt ttattagata aacaaggtta tgtaaaacta   2040

atcgattttg gttgtgccaa aaaggtacaa ggtagagctt atacattagt aggtacacct   2100

cattatatgg cacctgaggt tattttagga aaaggttatg gatgtactgt tgacatatgg   2160

gcattgggaa tatgcctata tgaatttata tgtggtccat taccatttgg taatgatgaa   2220

gaagatcaat tagaaatttt ccgtgatata ttaaccggcc aacttacatt tccagattat   2280

gtaacagaca cagatagcat aaatttgatg aaaagacttc tatgtagatt acctcaagga   2340

agaattggtt gttcaataaa tggcttcaaa gacataaagg atcacccatt tttctcaaac   2400

tttaattggg ataaattggc tggtcgtttg cttgatccgc ctttagtatc aaaaagtgaa   2460

acttatgcag aagatattga tattaaacaa atagaggagg aggatgctga ggatgatgag   2520

gaaccattga acgatgaaga caactgggac atagattttt aa                      2562
```

<210> SEQ ID NO 76
<211> LENGTH: 853
<212> TYPE: PRT
<213> ORGANISM: Artificial Sequence
<220> FEATURE:
<223> OTHER INFORMATION: PKG (cGMP-dependent protein kinase)

<400> SEQUENCE: 76

```
Met Glu Glu Asp Asp Asn Leu Lys Lys Gly Asn Glu Arg Asn Lys Lys
1               5                   10                  15

Lys Ala Ile Phe Ser Asn Asp Asp Phe Thr Gly Glu Asp Ser Leu Met
            20                  25                  30

Glu Asp His Leu Glu Leu Arg Glu Lys Leu Ser Glu Asp Ile Asp Met
        35                  40                  45

Ile Lys Thr Ser Leu Lys Asn Asn Leu Val Cys Ser Thr Leu Asn Asp
    50                  55                  60

Asn Glu Ile Leu Thr Leu Ser Asn Tyr Met Gln Phe Phe Val Phe Lys
65                  70                  75                  80

Ser Gly Asn Leu Val Ile Lys Gln Gly Glu Lys Gly Ser Tyr Phe Phe
                85                  90                  95

Ile Ile Asn Ser Gly Lys Phe Asp Val Tyr Val Asn Asp Lys Lys Val
            100                 105                 110

Lys Thr Met Gly Lys Gly Ser Ser Phe Gly Glu Ala Ala Leu Ile His
        115                 120                 125
```

```
Asn Thr Gln Arg Ser Ala Thr Ile Ile Ala Glu Thr Asp Gly Thr Leu
    130                 135                 140

Trp Gly Val Gln Arg Ser Thr Phe Arg Ala Thr Leu Lys Gln Leu Ser
145                 150                 155                 160

Asn Arg Asn Phe Asn Glu Asn Arg Thr Phe Ile Asp Ser Val Ser Val
                165                 170                 175

Phe Asp Met Leu Thr Glu Ala Gln Lys Asn Met Ile Thr Asn Ala Cys
            180                 185                 190

Val Ile Gln Asn Phe Lys Ser Gly Glu Thr Ile Val Lys Gln Gly Asp
        195                 200                 205

Tyr Gly Asp Val Leu Tyr Ile Leu Lys Glu Gly Lys Ala Thr Val Tyr
    210                 215                 220

Ile Asn Asp Glu Glu Ile Arg Val Leu Glu Lys Gly Ser Tyr Phe Gly
225                 230                 235                 240

Glu Arg Ala Leu Leu Tyr Asp Glu Pro Arg Ser Ala Thr Ile Ile Ala
                245                 250                 255

Lys Glu Pro Thr Ala Cys Ala Ser Ile Cys Arg Lys Leu Leu Asn Ile
            260                 265                 270

Val Leu Gly Asn Leu Gln Val Val Leu Phe Arg Asn Ile Met Thr Glu
        275                 280                 285

Ala Leu Gln Gln Ser Glu Ile Phe Lys Gln Phe Ser Gly Asp Gln Leu
    290                 295                 300

Asn Asp Leu Ala Asp Thr Ala Ile Val Arg Asp Tyr Pro Ala Asn Tyr
305                 310                 315                 320

Asn Ile Leu His Lys Asp Lys Val Lys Ser Val Lys Tyr Ile Ile Val
                325                 330                 335

Leu Glu Gly Lys Val Glu Leu Phe Leu Asp Asp Thr Ser Ile Gly Ile
            340                 345                 350

Leu Ser Arg Gly Met Ser Phe Gly Asp Gln Tyr Val Leu Asn Gln Lys
        355                 360                 365

Gln Pro Phe Lys His Thr Ile Lys Ser Leu Glu Val Cys Lys Ile Ala
    370                 375                 380

Leu Ile Thr Glu Thr Cys Leu Ala Asp Cys Leu Gly Asn Asn Asn Ile
385                 390                 395                 400

Asp Ala Ser Ile Asp Tyr Asn Asn Lys Lys Ser Ile Ile Lys Lys Met
                405                 410                 415

Tyr Ile Phe Arg Tyr Leu Thr Asp Lys Gln Cys Asn Leu Leu Ile Glu
            420                 425                 430

Ala Phe Arg Thr Thr Arg Tyr Glu Glu Gly Asp Tyr Ile Ile Gln Glu
        435                 440                 445

Gly Glu Val Gly Ser Arg Phe Tyr Ile Ile Lys Asn Gly Glu Val Glu
    450                 455                 460

Ile Val Lys Asn Lys Lys Arg Leu Arg Thr Leu Gly Lys Asn Asp Tyr
465                 470                 475                 480

Phe Gly Glu Arg Ala Leu Leu Tyr Asp Glu Pro Arg Thr Ala Ser Val
                485                 490                 495

Ile Ser Lys Val Asn Asn Val Glu Cys Trp Phe Val Asp Lys Ser Val
            500                 505                 510

Phe Leu Gln Ile Ile Gln Gly Pro Met Leu Ala His Leu Glu Glu Arg
        515                 520                 525

Ile Lys Met Gln Asp Thr Lys Val Glu Met Asp Glu Leu Glu Thr Glu
    530                 535                 540
```

```
Arg Ile Ile Gly Arg Gly Thr Phe Gly Thr Val Lys Leu Val His His
545                 550                 555                 560

Lys Pro Thr Lys Ile Arg Tyr Ala Leu Lys Cys Val Ser Lys Arg Ser
                565                 570                 575

Ile Ile Asn Leu Asn Gln Gln Asn Asn Ile Lys Leu Glu Arg Glu Ile
            580                 585                 590

Thr Ala Glu Asn Asp His Pro Phe Ile Ile Arg Leu Val Arg Thr Phe
        595                 600                 605

Lys Asp Ser Lys Tyr Phe Tyr Phe Leu Thr Glu Leu Val Thr Gly Gly
    610                 615                 620

Glu Leu Tyr Asp Ala Ile Arg Lys Leu Gly Leu Leu Ser Lys Ser Gln
625                 630                 635                 640

Ala Gln Phe Tyr Leu Gly Ser Ile Ile Leu Ala Ile Glu Tyr Leu His
                645                 650                 655

Glu Arg Asn Ile Val Tyr Arg Asp Leu Lys Pro Glu Asn Ile Leu Leu
            660                 665                 670

Asp Lys Gln Gly Tyr Val Lys Leu Ile Asp Phe Gly Cys Ala Lys Lys
        675                 680                 685

Val Gln Gly Arg Ala Tyr Thr Leu Val Gly Thr Pro His Tyr Met Ala
    690                 695                 700

Pro Glu Val Ile Leu Gly Lys Gly Tyr Gly Cys Thr Val Asp Ile Trp
705                 710                 715                 720

Ala Leu Gly Ile Cys Leu Tyr Glu Phe Ile Cys Gly Pro Leu Pro Phe
                725                 730                 735

Gly Asn Asp Glu Glu Asp Gln Leu Glu Ile Phe Arg Asp Ile Leu Thr
            740                 745                 750

Gly Gln Leu Thr Phe Pro Asp Tyr Val Thr Asp Thr Asp Ser Ile Asn
        755                 760                 765

Leu Met Lys Arg Leu Leu Cys Arg Leu Pro Gln Gly Arg Ile Gly Cys
    770                 775                 780

Ser Ile Asn Gly Phe Lys Asp Ile Lys Asp His Pro Phe Phe Ser Asn
785                 790                 795                 800

Phe Asn Trp Asp Lys Leu Ala Gly Arg Leu Leu Asp Pro Pro Leu Val
                805                 810                 815

Ser Lys Ser Glu Thr Tyr Ala Glu Asp Ile Asp Ile Lys Gln Ile Glu
            820                 825                 830

Glu Glu Asp Ala Glu Asp Asp Glu Glu Pro Leu Asn Asp Glu Asp Asn
        835                 840                 845

Trp Asp Ile Asp Phe
    850


<210> SEQ ID NO 77
<211> LENGTH: 88
<212> TYPE: PRT
<213> ORGANISM: Artificial Sequence
<220> FEATURE:
<223> OTHER INFORMATION: peptide fragment

<400> SEQUENCE: 77

Asp Tyr Thr Glu Phe Leu Ala Ala Cys Leu Asp His Ser Ile Phe Gln
1               5                   10                  15

Gln Asp Val Ile Cys Arg Asn Ala Phe Asn Val Phe Asp Leu Asp Gly
            20                  25                  30

Asp Gly Val Ile Thr Lys Asp Glu Leu Phe Lys Ile Leu Ser Phe Ser
        35                  40                  45
```

-continued

```
Ala Val Gln Val Ser Phe Ser Lys Glu Ile Ile Glu Asn Leu Ile Lys
    50                  55                  60

Glu Val Asp Ser Asn Asn Asp Gly Phe Ile Asp Tyr Asp Glu Phe Tyr
65                  70                  75                  80

Lys Met Met Thr Gly Val Lys Glu
                85
```

VACCINE FOR FALCIPARUM MALARIA

REFERENCE TO RELATED APPLICATIONS

This application is a continuation of U.S. application Ser. No. 16/283,472 filed on Feb. 22, 2019, which is a divisional application of U.S. application Ser. No. 15/607,203 filed on May 26, 2017 (now, U.S. Pat. No. 10,213,502), which is a continuation application of U.S. application Ser. No. 14/361,573 filed on May 29, 2014 (now, U.S. Pat. No. 9,662,379), which is a national stage application, filed under 35 U.S.C. § 371, of International Application No. PCT/US2012/067404 filed on Nov. 30, 2012, which claims priority to U.S. Provisional Application No. 61/641,445, filed May 2, 2012 and U.S. Provisional Application No. 61/566,365, filed Dec. 2, 2011, the contents of each are hereby incorporated by reference in their entireties.

STATEMENT AS TO FEDERALLY SPONSORED RESEARCH

This invention was made with government support under Grant No. AI076353 awarded by the National Institutes of Health. The Government has certain rights in the invention.

INCORPORATION OF SEQUENCE LISTING

The contents of the text file named "021486-607D02US_Sequence Listing_ST25.txt", which was created on Feb. 6, 2019 and is 232 KB in size, are hereby incorporated by reference in their entireties.

FIELD OF THE INVENTION

The invention relates generally to the field of malaria vaccines.

BACKGROUND OF THE INVENTION

Malaria is a mosquito-borne infectious disease caused by a parasite. At least four species of malaria parasites can infect humans under natural conditions: *Plasmodium falciparum* (*P. falciparum*), *P. vivax, P. ovale* and *P. malariae*. The first two species cause the most infections worldwide. *P. vivax* and *P. ovale* have dormant liver stage parasites (hypnozoites) that can reactivate (or "relapse") and cause malaria several months or years after the infecting mosquito bite; consequently, these species can be difficult to detect in infected individuals. Severe disease is largely caused by *P. falciparum* while the disease caused by *P. vivax, P. ovale*, and *P. malariae* is generally a milder disease that is rarely fatal.

In humans, the parasites grow and multiply first in the liver cells and then in the red blood cells. In the blood, successive broods of parasites grow inside the red cells and destroy them, releasing daughter parasites (merozoites) that continue the cycle by invading other red cells. The blood stage parasites cause the symptoms of malaria. When certain forms of blood stage parasites, gametocytes, are picked up by a female *Anopheles* mosquito during a blood meal, they start another, different cycle of growth and multiplication in the mosquito. After 10-18 days, the parasites are found as sporozoites in the mosquito's salivary glands. When the *Anopheles* mosquito takes a blood meal from another human, the sporozoites are injected with the mosquito's saliva and start another human infection when they parasitize the liver cells.

Infection with malaria parasites can result in a wide variety of symptoms, typically including fever and headache, in severe cases progressing to coma or death. There were an estimated 225 million cases of malaria worldwide in 2009. An estimated 781,000 people died from malaria in 2009 according to the World Health Organization's 2010 World Malaria Report, accounting for 2.23% of deaths worldwide. Ninety percent of malaria-related deaths occur in sub-Saharan Africa, with the majority of deaths being young children. *Plasmodium falciparum*, the most severe form of malaria, is responsible for the vast majority of deaths associated with the disease. Children suffer the greatest morbidity and mortality from malaria, yet this age group has not been targeted at the identification stage of vaccine development. Of the 100 vaccine candidates currently under investigation, more than 60% are based on only four parasite antigens—a fact that has caused considerable concern. New antigen candidates are urgently needed.

SUMMARY OF THE INVENTION

The vaccine of the invention successfully and surprisingly elicits an immune response that blocks the Schizont rupture of RBCs (parasite egress from RBCs), therefore protecting vaccinated individuals from severe malaria. The vaccines elicit a strong antibody response to the vaccine antigen, such as PfSEP1 or PfSEP-1A. Due to the permeability of parasitized red blood cells (RBCs) at the later stages of schizogony, antibodies gain access into the infected RBCs. Antibodies to the vaccine antigen, e.g., a Schizont Egress Protein (SEP) such as PfSEP-1A (SEQ ID NO:2, and other antigenic fragments of the whole protein PfSEP-1 (SEQ ID NO:3)) decrease parasite replication by at least 10% (e.g., 20, 40, 60%, 70% or more) by arresting schizont rupture.

Accordingly, the invention features a vaccine for preventing or reducing the severity of malaria comprising a composition that leads to inhibition of parasite egress from red blood cells or inhibits parasite egress. For example, the composition comprises a purified polypeptide comprising the amino acid sequence of SEQ ID NO:2 or a purified nucleic acid encoding a gene product that comprises the amino acid sequence of SEQ ID NO:2. The vaccine contains one or more compositions of a class of proteins that are involved in schizont egress such as PfSEP-1/1A (SEQ ID NO:3, 2, respectively), PbSEP-1/1A (SEQ ID NO:67, 68, respectively), PfCDPK5 (SEQ ID NO:47), SERA5 (SEQ ID NO:70, 72), PfSUB1 (SEQ ID NO:74), or PfPKG (SEQ ID NO:76). An immune response elicited by immunization with these vaccine antigens inhibits schizont egress. For example, the composition comprises a purified antigen that elicits an anti-PfSEP-1 antibody response. Alternatively, a passive immunization approach is used. In the latter case, the composition comprises a purified antibody that specifically binds to one or more of the vaccine antigens that are involved in schizont egress (listed above). For example, the composition comprises an anti-PfSEP-1 antibody or antigen binding fragment thereof. Thus, a method for preventing or reducing the severity of malaria is carried out by administering to a subject a composition that inhibits parasite egress from red blood cells.

The invention also includes a vaccine for preventing or reducing the severity of malaria comprising a polypeptide composition, wherein the polypeptide comprising an amino acid sequence selected from the group consisting of SEQ ID NO: 2, 10, 14, 18, 22, 26, 30, 34, 38, 42, and 46, 66 and 72 (antigenic polypeptides or protein fragments). A vaccine for preventing or reducing the severity of malaria comprising a polypeptide composition comprising whole protein antigens such as proteins comprising the following amino acid sequences: SEQ ID NO: 3, 8, 11, 15, 19, 22, 27, 31, 35, 39, 43, 47, 67, 70, 74, and/or 76.

In a preferred embodiment, the invention features an isolated peptide comprising a peptide having at least 90%, 95% or 99% identity with the sequence of SEQ ID NO: 2; a peptide encoded by a nucleic acid sequence having at least 90%, 95% or 99% identity with the sequence of SEQ ID NO: 1, or a fragment thereof in a vaccine composition for treatment or prevention of P. falciparum malaria. Alternatively, the isolated peptide of the present invention can be a peptide of SEQ ID NO: 3, a peptide encoded by a nucleic acid of SEQ ID NO: 4, or a fragment thereof.

The present invention also features an isolated nucleic acid sequence comprising a nucleic acid sequence having at least 90%, 95% or 99% identity with the sequence of SEQ ID NO: 1 or SEQ ID NO: 4, or any fragment thereof in a vaccine composition for treatment or prevention of P. falciparum malaria.

Antigens for use in a malaria vaccine include one or more of the following polypeptides (or fragments thereof) that elicit a clinically relevant decrease in the severity of the disease or that reduce/prevent infection or spread of parasites, reduce or inhibit parasite egress from a red blood cell (RBC), reduce or inhibit gametocyte egress (thereby reducing/inhibiting human→mosquito transmission), elicit a parasite-specific antibody or cellular immune response or nucleotides encoding such polypeptides/fragments: SEQ ID NO: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76. For example, the vaccine composition comprises polypeptides (or nucleic acids encoding them) comprising the following sequences: SEQ ID NO: 2, 10, 14, 18, 22, 26, 30, 34, 38, 42, 46, 47, 66, 67, 70, 72, 74, and/or 76.

Also provided herein is a vector or a host cell expressing one or more isolated peptides or one or more isolated nucleic acid sequences described herewith.

Another aspect of the present invention relates to a vaccine composition. The vaccine composition contains one or more isolated peptides or one or more isolated nucleic acid sequences described herewith. The peptide vaccine may also contain an adjuvant. Exemplary adjuvants include aluminum salts, such as aluminum phosphate and aluminum hydroxide. Another exemplary adjuvant is an oil adjuvant such as the Montanide ISA series, e.g., ISA 50 V2 or ISA 720 VG. The DNA vaccine contains a eukaryotic vector to direct/control expression of the antigen in the subject to be treated.

The vaccine of the present invention provides a new regimen in treating or preventing P. falciparum malaria in a subject. Accordingly, the present invention further provides a method of treating or preventing P. falciparum malaria in a subject in need by administering the vaccine to the subject. Preferably, the subject is a child under 5 years of age. More preferably, the subject is at least about 6-8 weeks of age. The vaccine is also suitable for administration to older children or adults. The vaccine can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. Preferably, the vaccine is administered intramuscularly. The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The vaccine of the present invention can be administered intramuscularly once every two weeks for 1, 2, 3, 4, or more times alone or in combination with 1, 2, 3, 4, or more additional vaccines in a subject, preferably a human subject. One exemplary additional vaccine contains an inhibitor of parasite liver invasion, such as RTS,S (Mosquirix). Another exemplary additional vaccine contains an inhibitor of parasite red blood cell invasion, such as MSP-1. The vaccine can be made by any known method in the art.

Also provided herein are an antibody that specifically binds to an antigen comprising the isolated peptide of the present invention and a method of treating P. falciparum malaria in a subject in need of by administering a therapeutically effective amount of such antibody to the subject. The P. falciparum malaria can be acute P. falciparum malaria.

Also provided herein is a method of treating P. falciparum malaria in a subject in need of by administering a therapeutically effective amount of an antibody described herewith to the subject. Preferably, the antibody is a purified monoclonal antibody, e.g., one that has been raised to and is specific for the protein of SEQ ID NO:2. For example, the monoclonal antibody is a humanized antibody. The treatment can be initiated at an early stage after the appearance of recrudescent parasites. The symptoms of the subject may be mild or absent and parasitemia is low but increasing, for example from range 4,000-10,000/ul. Alternative, the subject may have fever <38.5° C. without any other accompanying symptom. The subject can be a child under 10 years of age. The subject can also be an elder child or an adult. In one example, the subject is characterized as suffering from acute P. falciparum malaria but has not responded to treatment with anti-malarial drugs. In this passive immunity approach, the purified humanized monoclonal antibody that binds specifically to the protein of SEQ ID NO:2 is administered to the subject to kill the infective agent and/or inhibit RBC invasion.

The antibody can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. Preferably, the antibody is administered intravenously or intramuscularly. For example, the antibody is administered in 1-2 gram amounts, 1, 2, 3, or 4 times. The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The antibody of the present invention can be administered intravenously once, twice or three times alone or in combination with 1, 2, 3, 4, or more additional therapeutic agents in a subject, preferably a human subject. The additional therapeutic agent is, for example, one, two, three, four, or more additional vaccines or antibodies, an antimalarials artemisinin-combination therapy, or an immunotherapy. Any suitable therapeutic treatment for malaria may be administered. The additional vaccine may comprise an inhibitor of parasite liver invasion or an inhibitor of parasite RBC invasion. Such additional vaccines include, but are not limited to, anti-RBC invasion vaccines (MSP-1), RTS,S (Mosquirix), NYVAC-Pf7, CSP, and [NANP]19-5.1. The antibody of the invention can be administered prior to, concurrently, or after other therapeutic agents.

Amounts effective for this use will depend on, e.g., the antibody composition, the manner of administration, the stage and severity of *P. falciparum* malaria being treated, the weight and general state of health of the patient, and the judgment of the prescribing physician, but generally range for the treatment from about 10 mg/kg (weight of a subject) to 300 mg/kg, preferably 20 mg/kg-200 mg/kg.

The present invention further provides a kit for determining the presence of antibody to *P. falciparum* in a sample obtained from a subject. A "sample" is any bodily fluid or tissue sample obtained from a subject, including, but is not limited to, blood, blood serum, urine, and saliva. The kit contains an antigen or an antibody of the present invention and optionally one or more reagents for detection.

The kit may also contain a sample collection means, storage means for storing the collected sample, and for shipment. The kit further comprises instructions for use or a CD, or CD-ROM with instructions on how to collect sample, ship sample, and means to interpret test results. The kit may also contain an instruction for use to diagnose malaria or a receptacle for receiving subject derived bodily fluid or tissue.

The kit may also contain a control sample either positive or negative or a standard and/or an algorithmic device for assessing the results and additional reagents and components. The kit may further comprise one or more additional compounds to generate a detectable product.

A "vaccine" is to be understood as meaning a composition for generating immunity for the prophylaxis and/or treatment of diseases. Accordingly, vaccines are medicaments which comprise antigens and are intended to be used in humans or animals for generating specific defense and protective substance by vaccination.

A "subject" in the context of the present invention is preferably a mammal. The mammal can be a human, non-human primate, mouse, rat, dog, cat, horse, or cow, but are not limited to these examples. A subject can be male or female. A subject can be a child or an adult. A subject can be one who has been previously diagnosed or identified as having malaria, and optionally has already undergone, or is undergoing, a therapeutic intervention for the malaria. Alternatively, a subject can also be one who has not been previously diagnosed as having malaria, but who is at risk of developing such condition, e.g. due to infection or due to travel within a region in which malaria is prevalent. For example, a subject can be one who exhibits one or more symptoms for malaria.

A subject "at risk of developing malaria" in the context of the present invention refers to a subject who is living in an area where malaria is prevalent, such as the tropics and subtropics areas, or a subject who is traveling in such an area. Alternatively, a subject at risk of developing malaria can also refer to a subject who lives with or lives close by a subject diagnosed or identified as having malaria.

As used herein, an "isolated" or "purified" nucleotide or polypeptide is substantially free of other nucleotides and polypeptides. Purified nucleotides and polypeptides are also free of cellular material or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified nucleotides and polypeptides is one that is at least 90%, 91%, 92%, 93%, 94%, 95%, 98%, 99%, or 100% (w/w) of the desired nucleic acid or polypeptide by weight.

Purity is measured by any appropriate standard method, for example, by column chromatography, thin layer chromatography, or high-performance liquid chromatography (HPLC) analysis. The nucleotides and polypeptides are purified and used in a number of products for consumption by humans as well as animals, such as companion animals (dogs, cats) as well as livestock (bovine, equine, ovine, caprine, or porcine animals, as well as poultry). A purified or isolated polynucleotide (ribonucleic acid (RNA) or deoxyribonucleic acid (DNA)) is free of the genes or sequences that flank it in its naturally-occurring state. For example, the DNA is a cDNA. "Purified" also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By the terms "effective amount" and "therapeutically effective amount" of a formulation or formulation component is meant a sufficient amount of the formulation or component to provide the desired effect. For example, "an effective amount" of a vaccine is an amount of a compound required to blocking red blood cells (RBCs) rupture, block egress of parasites from RBCs, block gametocyte egress, or elicit an antibody or cellular immune response to the vaccine antigen(s). Ultimately, the attending physician or veterinarian decides the appropriate amount and dosage regimen.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps and permits those that do not materially affect the basic and the characteristic(s) of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIGS. 4A-C show that vaccination with rPbSEP-1A (recombinant SEP-1A antigenic polypeptide from *P. berghei*) protects mice from challenge with the infectious agent, e.g., *P. berghei* ANKA. A) rPbSEP-1A was expressed and purified from induced, clarified *E. coli* soluble lysates. Recombinant protein containing fractions were resolved on an 8-15% SDS PAGE-gel and stained with Gel-Code Blue. Lane 1) nickel chelate chromatography of soluble *E. coli* lysate, lane 2) hydrophobic interaction chromatography of lane 1, lane 3) anion exchange chromatography of lane 2. B) Antibody response of mice vaccinated with rPbSEP-1A. Following vaccination, mice generated high-titer anti-rPbSEP-1A IgG responses. C) Mice vaccinated with rPbSEP-1A had markedly reduced parasitemia (4.5 fold reduction on day 7 post challenge, P<0.002) and parasite growth rate compared to control mice. All control mice were euthanized on day 7 due to high parasitemia and associated illness.

FIG. 14A is a bar graph, and FIG. 14B is a photomicrograph showing that anti-rPfSEP-1A antibodies generated by protein immunization inhibit schizont egress across 2 parasite strains in vitro. A) Ring stage 3D7 (top panel), and W2 (bottom panel) parasites were synchronized three times using sorbitol, plated at 3.5% parasitemia, and cultured to obtain early schizonts. Parasites were incubated in in the presence of of anti-PfSEP-1 mouse sera (1:10 dilution). Negative controls included no mouse sera and pre-immune mouse sera (1:10 dilution). Sera was heat inactivated and dialyzed prior to use. Schizonts were enumerated at 12 hrs post-treatment. Bars represent the mean of 5 independent replicates with each replicate performed in triplicate. Error bars represent SEMs. P<0.009 for comparison between pre and post immune mouse sera by non-parametric Mann-Whitney U test. Schizontemia was 4.3-6.0 fold higher in post versus pre-immune sera treated cultures. B) Representative micrographs of giemsa stained blood films prepared from 3D7 cultures treated with pre-immune (top panel) and post-immune (bottom panel) sera.

FIG. 16 is a table showing epidemiological characteristics of resistant and susceptible individuals used in differential screening assays.

FIG. 17 is a table showing epidemiological characteristics of resistant and susceptible individuals used in confirmatory ELISA assays.

FIGS. 18A-G are photomicrographs showing the results of an immunofluorescence analysis on methanol fixed infected red blood cells (iRBCs) using mouse anti-PfSEP-1 sera.

FIG. 21 B illustrates the role of PfSEP in and protein-protein interactions involved in schizont egress.

DETAILED DESCRIPTION

Figure 1A:
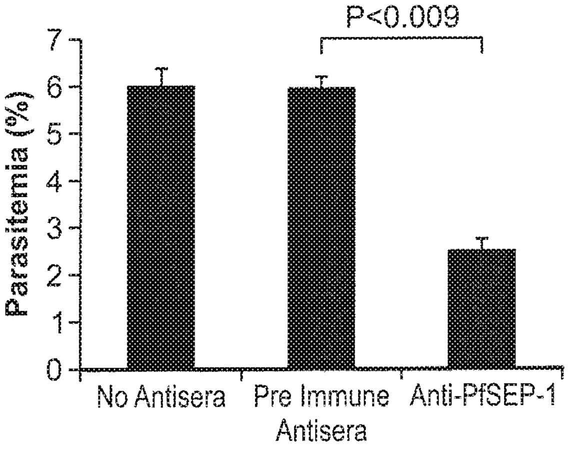
FIGS. 1A-C are bar graphs showing that anti-PfSEP-1 antibodies generated by DNA vaccination inhibit parasite growth/invasion by 58-65% across 3 parasite strains in vitro. Ring stage 3D7 (A), W2 (B) and D10 (C) parasites were synchronized three times using sorbitol, plated at 0.3-0.4% parasitemia, and cultured to obtain mature trophozoites. Mature trophozoites were cultured in the presence of anti-PfSEP-1 mouse sera (1:10 dilution). Negative controls included no mouse sera and pre-immune mouse sera (1:10 dilution). Sera was heat inactivated and dialyzed prior to use. Parasites were cultured for 24 hrs and ring stage parasites were enumerated by microscopic examination. Bars represent the mean of 5 independent replicates with each replicate performed in triplicate. Error bars represent SEMs. P<0.009 for comparison between pre and post immune mouse sera by non-parametric Mann-Whitney U test.
Figure 1B:
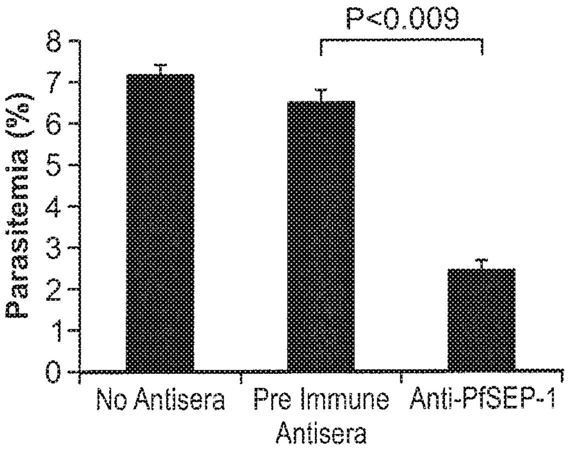
Figure 1C:
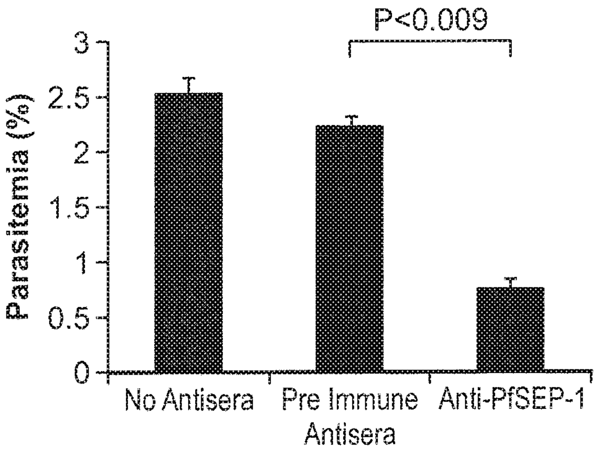

The invention represents a significant breakthrough in the treatment or prevention of malaria, for example, such as *P. falciparum* malaria. Prior to the present invention, an effective vaccine was not yet available for malaria, although several vaccines are under development. The vaccine, SPf66, was tested extensively in endemic areas in the 1990s, but clinical trials showed it to be insufficiently effective. Other vaccine candidates, targeting the blood-stage of the parasite's life cycle, such as anti-red blood cell (RBC) invasion (*P. falciparum* merozoite specific protein 1 (MSP-1) antigen and *P. falciparum* merozoites Apical Membrane Antigen 1 (AMA-1) antigen), have also been insufficient on their own. Several potential vaccines, for example, RTS,S (also called Mosquirix) targeting the pre-erythrocytic stage are being developed. One major challenge in the field is short acting time for a vaccine due to the quick infection/life cycle of the parasite. A vaccine, such as RTS,S, functioning at pre-liver stage has only 5 minutes to act before sporazoite enters hepatocytes. Anti-RBC invasion vaccines have only 15 seconds before merozoite enters RBCs.

*P. falciparum* remains a leading cause of morbidity and mortality in developing countries and vaccines for this parasite are urgently needed. Human residents of endemic areas develop protective immunity that limits parasitemia and disease. The subject invention relates to nucleic acid and polypeptide sequences designed from *P. falciparum* in a vaccine composition. The vaccine antigens were identified using a differential screening strategy using sera from resistant individuals and from susceptible ones. Antigens were identified by binding to antisera from resistant individuals were further characterized. Such nucleic acid sequences and polypeptides were found to be useful for therapeutic as well as diagnostic purposes.

Polynucleotide Sequence and Encoded Polypeptides

The invention is directed in part to *P. falciparum* polynucleotides and polypeptides that are useful, for example, for antigens for vaccines against *P. falciparum* malaria.

Human residents of endemic areas develop protective immunity that limits parasitemia and disease, and naturally acquired human immunity provides an attractive model for vaccine antigen identification. Plasma samples and parasitologic data collected during a longitudinal birth cohort study in Muheza, Tanzania (TZN) were used to identify previously unknown *P. falciparum* antigens associated with resistance during early life. The antigens were then validated as targets of antibodies associated with resistance to parasitemia in a large cohort of young children.

Using plasma obtained from maximally resistant and susceptible members of the Muheza cohort, parasite antigens recognized by host antibodies that mediate resistance to parasitemia were identified.

750,000 phage from a 3D7 based blood stage *P. falciparum* library were differentially screened using pooled plasma from the resistant and susceptible individuals. Three clones that are uniquely recognized by antibodies in the plasma of resistant but not susceptible pools were identified. These clones encode MSP-7 (MSP-7 nts 200-1,052), a unique hypothetical gene on Ch10 (Chromosome #10 bp 901175 to 900359), and a unique hypothetical gene on Ch11 (Chromosome #11 nts. 1333936 to 1335849). The gene on Ch11 has the gene ID of PF10_0212a.

Clone #2: Plasmodb.org designation:
Gene PF10_0212a (Version 9.2)

```
Nucleic acid sequence of Clone #2, 819 bp (Sequence 2,431-3,249 of
gene PF10_0212a)
AACGAGGATAGAGGAATATACGATGAATTATTAGAAAATGATATGTGTGATTTATACAATTTAAAAAT
GCATGATTTGCATAATTTAAAATCCTATGATTTTGGATTATCTAAAGATTTATTAAAAAAGGATATTT
TTATATATAGTAATAATTTGAAAAATGATGATATGGATGATGATGATAATAATAATATGAATGATATT
GCTATAGGTGAAAATGTAATATATGAAAATGATATACATGAAAATAATATAGATGATAATGATATGTA
TAATAATTACGTGAATGGAAATGATTTATATATTAACAATATGCAGGATGATGCCATGGACGATATTG
TATATGATGAGGAAGAAATTAAAAGCTTCCTAGATAAATTAAAATCTGATATATCAAATCAAATGAAT
GTAAAAAATGGAAATGTCGAAGTTACAGGAAATGGTGGTAATGAAGAAATGTCTTATATAAATAATGA
TGAAAATTTACAAGCTTTTGATTTGTTAGATAATTTCCATATGGATGATTATGGTAATAATTATAATG
ATAATGAAGAAGATGGGGATGGGGATGGGGATGACGATGAACAGAAGAAAAGAAAACAAAAAGAGTTA
CATAATGTAAATGGAAAATTAAACTTATCAGATTTAAATGAATTAAATGTAGATGATATAAATAATAA
TTTTTATATGTCAACTCCTCGAAAATCTATAGATGAACGTAAAGATACGGAATGTCAAACAGATTTTC
CCTTATTAGATGTATCAAGGAATACTAATAGGACTCCTAGAAGAAAAAGTGTGGAAGTAATACTTGTA
GAA (SEQ ID NO: 1) Sequence Length: 819

Amino acid sequence of Clone #2 (a.k.a., PfSEP-1A)
NEDRGIYDELLENDMCDLYNLKMHDLHNLKSYDFGLSKDLLKKDIFIYSNNLKNDDMDDDDNNNMNDI
AIGENVIYENDIHENNIDDNDMYNNYVNGNDLYINNMQDDAMDDIVYDEEEIKSFLDKLKSDISNQMN
VKNGNVEVTGNGGNEEMSYINNDENLQAFDLLDNFHMDDYGNNYNDNEEDGDGDGDDDEQKKRKQKEL
HNVNGKLNLSDLNELNVDDINNNFYMSTPRKSIDERKDTECQTDFPLLDVSRNTNRTPRRKSVEVILV
E (SEQ ID NO: 2) Sequence Length: 273

Amino acid sequence of PF10_0212a (PfSEP-1)
MMENKYPNELFCYINRYNINEIIENGEEKYVNEYDEDKNMSINHMNENDGICEYEIPFLL
DYVDDSNKEDSEKNSLKSYLDDGASTILSKPDELENYNKQNENEFDENNNNKNNKIDQLK
EKINIIIIPNKGVINNFEEILSMANRNDKNIEKKLNDRFYQICCKSIADINTHNLNKIKD
LKKKKNNKGSLNIEHIDYGDIFLTIHDTLKSNNKIKGNNKTNLLHDSSYEIKKKTRRGTN
IYKNPFHHRGSYLTSYENQKDIIYLNNLNNIMMDKYSNCSDSRKKEYSHFNSQEFSYDKY
SMKDRMFLKNLYMKQNRLRDKRGKYHKLGDYQNIENYRKTGEHSFDCMNMSDIMHSNKMS
HVNIMDHMIYKDNNNMSKLVDTINSREKDVKNYDDNFESYNNFFKNNNDEQHICLEYDDT
YNLKDTVKNIIVEEEQCGKGVACICDKNEDVDDLFVSKKTNYSSNKKREDYEKVFLEDNL
HLKQTPSKRTKINIIPDYYDNNRSNKSYKENEEDALFEVCGSLKNDDILYKDNKLNVINE
DNIKEEDDKESVVHLDNDEDKKEEMYKDVYPNVLSCEKETIRRNEKYNKSLNSTSSFEKI
DNPSEINVESKEDTEYFDLLIKKYEDTKINVYDNESLLLDLSNELREEMAKGDSNKNVNK
VEDNDNKKENICHDNIMEDICHNNNVEDMYRNNNVEDMYRNNNVEDMYRNNNVEDMYRNN
NVEDVCHNNNVEDVCHNNNVEDVCHNNNVEDVYHNNNVEDMYHDNNIEDVCHNNNVEDVC
HNNNVEDHVNYDNEELNKKMDEMKEEKEERNEDRGIYDELLENDMCDLYNLKMHDLHNLK
SYDFGLSKDLLKKDIFIYSNNLKNDDMDDDDNNNMNDIAIGENVIYENDIHENNIDDNDM
YNNYVNGNDLYINNMQDDAMDDIVYDEEEIKSFLDKLKSDISNQMNVKNGNVEVTGNGGN
EEMSYINNDENLQAFDLLDNFHMDDYGNNYNDNEEDGDGDGDDDEQKKRKQKELHNVNGK
LNLSDLNELNVDDINNNFYMSTPRKSIDERKDTECQTDFPLLDVSRNTNRTPRRKSVEVI
LVEKKLKKKKQKCMDKYTDANEDSNRRYPKRNRIKTLRYWIGERELTERNPYTGEIDVVG
FSECKNLQDLSPHIIGPIEYKKIYLKNLNSNEHEENEDNNGDIIENNNGDVIENNNGDII
EDNNANEKNHNNLESEGKGIVYDDVNNLHVHTNSDNSAHSKKIKGAPSRFSNTNNGRKKR
RRRKFINVVNYIKKKKKKKLIKSMDNMEVTDNFKNDMSDENKQSGDENKQSGDENKQSGD
ENKQSGDENKQTNNDIKQSDNDIKQSDDIYMNEDMNLFNDLNDNFDNNEYFINNGDKDSH
AEEEMAIENIQSKSIEKDILNNEEQDNNNIFDIDNELIDMKDGNVDEMESDEKLKTFEKL
ESLKSTTHLNNTDNCDVNLSEQTNEINYDEEKKVNKKTNHEKMKKKKKKKKKKKKKKKE
KKQIDIMYKNLSRLNLNLLLPTKKKVKKSKNSFKKEEEKQKKKNKKVKKIKGINKGEKIK
SNKKENKDNNNDSSTECVVEGEKGKDLHEFNKNGNLEDEQMDVDISMNISSINCESDNKN
VSKEGEEEKKDIAENKEEVDKNKEEVYMDKHEMDLNNEEVYMDKNEMDLNNEEVYMDKHE
MDLNNEEVYMDKHEMDLNNEEVYMDKHEMDLNKEEVYMDKHEMDLNNEEVDKENEYDENI
LSDNIIYNENNSFGNNKNSFFNNTSPLKTEIINEEENSLNEMKEDINEYVEMENKLDTEK
IKDSEKIGGKIEVDNKMISPINRHNFYLTILEGMNKNFPRQWNKNNITLSKNQGQIYKGR
KEKKRKRSYRNDEKLLDHSILNDINISDKMDERNELLESIKSNSTINNVLEIIKYDNRKK
```

-continued

| Clone #2: Plasmodb.org designation: Gene PF10_0212a (Version 9.2) |
|---|

IKKNDTNKEIIKYDNFTSKYNNKSNDIQLNGGIYINKFKLSLDMPINKLAVSSNLGPPSS
IGSTEIQPIQKNFNDFKMNINVYCIRMEPHEKYSSYSHKNNLVVYIDKGEKINIIINMSK
TYEKGDFFYIPRFSNFQIINDSRCDCVLYVCPLI (SEQ ID NO: 3) Sequence
Length: 2074 aa; underlined sequence corresponds to PfSEP-1A
antigenic fragment.

Coding Nucleotide sequence of PF10_0212a (PfSEP-1)
ATGATGGAAAATAAATACCCAAATGAATTATTCTGTTATATAAATAGATATAATATAAAC
GAAATAATAGAAAATGGAGAAGAGAAGTATGTAAATGAATATGATGAAGATAAGAATATG
TCAATAAATCATATGAATGAAAACGATGGTATATGTGAATATGAAATACCATTTTTATTA
GACTATGTGGATGATAGTAATAAAGAAGATTCAGAGAAAAATTCATTAAAGAGTTATCTC
GATGATGGTGCATCCACTATCCTTTCAAAACCAGATGAACTGGAAAATTATAATAAACAA
AATGAAAATGAATTTGACGAAAATAATAATAATAAAAATAATAAAATTGACCAATTGAAG
GAAAAAATAAATATTATAATAATACCAAATAAAGGTGTTATAAACAATTTTGAAGAGATA
TTAAGCATGGCAAATCGTAATGATAAAAATATAGAGAAAAAGTTGAATGATAGATTTTAT
CAAATATGTTGTAAAAGTATAGCTGATATAAACACACACAATTTAAATAAAATTAAAGAT
TTGAAAAAAAAAAAAAATAATAAAGGATCCTTAAATATTGAACATATAGATTATGGAGAT
ATTTTTCTTACTATACATGATACATTAAAAAGTAATAATAAAATAAAAGGAAACAATAAA
ACTAACTTATTACACGATTCTTCTTATGAAATAAAAAAGAAAACAAGAAGAGGAACAAAT
ATATATAAAAATCCATTTCATCATAGAGGTTCCTATTTAACTTCGTATGAAAATCAAAAG
GATATCATTTACCTTAATAATTTAAACAACATTATGATGGATAAATATAGTAATTGTAGT
GATTCACGAAAAAAGGAATATTCGCATTTCAATTCGCAGGAGTTTTCATATGATAAATAT
AGTATGAAAGACAGAATGTTTCTCAAAAATTTGTATATGAAACAAAATAGATTAAGAGAT
AAAAGGGGGAAATATCACAAATTGGGAGATTATCAAAATATTGAAAACTATCGTAAAACG
GGTGAACATAGTTTTGATTGTATGAATATGTCAGATATTATGCATTCAAATAAAATGAGC
CATGTTAATATCATGGATCATATGATATATAAAGATAATAACAATATGAGCAAACTAGTA
GATACAATAAATTCTCGTGAAAAGGATGTAAAAAATTATGACGATAACTTTGAAAGCTAT
AATAATTTTTTTAAGAATAATAATGATGAACAACATATATGTTTGGAGTATGACGATACA
TATAACTTAAAAGATACAGTTAAAAATATTATTGTTGAAGAAGAACAATGTGGTAAGGGT
GTTGCTTGTATATGTGATAAGAACGAAGATGTTGACGATTTGTTTGTTTCAAAGAAAACG
AATTATTCTTCTAATAAAAAAAGAGAAGATTATGAGAAAGTATTTCTTGAAGATAATTTA
CATTTAAAACAAACTCCATCAAAAAGAACAAAAATTAATATAATCCCAGATTATTATGAT
AACAATAGAAGTAATAAGAGTTATAAGGAAAATGAAGAGGATGCTTTGTTTGAGGTATGT
GGTAGTTTAAAAAACGATGATATATTGTATAAAGATAATAAGTTGAATGTCATAAATGAA
GATAATATAAAGGAAGAGGATGACAAAGAAAGTGTTGTTCATTTAGATAATGATGAGGAT
AAAAAAGAAGAAATGTATAAAGATGTATATCCCAATGTATTGTCTTGTGAAAAAGAAACG
ATTAGGAGGAATGAAAAGTATAACAAATCATTGAACAGTACAAGTAGCTTTGAAAAAATT
GATAATCCAAGTGAAATTAATGTTGAAAGTAAGGAAGATACAGAATATTTTGATTTATTA
ATAAAAAAATATGAGGATACAAAAATAAACGTATATGATAATGAATCTCTTTTATTGGAT
CTTAGTAATGAGCTACGTGAAGAAATGGCCAAGGGGGATTCTAATAAAAATGTAAATAAA
GTGGAAGATAATGATAATAAAAAGGAAAATATTTGTCATGATAATATCATGGAAGATATT
TGTCATAATAATAACGTGGAAGATATGTATCGTAATAATAACGTGGAAGATATGTATCGT
AATAATAACGTGGAAGATATGTATCGTAATAATAACGTGGAAGATATGTATCGTAATAAT
AACGTGGAAGATGTTTGTCATAATAATAACGTGGAAGATGTTTGTCATAATAATAACGTG
GAAGATGTTTGTCATAATAATAACGTGGAAGATGTTTATCATAATAATAACGTGGAAGAT
ATGTATCATGATAATAACATTGAAGATGTTTGTCATAATAATAACGTGGAAGATGTTTGT
CATAATAATAACGTGGAAGACCATGTTAATTATGATAATGAAGAATTGAATAAAAAAATG
GATGAGATGAAAGAAGAAAAGGAAGAAAGAAACGAGGATAGAGGAATATACGATGAATTA
TTAGAAAATGATATGTGTGATTTATACAATTTAAAAATGCATGATTTGCATAATTTAAAA
TCCTATGATTTTGGATTATCTAAAGATTTATTAAAAAAGGATATTTTTATATATAGTAAT
AATTTGAAAAATGATGATATGGATGATGATGATAATAATAATATGAATGATATTGCTATA
GGTGAAAATGTAATATATGAAAATGATATACATGAAAATAATATAGATGATAATGATATG
TATAATAATTACGTGAATGGAAATGATTTATATATTAACAATATGCAGGATGATGCCATG
GACGATATTGTATATGATGAGGAAGAAATTAAAAGCTTCCTAGATAAATTAAAATCTGAT
ATATCAAATCAAATGAATGTAAAAAATGGAAATGTCGAAGTTACAGGAAATGGTGGTAAT
GAAGAAATGTCTTATATAAATAATGATGAAAATTTACAAGCTTTTGATTTGTTAGATAAT
TTCCATATGGATGATTATGGTAATAATTATAATGATAATGAAGAAGATGGGGATGGGGAT
GGGGATGACGATGAACAGAAGAAAAGAAAACAAAAAGAGTTACATAATGTAAATGGAAAA
TTAAACTTATCAGATTTAAATGAATTAAATGTAGATGATATAAATAATAATTTCTATATG
TCAACTCCTCGAAAATCTATAGATGAACGTAAAGATACGGAATGTCAAACAGATTTTCCA
TTATTAGATGTATCAAGGAATACTAATAGGACTCCTAGAAGAAAAAGTGTGGAAGTAATA
CTTGTAGAAAAAAAAATTAAAAAAAAAAAAAACAGAAATGTATGGATAAATATACAGATGCA
AATGAGGATAGTAATAGAAGATATCCCAAAAGAAATCGAATTAAAACTTTGCGTTATTGG
ATAGGAGAAAGAGAGTTAACTGAAAGAAACCCTTACACAGGAGAAATAGATGTTGTAGGA
TTTAGTGAGTGTAAAAATTTGCAAGATTTGTCACCTCATATTATTGGTCCGATTGAATAT
AAAAAAATATATTTGAAAAATCTTAATAGTAATGAACATGAGGAAAATGAAGATAATAAT
GGAGACATTATTGAAAATAATAATGGGGACGTTATTGAAAATAATAATGGAGACATTATT
GAAGATAATAATGCAAACGAAAAAAATCATAATAATCTTGAATCTGAAGGTAAGGGTATC
GTATATGATGATGTAAATAATTTACATGTTCACACAAACAGTGATAATAGTGCTCATTCG
AAGAAAATAAAGGGAGCCCCCAGTAGGTTTAGTAATACAAATAATGGAAGGAAGAAACGA
AGAAGGAGAAAATTCATCAATGTAGTTAATTATATAAAGAAGAAGAAAAAGAAGAAACTG
ATAAAAAGTATGGATAATATGGAGGTTACAGATAATTTTAAGAATGATATGAGTGATGAA
AATAAACAAAGTGGTGATGAAAATAAACAAAGTGGTGATGAAAATAAACAAAGTGGTGAT
GAAAATAAACAAAGTGGTGATGAAAATAAACAAACTAATAATGATATTAAACAGAGTGAT
AATGATATTAAACAGAGTGATGATATTTACATGAATGAAGATATGAATTTGTTCAATGAT
TTAAATGATAACTTCGATAACAATGAATATTTCATAAACAATGGTGATAAGGATTCTCAT -continued

| Clone #2: Plasmodb.org designation: Gene PF10_0212a (Version 9.2) |
|---|
| GCTGAAGAAGAAATGGCCATAGAAAATATTCAAAGTAAAAGTATAGAAAAGGATATTTTA |
| AATAATGAAGAGCAGGATAATAATAACATCTTTGATATTGATAATGAACTTATAGATATG |
| AAGGATGGAAATGTAGATGAAATGGAAAGTGATGAAAAATTAAAAACTTTTGAAAAATTG |
| GAAAGTTTGAAAAGTACAACACATTTAAACAATACCGATAATTGTGATGTAAATTTGAGT |
| GAACAGACCAATGAAATAAATTATGATGAGGAAAAAAAAAGTTAATAAAAAAACAAATCAT |
| GAAAAAATGAAGAAGAAGAAGAAGAAAAAAAAAAAAAAAAAGAAAAAGAAGAAGAAAGAA |
| AAAAAACAAATAGATATTATGTACAAAAATTTGTCCAGACTTAATTTAAATTTGTTACTT |
| CCAACCAAAAAAAAAGTTAAGAAATCGAAAAACTCATTTAAAAAAGAGGAAGAAAAACAA |
| AAGAAGAAAAATAAAAAGTTAAAAAAATCAAAGGTATTAACAAGGGGGAAAAAATAAAA |
| AGTAATAAGAAAGAAAATAAGGACAATAATAATGATAGTAGTACAGAATGTGTTGTAGAA |
| GGAGAAAAAGGAAAAGATTTACATGAGTTTAATAAAAATGGAAATCTTGAAGATGAACAA |
| ATGGATGTTGATATTTCTATGAATATTTCAAGTATAAATTGTGAAAGTGATAATAAAAAT |
| GTGAGTAAGGAAGGAGAGGAAGAAAAAAAAAGACATAGCTGAAAACAAAGAAGAGGTGGAT |
| AAAAACAAAGAAGAGGTATATATGGACAAACATGAGATGGATTTGAACAATGAAGAGGTA |
| TATATGGACAAAAATGAGATGGATTTGAACAATGAAGAGGTATATATGGACAAACATGAG |
| ATGGATTTGAACAATGAAGAGGTATATATGGACAAACATGAAATGGATTTGAACAATGAA |
| GAGGTATATATGGACAAACATGAAATGGATTTGAACAAAGAAGAGGTATATATGGACAAA |
| CATGAGATGGATTTGAACAATGAAGAGGTAGATAAAGAAAACGAATATGATGAAAATATA |
| CTTAGTGATAACATAATATATAATGAAAACAATTCATTTGGAAACAATAAGAACTCTTTT |
| TTTAATAATACAAGTCCATTAAAAACAGAAATAATAAATGAAGAGGAAAATAGTTTGAAC |
| GAAATGAAAGAAGACATAAATGAATACGTTGAAATGGAAAACAAGTTGGATACGGAAAAA |
| ATAAAAGATTCAGAAAAAATAGGTGGAAAAATAGAGGTAGATAATAAAATGATTTCTCCT |
| ATTAATAGACATAATTTTTATTTAACAATTCTTGAAGGAATGAATAAGAATTTTCCTAGG |
| CAATGGAATAAAAATAATATAACTTTATCAAAAAATCAAGGACAAATTTATAAAGGAAGG |
| AAAGAAAAGAAAAGAAAACGTTCCTATAGAAATGATGAAAAATTACTTGATCATAGTATA |
| TTAAATGATATCAATATAAGTGACAAAATGGATGAAAGAAATGAATTATTAGAGAGTATA |
| AAATCTAATAGTACTATAAATAATGTATTAGAAATTATAAAATATGATAATAGGAAAAAA |
| ATAAAGAAGAATGATACAAACAAGGAAATAATCAAATATGATAACTTCACATCTAAATAT |
| AATAATAAAAGTAATGATATTCAATTGAATGGTGGAATATATATAAATAAATTCAAACTT |
| TCTTTAGATATGCCTATAAATAAATTAGCGGTATCTTCAAATCTTGGACCTCCATCATCT |
| ATAGGATCAACAGAAATACAGCCTATTCAAAAGAATTTCAACGATTTCAAAATGAATATT |
| AACGTGTACTGTATTAGGATGGAGCCGCATGAAAAATACAGCTCATATAGCCATAAAAAT |
| AATTTAGTTGTATATATTGATAAGGGAGAAAAAATTAACATAATAATCAACATGTCAAAG |
| ACTTATGAAAAAGGTGATTTTTTTTACATACCTAGATTTTCTAACTTCCAAATAATTAAT |
| GATAGCAGATGTGATTGTGTTTTATATGTTTGTCCTTTAATTTAA |
| (SEQ ID NO: 4) Sequence Length: 6225 bp; underlined sequence corresponds to nucleotide sequence encoding; PfSEP-1A antigenic fragment. |

The invention is also directed in part to polynucleotides and polypeptides shown in the Table below that are useful, for example, for antigens for vaccines against *P. falciparum* malaria.

| Serial Number | Clone Name | Plasmodb.org GENE ID | Gene Name/Function | Length of peptide in aa | Length of Protein aa | Clone size in bp | Gene size in bp |
|---|---|---|---|---|---|---|---|
| 1 | Clone#2 | PF10_0212a Version 9.2 | PfSEP-1/Schizont egress | 273 | 2074 | 819 (2431-3249) | 6225 |
| 2 | Clone#5 | PF13_0197 | MSP-7/Merozoite surface protein/ RBC invasion | 284 | 351 | 852 (201-1052) | 1056 |
| 3 | Clone#10 | PF11_0354 | Schizont egress | 641 | 2227 | 1923 (3490-5412) | 6684 |
| 4 | Clone#T108 | PFB0310c | MSP-4/Merozoite surface protein/ RBC invasion | 79 | 272 | 238 (124-361) | 819 |
| 5 | Clone#T32 | MAL8P1.58 | Pf-PGPS/phosphatidyl glycerophosphate synthase | 100 | 661 | 300 (1023-1322) | 1986 |
| 6 | Clone#T9 | PFE0040c | MESA/Mature Erythrocyte Surface Antigen | 153 | 1434 | 459 (2080-2538) | 4305 |

-continued

| | | | | | | | |
|---|---|---|---|---|---|---|---|
| 7 | Clone#TL22 | PFA0620c | Pf-GARP/glutamic acid rich protein | 263 | 673 | 792 (1231-2022) | 2022 |
| 8 | Clone#TL27 | PFI1780w | Plasmodium exported protein | 101 | 383 | 303 (691-993) | 1152 |
| 9 | Clone#TL5 | PFB0100c | Pf-KAHRP/Pathogenicity, Adhesion/Knob Associated Histidine Rich Protein | 80 | 654 | 242 (1309-1550) | 1965 |
| 10 | Clone#TL16 | MAL7P1.208 | RAMA/Rhoptry Associated membrane antigen/RBC invasion/DNA mismatch repair protein | 144 | 873 | 432 (953-1384) | 2114 |
| 11 | Clone#TL45 | PF07_0033 | Cg4 protein/ parasite heat shock protein 70/ protein transport | 216 | 873 | 650 (1764-2413) | 2622 |
| 12 | PF3D7 | PF13_0211 | $Ca^{++}$ dep. Protein kinase | 84 | 568 | 255 | 1707 |

Clone #5: MSP-7 (PF13_0197)
Nucleic acid sequence of Clone #5, 852 bp (Sequence 201-1,052 of gene PF13_0197)

(SEQ ID NO: 5)

ATTAAACAAAAAAATTGAAGAATTACAAAACAGTAAAGAAAAAAATGTACATGTAT

TAATTAATGGAAATTCAATTATTGATGAAATAGAAAAAAATGAAGAAAATGATGAT

AACGAAGAAAATAATGATGATGACAATACATATGAATTAGATATGAATGATGACAC

ATTCTTAGGACAAAATAACGATTCACATTTTGAAAATGTTGATGATGACGCAGTAGA

AAATGAACAAGAAGATGAAAACAAGGAAAAATCAGAATCATTTCCATTATTCCAAA

ATTTAGGATTATTCGGTAAAAACGTATTATCAAAGGTAAAGGCACAAAGTGAAACA

GATACTCAATCTAAAAATGAACAAGAGATATCAACACAAGGACAAGAAGTACAAA

AACCAGCACAAGGAGGAGAATCGACATTTCAAAAAGACCTAGATAAGAAATTATAT

AATTTAGGAGATGTTTTTAATCATGTAGTTGATATTTCAAACAAAAAGAACAAAATA

AATCTCGATGAATATGGTAAAAAATATACAGATTTCAAAAAAGAATATGAAGACTT

CGTTTTAAATTCTAAAGAATATGATATAATCAAAAATCTAATAATTATGTTTGGTCA

AGAAGATAATAAGAGTAAAAATGGCAAAACGGATATTGTAAGTGAAGCTAAACATA

TGACTGATATTTTCATAAAACTATTTAAAGATAAGGAATACCATGAACAATTTAAAA

ATTATATTTATGGTGTTTATAGTTATGCAAAACAAAATAGTCACTTAAGTGAGAAAA

AAATAAAACCAGAAGAGGAATATAAAAAATTTTTAGAATATTCATTTAATTTACTAA

ACACAAT

Sequence Length: 852 bp

Amino acid sequence of Clone #5

(SEQ ID NO: 6)

LNKKIEELQNSKEKNVHVLINGNSIIDEIEKNEENDDNEENNDDDNTYELDMNDDTFLG

QNNDSHFENVDDDAVENEQEDENKEKSESFPLFQNLGLFGKNVLSKVKAQSETDTQSK

NEQEISTQGQEVQKPAQGGESTFQKDLDKKLYNLGDVFNHVVDISNKKNKINLDEYGK

KYTDFKKEYEDFVLNSKEYDIIKNLIIMFGQEDNKSKNGKTDIVSEAKHMTDIFIKLFKD

KEYHEQFKNYIYGVYSYAKQNSHLSEKKIKPEEEYKKFLEYSFNLLNTM

-continued

Sequence Length: 284 aa

Amino acid sequence of MSP7 gene (PF13_0197)

(SEQ ID NO: 7)

MKSNIIFYFSFFFVYLYYVSCNQSTHSTPVNNEEDQEELYIKNKKLEKLKNIVSGDFVGN

*YKNNEELLNKKIEELQNSKEKNVHVLINGNSIIDEIEKNEENDDNEENNDDDNTYELDMN*

*DDTFLGQNNDSHFENVDDDAVENEQEDENKEKSESFPLFQNLGLFGKNVLSKVKAQSETD*

*TQSKNEQEISTQGQEVQKPAQGGESTFQKDLDKKLYNLGDVFNHVVDISNKKNKINLDEY*

*GKKYTDFKKEYEDFVLNSKEYDIIKNLIIMFGQEDNKSKNGKTDIVSEAKHMTEIFIKLF*

*KDKEYHEQFKNYIYGVYSYAKQNSHLSEKKIKPEEEYKKFLEYSFNLLNTM*
Sequence Length: 351 aa

Nucleic acid sequence of MSP7 gene (PF13_0197)

(SEQ ID NO: 8)

ATGAAGAGTAATATCATATTTTATTTTTCTTTTTTTTTTGTGTACTTATACTATGTTTC

GTGTAATCAATCAACTCATAGTACACCAGTAAATAATGAAGAAGATCAAGAAGAAT

TATATATTAAAAATAAAAAATTGGAAAAACTAAAAAATATAGTATCAGGAGATTTT

GTTGGAAATTATAAAAATAATGAAGAATT*ATTAAACAAAAAAATTGAAGAATTACAAAAC*

*AGTAAAGAAAAAAATGTACATGTATTAATTAATGGAAATTCAATTATTGATGAAATAGAAAAA*

*AATGAAGAAAATGATGATAACGAAGAAAATAATGATGATGACAATACATATGAATTAGATAT*

*GAATGATGACACATTCTTAGGACAAAATAACGATTCACATTTTGAAAATGTTGATGATGACG*

*CAGTAGAAAATGAACAAGAAGATGAAAACAAGGAAAAATCAGAATCATTTCCATTATTCCAA*

*AATTTAGGATTATTCGGTAAAAACGTATTATCAAAGGTAAAGGCACAAAGTGAAACAGATAC*

*TCAATCTAAAAATGAACAAGAGATATCAACACAAGGACAAGAAGTACAAAAACCAGCACAA*

*GGAGGAGAATCGACATTTCAAAAAGACCTAGATAAGAAATTATATAATTTAGGAGATGTTTT*

*TAATCATGTAGTTGATATTTCAAACAAAAAGAACAAAATAAATCTCGATGAATATGGTAAAAA*

*ATATACAGATTTCAAAAAAGAATATGAAGACTTCGTTTTAAATTCTAAAGAATATGATATAAT*

*CAAAAATCTAATAATTATGTTTGGTCAAGAAGATAATAAGAGTAAAAATGGCAAAACGGATA*

*TTGTAAGTGAAGCTAAACATATGACTGAAATTTTCATAAAACTATTTAAAGATAAGGAATACC*

*ATGAACAATTTAAAAATTATATTTATGGTGTTTATAGTTATGCAAAACAAAATAGTCACTTAA*

*GTGAGAAAAAAATAAAACCAGAAGAGGAATATAAAAAATTCTTAGAATATTCATTTAATTTAC*

*TAAACACAAT*GTAA
Sequence Length: 1056 bp

Clone#10 (PF11_0354)
Nucleic acid sequence of Clone #10, 1923 bp (Sequence
3490-5412 of gene PF11_0354

(SEQ ID NO: 9)

GATAATGTTAATAATAATAATAATAAAGAAAGTTGTGATAATATTAAACATATGAG

AACAAAAAGTTTAAATTTTGTAAGTAGAGAATCCTATGGCGAACATAAAAGTCTAG

ATGTTTACCAGGAATGTTATGTAAAAAATAATAAACTTATTAATAAGGTAAATGATA

AAAAATATGAGGACAATAATAATTCCTATCTTAATGAAGATGATAACGCTAGTATG

CAATTTTATGAAGAAACTAATAGTAATCCATATATTGTAGACCAGGAAAATAATAT

GAAAAATTATGTCAATAATGTTTTATATAACAACAATAGCAATTATTATGTTGATTC

AAAGAATTATGATAAATCTAAAGAGAATGCAGAAAATAAATCAGATGATATATTAA

ATAATGAAAATATACATACCTTAAAAGATCAAAAAAAGAAAATACAAAATAATAAT

GAATTCATTAGTGAACAGGCTGATATAGAAAATATAAGAAATTCTCAAGAAGAAGT

ATATGAGAAAGAACACGAACCTTTGTGGGTAATAAATGCATCTAATGAAGAAAAGA

-continued

AATCATATGAAGAATTGATATACAGCGATATGTCATCTAATCGTGTTACGAAAAATA

AATATAGTGATATGAATAATGTTGAGGTATTATTAAATGAAGATAATTTATTAACTA

CTGAAAAATACAAGGTGCAATTAGAAAAAGAAAATAAAATGATTGATATGTATGAA

ACGGTAGAGGAGAATATAAATACAATTAAAACAGAAAATACGAACGACATAAATG

AAGAAGTTAGAAACGAACAAAAAAGAGAAAGTATCAATCATATTAATGATACAAA

TATAAATCATATAATAGATGAATATCCCAATGATACATATAATTTCATAAAAGATAT

AGAATGTGTACATAACAATGAAAATAACATGTACAATTCTATTGAACAATATACATT

TTATCATGATACACGTAATAATCATTTAGTTGATAAAAATAATCAAAATTTTATATT

CGAAGAGGAAGGTTTAAATGAATTGAACTTTGAAGAAAAAAAGGTATATATAGAAA

ATAATACCAAGGATGATCACAAGGGAGATAGCAAAACAAGTAACTTAACATCTTTA

AGGAATACCATATGTAAAAGTGAAAACGATCATAATGAAAAAAATGAAAACACAT

ATGTGGTTAGAAAAGGCGAAAAAGGAATTAAACGTAAGGTTTCCATGAAGAAAAG

AAATGAAAAGCTAAATGAAGAAAATTATATTAATAATATATACGATAAAATGGATA

ACCATAGACAAAATGATATTACAAAAAAAGAAAATGACGAAGAAAATTATATTTTG

TACAACAACGTAAAGGTTAATTATGATGAATATATAGAAAATGGAAATAAAATAAA

AATAACGGAAGAATCATTAAATGTCTTTTATAAAGAAAATCAAAATGAGGAAGATT

CTTCTACAAAAAAGTTGAATAGTACAAGTAAAATAAAACGTGCAAACAAAGGGAA

AACAAAAAAAAAGAATGTTATCACAAGGGTACATAAAACAAAACAAAAAATTGAA

TATGTTACAAATAGTTTTAATAAATCTTCCAAAGGTGAAAATTCAGAAATAGGAAA

AATTGGAGGTAGGAGTAAATCATTATTAACACACAGCAAGAAAGTTAGTGAACGAA

ATAAAAATAAAATAGAAAAAATTAATGATACAAATTCAAAGATAATAAAAGGAAA

AAAGAGTAATAGCCAAAGCAAACTTGGGAAGGATACAAAAATTAGAGGGAAATCA

AAAACTGGGGAATATATAAAAAATAAAGATTTAAGAAAAAAATCTAACGAAAAAA

ACAAAACAGTGATGGATAATATAAATACTATAAATAATTCTTCAGTATCTAACCTAA

AAAGCAAAAAACATAAATTG
Sequence Length: 1923

Amino acid sequence of Clone # 10, (PF11_0354)

(SEQ ID NO: 10)

DNVNNNNNKESCDNIKHMRTKSLNFVSRESYGEHKSLDVYQECYVKNNKLINKVNDK

KYEDNNNSYLNEDDNASMQFYEETNSNPYIVDQENNMKNYVNNVLYNNNSNYYVDS

KNYDKSKENAENKSDDILNNENIHTLKDQKKKIQNNNEFISEQADIENIRNSQEEVYEKE

HEPLWVINASNEEKKSYEELIYSDMSSNRVTKNKYSDMNNVEVLLNEDNLLTTEKYKV

QLEKENKMIDMYETVEENINTIKTENTNDINEEVRNEQKRESINHINDTNINHIIDEYPND

TYNFIKDIECVHNNENNMYNSIEQYTFYHDTRNNHLVDKNNQNFIFEEEGLNELNFEEK

KVYIENNTKDDHKGDSKTSNLTSLRNTICKSENDHNEKNENTYVVRKGEKGIKRKVSM

KKRNEKLNEENYINNIYDKMDNHRQNDITKKENDEENYILYNNVKVNYDEYIENGNKI

KITEESLNVFYKENQNEEDSSTKKLNSTSKIKRANKGKTKKKNVITRVHKTKQKIEYVT

NSFNKSSKGENSEIGKIGGRSKSLLTHSKKVSERNKNKIEKINDTNSKIIKGKKSNSQSKL

GKDTKIRGKSKTGEYIKNKDLRKKSNEKNKTVMDNINTINNSSVSNLKSKKHKL,

-continued

Sequence Length: 641

Amino acid sequence of PF11_0354

(SEQ ID NO: 11)

MRSKSISYFLFFKKNKKKNDSCDSVIISSNKNLSIQLSKGEDDEKNEINEEKSYIKNEDVY

KKEKLKKKKENKENNKKKDKNEVVYDYHDISNDATSDYVNNYKVYEMNTCNIKKKR

ESFFKKINILQKYKNYKIRKAASTFHTIGHKTSFSGTDDEIENNQKKQKKYKIKISEWKD

DKSHTFHKKNDILVFDKMDKNKKFKIDNNKNNQINIDNEERVNKNYPMATNVQNFNIK

YTSIDVTNDEYIIDSNKPEGSIMSTDKKNNKLNYNNDTYDVDKSSDINKLGNIKKNKFDII

TKTTHNINNNVNNIHNYMMYTNKENIKININHGNLNGREQNNYDEERKANVYEIFENA

KKLEPNNININTEEHIHISEPSIPFDMKDHKNDINEKDIILKLMYNNNGIYFDDDDENHKN

LLYKNKDTHVKHLNNKFNHNFIIYNDREEGVNQKHAQKKLKKKNTILNKNENEDINHN

SFKRPLSNTNICYKDKDDKIKNGSNKYDILNNDYSNEHEKNKYNDHITKNKRNQSANE

VKSNNNDNHNNKKNNNFNININDSYSTNINRNQNVMINDVNDVIKDPNMQENTQGDD

EGGIINKYLINPIYNLFLRANEEIQNSNSTNNKLKMNNITKSYTNELQKTYKSMYDINDIS

NKRKINNKDIRGTNLYNTKLCNNKLYNSNPYNMIPYNINTYNNNNNNKETCTSINIKHS

ENKYPFNKSHVNSYMKNTNHLPHRNAITSNNRNNEEYEKEKEKDRNITNGNNNYLVEY

NNSCIPPPLKKMIPIDGVRNKSINKLNNVTNTQRTSSVSYTNKNIDENSFDMPIINGIRESK

YISNNNNINGNSIGFNSSKLDNYHHQSMNVNESYPLKNMMKNNYIEHNYDDKNNIFLV

KNYEDTYSNIHNGIHENSMLKNYNLKKACTFHGYSRNHQKNMYTEENLNINQKKNYS

HYHNNGTVLKPLVNTNNVAVNEFADINLSAQKRLHSLKSMGYEDKSMENYRNKIYNNI

NNNNNNNNDNNIYNDNEYCQYNNSYCFDHSDLKNMFPLNHQNSKLLTHSNNKNSFFN

GINVESKHHLANPEIKTFAHNSYPILNQGLINCNPLQCLGYDSNQRNKHNVVYIKKNEY

LNKNIGSIINVLKREGLRKISTHNGKFESFSNMDNKNVYMEGLNIQ*DNVNNNNNKESCDN*

*IKHMRTKSLNFVSRESYGEHKSLDVYQECYVKNNKLINKVNDKKYEDNNNSYLNEDDNASMQ*

*FYEETNSNPYIVDQENNMKNYVNNVLYNNNSNYYVDSKNYDKSKENAENKSDDILNNENIHTL*

*KDQKKKIQNNNEFISEQADIENIRNSQEEVYEKEHEPLWVINASNEEKKSYEELIYSDMSSNRV*

*TKNKYSDMNNVEVLLNEDNLLTTEKYKVQLEKENKMIDMYETVEENINTIKTENTNDINEEVR*

*NEQKRESINHINDTNINHIIDEYPNDTYNFIKDIECVHNNENNMYNSIEQYTFYHDTRNNHLVD*

*KNNQNFIFEEEGLNELNFEEKKVYIENNTKDDHKGDSKTSNLTSLRNTICKSENDHNEKNEN*

*TYVVRKGEKGIKRKVSMKKRNEKLNEENYINNIYDKMDNHRQNDITKKENDEENYILYNNVK*

*VNYDEYIENGNKIKITEESLNVFYKENQNEEDSSTKKLNSTSKIKRANKGKTKKKNVITRVHKT*

*KQKIEYVTNSFNKSSKGENSEIGKIGGRSKSLLTHSKKVSERNKNKIEKINDTNSKIIKGKKSNS*

*QSKLGKDTKIRGKSKTGEYIKNKDLRKKSNEKNKTVMDNINTINNSSVSNLKSKKHKL*KKKK

KKNISMENINKNITNEFCSMERKGTVLLSNMSIKKIDNANSCTLNEPLEENTLNYESNNN

CSNSNLSKDKEKDRNILCNKYYSDEETNSLNKMYTSNIPEISNYYKEIQAINYILSNINNP

NFLNSLELNDLINIEKKFINENIYINKQIIACNVKNEKSNDEMVEKNERKVDEEKGEDEQ

EIKAKENNNKEENQDNENNNKEENHDNENNNKEENQDNENNNKEENQDNENNNKEE

NQDNENNNKEENQKNENGIIYDSRFSIIYLEHDLIYLKKNNLKVILNVLLSNVYCFFEIKL

TIILLNFFISNNCQWSFSLFPLSLINKLIHKFSLKINKKVPKYKLENMNINSPNIPYTYLFIC

DGSNYLCINDNSLNNEVYENKMKLNNIIGYYHYINLNRLTYYLEKVNANFVYNHHIYE,

-continued

Sequence Length: 2227

Coding Nucleic acid sequence gene PF11_0354

(SEQ ID NO: 12)

ATGAGATCGAAATCCATTTCGTATTTCTTATTTTTTAAAAAAAACAAAAAGAAAAAT

GATTCTTGTGATAGTGTCATAATATCTAGCAATAAGAATTTATCCATTCAATTATCG

AAAGGTGAGGATGATGAAAAAAATGAAATAAATGAGGAAAAGAGTTATATAAAAA

ATGAAGATGTATATAAAAAGGAAAAATTAAAAAAGAAGAAAGAAAACAAGGAAAA

TAATAAAAAGAAAGATAAAAATGAAGTAGTATATGATTATCATGACATTTCAAATG

ATGCTACTAGTGATTATGTTAATAATTATAAAGTATATGAAATGAATACTTGTAATA

TAAAAAAGAAGAGAGAAAGTTTTTTTAAAAAAATTAATATTTTACAAAAATATAAA

AATTACAAAATTAGAAAGGCAGCTAGTACCTTTCATACCATAGGACATAAAACATC

TTTTTCTGGTACAGATGATGAAATAGAAAATAATCAAAAGAAACAAAAAAAATATA

AAATAAAAATTTCTGAATGGAAGGATGATAAATCACATACTTTTCATAAAAAAAAT

GACATATTGGTATTTGATAAGATGGATAAAAATAAAAAATTTAAAATTGATAACAA

CAAAAACAATCAAATTAATATAGATAATGAAGAAAGAGTTAATAAAAATTATCCTA

TGGCTACTAATGTACAAAATTTTAATATAAAATATACATCAATAGATGTAACAAATG

ACGAATATATTATAGATTCTAATAAACCTGAAGGTTCTATTATGTCTACAGATAAAA

AGAATAATAAACTTAATTATAATAATGATACATATGATGTAGACAAAAGCTCTGAT

ATAAATAAGTTAGGTAATATAAAAAAGAATAAATTTGATATTATTACTAAAACAAC

ACATAATATTAATAATAATGTAAATAATATACATAATTATATGATGTATACAAATAA

AGAAAATATAAAAATAAATATAAATCATGGAAATCTAAATGGAAGAGAACAAAAC

AATTATGATGAAGAAAGGAAAGCAAATGTTTATGAAATATTTGAAAATGCAAAAAA

ATTAGAACCTAATAATATTAATATCAACACAGAAGAACATATTCATATTAGTGAACC

CAGCATACCATTTGATATGAAGGATCATAAAAATGATATAAATGAAAAAGATATAA

TATTAAAATTGATGTATAACAATAACGGTATTTATTTTGATGATGATGATGAAAATC

ACAAGAATTTATTATACAAAAATAAAGATACACATGTAAAACATTTAAATAATAAA

TTTAACCATAATTTTATTATATATAATGATCGCGAAGAAGGGGTAAATCAGAAACAC

GCACAAAAAAAATTAAAAAAAAAAAATACTATTCTTAACAAAAACGAAAATGAAG

ATATTAATCATAATAGTTTCAAAAGACCTTTATCTAATACGAATATATGTTATAAGG

ACAAAGATGATAAAATTAAAAATGGTTCTAATAAGTATGATATATTAAATAATGAC

TATTCTAATGAACACGAAAAAAATAAATATAATGATCATATAACAAAAAATAAAAG

AAATCAATCAGCAAATGAAGTAAAATCTAATAATAATGATAACCACAATAATAAAA

AAAATAATAATTTTAATATTAATATTAATGATTCATATTCTACAAATATAAATAGAA

ACCAAAATGTGATGATAAATGATGTAAACGATGTTATTAAGGATCCAAATATGCAG

GAAAATACACAAGGTGATGACGAAGGTGGTATTATAAACAAATATTTAATTAACCC

TATTTACAATTTATTTCTACGTGCTAATGAAGAAATACAAAATTCAAATAGTACAAA

CAATAAATTAAAAATGAATAATATAACAAAAAGTTATACAAACGAACTACAAAAGA

CATATAAAAGTATGTACGATATAAATGATATATCAAATAAGAGAAAAATTAATAAT

AAAGATATACGTGGAACTAATTTGTATAACACCAAATTATGTAATAATAAATTATAT

AATTCGAATCCATATAATATGATTCCATATAATATAAACACATATAATAATAATAAT

AATAATAAGGAAACTTGTACCAGCATAAATATCAAACATTCCGAAAATAAATATCC

-continued

CTTCAATAAATCTCATGTAAACTCATATATGAAAAATACAAATCATCTTCCTCATAG

AAATGCGATTACATCAAATAATAGAAACAATGAAGAATATGAGAAAGAAAAAGAA

AAAGATCGTAACATTACTAATGGGAACAATAATTATTTGGTTGAATATAATAATTCT

TGTATACCTCCACCACTCAAAAAAATGATACCAATAGATGGTGTGAGAAATAAAAG

TATAAATAAATTAAATAATGTAACTAATACGCAACGTACATCAAGTGTTTCATATAC

GAATAAGAATATTGATGAGAATTCGTTTGATATGCCTATAATAAATGGAATAAGAG

AATCTAAATATATAAGTAATAATAATAATATTAATGGTAATTCCATTGGTTTTAATT

CATCTAAGTTAGATAATTATCATCACCAATCTATGAATGTGAATGAATCTTATCCTC

TAAAAAATATGATGAAAAATAATTATATTGAACATAATTATGATGATAAAAATAAT

ATTTTCCTTGTTAAAAATTATGAAGATACATATTCAAATATTCATAATGGCATACAT

GAAAATAGCATGCTAAAAAATTATAATTTAAAAAAAGCGTGCACTTTTCATGGGTA

CTCTAGAAATCACCAAAAAAATATGTATACGGAAGAAAATTTAAATATTAATCAAA

AAAAGAATTATAGTCATTATCATAATAATGGAACGGTATTAAAACCTTTGGTAAATA

CTAATAATGTTGCAGTGAACGAATTTGCAGATATTAATTTATCGGCTCAAAAAAGAT

TACATAGTTTAAAAAGTATGGGGTACGAGGATAAGAGTATGGAAAATTACAGAAAC

AAAATATACAACAACATCAATAATAATAATAATAATAATGATAATAATATATA

TAATGATAATGAATATTGTCAGTATAATAATAGTTATTGTTTCGATCATAGTGATTT

AAAAAATATGTTTCCATTAAATCATCAGAATAGCAAGTTATTAACACATAGTAATAA

TAAAAATTCATTTTTTAACGGAATAAATGTAGAATCGAAACATCATTTAGCAAATCC

TGAAATAAAAACATTTGCACACAATAGTTATCCTATATTAAATCAAGGTTTAATAAA

TTGTAACCCCTTACAATGCTTGGGTTATGATTCAAATCAAAGGAATAAGCATAATGT

AGTATACATAAAAAAAAATGAATACCTTAATAAAAACATTGGCTCTATTATAAATG

TTCTTAAAAGAGAAGGACTAAGAAAAATTTCTACACATAATGGAAAATTCGAATCA

TTTAGTAATATGGATAATAAAAATGTATATATGGAAGGACTAAACATACAA*GATAAT*

*GTTAATAATAATAATAATAAAGAAAGTTGTGATAATATTAAACATATGAGAACAAAAAGTTTA*

*AATTTTGTAAGTAGAGAATCCTATGGCGAACATAAAAGTCTAGATGTTTACCAGGAATGTTA*

*TGTAAAAAATAATAAACTTATTAATAAGGTAAATGATAAAAAATATGAGGACAATAATAATTC*

*CTATCTTAATGAAGATGATAACGCTAGTATGCAATTTTATGAAGAAACTAATAGTAATCCATA*

*TATTGTAGACCAGGAAAATAATATGAAAAATTATGTCAATAATGTTTTATATAACAACAATAG*

*CAATTATTATGTTGATTCAAAGAATTATGATAAATCTAAAGAGAATGCAGAAAATAAATCAGA*

*TGATATATTAAATAATGAAAATATACATACCTTAAAAGATCAAAAAAAGAAAATACAAAATAA*

*TAATGAATTCATTAGTGAACAGGCTGATATAGAAAATATAAGAAATTCTCAAGAAGAAGTAT*

*ATGAGAAAGAACACGAACCTTTGTGGGTAATAAATGCATCTAATGAAGAAAAGAAATCATAT*

*GAAGAATTGATATACAGCGATATGTCATCTAATCGTGTTACGAAAAATAAATATAGTGATAT*

*GAATAATGTTGAGGTATTATTAAATGAAGATAATTTATTAACTACTGAAAAATACAAGGTGCA*

*ATTAGAAAAAGAAAATAAAATGATTGATATGTATGAAACGGTAGAGGAGAATATAAATACAA*

*TTAAAACAGAAAATACGAACGACATAAATGAAGAAGTTAGAAACGAACAAAAAAGAGAAAG*

*TATCAATCATATTAATGATACAAATATAAATCATATAATAGATGAATATCCCAATGATACATAT*

*AATTTCATAAAAGATATAGAATGTGTACATAACAATGAAAATAACATGTACAATTCTATTGAA*

-continued

*CAATATACATTTTATCATGATACACGTAATAATCATTTAGTTGATAAAAATAATCAAAATTTTA*

*TATTCGAAGAGGAAGGTTTAAATGAATTGAACTTTGAAGAAAAAAAGGTATATATAGAAAAT*

*AATACCAAGGATGATCACAAGGGAGATAGCAAAACAAGTAACTTAACATCTTTAAGGAATA*

*CCATATGTAAAAGTGAAAACGATCATAATGAAAAAAATGAAAACACATATGTGGTTAGAAAA*

*GGCGAAAAAGGAATTAAACGTAAGGTTTCCATGAAGAAAAGAAATGAAAAGCTAAATGAAG*

*AAAATTATATTAATAATATATACGATAAAATGGATAACCATAGACAAAATGATATTACAAAAA*

*AAGAAAATGACGAAGAAAATTATATTTTGTACAACAACGTAAAGGTTAATTATGATGAATATA*

*TAGAAAATGGAAATAAAATAAAAATAACGGAAGAATCATTAAATGTCTTTTATAAAGAAAATC*

*AAAATGAGGAAGATTCTTCTACAAAAAAGTTGAATAGTACAAGTAAAATAAAACGTGCAAAC*

*AAAGGGAAAACAAAAAAAAAGAATGTTATCACAAGGGTACATAAAACAAAACAAAAAATTGA*

*ATATGTTACAAATAGTTTTAATAAATCTTCCAAAGGTGAAAATTCAGAAATAGGAAAAATTGG*

*AGGTAGGAGTAAATCATTATTAACACACAGCAAGAAAGTTAGTGAACGAAATAAAAATAAAA*

*TAGAAAAAATTAATGATACAAATTCAAAGATAATAAAAGGAAAAAAGAGTAATAGCCAAAGC*

*AAACTTGGGAAGGATACAAAAATTAGAGGGAAATCAAAAACTGGGGAATATATAAAAAATA*

*AAGATTTAAGAAAAAAATCTAACGAAAAAAACAAAACAGTGATGGATAATATAAATACTATAA*

*ATAATTCTTCAGTATCTAACCTAAAAAGCAAAAAACATAAATTG*AAAAAAAAAAAAAAAA

AAAATATATCTATGGAAAATATAAATAAAAATATAACAAATGAATTTTGTTCTATGG

AAAGAAAAGGAACCGTTCTATTATCTAATATGAGTATTAAGAAGATTGATAATGCA

AATAGTTGTACATTAAATGAACCATTAGAGGAAAATACCTTAAATTATGAAAGTAA

TAATAACTGTAGTAATAGTAATTTATCTAAGGATAAAGAAAAAGATAGAAATATAT

TGTGTAATAAATATTATAGTGATGAGGAAACAAACTCTTTAAACAAAATGTATACAT

CGAATATACCAGAAATAAGTAATTATTATAAGGAAATTCAAGCAATTAATTACATA

TTAAGTAATATTAATAATCCAAATTTTTTAAATTCCCTCGAACTGAATGATTTAATA

AATATTGAAAAAAAATTTATTAACGAAAATATATATATTAATAAGCAGATAATAGC

CTGTAATGTAAAAAATGAAAAATCAAATGATGAGATGGTCGAGAAAAATGAACGC

AAAGTGGATGAAGAAAAAGGAGAAGACGAACAAGAAATAAAAGCAAAGGAAAAT

AATAATAAAGAAGAAAACCAAGATAATGAAAATAATAATAAAGAAGAAAACCATG

ATAATGAAAATAATAATAAAGAAGAAAATCAAGATAATGAAAATAATAATAAAGA

AGAAAACCAAGATAATGAAAATAATAATAAAGAAGAAAATCAAGATAATGAAAAT

AATAATAAAGAAGAAAACCAAAAAAATGAAAATGGTATTATTTATGATAGCAGGTT

TAGTATTATCTATTTAGAACACGATTTAATATATTTAAAAAAAAATAATTTAAAAGT

GATACTTAATGTTTTGCTGTCAAATGTGTATTGCTTTTTTGAAATTAAATTAACCATA

ATATTGTTAAATTTCTTTATATCTAATAATTGTCAATGGAGTTTCAGTTTATTTCCCC

TTTCATTAATTAATAAATTAATACATAAATTCAGTTTAAAGATAAATAAGAAAGTTC

CTAAATATAAATTGGAAAATATGAATATTAACTCACCAAATATTCCATATACATATC

TTTTTATATGTGATGGAAGTAACTATTTATGTATTAATGACAATTCATTAAATAACG

AGGTATATGAAAACAAGATGAAATTGAACAATATCATTGGATATTACCATTATATTA

ATTTGAATAGATTAACATATTATTTAGAAAAGGTAAATGCTAATTTTGTTTATAACC

ATCATATATATGAATAA,

-continued

Sequence Length: 6684 bp

Clone # T108: MSP-4 (PFB0310c)
Nucleic acid sequence of Clone# T108, 238 bp (Sequence 124-361 of gene PFB0310c 1-819)

(SEQ ID NO: 13)

AGAATTCTAGGGGAAGAAAAACCAAATGTGGACGGAGTAAGTACTAGTAATACTCC

TGGAGGAAATGAATCTTCAAGTGCTTCCCCCAATTTATCTGACGCAGCAGAAAAAA

AGGATGAAAAAGAAGCTTCTGAACAAGGAGAAGAAAGTCATAAAAAAGAAAATTC

CCAAGAAAGCGCGAATGGTAAGGATGATGTTAAAGAAGAAAAAAAAACTAATGAA

AAAAAAGATGATGGAA
Sequence Length: 238 bp

Amino acid sequence of Clone# T108

(SEQ ID NO: 14)

RILGEEKPNVDGVSTSNTPGGNESSSASPNLSDAAEKKDEKEASEQGEESHKKENSQESA

NGKDDVKEEKKTNEKKDDG
Sequence Length: 79 aa

Amino acid sequence of PFB0310c (MSP-4)

(SEQ ID NO: 15)

MWIVKFLIVVHFFIICTINFDKLYISYSYNIVPENGRMLNM*RILGEEKPNVDGVSTSNTPGG*

*NESSSASPNLSDAAEKKDEKEASEQGEESHKKENSQESANGKDDVKEEKKTNEKKDDG*KTD

KVQEKVLEKSPKESQMVDDKKKTEAIPKKVVQPSSSNSGGHVGEEEDHNEGEGEHEEE

EEHEEDDDDEDDDTYNKDDLEDEDLCKHNNGGCGDDKLCEYVGNRRVKCKCKEGYK

LEGIECVELLSLASSSLNLIFNSFITIFVVILLIN,
Sequence Length: 272 aa

Coding Nucleotide Sequence of PFB0310c (MSP-4)

(SEQ ID NO: 16)

ATGTGGATAGTTAAATTTTTAATAGTAGTTCATTTTTTTATAATTTGTACCATAAACT

TTGATAAATTGTATATCAGTTATTCTTATAATATAGTACCAGAAAATGGAAGAATGT

TAAATATGA*GAATTCTAGGGGAAGAAAAACCAAATGTGGACGGAGTAAGTACTAGTAATA*

*CTCCTGGAGGAAATGAATCTTCAAGTGCTTCCCCCAATTTATCTGACGCAGCAGAAAAAA*

*GGATGAAAAAGAAGCTTCTGAACAAGGAGAAGAAAGTCATAAAAAAGAAAATTCCCAAGAA*

*AGCGCGAATGGTAAGGATGATGTTAAAGAAGAAAAAAAAACTAATGAAAAAAAAGATGATG*

*GAA*AAACAGACAAGGTTCAAGAAAAGGTTCTAGAAAAGTCTCCAAAAGAATCCCAA

ATGGTTGATGATAAAAAAAAAACTGAAGCTATCCCTAAAAAGGTAGTTCAACCAAG

TTCATCAAATTCAGGTGGCCATGTTGGAGAGGAGGAAGACCACAACGAAGGAGAA

GGAGAACATGAAGAGGAGGAAGAACATGAAGAAGATGACGATGACGAAGATGATG

ATACTTATAATAAGGACGATTTGGAAGATGAAGATTTATGTAAACATAATAATGGG

GGTTGTGGAGATGATAAATTATGTGAATATGTTGGGAATAGAAGAGTAAAATGTAA

ATGTAAAGAAGGATATAAATTAGAAGGTATTGAATGTGTTGAATTATTATCCTTAGC

ATCTTCTTCTTTAAATTTAATTTTTAATTCATTTATAACAATATTTGTTGTTATATTGT

TAATAAATTAA,
Sequence Length: 819 bp

Clone # T32: Pf-PGPS(MAL8P1.58)
Nucleic acid sequence of Clone#T32, 300 bp (Sequence 1,023-1,3,22 of gene MAL8P1.58 (Pf-PGPS) 1-1986

(SEQ ID NO: 17)

TTCTTTTATCCTTTATTTGAAAAAAATAAAAGCATTTTAGTACTTGAACTTTCCTTGC

AGTGTGGATTTTCCATACCTCCAATATATGATGAAACAGATATGTTAGAAAACTTAT

TAAAAAATATCGAAAAATATGATCAAAGCTTAGTTATTTCTTCGGGATATTTAAACT

TCCCAATGAATTTTCTTAAATTAATTAGAAATATATATATCAACGTTATGCAAAAAA

AAAATGGTATTTTACAATTAATCACAGCGTCCCCATGCGCTAATATTTTTTATAAATC

TAAAGGGATATCT
Sequence Length: 300 bp

Amino acid sequence of Clone#T32

(SEQ ID NO: 18)

FFYPLFEKNKSILVLELSLQCGFSIPPIYDETDMLENLLKNIEKYDQSLVISSGYLNFPMNF

LKLIRNIYINVMQKKNGILQLITASPCANSFYKSKGIS,
Sequence Length: 100

Amino acid sequence of MAL8P1.58 (PfPGPS)

(SEQ ID NO: 19)

MALKFVIHEPKAKLLFTPKEFFNTLNDIFKNSQNRIVISCLYMGIGELEKELIDSIKKNVNI

KDLKVDILLDRQRGTRLEGKFNESSVSILSELFKCSDNINISLFHNPLLGPILYNILPPRAN

EAIGVMHMKIYIGDNILMLSGANLSDSYLRNRQDRYFVIENKFLADSIHNIINTIQGMSFT

LNRDLTIKWENDLMNPLIDAYVFREQYYRRIRFMLQGIQKHISQYNKNYSYNNYYKNIK

NDPINDKTYIYNNQNNNKYSYTSNEFRMLNSFSTDIFDKDTYNNKNQKNNHKKENMET

HTLLDTNHGTCDSTINLLNNNQNENHTNNLFTYLNEKDE*FFYPLFEKNKSILVLELSLQCG*

*FSIPPIYDETDMLENLLKNIEKYDQSLVISSGYLNFPMNFLKLIRNIYINVMQKKNGILQLITASP*

*CANSFYKSKGIS*YYIPSSYSAMANVCIEYITKNLTNFLKKVNGQNVSEQNDISNQKIYIEY

YKPSWTFHSKGIWIMDNMKSMKNVSNDNDNDNDNNNNDNNNNNNINNNNEFHSAKKY

EQNVNNSPNVKNNLNKSEYFNNENFDKNIDEENDYYDNLPWCTVIGSSNYGYRAKYR

DLEMSFIIKTNDYNLRCQLKKELNIIYESSHFVQVDELKLRYAFWLKFLVKYIFKWLL,
Sequence Length: 661

Coding Nucleic acid sequence of gene MAL8P1.58 (PfPGPS) 1-1986

(SEQ ID NO: 20)

ATGGCTCTGAAGTTTGTCATTCATGAACCTAAAGCAAAATTATTATTTACTCCTAAA

GAATTTTTTAATACCTTAAATGACATTTTTAAGAACTCACAAAATCGTATTGTGATTA

GCTGTTTATATATGGGAATAGGAGAATTAGAAAAAGAATTAATAGATAGTATAAAA

AAGAATGTGAATATAAAAGATTTAAAAGTTGATATATTATTAGATAGACAAAGAGG

TACAAGACTAGAAGGGAAATTTAATGAAAGTTCAGTTAGTATTTTATCAGAACTTTT

TAAATGTTCAGATAATATTAATATAAGCTTATTTCATAATCCTTTATTAGGTCCTATA

CTTTATAATATCTTACCTCCTAGAGCAAATGAAGCTATAGGTGTAATGCATATGAAA

ATTTATATTGGGGATAATATTCTAATGTTATCAGGAGCCAATTTAAGTGATAGCTAT

TTACGAAATAGACAAGATAGATATTTTGTTATTGAAAATAAATTCTTAGCTGATTCT

ATTCATAATATTATTAATACCATACAAGGTATGTCATTTACTCTAAATCGAGATTTA

ACCATAAAGTGGGAAAATGATTTAATGAACCCACTTATAGATGCTTACGTATTTCGT

GAACAATATTATAGAAGAATACGTTTTATGTTACAAGGAATTCAAAAACATATTTCA

CAATATAATAAAAATTATTCATATAATAATTATTATAAAAATATAAAAAATGATCCA

ATAAATGATAAGACATATATTTATAATAATCAAAATAACAATAAATATAGTTATACA

TCAAACGAATTTCGCATGTTAAATTCTTTCAGTACAGATATATTCGATAAAGATACT

TATAATAATAAAAACCAAAAAAATAATCATAAAAAAGAAAATATGGAAACACATA

CTTTATTAGATACTAATCATGGAACATGTGATTCAACAATTAATCTTCTAAATAATA

ATCAAAATGAAAACCATACAAATAATTTATTTACATATCTAAATGAAAAAGATGAA

*TTCTTTTATCCATTATTTGAAAAAAATAAAAGCATTTTAGTACTTGAACTTTCCTTGCAGTGT*

-continued

*GGATTTTCCATACCTCCAATATATGATGAAACAGATATGTTAGAAAACTTATTTAAAAAATATC*

*GAAAAATATGATCAAAGCTTAGTTATTTCTTCGGGATATTTAAACTTCCCAATGAATTTTCTT*

*AAATTAATTAGAAATATATATATCAACGTTATGCAAAAAAAAAATGGTATTTTACAATTAATCA*

*CAGCGTCACCATGCGCTAATAGTTTTTATAAATCTAAAGGGATATCT*TATTATATACCAAG

TTCATATTCAGCTATGGCTAATGTGTGTATTGAATATATTACCAAAAATTTAACCAA

TTTTCTAAAAAAAGTAAATGGACAAAATGTTTCTGAACAAAATGATATTTCAAATCA

AAAAATATATATTGAATATTACAAACCTTCATGGACATTTCATTCGAAAGGTATATG

GATAATGGACAATATGAAAAGTATGAAAAATGTGAGTAATGATAATGATAATGATA

ATGATAATAATAATAATGATAATAATAATAATAATAATATTAATAATAATGAATTTC

ATTCAGCTAAAAAATATGAACAAAATGTTAATAACTCACCAAATGTAAAAAATAAC

CTGAACAAGTCAGAATATTTTAACAACGAAAATTTTGATAAGAATATTGATGAAGA

GAATGATTATTATGATAATTTACCCTGGTGTACAGTGATTGGAAGTTCTAATTATGG

GTATAGAGCAAAATATAGAGATTTGGAGATGAGTTTTATAATAAAAACAAATGATT

ATAATTTGAGGTGTCAGTTAAAGAAAGAATTAAATATAATATATGAGTCATCTCATT

TTGTACAAGTGGATGAATTGAAATTACGATATGCTTTTTGGTTAAAATTTTTAGTGA

AATATATATTCAAATGGCTTTTATAA
Sequence Length: 1986 bp

Clone #T9: Mature parasite-infected erythrocyte surface antigen, erythrocyte membrane protein 2 (MESA)
Nucleic acid sequence of Clone# T9, 459 bp (Sequence 2,080-2,538 of PFE0040c (MESA)

(SEQ ID NO: 21)

GTAAAAGAAGGAATTAAAGAAAATGATACTGAAAATAAAGATAAAGTGATAGGAC

AAGAAATAATAACTGAAGAAGTAAAAGAAGGAATTAAAGAAAATGATACTGAAAA

TAAAGATAAAGTGATAGGACAAGAAATAATAACTGAAGAAGTAAAAAAAGAAATT

GAAAAACAAGAAGAAAAAGGAAATAAAGAAAATATTCTTGAAATTAAAGATATAG

TAATTGGACAAGAAGTAATAATAGAAGAAGTAAAAAAAGTAATTAAAAAAAAAGT

AGAAAAAGGAATTAAAGAAAATCATACTGAAAGTAAAGATAAAGTGATAGGACAA

GAAATAATAGTTGAAGAAGTAAAAGAAGAAATTGAAAAACAAGTAGAAGAAGGAA

TTAAAGAAAATGATACTGAAAGTAAAGATAAAGTGATAGGACAAGAAGTGATAAA

AGGAGATGTTAATGAAGAA
Sequence Length: 459 bp

Amino acid sequence of Clone# T9

(SEQ ID NO: 22)

VKEGIKENDTENKDKVIGQEIITEEVKEGIKENDTENKDKVIGQEIITEEVKKEIEKQEEK

GNKENILEIKDIVIGQEVIIEEVKKVIKKKVEKGIKENHTESKDKVIGQEIIVEEVKEEIEKQ

VEEGIKENDTESKDKVIGQEVIKGDVNEE
Sequence Length 153 aa

Amino acid sequence of PFE0040c (MESA)

(SEQ ID NO: 23)

MEVICRNLCYDKKNNMMENEGNKVKKVYNNSSLKKYMKFCLCTIICVFLLDIYTNCES

PTYSYSSIKNNNDRYVRILSETEPPMSLEEIMRTFDEDHLYSIRNYIECLRNAPYIDDPLW

GSVVTDKRNNCLQHIKLLEMQESERRKQQEEENAKDIEEIRKKEKEYLMKELEEMDESD

VEKAFRELQFIKLRDRTRPRKHVNVMGESKETDESKETDESKETGESKETGESKETGES

KETGESKETGESKETGESKETGESKETGESKETGESKETGESKETGESKETGESKETGES

-continued

KETGESKETRIYEETKYNKITSEFRETENVKITEESKDREGNKVSGPYENSENSNVTSESE

ETKKLAEKEENEGEKLGENVNDGASENSEDPKKLTEQEENGTKESSEETKDDKPEENEK

KADNKKKSKKKKKSFFQMLGCNFLCNKNIETDDEEETLVVKDDAKKKHKFLREANTE

KNDNEKKDKLLGEGDKEDVKEKNDEQKDKVLGEGDKEDVKEKNDEQKDKVLGEGDK

EDVKEKNDGKKDKVIGSEKTQKEIKEKVEKRVKKKCKKKVKKGIKENDTEGNDKVKG

PEIIIEEVKEEIKKQVEDGIKENDTEGNDKVKGPEIITEEVKEEIKKQVEEGIKENDTEGND

KVKGPEIITEEVKEEIKKQVEEGIKENDTESKDKLIGQEIITEEVKEGIKENDTENKDKVIG

QEIITEEVKEGIKENDTENKDKVIGQEIITEEVKKEIEKQEEKGNKENILEIKDIVIGQEVIIE

EVKKVIKKKVEKGIKENHTESKDKVIGQEIIVEEVKEEIEKQVEEGIKENDTESKDKVIGQ

EVIKGDVNEEGPENKDKVTKQEKVKEVKKEVKKKVKKRVKKRNNKNERKDNVIGKEI

MKEDVNEKDTANKDKEIEQEKEKEEVKEKEEVKEKEEVKEKEEVKEKEEVKEKEEVKE

KEEVKEKEEVKEKDTESKDKEIEQEKEKEEVKEVKEKDTENKDKVIGQEIIIEEIKKEVK

KRVKKRNNKNENKDNVIVQEIMNEDVNEKDTANKDKVIEQEKEKEEVKEKEEVKEKE

EVKEKEEVKEKEEVKEKEEVKEKDTESKDNVIVQEIMNEDVNEKDTESKDKMIGKEVII

EEVKEEVKKRVNKEVNKRVNRRNRKNERKDVIEQEIVSEEVNEKDTKNNDKKIGKRVK

KPIDDCKKEREVQEESEEESEEESEEESEEESEEESEEESEEESEEESEEESEEESEEESEEE

SEEESEEESEEESEEESEEESDEEKNTSGLVHRRNCKKEKKYNNGELEEYYKEKQNEEYF

DEEYIIQSKEHNTLNTFPNMALNEDFRREFHNILSIHEDTDLMELKRILYNLFLEYNPHM

NNKQKAELDKKFSEMNVVHQILNYEERIRMYEENAARGRLNTVILDPIITFNVIFGDDT

MFKFIDE

Sequence Length: 1434 aa

Coding Nucleotide sequence of PFE0040c (MESA)

(SEQ ID NO: 24)

TGGAGGTAATTTGTAGAAATTTATGCTACGATAAGAAAAATAATATGATGGAAAAT

GAAGGGAACAAAGTGAAAAAAGTGTATAATAATTCTTCTTTAAAGAAATATATGAA

GTTTTGTTTATGCACTATAATATGTGTTTTTTTATTAGATATCTATACGAATTGTGAA

TCACCCACCTATTCATACAGTTCAATAAAGAATAATAATGACAGATATGTAAGAATT

TTAAGTGAAACTGAACCACCGATGAGTTTAGAGGAAATAATGAGAACATTTGATGA

AGATCATCTATATTCTATAAGAAACTATATTGAATGTTTAAGAAACGCTCCATATAT

CGATGATCCTTTGTGGGGTTCGGTTGTTACAGATAAACGTAATAATTGTCTTCAGCA

TATTAAATTATTGGAAATGCAAGAATCCGAAAGAAGAAAACAACAAGAAGAGGAG

AATGCTAAGGATATTGAAGAAATAAGAAAGAAAGAAAAAGAATACCTTATGAAAG

AATTAGAAGAAATGGATGAATCCGATGTAGAAAAGGCATTTAGAGAATTACAATTT

ATTAAGTTAAGAGATAGAACTAGACCTAGAAAACATGTGAATGTAATGGGAGAATC

TAAGGAAACAGATGAATCTAAGGAAACAGATGAATCTAAGGAAACTGGTGAATCTA

AGGAAACTGGTGAATCTAAGGAAACTGGTGAATCTAAGGAAACTGGTGAATCTAAG

GAAACTGGTGAATCTAAGGAAACTGGTGAATCTAAGGAAACTGGTGAATCTAAGGA

AACTGGTGAATCTAAGGAAACTGGTGAATCTAAGGAAACTGGTGAATCTAAGGAAA

CTGGTGAATCTAAGGAAACTGGTGAATCTAAGGAAACTGGTGAATCTAAGGAAACT

GGTGAATCTAAGGAAACAAGAATATATGAGGAAACAAAATATAACAAAATAACGA

GTGAATTTAGAGAAACAGAAAACGTGAAGATAACAGAGGAATCTAAGGATAGAGA

-continued

AGGTAACAAAGTATCAGGTCCATATGAAAACTCAGAAAATTCCAATGTAACAAGTG

AATCTGAAGAGACCAAAAAATTAGCCGAAAAAGAGGAGAATGAGGGAGAAAAATT

AGGAGAAAATGTTAATGATGGGGCATCAGAAAATTCAGAAGATCCCAAAAAATTAA

CAGAACAAGAAGAAAATGGTACAAAGGAAAGTTCTGAAGAAACAAAAGATGATAA

ACCGGAAGAAAATGAGAAAAAGGCAGATAATAAAAAAAAAAGTAAAAAAAAGA

AAAATCATTTTTTCAAATGTTAGGATGTAATTTCCTATGTAATAAAAATATTGAAAC

TGATGATGAAGAAGAAACGTTGGTAGTAAAAGATGATGCTAAAAAGAAACATAAAT

TTTTAAGAGAAGCTAATACTGAAAAAAATGATAATGAAAAGAAAGATAAATTATTA

GGAGAAGGAGATAAAGAAGATGTTAAAGAAAAGAATGATGAACAGAAAGATAAAG

TATTAGGAGAAGGAGATAAAGAAGATGTTAAAGAAAAGAATGATGAACAGAAAGA

TAAAGTATTAGGAGAAGGAGATAAAGAAGATGTTAAAGAAAAGAATGATGGAAAG

AAAGATAAAGTGATAGGATCAGAAAAAACACAAAAGGAAATTAAAGAAAAAGTAG

AAAAAAGAGTTAAAAAAAAGTGTAAAAAAAAAGTAAAAAAAGGAATTAAAGAAAA

TGATACTGAAGGTAACGATAAAGTGAAAGGACCAGAAATAATAATTGAAGAAGTA

AAAGAAGAAATTAAAAAACAAGTAGAAGATGGAATTAAAGAAAATGATACTGAAG

GTAACGATAAAGTGAAAGGGCCAGAAATAATAACTGAAGAAGTAAAAGAAGAAAT

TAAAAAACAAGTAGAAGAAGGAATTAAAGAAAATGATACTGAAGGTAACGATAAA

GTGAAAGGGCCAGAAATAATAACTGAAGAAGTAAAAGAAGAAATTAAAAAACAAG

TAGAAGAAGGAATTAAAGAAAATGATACTGAAAGTAAGGATAAATTGATAGGACA

AGAAATAATAACTGAAGAA*GTAAAAGAAGGAATTAAAGAAAATGATACTGAAAATAAAGA*

*TAAAGTGATAGGACAAGAAATAATAACTGAAGAAGTAAAAGAAGGAATTAAAGAAAATGATA*

*CTGAAAATAAAGATAAAGTGATAGGACAAGAAATAATAACTGAAGAAGTAAAAAAAGAAATT*

*GAAAAACAAGAAGAAAAAGGAAATAAAGAAAATATTCTTGAAATTAAAGATATAGTAATTGG*

*ACAAGAAGTAATAATAGAAGAAGTAAAAAAAGTAATTAAAAAAAAAGTAGAAAAAGGAATTA*

*AAGAAAATCATACTGAAAGTAAAGATAAAGTGATAGGACAAGAAATAATAGTTGAAGAAGTA*

*AAAGAAGAAATTGAAAAACAAGTAGAAGAAGGAATTAAAGAAAATGATACTGAAAGTAAAGA*

*TAAAGTGATAGGACAAGAAGTGATAAAAGGAGATGTTAATGAAGAA*GGTCCCGAAAACAA

AGATAAAGTGACAAAACAGGAAAAAGTAAAAGAAGTTAAAAAAGAAGTAAAAAAA

AAAGTTAAAAAAAGAGTAAAAAAAAGAAATAATAAGAATGAAAGAAAAGATAATG

TGATAGGAAAAGAAATAATGAAAGAAGATGTTAATGAAAAAGATACCGCAAACAA

AGATAAAGAGATAGAACAAGAAAAAGAAAAAGAAGAAGTTAAAGAAAAAGAAGA

AGTTAAAGAAAAAGAAGAAGTTAAAGAAAAAGAAGAAGTAAAAGAAAAAGAAGA

AGTAAAAGAAAAAGAAGAAGTAAAAGAAAAAGAAGAAGTAAAAGAAAAAGAAGA

AGTAAAAGAAAAAGATACCGAAAGCAAAGATAAAGAGATAGAACAAGAAAAAGA

AAAAGAAGAAGTAAAAGAAGTTAAAGAAAAAGATACCGAAAACAAAGATAAAGTG

ATAGGACAAGAAATAATAATAGAAGAAATAAAAAAAGAAGTTAAAAAAAGAGTAA

AAAAAAGAAATAATAAAAATGAAAACAAAGATAATGTGATAGTACAAGAAATAAT

GAACGAAGATGTTAACGAAAAAGATACCGCAAACAAAGATAAGGTGATAGAACAA

GAAAAAGAAAAAGAAGAAGTTAAAGAAAAAGAAGAAGTTAAAGAAAAAGAAGAA

GTAAAAGAAAAAGAAGAAGTAAAAGAAAAAGAAGAAGTAAAAGAAAAAGAAGAA

-continued

GTAAAAGAAAAAGATACCGAAAGCAAAGATAATGTGATAGTACAAGAAATAATGA

ACGAAGATGTTAACGAAAAAGATACCGAAAGCAAAGATAAAATGATAGGAAAAGA

AGTAATAATAGAAGAAGTAAAAGAAGAAGTTAAAAAAAGAGTAAACAAAGAAGTT

AACAAAAGAGTAAACAGAAGAAATAGAAAAAATGAAAGAAAAGATGTGATAGAAC

AAGAAATAGTAAGCGAAGAAGTTAACGAAAAAGATACCAAAAACAACGATAAAAA

GATAGGAAAAAGAGTCAAAAAACCAATAGATGATTGTAAAAAAGAAAGAGAAGTA

CAAGAAGAATCTGAAGAAGAGTCTGAAGAAGAGTCTGAAGAAGAATCTGAAGAAG

AGTCTGAAGAAGAATCTGAAGAAGAGTCTGAAGAAGAATCTGAAGAAGAGTCTGA

AGAAGAATCTGAAGAAGAATCTGAAGAAGAGTCTGAAGAAGAATCTGAAGAAGAG

TCTGAAGAAGAGTCTGAAGAAGAGTCTGAAGAAGAATCTGAAGAAGAATCTGATGA

AGAAAAAAAATACATCAGGTTTGGTACATAGAAGAAATTGTAAAAAAGAAAAGAAA

TATAATAATGGAGAATTAGAAGAATATTATAAAGAGAAACAGAATGAAGAATATTT

TGATGAAGAATATATTATTCAATCAAAAGAACATAATACTTTGAATACATTCCCAAA

TATGGCATTAAATGAAGATTTCAGAAGAGAATTTCACAATATATTAAGTATTCATGA

AGATACAGATTTGATGGAACTAAAAAGAATCTTATATAATTTATTTTTAGAATATAA

TCCACATATGAATAATAAACAGAAAGCAGAATTGGATAAGAAATTTAGTGAAATGA

ATGTGGTACATCAAATATTAAATTATGAAGAGAGAATACGCATGTATGAAGAAAAT

GCAGCACGAGGAAGACTAAATACAGTTATTCTGGATCCAATTATTACATTTAATGTA

ATATTCGGAGATGATACAATGTTTAAGTTTATTGATGAATAA
Sequence Length: 4305 bp

Clone #TL22: Plasmodium falciparum glutamic acid-rich protein (Pf-GARP)
Nucleic acid sequence of Clone#TL22, 792 bp (Sequence
1,231-2,022 of gene PFA_0620c)

(SEQ ID NO: 25)

TCAAAAGAACACAAATCAAAAGGAAAGAAAGATAAAGGAAAGAAAGATAAAGGA

AAACATAAAAAAGCAAAAAAAGAAAAAGTAAAAAAACACGTAGTTAAAAATGTTA

TAGAAGATGAAGACAAAGATGGTGTAGAAATAATAAACTTAGAAGATAAAGAGGC

ATGTGAAGAACAACACATAACAGTAGAAAGTAGACCACTAAGCCAACCACAATGTA

AACTAATAGATGAACCAGAACAATTAACATTAATGGATAAATCAAAAGTTGAAGAA

AAAAACTTATCCATACAAGAGCAATTAATAGGTACCATAGGACGTGTTAATGTAGT

ACCCAGAAGAGATAATCATAAGAAAAAAATGGCGAAGATAGAGGAAGCTGAACTT

CAAAAACAGAAACATGTTGATAAGGAAGAAGACAAAAAAGAAGAATCCAAAGAAG

TAGAAGAAGAATCTAAAGAGGTACAAGAAGATGAAGAAGAAGTAGAAGAAGATGA

AGAAGAAGAAGAAGAAGAAGAGGAAGAAGAAGAAGAAGAAGAAGAAGAAGAGG

AAGAAGAAGAAGATGAAGTAGAAGAAGATGAAGATGATGCTGAAGAAGATGAAGA

TGATGCTGAAGAAGATGAAGATGATGCTGAAGAAGATGATGATGATGCTGAAGAAG

ATGATGATGATGCTGAAGAAGATGATGATGAAGATGAAGATGAAGATGAAGAAGA

AGAAGAAGATGAAGAAGAAGAAGAAGAATCAGAAAAAAAAAATAAAAAGAAATTT

GAGAAAAAAATGCCAAAATTTAA

-continued

Sequence Length: 792

Amino acid sequence of Clone#TL22

(SEQ ID NO: 26)

SKEHKSKGKKDKGKKDKGKHKKAKKEKVKKHVVKNVIEDEDKDGVEIINLEDKEACE

EQHITVESRPLSQPQCKLIDEPEQLTLMDKSKVEEKNLSIQEQLIGTIGRVNVVPRRDNHK

KKMAKIEEAELQKQKHVDKEEDKKEESKEVEEESKEVQEDEEEVEEDEEEEEEEEEEEE

EEEEEEEEEEDEVEEDEDDAEEDEDDAEEDEDDAEEDDDDAEEDDDDAEEDDDEDEDE

DEEEEEDEEEEEESEKKIKRNLRKNAKI

Sequence Length: 263

Amino acid sequence of Pf-GARP (PFA_0620c)

(SEQ ID NO: 27)

MNVLFLSYNICILFFVVCTLNFSTKCFSNGLLKNQNILNKSFDSITGRLLNETELEKNKDD

NSKSETLLKEEKDEKDDVPTTSNDNLKNAHNNNEISSSTDPTNIINVNDKDNENSVDKK

KDKKEKKHKKDKKEKKEKKDKKEKKDKKEKKHKKEKKHKKDKKKEENSEVMSLYK

TGQHKPKNATEHGEENLYEEMVSEINNNAQGGLLLSSPYQYREQGGCGIISSVHETSND

TKDNDKENISEDKKEDHQQEEMLKTLDKKERKQKEKEMKEQEKIEKKKKKQEEKEKK

KQEKERKKQEKKERKQKEKEMKKQKKIEKERKKKEEKEKKKKKHDKENEETMQQPD

QTSEETNNEIMVPLPSPLTDVTTPEEHKEGEHKEEEHKEGEHKEGEHKEEEHKEEEHKK

EEHK*SKEHKSKGKKDKGKKDKGKHKKAKKEKVKKHVVKNVIEDEDKDGVE*IINLEDKEAC

*EEQHITVESRPLSQPQCKLIDEPEQLTLMDKSKVEEKNLSIQEQLIGTIGRVNVVPRRDNHKK*

*KMAKIEEAELQKQKHVDKEEDKKEESKEVEEESKEVQEDEEEVEEDEEEEEEEEEEEEEEEE*

*EEEEEEDEVEEDEDDAEEDEDDAEEDEDDAEEDDDDAEEDDDDAEEDDDEDEDEDEEEE*

*EDEEEEEESEKKIKRNLRKNAKI*

Sequence Length: 673 aa

Coding Nucleic acid sequence gene Pf-GARP (PFA_0620c)

(SEQ ID NO: 28)

ATGAATGTGCTATTTCTTTCGTATAATATTTGTATTCTTTTTTTTGTTGTATGCACATT

AAATTTTTCTACTAAGTGCTTTTCCAATGGTTTATTGAAGAATCAAAATATCCTAAAC

AAAAGTTTTGATTCCATAACGGGAAGATTATTAAACGAAACCGAATTAGAAAAAAA

TAAAGATGATAATTCAAAATCTGAAACGTTGTTAAAAGAGGAAAAAGATGAAAAGG

ATGATGTACCTACAACGAGTAATGACAACCTTAAGAATGCTCATAATAATAATGAA

ATTTCAAGTTCAACTGATCCAACGAATATTATTAATGTTAATGATAAAGATAATGAA

AACTCTGTAGATAAAAAAAAAGATAAAAAAGAAAAAAAGCATAAAAAAGATAAAA

AAGAAAAAAAAGAAAAAAAAGATAAAAAAGAAAAAAAAAGATAAAAAAGAAAAAA

AACATAAAAAAGAAAAAAAACATAAAAAAGATAAAAAAAAAGAAGAAAACAGTG

AAGTGATGTCTTTATATAAAACGGGTCAACATAAACCAAAAAACGCAACAGAACAT

GGTGAAGAAAATTTATATGAAGAAATGGTAAGTGAAATAAATAATAATGCACAAGG

TGGACTCCTTTTATCAAGCCCATATCAATATAGAGAACAAGGAGGATGTGGAATCA

TATCTAGTGTTCATGAGACGTCTAATGATACAAAAGATAATGATAAAGAAAATATA

TCCGAAGACAAAAAGGAGGACCATCAACAAGAAGAAATGTTGAAAACACTTGATA

AAAAAGAACGTAAACAAAAAGAAAAAGAAATGAAAGAACAAGAAAAAAATCGAAA

AAAAAAAAAAAAAGCAAGAAGAAAAGGAAAAGAAAAAACAAGAAAAAGAAAGAA

AAAAACAAGAAAAGAAAGAACGTAAACAAAAAGAAAAAGAAATGAAAAAACAAA

AAAAAATAGAAAAAGAAAGAAAAAAGAAAGAAGAAAAGGAAAAGAAAAAGAAAA

-continued

AACATGATAAGGAAAATGAAGAAACAATGCAACAACCAGATCAAACAAGTGAAGA

AACCAACAATGAAATTATGGTACCATTACCAAGTCCATTGACAGACGTAACTACAC

CAGAAGAACACAAAGAAGGAGAACACAAAGAAGAAGAACACAAAGAAGGAGAAC

ACAAAGAAGGAGAACACAAAGAAGAAGAACACAAAGAAGAAGAACACAAAAAAG

AAGAACACAAA*TCAAAAGAACACAAATCAAAAGGAAAGAAAGATAAAGGAAAGAAAGATA*

*AAGGAAAACATAAAAAAGCAAAAAAAGAAAAAGTAAAAAAACACGTAGTTAAAAATGTTATA*

*GAAGATGAAGACAAAGATGGTGTAGAAATAATAAACTTAGAAGATAAAGAGGCATGTGAAG*

*AACAACACATAACAGTAGAAAGTAGACCACTAAGCCAACCACAATGTAAACTAATAGATGA*

*ACCAGAACAATTAACATTAATGGATAAATCAAAAGTTGAAGAAAAAAACTTATCCATACAAG*

*AGCAATTAATAGGTACCATAGGACGTGTTAATGTAGTACCCAGAAGAGATAATCATAAGAA*

*AAAAATGGCGAAGATAGAGGAAGCTGAACTTCAAAAACAGAAACATGTTGATAAGGAAGAA*

*GACAAAAAAGAAGAATCCAAAGAAGTAGAAGAAGAATCTAAAGAGGTACAAGAAGATGAAG*

*AAGAAGTAGAAGAAGATGAAGAAGAAGAAGAAGAAGAGGAAGAAGAAGAAGAAG*

*AAGAAGAAGAGGAAGAAGAAGAAGATGAAGTAGAAGAAGATGAAGATGATGCTGAAGAAG*

*ATGAAGATGATGCTGAAGAAGATGAAGATGATGCTGAAGAAGATGATGATGATGCTGAAG*

*AAGATGATGATGATGCTGAAGAAGATGATGATGAAGATGAAGATGAAGATGAAGAAGAAG*

*AAGAAGATGAAGAAGAAGAAGAAGAATCAGAAAAAAAAATAAAAAGAAATTTGAGAAAAAAT*

*GCCAAAATTTAA*
Sequence Length: 2022 bp

Clone #TL27: Plasmodium falciparum 3D7 Plasmodium exported protein (PHISTc), unknown function (PFI1780w) mRNA, complete cds
Nucleic acid sequence of Clone#TL27, 303 bp (Sequence 691-998 of gene (PFI1780w)

(SEQ ID NO: 29)

GAACATGGTGAAATGCTAAATCAAAAAAGAAAACTTAAACAACATGAACTTGATAG

AAGAGCACAAAGGGAAAAAATGTTAGAAGAACATAGTAGAGGAATATTTGCTAAA

GGATATTTGGGAGAAGTAGAATCAGAAACTATAAAAAAGAAAACGGAACACCATG

AAAATGTAAATGAAGATAATGTAGAAAAACCAAAATTGCAACAACATAAAGTTCAA

CCACCAAAAGTCCAACAACAAAAAGTTCAACCACCAAAATCACAACAACAAAAAG

TTCAACCACCAAAATCACAACAACAA
Sequence Length: 303

Amino acid sequence of Clone#TL27

(SEQ ID NO: 30)

EHGEMLNQKRKLKQHELDRRAQREKMLEEHSRGIFAKGYLGEVESETIKKKTEHHENV

NEDNVEKPKLQQHKVQPPKVQQQKVQPPKSQQQKVQPPKSQQQ
Sequence Length: 101

Amino acid sequence of PFI1780w (SEQ ID NO: 31)

MAVSTYNNTRRNGLRYVLKRRTILSVFAVICMLSLNLSIFENNNNNYGFHCNKRHFKSL

AEASPEEHNNLRSHSTSDPKKNEEKSLSDEINKCDMKKYTAEEINEMINSSNEFINRNDM

NIIFSYVHESEREKFKKVEENIFKFIQSIVETYKIPDEYKMRKFKFAHFEMQGYALKQEKF

LLEYAFLSLNGKLCERKKFKEVLEYVKREWIEFRKSMFDVWKEKLASEFREHGEMLNQ

KRKLKQHELDRRAQREKMLEEHSRGIFAKGYLGEVESETIKKKTEHHENVNEDNVEKP

KLQQHKVQPPKVQQQKVQPPKSQQQKVQPPKSQQQKVQPPKVQQQKVQPPKVQKPKL

QNQKGQKQVSPKAKGNNQAKPTKGNKLKKN

Sequence Length: 383 aa

Coding Nucleic acid sequence gene PFI1780w (SEQ ID NO: 32)

ATGGCTGTTAGTACATATAATAATACTCGAAGGAATGGTCTAAGATATGTCCTTAAA

AGACGTACCATTCTATCTGTTTTTGCTGTCATTTGTATGTTATCATTGAATTTATCAA

TATTTGAAAATAATAATAATAATTATGGATTCCATTGCAATAAAAGACATTTTAAAA

GTTTAGCTGAAGCAAGTCCAGAAGAACATAACAATTTAAGAAGTCATTCAACAAGT

GATCCAAAGAAGAATGAAGAGAAATCATTAAGTGACGAAATAAATAAATGTGATAT

GAAAAAATACACTGCTGAAGAAATAAATGAAATGATTAACAGTTCTAATGAATTTA

TAAATAGAAATGATATGAATATAATATTTAGTTATGTACATGAATCTGAGAGAGAA

AAATTTAAAAAGGTAGAAGAAAATATATTTAAATTTATTCAAAGTATAGTAGAAAC

ATATAAAATACCAGATGAATATAAAATGAGAAAATTCAAATTTGCACACTTTGAAA

TGCAAGGATATGCATTAAAACAAGAAAAGTTCCTTTTAGAATATGCTTTTCTTTCCTT

AAATGGTAAATTATGTGAACGTAAAAAATTTAAAGAAGTTTTAGAATATGTAAAAA

GGGAATGGATTGAGTTTAGAAAATCAATGTTTGACGTATGGAAGGAAAAATTAGCT

TCTGAATTCAGAGAACATGGTGAAATGCTAAATCAAAAAAGAAAACTTAAACAACA

TGAACTTGATAGAAGAGCACAAAGGGAAAAAATGTTAGAAGAACATAGTAGAGGA

ATATTTGCTAAAGGATATTTGGGAGAAGTAGAATCAGAAACTATAAAAAAGAAAAC

GGAACACCATGAAAATGTAAATGAAGATAATGTAGAAAAACCAAAATTGCAACAA

CATAAAGTTCAACCACCAAAAGTCCAACAACAAAAAGTTCAACCACCAAAATCACA

ACAACAAAAAGTTCAACCACCAAAATCACAACAACAAAAAGTTCAACCACCAAAA

GTACAACAACAAAAAGTTCAACCACCAAAAGTGCAAAAACCAAAACTTCAAAATCA

AAAAGGACAAAAGCAAGTATCTCCCAAAGCAAAGGGTAATAATCAAGCGAAACCA

ACCAAAGGAAACAAGTTAAAGAAAAATTAA
Sequence Length: 1152 bp

Clone #TL5: Plasmodium falciparum 3D7 knob-associated
histidine-rich protein (PFB0100c)
Nucleic acid sequence of Clone#TL5, 242 bp (Sequence
1309-1550 of gene (PFB0100c)

(SEQ ID NO: 33)

GTTAAAGAAAAGGGAGAAAAGCATAATGGAAAAAAACCATGCAGCAAAAAAACTA

ACGAAGAAAATAAAAATAAAGAAAAAACCAATAATTCAAAATCAGATGGATCAAA

AGCTCATGAAAAAAAAGAAAATGAAACAAAAAACACCGCTGGAGAAAATAAAAAA

GTAGATTCTACTTCAGCTGATAATAAATCAACAAATGCTGCTACACCAGGCGCAAA

AGATAAAACTCAAGGAGGAAA
Sequence Length: 242 bp

Amino acid sequence of Clone#TL5

(SEQ ID NO: 34)

VKEKGEKHNGKKPCSKKTNEENKNKEKTNNSKSDGSKAHEKKENETKNTAGENKKVD

STSADNKSTNAATPGAKDKTQGG
Sequence Length: 80 aa

Amino acid sequence of PFB0100c (SEQ ID NO: 35)

MKSFKNKNTLRRKKAFPVFTKILLVSFLVWVLKCSNNCNNGNGSGDSFDFRNKRTLAQ

KQHEHHHHHHHQHQHQHQAPHQAHHHHHHGEVNHQAPQVHQQVHGQDQAHHHHH

HHHHQLQPQQPQGTVANPPSNEPVVKTQVFREARPGGGFKAYEEKYESKHYKLKENV

VDGKKDCDEKYEAANYAFSEECPYTVNDYSQENGPNIFALRKRFPLGMNDEDEEGKEA

LAIKDKLPGGLDEYQNQLYGICNETCTTCGPAAIDYVPADAPNGYAYGGSAHDGSHGN

LRGHDNKGSEGYGYEAPYNPGFNGAPGSNGMQNYVPPHGAGYSAPYGVPHGAAHGSR

YSSFSSVNKYGKHGDEKHHSSKKHEGNDGEGEKKKKSKKHKDHDGEKKKSKKHKDN

EDAESVKSKKHKSHDCEKKKSKKHKDNEDAESVKSKKS*VKEKGEKHNGKKPCSKKTNE*

*ENKNKEKTNNSKSDGSKAHEKKENETKNTAGENKKVDSTSADNKSTNAATPGAKDKTQGG*K

TDKTGASTNAATNKGQCAAEGATKGATKEASTSKEATKEASTSKEATKEASTSKEATK

EASTSKGATKEASTTEGATKGASTTAGSTTGATTGANAVQSKDETADKNAANNGEQV

MSRGQAQLQEAGKKKKKRGCCG
Sequence Length: 654 aa

Coding Nucleic acid sequence gene PFB0100c (SEQ ID NO: 36)

ATGAAAAGTTTTAAGAACAAAAATACTTTGAGGAGAAAGAAGGCTTTCCCTGTTTTT

ACTAAAATTCTTTTAGTCTCTTTTTTAGTATGGGTTTTGAAGTGCTCTAATAACTGCA

ATAATGGAAACGGATCCGGTGACTCCTTCGATTTCAGAAATAAGAGAACTTTAGCA

CAAAAGCAACATGAACACCATCACCACCATCACCATCAACATCAACACCAACACCA

AGCTCCACACCAAGCACACCACCATCATCATCATGGAGAAGTAAATCACCAAGCAC

CACAGGTTCACCAACAAGTACATGGTCAAGACCAAGCACACCATCACCATCATCAC

CACCATCATCAATTACAACCTCAACAACCCCAGGGAACAGTTGCTAATCCTCCTAGT

AATGAACCAGTTGTAAAAACCCAAGTATTCAGGGAAGCAAGACCAGGTGGAGGTTT

CAAAGCATATGAAGAAAAATACGAATCAAAACACTATAAATTAAAGGAAAATGTTG

TCGATGGTAAAAAAGATTGTGATGAAAAATACGAAGCTGCCAATTATGCTTTCTCCG

AAGAGTGCCCATACACCGTAAACGATTATAGCCAAGAAAATGGTCCAAATATATTT

GCCTTAAGAAAAAGATTCCCTCTTGGAATGAATGATGAAGATGAAGAAGGTAAAGA

AGCATTAGCAATAAAAGATAAATTACCAGGTGGTTTAGATGAATACCAAAACCAAT

TATATGGAATATGTAATGAGACATGTACCACATGTGGACCTGCCGCTATAGATTATG

TTCCAGCAGATGCACCAAATGGCTATGCTTATGGAGGAAGTGCACACGATGGTTCTC

ACGGTAATTTAAGAGGACACGATAATAAAGGTTCAGAAGGTTATGGATATGAAGCT

CCATATAACCCAGGATTTAATGGTGCTCCTGGAAGTAATGGTATGCAAAATTATGTC

CCACCCCATGGTGCAGGCTATTCAGCTCCATACGGAGTTCCACATGGTGCAGCCCAT

GGTTCAAGATATAGTTCATTCAGTTCCGTAAATAAATATGGAAAACACGGTGATGA

AAAACACCATTCCTCTAAAAAGCATGAAGGAAATGACGGTGAAGGAGAAAAAAAG

AAAAAATCAAAAAAACACAAAGACCACGATGGAGAAAAGAAAAAATCAAAAAAA

CACAAAGACAATGAAGATGCAGAAAGCGTAAAATCAAAAAAACACAAAAGCCACG

ATTGTGAAAAGAAAAAATCAAAAAAACACAAAGACAATGAAGATGCAGAAAGCGT

AAAATCAAAAAAAAGT*GTTAAAGAAAAGGGAGAAAAGCATAATGGAAAAAAACCATGCA*

*GCAAAAAAACTAACGAAGAAAATAAAAATAAAGAAAAAACCAATAATTCAAAATCAGATGGA*

*TCAAAAGCTCATGAAAAAAAAGAAAATGAAACAAAAAACACCGCTGGAGAAAATAAAAAAGT*

*AGATTCTACTTCAGCTGATAATAAATCAACAAATGCTGCTACACCAGGCGCAAAAGATAAAA*

*CTCAAGGAGGAAA*AACTGACAAAACAGGAGCAAGTACTAATGCCGCAACAAATAAA

GGACAATGTGCTGCTGAAGGAGCAACTAAGGGAGCAACTAAAGAAGCAAGTACTTC

TAAAGAAGCAACAAAAGAAGCAAGTACTTCTAAAGAAGCAACAAAAGAAGCAAGT

-continued

ACTTCTAAAGAAGCAACAAAAGAAGCAAGTACTTCTAAAGGAGCAACTAAAGAAG

CAAGTACTACTGAAGGAGCAACTAAAGGAGCAAGTACTACTGCAGGTTCAACTACA

GGAGCAACTACAGGAGCTAATGCAGTACAATCTAAAGATGAAACTGCCGATAAAAA

TGCTGCAAATAATGGTGAACAAGTAATGTCAAGAGGACAAGCACAATTACAAGAAG

CAGGAAAGAAAAAGAAGAAAAGAGGATGCTGTGGTTAA
Sequence Length: 1965 bp

Clone #TL16: Plasmodium falciparum isolate 822 rhoptry associated membrane antigen gene (MAL7P1.208)
Nucleic acid sequence of Clone#TL16, 432 bp (Sequence 953-,1384 of gene MAL7P1.208)

(SEQ ID NO: 37)

GAAGAATCCAAAAATGAAGAATTTAAAAATGAAGAATTCAAAAATGTAGATAAAG

AAAATTATGATGATAAAAATATTTTCTATGGTTATAGTGATAATGATGATGAAAGCT

TTTTAGAAACTGATTCTTATGAAGAATATGAAGACGAAGATAAAGATGTTGAAGAT

GAGTATGAAGAAAGTTTCTTACAAAATGATGAGAAAAAAATGGTCTTTTATGATTTA

TACAAGCCAGAAGAAAATGAATCTTATTATGAAAAGAAACAAAAGAAAGAAGAAA

AAGAAGAGAAAGAAGAGAAAGAACAAAGTTTGAACAAACAAAACGATATGGAAG

ACCAAGAAGATAATGAAGAATATAAATTTGAAGAAGAAAATAAAGAAGACCTTCTA

GATGTCCAACAAGATGAAGAATTACCAAGTGAAGGAAAACAA
Sequence Length: 432

Amino acid sequence of Clone#TL16

(SEQ ID NO: 38)

EESKNEEFKNEEFKNVDKENYDDKNIFYGYSDNDDESFLETDSYEEYEDEDKDVEDEYE

ESFLQNDEKKMVFYDLYKPEENESYYEKKQKKEEKEEKEEKEQSLNKQNDMEDQEDN

EEYKFEEENKEDLLDVQQDEELPSEGKQ
Sequence Length: 144

Amino acid sequence of MAL7P1.208

(SEQ ID NO: 39)

ISFSDYERSIKNFSISSHAENNYDNIINEYKKIKDINNNINILSSVHRKGRILYDSFLEINKLE

NDKKEKHEKEDEYEDNDESFLETEEYEDNEDEKYNKDEDDYAESFIETDEYEDNEDDK

YNKDEDDYSESFIETDEYDDNEEEQYNKDEDDYADSFIETDHYENNDDKNEEEEEYND

QDNDYGYNFLETDEYDDSEEYDYDDKEYGESFLEKEEGEEMKDEEMKDEEMKDVEM

KDEEMKDEEIKYDEMKNEEMKYDEMKDEVMKDEEMKDEVMKDEEMKDEQMKYEEF

KN<u>EESKNEESKNEESKNEESKNEEFKNEESKNEEFKNEEFKNVDKENYDDKNIFYGYSDND</u>

<u>DESFLETDSYEEYEDEDKDVEDEYEESFLQNDEKKMVFYDLYKPEENESYYEKKQKKEEKEE</u>

<u>KEEKEQSLNKQNDMEDQEDNEEYKFEEENKEDLLDVQQDEELPSEGKQ</u>KVKGKSFDNEH

LNEIQNVSDVHAFIQKDMKYLDDLIDEEQTIKDAVKKSAYKGNKKLGNNKKSQMILEE

EPEENFEEDADEELNKLMEQEKNIVDKEIKNSKANKSNKKLQFNNTNKQNKMYMKNE

YNNKTKNNKNNKFEQQNYDESYMDDDYEQNEEFNDNNQSEDMKETNELDKINDELLT

DQGPNEDTLLENNNKIFDNKFVAHKKREKSISPHSYQKVSTKVQNKEDMENKEEKQLIS
Sequence Length: 704

Coding Nucleic acid sequence gene MAL7P1.208

(SEQ ID NO: 40)

ATTAGCTTTTCTGATTATGAGAGATCAATAAAAAACTTTTCTATTTCTTCTCATGCAG

AAAATAATTATGATAATATAATAAATGAATATAAAAAAATAAAAGATATTAACAAC

AATATAAACATATTATCATCAGTACATAGAAAAGGAAGAATATTGTACGACAGCTT

TTTAGAAATAAATAAGTTGGAAAATGACAAAAAAGAGAAACATGAAAAAGAAGAT

GAATATGAAGATAATGATGAAAGCTTTTTAGAAACTGAAGAATATGAAGATAATGA

AGATGAAAAATATAACAAAGATGAAGATGATTATGCAGAAAGTTTTATTGAGACTG

ATGAATATGAAGATAATGAAGATGATAAATATAATAAAGATGAAGATGATTATTCA

GAAAGCTTTATTGAGACTGATGAATATGATGATAATGAAGAAGAACAATATAATAA

AGATGAAGATGATTATGCAGATAGTTTTATTGAGACAGACCATTATGAAAATAACG

ATGATAAAAATGAAGAAGAAGAAGAATATAATGATCAAGATAATGATTATGGATAT

AACTTTTTAGAAACTGACGAATACGATGATAGCGAAGAATATGATTACGACGATAA

GGAATACGGAGAGAGTTTCCTCGAAAAAGAAGAAGGTGAAGAAATGAAAGATGAA

GAGATGAAAGATGAAGAAATGAAAGATGTAGAAATGAAAGATGAAGAGATGAAAG

ATGAAGAGATAAAAATATGACGAGATGAAAAATGAAGAGATGAAATATGACGAGAT

GAAAGATGAAGTGATGAAAGATGAAGAGATGAAAGATGAAGTGATGAAAGATGAA

GAGATGAAAGACGAACAAATGAAATATGAAGAATTCAAAAAT*GAAGAATCCAAAAAT*

*GAAGAATCCAAAAATGAAGAATCCAAAAATGAAGAATCCAAAAATGAAGAATTCAAAAATGA*

*AGAATCCAAAAATGAAGAATTTAAAAATGAAGAATTCAAAAATGTAGATAAAGAAAATTATGA*

*TGATAAAAATATTTTCTATGGTTATAGTGATAATGATGATGAAAGCTTTTTAGAAACTGATTC*

*TTATGAAGAATATGAAGACGAAGATAAAGATGTTGAAGATGAGTATGAAGAAAGTTTCTTAC*

*AAAATGATGAGAAAAAAATGGTCTTTTATGATTTATACAAGCCAGAAGAAAATGAATCTTATT*

*ATGAAAAGAAACAAAAGAAAGAAGAAAAAGAAGAGAAAGAAGAGAAAGAACAAAGTTTGAA*

*CAAACAAAACGATATGGAAGACCAAGAAGATAATGAAGAATATAAATTTGAAGAAGAAAATA*

*AAGAAGACCTTCTAGATGTCCAACAAGATGAAGAATTACCAAGTGAAGGAAAACAAAAAGT*

*AAAAGGAAAATCATTCGATAATGAACATTTGAATGAAATACAAAATGTTAGCGACGTACATG*

*CATTTATACAAAAAGATATGAAATATTTAGATGATCTCATAGATGAAGAGCAAACTATTAAAG*

*ATGCCGTCAAAAAAAGTGCTTATAAAGGAAATAAGAAATTAGGAAATAATAAAAAATCACAA*

*ATGATACTGGAAGAAGAACCAGAAGAAAAATTTTGAAGAAGATGCTGATGAAGAATTAAATA*

*AACTAATGGAACAAGAAAAAAAATATTGTAGATAAAGAAATCAAAAATAGTAAAGCAAATAAA*

*AGCAACAAAAAATTACAATTCAATAACACTAATAAACAAAACAAAATGTATATGAAAAACGAA*

*TATAATAATAAGACAAAAAATAATAAAAACAA*TAAATTTGAACAACAAAATTATGATGAA

TCATATATGGATGATGATTATGAACAAAATGAAGAATTTAATGATAATAATCAAAG

CGAAGATATGAAAGAAACAAATGAACTCGATAAAATTAATGATGAACTATTAACTG

ATCAAGGACCAAACGAAGATACATTATTAGAAAATAATAATAAAATTTTCGATAAT

AAATTTGTAGCACATAAAAAAAGAGAAAAAAGTATATCCCCACACAGTTACCAAAA

GGTATCTACCAAAGTACAAAATAAGGAAGACATGGAAAATAAGGAAGAGAAACAA

TTGATAAGTAA
Sequence Length: 2114

Clone #TL45: Plasmodium falciparum 3D7 Cg4 protein (PF07_0033)
Nucleic acid sequence of Clone#TL45, 650 bp
(Sequence 1,764-2413 of gene PF07_0033)

(SEQ ID NO: 41)

TCACCAAATAAAACAGAATTAAAAAAAGGAGAAGAAGGAAAAGTACAAACATGTT

ATACAACAATACCTATTGAAACATTATTAGCTCAAGGATCTTATAGTTCTAAAGATA

TATTCAATTTTAGTGAACAGGAAATTAATATGCAACATAGTGATATATTAGAAGGAG

AACGATTAAAACATCTTAATGAACTAGAAACTATTATATATGAAAGTAGAAGTAGA

CTTAATGGTATATATAAAAATTTTGTTATGGATGATGAAAGAGATCGTATTTTACTTT

CCTTAGATGATTATGAAAATTGGTTATATGATAATATAGAAGAAAATAAAAATATGT

TTATTAAAAAAAAAGAAGAAATTAGAGATCTTATAAAAAATATTGTACAAAAATTT

GATGTATATAATTCAAAACAACAAAATCTAGGAAATATAATTAATCATCTTAATAAT

ATCATAACACAATGTTCAAATAAACCATCGGATGAAAGTCAAAATATAATTAATAG

AACAACGAAATTCTTAAATAATATTAATTCTTTACAAGAACAAGAAAAAAAATAAAC

CACTATACGAACCACCTGTATATACACTTAACGATATTGAAGCAGAATTTAATGAAG

TCACACAACTCGCTCAAAAATTCTTTTC
Sequence Length: 650 bp

Amino acid sequence of Clone#TL45

(SEQ ID NO: 42)

SPNKTELKKGEEGKVQTCYTTIPIETLLAQGSYSSKDIFNFSEQEINMQHSDILEGERLKH

LNELETIIYESRSRLNGIYKNFVMDDERDRILLSLDDYENWLYDNIEENKNMFIKKKEEIR

DLIKNIVQKFDVYNSKQQNLGNIINHLNNIITQCSNKPSDESQNIINRTTKFLNNINSLQEQ

EKNKPLYEPPVYTLNDIEAEFNEVTQLAQKFF
Sequence Length: 216 aa

Amino acid sequence of gene PF07_0033

(SEQ ID NO: 43)

MSVLGIDIGNDNSVVATINKGAINVVRNDISERLTPTLVGFTEKERLIGDSALSKLKSNYK

NTCRNIKNLIGKIGTDVKDDIEIHEAYGDLIPCEYNYLGYEVEYKNEKVVFSAVRVLSALL

SHLIKMAEKYIGKECKEIVLSYPPTFTNCQKECLLAATKIINANVLRIISDNTAVALDYGM

YRMKEFKEDNGSLLVFVNIGYANTCVCVARFFSNKCEILCDIADSNLGGRNLDNELIKYI

TNIFVNNYKMNPLYKNNTPELCPMGTGRLNKFLVTSTASDQQNGINNKVRIKLQEVAIK

TKKVLSANNEASIHVECLYEDLDCQGSINRETFEELCSNFFLTKLKHLLDTALCISKVNIQ

DIHSIEVLGGSTRVPFIQNFLQQYFQKPLSKTLIADESIARGCVLSAAMVSKHYKVKEYEC

VEKVTHPINVEWHNINDASKSNVEKLYTRDSLKKKVKKIVIPEKGHIKLTAYYENTPDLP

SNCIKELGSCIVKINEKNDKIVESHVMTTFSNYDTFTFLGAQTVTKSVIKSKDEKKKADD

KTEDKGEKKDAKDQEQNDDKDQTNDNNMNEKDTNDKKEKNNETNSPNKTELKKGEE

GKVQTCYTTIPIETLLAQGSYSSKDIFNFSEQEINMQHSDILEGERLKHLNELETIIYESRSR

LNGIYKNFVMDDERDRILLSLDDYENWLYDNIEENKNMFIKKKEEIRDLIKNIVQKFDVY

NSKQQNLGNIINHLNNIITQCSNKPSDESQNIINRTTKFLNNINSLQEQEKNKPLYEPPVYT

LNDIEAEFNEVTQLAQKFFSKLEVEELAKQKAKQEKEKEKEKEKEKEKEKEKNEETNLD

ANEEQNNEAKNNEEKENSTKNENSANPEE
Sequence Length: 873 aa

Coding Nucleic acid sequence gene PF07_0033

(SEQ ID NO: 44)

ATGTCGGTTTTAGGTATAGATATAGGAAATGACAATTCTGTTGTAGCTACTATTAAT

AAAGGTGCTATAAATGTTGTGAGGAATGACATATCCGAAAGGTTAACCCCGACATT

AGTTGGTTTCACCGAAAAAGAAAGATTAATAGGTGATAGTGCTTTATCTAAATTGAA

ATCTAATTATAAGAATACATGTAGGAATATAAAGAATTTGATAGGTAAAATAGGTA

CCGATGTAAAAGATGATATAGAAATACATGAAGCATATGGGGATTTAATACCATGT

GAATATAATTATTTAGGTTATGAAGTTGAATATAAAAATGAAAAAGTTGTATTTAGT

GCTGTTCGTGTTTTATCAGCCTTATTATCACATTTGATTAAAATGGCTGAAAAATATA

TTGGAAAGGAATGTAAAGAAATTGTCTTATCATATCCTCCAACATTTACAAATTGTC

-continued

AAAAAGAATGTTTATTAGCTGCAACTAAAATTATTAATGCTAATGTTTTGAGAATTA

TTAGTGATAATACAGCTGTTGCTCTAGATTATGGAATGTACAGAATGAAAGAATTCA

AAGAAGATAATGGATCCTTACTAGTTTTTGTTAACATTGGTTATGCAAATACTTGTG

TATGTGTTGCGCGTTTTTTTTCTAATAAATGTGAAATCTTATGTGATATTGCTGATTC

AAATTTAGGTGGTAGAAATTTAGATAATGAACTTATTAAATATATTACAAATATATT

TGTTAATAATTATAAAATGAATCCATTATATAAAAACAATACTCCGGAATTATGCCC

CATGGGTACTGGTAGATTAAATAAGTTTTTAGTAACATCTACAGCATCTGATCAACA

AAATGGTATTAATAATAAAGTACGTATTAAATTACAAGAAGTTGCTATAAAAACAA

AGAAAGTACTTTCAGCAAATAATGAAGCGTCCATACATGTTGAATGTTTATATGAAG

ATTTAGATTGTCAAGGTTCCATTAATAGAGAAACCTTTGAAGAATTGTGTTCAAACT

TCTTCTTAACAAAATTAAAACATCTTCTAGATACTGCTCTATGTATTAGTAAAGTAA

ACATACAAGATATACATTCTATTGAAGTTTTGGGTGGATCCACAAGAGTTCCATTTA

TTCAAAATTTTTTACAACAATATTTTCAGAAACCATTATCTAAGACCCTTATAGCAG

ATGAATCTATAGCAAGAGGTTGTGTACTATCAGCTGCTATGGTTAGTAAACATTATA

AAGTAAAAGAATATGAATGTGTAGAAAAAGTTACACATCCAATTAATGTTGAATGG

CATAATATTAATGACGCATCTAAAAGTAATGTAGAAAAATTATATACAAGAGATTC

CTTAAAAAAGAAAGTTAAGAAAATTGTTATCCCAGAAAAAGGACACATTAAACTTA

CAGCTTATTATGAAAATACACCAGATTTACCATCCAATTGTATAAAAGAATTGGGAT

CATGTATTGTTAAAATAAATGAAAAGAATGATAAAATTGTTGAATCCCACGTTATGA

CCACCTTTTCAAATTATGATACATTTACATTTTTAGGTGCACAGACAGTAACCAAGT

CTGTTATTAAGTCCAAGGATGAAAAAAAAAAAGCAGATGACAAAACGGAGGATAA

GGGAGAAAAAAAAGATGCAAAAGATCAAGAACAAAATGATGATAAAGATCAAACA

AATGATAATAACATGAATGAGAAAGATACTAATGATAAAAAAGAAAAAAATAATG

AAACAAACTCACCAAATAAAACAGAATTAAAAAAAGGAGAAGAAGGAAAAGTACA

AACATGTTATACAACAATACCTATTGAAACATTATTAGCTCAAGGATCTTATAGTTC

TAAAGATATATTCAATTTTAGTGAACAGGAAATTAATATGCAACATAGTGATATATT

AGAAGGAGAACGATTAAAACATCTTAATGAACTAGAAACTATTATATATGAAAGTA

GAAGTAGACTTAATGGTATATATAAAAATTTTGTTATGGATGATGAAAGAGATCGTA

TTTTACTTTCCTTAGATGATTATGAAAATTGGTTATATGATAATATAGAAGAAAATA

AAAATATGTTTATTAAAAAAAAAGAAGAAATTAGAGATCTTATAAAAAATATTGTA

CAAAAATTTGATGTATATAATTCAAAACAACAAAATCTAGGAAATATAATTAATCAT

CTTAATAATATCATAACACAATGTTCAAATAAACCATCGGATGAAAGTCAAAATAT

AATTAATAGAACAACGAAATTCTTAAATAATATTAATTCTTTACAAGAACAAGAAA

AAAATAAACCACTATACGAACCACCTGTATATACACTTAACGATATTGAAGCAGAA

TTTAATGAAGTCACACAACTCGCTCAAAAATTCTTTTCAAAGCTTGAAGTAGAAGAA

CTAGCCAAACAAAAAGCAAAGCAAGAAAAGGAAAAGGAAAAGGAAAAAGAAAAA

GAGAAAGAAAAAGAAAAGGAAAAAAATGAAGAGACAAACTTGGATGCAAATGAG

GAACAAAATAATGAAGCAAAAAATAATGAAGAAAAGGAGAACTCAACAAAAAATG

AAAATTCAGCTAATCCAGAGGAATAA

Sequence Length: 2622 bp

Plasmodium falciparum calcium-dependent protein kinase (PF-CDPK5), putative Gene PF3D7_1337800 (fragment C)
Nucleic acid sequence 255 bp (Sequence 1452-1706(255) of gene PF3D7_1337800
(SEQ ID NO: 45)

TTCTTAGCAGCTTGTTTAGATCATAGTATATTTCAACAAGATGTTATCTGTAGAAATGCTTTCA

ATGTTTTTGATTTAGATGGTGATGGTGTTATAACAAAGGATGAATTATTTAAAATTCTATCCTT

TAGTGCTGTACAAGTATCCTTTAGTAAAGAAATTATTGAAAATCTTATTAAAGAAGTCGATTCT

AATAATGATGGATTTATAGATTATGATGAATTTTATAAGATGATGACGGGAGTTAAAGAATGA
Sequence Length: 255

Amino acid sequence of Fragment C (Pf-CDPK5)
(SEQ ID NO: 46)

FLAACLDHSIFQQDVICRNAFNVFDLDGDGVITKDELFKILSFSAVQVSFSKEIIENLIKEVDS

NNDGFIDYDEFYKMMTGVKE
Sequence Length: 84

Amino acid sequence of PF3D7_1337800(Pf-CDPK5)
(SEQ ID NO: 47)

MKETEVEDMDTNRKDGKIKKKEKIVNMKNEEVKSTTKSTLADSDEDYSIITLCTKCLSKK

LEDNKNRIILDSKAFKDNRLKGRCSVSSNEDPLDNKLNLSPYFDRSQIIQEIILMNNDEL

SDVYEIDRYKLGKGSYGNVVKAVSKRTGQQRAIKIIEKKKIHNIERLKREILIMKQMDHP

NIIKLYEVYEDNEKLYLVLELCDGGELFDKIVKYGSFSEYEAYKIMKQIFSALYYCHSKN

IMHRDLKPENILYVDNTEDSPIQIIDWGFASKCMNNHNLKSVVGTPYYIAPEILRGKYDK

RCDIWSSGVIMYILLCGYPPFNGKNNDEILKKVEKGEFVFDSNYWARVSDDAKDLICQCL

NYNYKERIDVEQVLKHRWFKKFKSNNLIINKTLNKTLIEKFKEFHKLCKIKKLAVTCIAY

QLNEKDIGKLKKTFEAFDHNGDGVLTISEIFQCLKVNDNEFDRELYFLLKQLDTDGNGLI

DYTEFLAACLDHSIFQQDVICRNAFNVFDLDGDGVITKDELFKILSFSAVQVSFSKEIIE

NLIKEVDSNNDGFIDYDEFYKMMTGVKE
Sequence Length: 568 aa

Coding Nucleotide sequence of PF3D7_1337800 (Pf-CDPK5)
(SEQ ID NO: 48)

ATGAAAGAGACGGAGGTCGAAGATATGGATACGAATAGAAAAGATGGTAAAATTAAAAAG

AAAGAAAAAATAGTAAATATGAAAAATGAAGAAGTGAAAAGTACGACAAAGAGTACGTTA

GCCGATAGTGATGAAGACTATTCGATTATAACTTTATGTACGAAATGTTTATCTAAAAAA

CTTGAAGATAATAAGAATCGAATAATTCTTGATAGTAAAGCTTTTAAAGATAATAGATTA

AAAGGTAGATGTAGTGTTAGTTCCAATGAAGATCCTTTAGATAACAAATTAAATTTATCA

CCATATTTTGATAGATCCCAAATAATTCAAGAAATAATTTTGATGAATAATGATGAATTA

AGTGATGTATATGAAATAGATAGATACAAGTTAGGCAAAGGATCTTATGGAAATGTTGTT

AAAGCCGTAAGTAAAAGAACTGGTCAACAGAGAGCTATAAAAATTATAGAGAAAAAGAAA

ATTCATAATATTGAAAGATTAAAAAGAGAAATATTAATAATGAAACAGATGGATCATCCT

AATATTATAAAATTATATGAAGTTTATGAAGACAATGAAAAATTATATTTAGTATTAGAA

TTATGTGACGGTGGAGAATTATTTGATAAAATTGTAAAATATGGTAGCTTCTCTGAATAT

GAAGCATATAAAATTATGAAACAAATATTTTCAGCTTTATATTATTGTCATAGTAAAAAT

ATTATGCATAGAGATTTAAAACCAGAAAATATTTTATATGTAGATAATACAGAAGATTCT

CCTATACAAATAATTGATTGGGGATTCGCTAGTAAATGTATGAATAATCATAATTTGAAA

TCAGTTGTTGGGACACCTTATTATATAGCACCCGAAATATTAAGAGGTAAATATGACAAA

AGATGTGATATATGGAGTAGTGGTGTAATTATGTATATTTTATTATGTGGATATCCACCA

-continued

TTTAATGGAAAAAATAATGATGAAATCTTAAAAAAAGTGGAAAAAGGAGAATTTGTTTTC

GATTCCAATTATTGGGCAAGAGTTAGTGATGATGCTAAAGATTTAATTTGTCAATGTTTA

AATTATAATTATAAAGAAAGAATAGATGTTGAGCAAGTTCTAAAACATAGATGGTTCAAA

AAATTTAAATCAAATAATCTTATTATAAATAAAACATTAAATAAAACTTTAATCGAAAAA

TTTAAAGAATTCCATAAATTATGTAAAATTAAAAAGCTAGCTGTAACATGTATAGCATAC

CAATTAAATGAAAAAGATATAGGGAAATTAAAAAAAACATTTGAAGCTTTTGATCATAAT

GGAGATGGAGTATTAACCATATCAGAAATTTTTCAATGTTTAAAAGTTAATGACAATGAA

TTTGATAGAGAATTATACTTTTTATTAAAACAACTTGATACAGATGGAAATGGATTAATT

GATTATACTGAATTCTTAGCAGCTTGTTTAGATCATAGTATATTTCAACAAGATGTTATC

TGTAGAAATGCTTTCAATGTTTTTGATTTAGATGGTGATGGTGTTATAACAAAGGATGAA

TTATTTAAAATTCTATCCTTTAGTGCTGTACAAGTATCCTTTAGTAAAGAAATTATTGAA

AATCTTATTAAAGAAGTCGATTCTAATAATGATGGATTTATAGATTATGATGAATTTTAT

AAGATGATGACGGGAGTTAAAGAATGA
Sequence Length: 1707 bp

PbSEP-1; Gene PBANKA_050600 (PbSEP-1A)
Nucleic acid sequence of PB Clone #2 828 bp (Sequence 2172-2991 of gene PBANKA_050600)

(SEQ ID NO: 65)

TTAAAAGATAGTGATGGATATGAGAAATTATTAAAAAATGACATGTACGATTTATATAATATTA

AGATGCATGATTTAAATAACTTAAAATCATATGATTTTGAATTTTCAAAAAATTTATTAAAAAA

CGAGATTTTTTTTTGTGGTGATAATATAAAAAGTGATGAAATAAATTTAAATGATAATGACATA

AATGAAAAGATTGATTCACTAATGAACAATTACAATATTATGAAAAACAAACGTGACAAATTTA

ATGAAGAAGAAAACGAAATTCAAAACTTTTTAGCAGAATTAAAAGCTGATGTAACTAATCAACT

CAATCTAAATAACGGGGAAGATGAACAGGCTTTTGATTTGCTTAATTCGTTTGATATAAACAAT

AACTTTGACGATTTTGTTGGCAACTTTGATGATACAAATGATAACATAGCTCAAAATAAATCAG

ACATAGACAATAATAAAGAGTTCGAACACGAAAATGATATAAATCATGATTATAACGATTGTGG

TACATATATGGATGATATATATAATAACAATAATGGTGATGATATTTCGAGAAAGGGATCACGT

CTGAAATTGTCTGATTTAAATGACGAAAAGAATTTATTTCCAGATGTCAACTCCTCTTTTAATA

CTCCTATAAAATCTTCTGAACTAAAGAGAGATTCAGAATGCCAAACAAATTCACCACTTATATT

TTCTAGAAGTAATAGAACTCCTAGGAAAAAAAGTGTAGAAGTAATATTAGTAAAGAAAAAATTA

AAAAAAAGAAAAGAAAAAGAATCAAATATATCATTTGAAAATACAACACATGATGATTAT
Sequence Length: 828 bp PBANKA_050600 (PbSEP-1A aa 724-997)

(SEQ ID NO: 66)

LKDSDGYEKLLKNDMYDLYNIKMHDLNNLKSYDFEFSKNLLKNEIFFCGDNIKSDEINLNDNDI

NEKIDSLMNNYNIMKNKRDKFNEEENEIQNFLAELKADVTNQLNLNNGEDEQAFDLLNSFDINN

NFDDFVGNFDDTNDNIAQNKSDIDNNKEFEHENDINHDYNDCGTYMDDIYNNNNGDDISRKGSR

LKLSDLNDEKNLFPDVNSSFNTPIKSSELKRDSECQTNSPLIFSRSNRTPRKKSVEVILVKKKL

KKRKEKESNISFENTTHDDY
Sequence Length: 276 aa

Amino acid sequence of Gene PBANKA_050600

(SEQ ID NO: 67)

MTDNEDQNKEDLIYYINRYSVNDILGNLEENDKLTNYDENSGICEYEIPFLLENVDNNNN

NNTKEHSDRNSVSSYFDDGTCSIISKNDEKHYIDKCEKDKMPKEKINIIFIQNKGEMNSF

EDILSMNNASSENLENKLNDRFYQLCCKSIADVNTHNLNKTKNIVKDKKGTLNIEHIDYG

-continued

DIFLTIRHRLRGREEKTNNMLNNNNNNDNNNNHLYSDMADSVISNWREIKNHENFIKYEN

YKEHEKEFIRRKLKKKCVNSLNGDKYFMANRKVFDYYRNNLDSYMTNGNEKDICKQENMS

LHFLPKKRKSMNNSSLYNSQIIGQNEYILKNRTFLKKFYIKKNFKQQEHIHNDDYYCDDN

HSENLYNDDIYNYNKNLSNRQGNLPSNDFIYSCEIQNKKNSIPHNICVDRNVITPRNSTW

NNENEIHEEDMVYYHSQNKGKNSHYVEAENEIQSNHYCEDKNTNSFNEYVNEIDKLDENY

NMFNKVEEDDNNNNKENFNIYDGDEIDNNEAFDIKIEENDDYETYNNELELEVEVDDGIG

NNIPFNNNDNFVNSNKNEDLDNINNCEHVSNSNHTKYGEEDNEQKAPSITSKDDKDYFDL

LIKKYEQTRMSINESSTASLSESIYLSKEGTKEPSLNAHEMLKIASNTKNDVNNKIECLN

ENLIDLKNNKEIINEGECFSNGFSIEKNDIEKENDNIVKLGSVYNNDKTEGERGNIGNKN

EKVDLKDSDGYEKLLKNDMYDLYNIKMHDLNNLKSYDFEFSKNLLKNEIFFCGDNIKSDE

INLNDNDINEKIDSLMNNYNIMKNKRDKFNEEENEIQNFLAELKADVTNQLNLNNGEDEQ

AFDLLNSFDINNNFDDFVGNFDDTNDNIAQNKSDIDNNKEFEHENDINHDYNDCGTYMDD

IYNNNNGDDISRKGSRLKLSDLNDEKNLFPDVNSSFNTPIKSSELKRDSECQTNSPLIFS

RSNRTPRKKSVEVILVKKKLKKRKEKESNISFENTTHDDYTVGTTTATSSINSKRRYPKR

NRIKTLRYWIGERELTRRNPETGEIDVVGFSECKNLEELSPHIIGPVYYKKMYLRDVNNL

HGKGNEDANNNIDRNDNTDEENEITIEINNGMYENEVYNKIQNKENSVNKNDNVSNILKK

SINGSIHNRSDNDAITRNGKKKRKKFINVVNYIKKKTKKKLVKVIDKEVEQENENVDNRN

TFSNNDNIINDITNVNHNSQNNLDQNFIAISNDFIENDDNIFFDAISLGDNAHINDIPEK

SEEIIEAPGVDAIETTKVNGNEKEINLEKEINLEKEINLEKNKDVHVKKKLLDKKKKKKK

KKNKGKEKEIDEMYKQLSFLNFNSFYSKGNEDKSKIEILKKTSTKKKGSKIDKEKVDEEN

DKHNKNSGKEAKELITKKKKAKNMKKNKKRNMQNKEMKNYYEYTNNEIEKFYNNPNDRIE

NEYNMGVDLEASIKTEEEKTEKIGELPILNSYTNEQYEHITNTNDITNSKSENFELHKNE

DEEVEKLQTSTRRKKKKKSESLIHDTNELNKKRRKTDGNNSGELISINENDEIKNVDADK

KINDKEGKYIKKVDKDTIMGSNGNNIDELNKDFEDNDQIKNIKKDEKKKETNTDGSNNMR

NINLLEEIDANEKNSTLCLVTHNKKNNTNSQSFIIDKLKSYFNIKELINVKKQKTNNVIL

NTFENKQIINNNPIRISLSYPSSVELSVENRCNQTRNGQFPLIQKNLSNFKVDINLFCVQ

IFPNKAHSSNSYDKILIGYIYQGKKVKIYFKNQERYFEKDEFFYIPKYSPFKIVNISRDN

CILYVYPINK
Sequence Length: 1810 aa

Coding Nucleotide sequence of PBANKA_050600

(SEQ ID NO: 68)

ATGACAGACAACGAGGATCAAAATAAAGAAGATCTGATATATTACATAAATAGATACAGT

GTCAATGATATATTGGGAAATTTAGAAGAAAATGATAAGTTAACAAATTATGATGAAAAT

AGCGGAATATGTGAATATGAAATTCCATTTCTTTTGGAAAATGTCGATAATAATAATAAT

AATAATACTAAAGAACATTCCGATAGAAATTCTGTATCTAGTTATTTCGATGATGGAACA

TGTTCGATTATTTCTAAAAATGATGAAAAACATTATATAGACAAATGTGAAAAAGACAAA

ATGCCAAAGGAAAAAATAAATATTATATTTATTCAGAATAAAGGTGAAATGAATAGCTTT

GAAGATATTTTATCCATGAATAATGCAAGCAGTGAAAATTTAGAAAACAAGTTAAATGAT

AGATTTTATCAACTATGTTGTAAAAGTATTGCTGATGTGAACACCCACAATTTAAATAAA

ACTAAAAATATTGTAAAAGATAAAAAAGGGACATTGAATATTGAGCATATAGATTATGGT

GATATATTTTTAACCATTCGTCATCGTCTAAGAGGGCGTGAAGAAAAAACGAATAACATG

-continued

CTAAATAATAATAATAATAATGATAATAATAATAATCATTTATATAGTGACATGGCTGAT

AGTGTTATTAGTAATTGGAGGGAAATAAAAAATCATGAAAATTTTATAAAATATGAAAAC

TATAAAGAGCATGAAAAGGAGTTTATAAGGAGGAAATTGAAAAAGAAATGCGTCAATAGT

TTAAATGGAGATAAATATTTTATGGCCAATAGAAAAGTATTTGATTATTATCGTAATAAT

TTAGATAGTTACATGACTAATGGGAATGAAAAAGATATATGCAAGCAAGAAAATATGTCT

CTACATTTTTTACCAAAAAAGAGAAAATCAATGAATAATAGTTCTTTATACAATTCTCAA

ATAATTGGACAAAATGAATATATTTTAAAGAATAGAACATTTTTAAAAAAATTTTATATA

AAAAAAAATTTTAAGCAACAAGAACATATCCATAATGATGATTATTATTGTGATGATAAT

CATAGTGAAAATTTATATAATGATGATATATATAATTATAATAAAAACTTGAGTAATAGA

CAAGGTAATCTACCCAGCAATGATTTTATTTATTCATGTGAAATTCAAAATAAGAAAAAT

TCAATACCACATAATATATGTGTCGATAGAAATGTAATAACCCCACGGAACAGTACATGG

AATAATGAAAACGAAATTCACGAAGAGGATATGGTTTATTATCATTCTCAAAATAAGGGA

AAAAATTCACATTATGTAGAAGCAGAAAATGAAATACAATCAAATCATTATTGTGAAGAT

AAAAATACAAACAGTTTTAACGAATATGTTAATGAAATTGATAAACTCGATGAAAATTAT

AATATGTTTAACAAAGTTGAAGAGGACGATAATAATAATAACAAAGAAAATTTTAACATT

TATGATGGTGATGAAATAGATAATAACGAAGCATTTGATATCAAAATCGAAGAAAATGAT

GATTATGAAACATATAACAACGAATTAGAATTAGAGGTAGAGGTAGATGATGGAATAGGT

AATAATATTCCATTTAATAATAATGATAATTTTGTAAATTCAAATAAGAATGAAGATTTG

GATAATATAAATAATTGTGAACATGTTTCAAATTCAAATCATACAAAATATGGGGAAGAA

GACAATGAGCAAAAAGCTCCATCAATAACCAGTAAAGATGATAAAGATTATTTTGATTTA

CTAATAAAAAAATATGAACAAACTAGAATGTCAATTAATGAATCTAGTACAGCCTCACTT

AGTGAAAGTATTTATTTATCAAAAGAAGGAACAAAAGAACCTTCTTTAAATGCTCACGAA

ATGTTAAAAATCGCATCTAACACAAAGAATGATGTAAATAATAAAATTGAATGTTTGAAT

GAAAACTTAATAGATTTAAAAAATAACAAGGAAATTATTAATGAAGGGGAATGTTTTAGT

AATGGTTTTTCTATCGAAAAAAATGACATAGAAAAGGAAAATGATAATATAGTAAAATTA

GGAAGTGTATATAATAATGACAAAACAGAGGGGGAAAGAGGGAATATTGGAAACAAAAAT

GAAAAAGTAGACCTTAAAAGATAGTGATGGATATGAGAAATTATTAAAAAATGACATGTAC

GATTTATATAATATTAAGATGCATGATTTAAATAACTTAAAATCATATGATTTTGAATTT

TCAAAAAATTTATTAAAAAACGAGATTTTTTTTGTGGTGATAATATAAAAAGTGATGAA

ATAAATTTAAATGATAATGACATAAATGAAAAGATTGATTCACTAATGAACAATTACAAT

ATTATGAAAAACAAACGTGACAAATTTAATGAAGAAGAAAACGAAATTCAAAACTTTTTA

GCAGAATTAAAAGCTGATGTAACTAATCAACTCAATCTAAATAACGGGGAAGATGAACAG

GCTTTTGATTTGCTTAATTCGTTTGATATAAACAATAACTTTGACGATTTTGTTGGCAAC

TTTGATGATACAAATGATAACATAGCTCAAAATAAATCAGACATAGACAATAATAAAGAG

TTCGAACACGAAAATGATATAAATCATGATTATAACGATTGTGGTACATATATGGATGAT

ATATATAATAACAATAATGGTGATGATATTTCGAGAAAGGGATCACGTCTGAAATTGTCT

GATTTAAATGACGAAAAGAATTTATTTCCAGATGTCAACTCCTCTTTTAATACTCCTATA

AAATCTTCTGAACTAAAGAGAGATTCAGAATGCCAAACAAATTCACCACTTATATTTTCT

AGAAGTAATAGAACTCCTAGGAAAAAAAGTGTAGAAGTAATATTAGTAAAGAAAAAATTA

AAAAAAAGAAAAGAAAAAGAATCAAATATATCATTTGAAAATACAACACATGATGATTAT

ACTGTTGGTACAACTACTGCTACTAGTAGCATCAATTCGAAAAGAAGATATCCTAAAAGA

AATAGAATAAAAACGTTGCGATACTGGATAGGTGAAAGGGAACTTACTAGAAGAAATCCT

GAAACAGGCGAAATAGATGTTGTAGGTTTTAGTGAATGCAAAAATTTAGAAGAATTATCT

CCTCATATTATTGGTCCAGTTTATTATAAAAAAATGTATTTACGAGATGTGAATAATTTA

CATGGAAAAGGAAACGAAGATGCTAACAACAATATAGATAGAAATGATAATACTGATGAA

GAAAATGAAATAACGATAGAAATCAATAATGGAATGTATGAAAATGAAGTGTATAATAAA

ATTCAGAATAAAGAGAATTCTGTGAATAAAAATGATAATGTTAGTAACATATTGAAAAAA

AGTATAAATGGTAGCATTCATAATAGAAGTGATAATGATGCAATAACTAGAAATGGGAAA

AAGAAAAGAAAAAAGTTTATTAATGTTGTTAATTATATTAAAAAAAAAACAAAAAAAAAA

TTAGTCAAAGTTATAGATAAAGAAGTAGAGCAGGAAAATGAAAATGTAGATAATCGTAAC

ACTTTTTCAAATAATGATAATATAATTAATGACATAACAAATGTCAATCACAATTCTCAA

AATAATTTGGATCAAAATTTTATTGCAATTAGTAATGATTTTATTGAAAATGATGACAAT

ATTTTTTTCGATGCGATTAGTCTTGGCGATAATGCTCACATAAATGATATTCCAGAAAAA

AGCGAAGAAATTATTGAAGCACCAGGAGTAGATGCAATTGAAACGACTAAAGTTAATGGA

AACGAAAAGGAAATCAATTTAGAAAAGGAAATCAATTTAGAAAAGGAAATCAATTTAGAA

AAGAATAAAGATGTACATGTGAAAAAGAAATTATTAGATAAAAAGAAAAAGAAAAAAAAA

AAGAAAAACAAGGGAAAAGAAAAGGAAATAGACGAAATGTACAAGCAATTATCATTTTTG

AATTTTAATTCGTTTTATTCTAAAGGAAATGAAGATAAATCAAAAATAGAAATTTTGAAA

AAAACAAGTACCAAAAAAAAAGGGAGTAAAATTGATAAAGAAAAGGTAGATGAGGAAAAT

GATAAACATAATAAAAATTCGGGAAAGGAAGCCAAAGAATTAATTACAAAAAAAAAGAAA

GCCAAGAATATGAAGAAAAATAAAAAGAGAAATATGCAGAATAAAGAAATGAAAAATTAT

TATGAATATACAAATAATGAAATCGAAAAGTTCTACAACAATCCAAATGATAGAATAGAG

AATGAATACAATATGGGAGTCGATTTAGAAGCATCAATAAAAACTGAAGAAGAAAAAACA

GAAAAAATTGGAGAGTTGCCCATTTTAAATTCATATACTAATGAGCAATATGAGCACATA

ACGAATACAAATGATATAACAAATTCGAAAAGTGAAAATTTTGAACTCCACAAAAATGAA

GACGAAGAAGTGGAAAAGCTACAAACTTCTACACGTCGAAAAAAGAAAAAAAAAAGTGAA

AGTTTAATTCATGATACAAATGAATTGAATAAAAAGCGAAGAAAAACAGATGGAAATAAT

TCAGGGGAATTAATTTCTATTAATGAAAATGATGAGATAAAAAATGTAGATGCTGATAAA

AAAATAAATGACAAAGAAGGTAAATATATAAAGAAAGTTGACAAGGATACAATTATGGGA

TCAAATGGAAATAATATTGATGAATTAAATAAGGATTTTGAAGATAATGATCAAATTAAA

AATATAAAAAAAGATGAAAAAAAAAAAGAGACAAATACAGATGGTTCTAATAATATGAGA

AATATAAATTTATTAGAAGAAATAGATGCAAATGAAAAAAATAGTACATTATGTTTGGTA

ACTCACAATAAAAAAAATAATACGAATAGTCAAAGTTTTATTATAGATAAATTAAAATCG

TATTTCAATATAAAAGAGTTAATAAATGTCAAAAAACAAAAAACAAATAATGTAATATTA

AATACTTTTGAAAATAAACAAATAATAAATAATAATCCTATACGTATTTCTCTTTCCTAT

CCTTCTAGTGTAGAATTATCAGTTGAAAATAGATGCAACCAAACAAGAAATGGACAATTT

CCACTTATACAAAAGAACTTAAGCAACTTCAAGGTAGACATAAATTTATTTTGTGTTCAA

ATTTTCCCAAACAAAGCACATAGCTCGAATAGTTATGATAAAATTTTGATTGGGTATATA

TATCAGGGAAAAAAGGTAAAGATTTATTTTAAGAACCAAGAAAGATATTTTGAAAAGGAT

-continued

GAGTTTTTTTACATACCCAAATACTCTCCTTTCAAAATTGTCAACATAAGCAGGGACAAT

TGTATTTTATATGTTTATCCAATAAATAAATAA
Sequence Length: 5434 bp

SERA5 (serine repeat antigen 5)
PlasmoDB ID: PF3D7_0207600
Chromosome 2; position 303,593-307,027
Full Sequence: base pairs 1-2994 (excluding introns)

(SEQ ID NO: 69)

ATGAAGTCATATATTTCCTTGTTTTTCATATTGTGTGTTATATTTAACAAAAATGTTATAAAAT

GTACAGGAGAAAGTCAAACAGGTAATACAGGAGGAGGTCAAGCAGGTAATACAGGAGGAGATCA

AGCAGGTAGTACAGGAGGAAGTCCACAAGGTAGTACGGGAGCAAGTCCACAAGGTAGTACGGGA

GCAAGTCCACAAGGTAGTACGGGAGCAAGTCAACCCGGAAGTTCCGAACCAAGCAATCCTGTAA

GTTCCGGACATTCTGTAAGTACTGTATCAGTATCACAAACTTCAACTTCTTCAGAAAAACAGGA

TACAATTCAAGTAAAATCAGCTTTATTAAAAGATTATATGGGTTTAAAAGTTACTGGTCCATGT

AACGAAAATTTCATAATGTTCTTAGTTCCTCATATATATATTGATGTTGATACAGAAGATACTA

ATATCGAATTAAGAACAACATTGAAAAAAACAAATAATGCAATATCATTTGAATCAAACAGTGG

TTCATTAGAAAAAAAAAAATATGTAAAACTACCATCAAATGGTACAACTGGTGAACAAGGTTCA

AGTACGGGAACAGTTAGAGGAGATACAGAACCAATTTCAGATTCAAGCTCAAGTTCAAGTTCAA

GCTCTAGTTCAAGTTCAAGTTCAAGTTCAAGTTCTAGTTCAAGTTCTAGTTCAAGTTCAGAAAG

TCTTCCTGCTAATGGACCTGATTCCCCTACTGTTAAACCGCCAAGAAATTTACAAAATATATGT

GAAACTGGAAAAAACTTCAAGTTGGTAGTATATATTAAGGAGAATACATTAATACTTAAATGGA

AAGTATACGGAGAAACAAAAGATACTACTGAAAATAACAAAGTTGATGTAAGAAAGTATTTGAT

AAATGAAAAGGAAACCCCATTTACTAATATACTAATACATGCGTATAAAGAACATAATGGAACA

AACTTAATAGAAAGTAAAAACTACGCAATAGGATCAGACATTCCAGAAAAATGTGATACCTTAG

CTTCCAATTGCTTTTTAAGTGGTAATTTTAACATTGAAAAATGCTTTCAATGTGCTCTTTTAGT

AGAAAAAGAAAATAAAAATGACGTATGTTACAAATACCTATCTGAAGATATTGTAAGTAAATTC

AAAGAAATAAAAGCTGAGACAGAAGATGATGATGAAGATGATTATACTGAATATAAATTAACAG

AATCTATTGATAATATATTAGTAAAAATGTTTAAAACAAATGAAAATAATGATAAATCAGAATT

AATAAAATTAGAAGAAGTAGATGATAGTTTGAAATTAGAATTAATGAATTACTGTAGTTTACTT

AAAGACGTAGATACAACAGGTACCTTAGATAATTATGGGATGGGAAATGAAATGGATATATTTA

ATAACTTAAAGAGATTATTAATTTATCATTCAGAAGAAAATATTAATACTTTAAAAAATAAATT

CCGTAATGCAGCTGTATGTCTTAAAAATGTTGATGATTGGATTGTAAATAAGAGAGGTTTAGTA

TTACCTGAATTAAATTATGATTTAGAATATTTCAATGAACATTTATATAATGATAAAAATTCTC

CAGAAGATAAAGATAATAAAGGAAAAGGTGTCGTACATGTTGATACAACTTTAGAAAAAGAAGA

TACTTTATCATATGATAACTCAGATAATATGTTTTGTAATAAAGAATATTGTAACAGATTAAAA

GATGAAAATAATTGTATATCTAATCTTCAAGTTGAAGATCAAGGTAATTGTGATACTTCATGGA

TTTTTGCTTCAAAATATCATTTAGAAACTATTAGATGTATGAAAGGATATGAACCTACCAAAAT

TTCTGCTCTTTATGTAGCTAATTGTTATAAAGGTGAACATAAAGATAGATGTGATGAAGGTTCT

AGTCCAATGGAATTCTTACAAATTATTGAAGATTATGGATTCTTACCAGCAGAATCAAATTATC

CATATAACTATGTGAAAGTTGGAGAACAATGTCCAAAGGTAGAAGATCACTGGATGAATCTATG

GGATAATGGAAAAATCTTACATAACAAAAATGAACCTAATAGTTTAGATGGTAAGGGATATACT

GCATATGAAAGTGAAAGATTTCATGATAATATGGATGCATTTGTTAAAATTATTAAAACTGAAG

TAATGAATAAAGGTTCAGTTATTGCATATATTAAAGCTGAAAATGTTATGGGATATGAATTTAG

-continued

TGGAAAGAAAGTACAGAACTTATGTGGTGATGATACAGCTGATCATGCAGTTAATATTGTTGGT

TATGGTAATTATGTGAATAGCGAAGGAGAAAAAAAATCCTATTGGATTGTAAGAAACAGTTGGG

GTCCATATTGGGGAGATGAAGGTTATTTTAAAGTAGATATGTATGGACCAACTCATTGTCATTT

TAACTTTATTCACAGTGTTGTTATATTCAATGTTGATTTACCTATGAATAATAAAACAACTAAA

AAAGAATCAAAAATATATGATTATTATTTAAAGGCCTCTCCAGAATTTTATCATAACCTTTACT

TTAAGAATTTTAATGTTGGTAAGAAAAATTTATTCTCTGAAAAGGAAGATAATGAAAACAACAA

AAAATTAGGTAACAACTATATTATATTCGGTCAAGATACGGCAGGATCAGGACAAAGTGGAAAG

GAAAGCAATACTGCATTAGAATCTGCAGGAACTTCAAATGAAGTCTCAGAACGTGTTCATGTTT

ATCACATATTAAAACATATAAAGGATGGCAAAATAAGAATGGGTATGCGTAAATATATAGATAC

ACAAGATGTAAATAAGAAACATTCTTGTACAAGATCCTATGCATTTAATCCAGAGAATTATGAA

AAATGTGTAAATTTATGTAATGTGAACTGGAAAACATGCGAGGAAAAAACATCACCAGGACTTT

GTTTATCCAAATTGGATACAAATAACGAATGTTATTTCTGTTATGTATAA

Full Sequence: 1-997 amino acids (SEQ ID NO: 70)

MKSYISLFFILCVIFNKNVIKCTGESQTGNTGGGQAGNTGGDQAGSTGGSPQGSTGASPQGSTG

ASPQGSTGASQPGSSEPSNPVSSGHSVSTVSVSQTSTSSEKQDTIQVKSALLKDYMGLKVTGPC

NENFIMFLVPHIYIDVDTEDTNIELRTTLKKTNNAISFESNSGSLEKKKYVKLPSNGTTGEQGS

STGTVRGDTEPISDSSSSSSSSSSSSSSSSSSSSSSSSSSSSESLPANGPDSPTVKPPRNLQNIC

ETGKNFKLVVYIKENTLILKWKVYGETKDTTENNKVDVRKYLINEKETPFTNILIHAYKEHNGT

NLIESKNYAIGSDIPEKCDTLASNCFLSGNFNIEKCFQCALLVEKENKNDVCYKYLSEDIVSKF

KEIKAETEDDDEDDYTEYKLTESIDNILVKMFKTNENNDKSELIKLEEVDDSLKLELMNYCSLL

KDVDTTGTLDNYGMGNEMDIFNNLKRLLIYHSEENINTLKNKFRNAAVCLKNVDDWIVNKRGLV

LPELNYDLEYFNEHLYNDKNSPEDKDNKGKGVVHVDTTLEKEDTLSYDNSDNMFCNKEYCNRLK

DENNCISNLQVEDQGNCDTSWIFASKYHLETIRCMKGYEPTKISALYVANCYKGEHKDRCDEGS

SPMEFLQIIEDYGELPAESNYPYNYVKVGEQCPKVEDHWMNLWDNGKILHNKNEPNSLDGKGYT

AYESERFHDNMDAFVKIIKTEVMNKGSVIAYIKAENVMGYEFSGKKVQNLCGDDTADHAVNIVG

YGNYVNSEGEKKSYWIVRNSWGPYWGDEGYEKVDMYGPTHCHFNFIHSVVIFNVDLPMNNKTTK

KESKIYDYYLKASPEFYHNLYFKNFNVGKKNLFSEKEDNENNKKLGNNYIIFGQDTAGSGQSGK

ESNTALESAGTSNEVSERVHVYHILKHIKDGKIRMGMRKYIDTQDVNKKHSCTRSYAFNPENYE

KCVNLCNVNWKTCEEKTSPGLCLSKLDTNNECYFCYV

Y2H Clone name: 1 7-1 (nucleotides 2433-2994; amino acids
561 base pairs (SEQ ID NO: 71)

AACTTTATTCACAGTGTTGTTATATTCAATGTTGATTTACCTATGAATAATAAAACAAC

TAAAAAAGAATCAAAAATATATGATTATTATTTAAAGGCCTCTCCAGAATTTTATCATAACCTT

TACTTTAAGAATTTTAATGTTGGTAAGAAAAATTTATTCTCTGAAAAGGAAGATAATGAAAACA

ACAAAAAATTAGGTAACAACTATATTATATTCGGTCAAGATACGGCAGGATCAGGACAAAGTGG

AAAGGAAAGCAATACTGCATTAGAATCTGCAGGAACTTCAAATGAAGTCTCAGAACGTGTTCAT

GTTTATCACATATTAAAACATATAAAGGATGGCAAAATAAGAATGGGTATGCGTAAATATATAG

ATACACAAGATGTAAATAAGAAACATTCTTGTACAAGATCCTATGCATTTAATCCAGAGAATTA

TGAAAAATGTGTAAATTTATGTAATGTGAACTGGAAAACATGCGAGGAAAAAACATCACCAGGA

CTTTGTTTATCCAAATTGGATACAAATAACGAATGTTATTTCTGTTATGTATAA

-continued 186 amino acids (SEQ ID NO: 72)

NFIHSVVIFNVDLPMNNKTTKKESKIYDYYLKASPEFYHNLYFKNFNVGKKNLFSEKEDNENNK

KLGNNYIIFGQDTAGSGQSGKESNTALESAGTSNEVSERVHVYHILKHIKDGKIRMGMRKYIDT

QDVNKKHSCTRSYAFNPENYEKCVNLCNVNWKTCEEKTSPGLCLSKLDTNNECYFCYV

SUB1 (subtilisin-like protease 1)
PlasmoDB ID: PF3D7_0507500
Chromosome 5; position 307,490-309,556
Full Sequence: base pairs 1-2067 (excluding introns)

(SEQ ID NO: 73)

ATGATGCTCAATAAAAAAGTTGTTGCTTTGTGCACACTTACCTTACATCTTTTTTGTATATTTC

TATGTCTAGGAAAGGAAGTAAGGTCTGAAGAAAATGGGAAAATACAAGATGATGCTAAAAAGAT

TGTTAGCGAATTACGATTCCTAGAAAAAGTAGAAGATGTTATTGAAAAGAGTAACATAGGAGGG

AATGAGGTAGATGCCGATGAAAATTCATTTAATCCGGATACTGAGGTTCCCATAGAAGAGATAG

AAGAAATAAAAATGAGGGAACTGAAAGATGTAAAGGAAGAAAAAAATAAAAATGACAACCATAA

TAATAATAATAATAATATTAGTAGTAGTAGTAGTAGTAGTAGTAATACTTTTGGTGAAGAAAAA

GAAGAAGTATCTAAGAAAAAAAAAAAGTTAAGACTTATAGTTAGCGAGAATCATGCAACTACCC

CCTCGTTTTTCCAAGAATCCCTTTTAGAACCTGATGTTTTATCCTTTTTAGAAAGTAAAGGGAA

TTTGTCCAACTTGAAAAATATCAATTCTATGATTATAGAACTAAAGGAAGATACAACGGATGAT

GAATTAATATCTTATATTAAAATTCTTGAGGAGAAGGGAGCTTTGATTGAATCAGATAAATTAG

TGAGTGCAGATAATATTGATATAAGTGGTATAAAAGATGCTATAAGAAGAGGTGAAGAAAATAT

TGATGTTAATGATTATAAAAGTATGTTAGAAGTCGAAAATGATGCTGAAGATTATGATAAAATG

TTTGGTATGTTTAATGAATCACATGCTGCAACATCTAAAAGGAAACGCCATTCAACAAATGAGC

GTGGATATGATACATTTTCATCACCTTCATATAAGACATATTCAAAAAGTGATTATTTATATGA

TGATGATAATAATAATAATAATTATTATTATAGTCATAGTAGTAATGGTCATAATAGTAGTAGT

CGTAATAGTAGTAGTAGTCGTAGTAGACCAGGTAAATATCATTTCAATGATGAATTTCGTAATT

TGCAATGGGGTTTAGATTTATCCAGATTAGATGAAACACAAGAATTAATTAACGAACATCAAGT

GATGAGTACTCGTATATGTGTTATAGATAGTGGTATTGATTATAATCATCCCGATTTAAAAGAT

AATATTGAATTAAATTTAAAAGAATTACATGGAAGGAAAGGTTTTGATGATGATAATAATGGTA

TAGTTGATGATATATATGGTGCTAATTTTGTAAATAATTCAGGAAACCCGATGGATGATAATTA

TCATGGTACTCATGTATCAGGAATTATATCTGCCATAGGAAATAATAATATAGGTGTTGTAGGT

GTTGATGTAAATTCAAAATTAATTATTTGTAAAGCATTAGATGAACATAAATTAGGAAGATTAG

GAGATATGTTCAAATGTTTAGATTATTGTATAAGTAGAAATGCACATATGATAAATGGAAGCTT

TTCATTTGATGAATATAGTGGTATTTTTAATTCTTCTGTAGAATATTTACAAAGAAAAGGTATC

CTCTTTTTTGTATCTGCAAGTAATTGTAGTCATCCTAAATCGTCAACACCAGATATTAGAAAAT

GTGATTTATCCATAAATGCAAAATATCCCCCTATCTTATCTACTGTTTATGATAATGTTATATC

TGTTGCTAATTTAAAAAAAAATGATAATAATAATCATTATTCATTATCCATTAATTCTTTTTAT

AGCAATAAATATTGTCAACTAGCTGCACCAGGAACTAATATATATTCTACTGCTCCACATAATT

CATATCGAAAATTAAATGGTACATCTATGGCTGCTCCACATGTAGCTGCAATAGCATCACTCAT

ATTTTCTATTAATCCTGACTTATCATATAAAAAAGTTATACAAATATTAAAAGATTCTATTGTA

TATCTCCCTTCCTTAAAAAATATGGTTGCATGGGCAGGATATGCAGATATAAATAAGGCAGTCA

ATTTAGCCATAAAATCAAAAAAAACATATATCAATTCTAATATATCTAACAAGTGGAAAAAAAA

AAGTAGATATTTGCATTAA

-continued

Full Sequence: 1-688 amino acids (SEQ ID NO: 74)

MMLNKKVVALCTLTLHLFCIFLCLGKEVRSEENGKIQDDAKKIVSELRFLEKVEDVIEKSNIGG

NEVDADENSFNPDTEVPIEEIEEIKMRELKDVKEEKNKNDNHNNNNNNISSSSSSSSNTFGEEK

EEVSKKKKKLRLIVSENHATTPSFFQESLLEPDVLSFLESKGNLSNLKNINSMIIELKEDTTDD

ELISYIKILEEKGALIESDKLVSADNIDISGIKDAIRRGEENIDVNDYKSMLEVENDAEDYDKM

FGMFNESHAATSKRKRHSTNERGYDTFSSPSYKTYSKSDYLYDDDNNNNNYYYSHSSNGHNSSS

RNSSSSRSRPGKYHFNDEFRNLQWGLDLSRLDETQELINEHQVMSTRICVIDSGIDYNHPDLKD

NIELNLKELHGRKGFDDDNNGIVDDIYGANFVNNSGNPMDDNYHGTHVSGIISAIGNNNIGVVG

VDVNSKLIICKALDEHKLGRLGDMFKCLDYCISRNAHMINGSFSFDEYSGIFNSSVEYLQRKGI

LFFVSASNCSHPKSSTPDIRKCDLSINAKYPPILSTVYDNVISVANLKKNDNNNHYSLSINSFY

SNKYCQLAAPGTNIYSTAPHNSYRKLNGTSMAAPHVAAIASLIFSINPDLSYKKVIQILKDSIV

YLPSLKNMVAWAGYADINKAVNLAIKSKKTYINSNISNKWKKKSRYLH

PKG (cGMP-dependent protein kinase)
PlasmoDB ID: PF3D7_1436600
Chromosome 14; position 1,490,654-1,494,214
Full Sequence: base pairs 1-2562 (excluding introns)

(SEQ ID NO: 75)

ATGGAAGAAGATGATAATCTAAAAAAAGGGAATGAAAGAAATAAAAAGAAGGCTATATTTTCAAATGATG

ATTTTACAGGAGAAGATAGTTTAATGGAGGATCATTTAGAACTTCGGGAAAAGCTTTCAGAAGATATTGA

TATGATAAAGACTTCCTTAAAAAATAATCTAGTTTGTAGTACATTAAACGATAATGAAATATTGACTCTG

TCTAATTATATGCAATTCTTTGTTTTTAAAAGTGGAAATTTAGTAATAAAACAAGGGGAAAAAGGGTCAT

ACTTTTTCATTATTAATAGTGGCAAATTTGACGTTTATGTAAATGATAAAAAAGTAAAGACTATGGGAAA

AGGTAGTTCTTTCGGTGAAGCTGCTTTAATTCATAATACCCAAAGAAGTGCAACTATTATTGCAGAAACT

GATGGAACTCTATGGGGAGTTCAAAGAAGTACATTTAGAGCTACCCTAAAACAATTATCTAATAGAAATT

TTAACGAAAACAGAACATTTATCGATTCCGTTTCAGTTTTTGATATGTTAACTGAAGCACAAAAAAACAT

GATTACTAATGCTTGTGTAATACAAAACTTTAAATCTGGTGAAACCATTGTTAAACAAGGAGATTATGGA

GATGTCTTATACATTTTGAAAGAAGGAAAGGCTACAGTATATATTAACGATGAAGAGATAAGGGTTTTAG

AGAAAGGTTCCTATTTTGGGGAAAGAGCTCTACTGTATGATGAACCAAGAAGTGCAACAATCATTGCAAA

AGAACCAACCGCTTGTGCATCCATTTGTAGGAAATTATTAAATATTGTTCTAGGAAACTTACAAGTAGTT

TTATTTCGTAATATTATGACTGAAGCTTTACAACAGAGTGAAATTTTTAAACAATTTAGTGGGGATCAAT

TAAACGATTTAGCAGATACCGCCATTGTTCGAGATTATCCAGCTAATTATAATATATTACATAAGGATAA

GGTAAAATCCGTTAAATATATTATTGTATTGGAAGGTAAAGTAGAATTATTTCTTGATGATACTTCTATT

GGTATATTATCCAGAGGAATGTCTTTTGGAGATCAATATGTATTAAATCAGAAACAACCATTTAAGCATA

CTATTAAATCATTAGAAGTTTGTAAAATCGCATTAATAACGGAAACTTGTTTAGCTGATTGTCTAGGAAA

TAATAATATTGATGCATCTATTGATTATAATAATAAAAAAAGTATTATAAAGAAAATGTATATCTTTAGA

TACTTAACTGATAAACAATGTAATTTATTAATTGAAGCTTTTAGAACCACAAGATATGAAGAAGGTGATT

ATATAATACAAGAAGGAGAAGTAGGATCTAGATTTTATATAATAAAAAATGGAGAAGTAGAAATAGTAAA

AAATAAAAAAAGGTTACGTACCTTAGGAAAGAATGATTACTTTGGTGAAAGAGCTTTATTATATGATGAA

CCAAGAACAGCTTCTGTTATAAGTAAAGTAAATAATGTTGAATGTTGGTTTGTTGATAAAAGTGTGTTTT

TACAAATTATACAAGGACCTATGTTAGCACATTTGGAAGAAAGAATAAAAATGCAAGATACTAAAGTAGA

AATGGATGAACTAGAAACAGAACGAATTATTGGAAGAGGTACTTTCGGAACAGTTAAATTAGTTCATCAT

AAACCAACAAAAAATAAGATATGCTTTAAAATGTGTTAGTAAAAGAAGTATTATTAATTTAAATCAACAAA

-continued

ACAATATAAAATTAGAAAGAGAAATAACAGCAGAAAATGATCATCCATTTATTATAAGATTAGTAAGAAC

ATTTAAAGATTCTAAATATTTCTATTTTCTAACAGAATTAGTAACAGGTGGAGAATTATATGATGCTATT

AGAAAATTAGGTTTATTATCTAAATCACAAGCTCAATTTTATTTAGGTTCTATCATTTTAGCTATTGAAT

ATTTACATGAAAGAAATATTGTATATAGAGATTTAAAACCAGAAAACATTTTATTAGATAAACAAGGTTA

TGTAAAACTAATCGATTTTGGTTGTGCCAAAAAGGTACAAGGTAGAGCTTATACATTAGTAGGTACACCT

CATTATATGGCACCTGAGGTTATTTTAGGAAAAGGTTATGGATGTACTGTTGACATATGGGCATTGGGAA

TATGCCTATATGAATTTATATGTGGTCCATTACCATTTGGTAATGATGAAGAAGATCAATTAGAAATTTT

CCGTGATATATTAACCGGCCAACTTACATTTCCAGATTATGTAACAGACACAGATAGCATAAATTTGATG

AAAAGACTTCTATGTAGATTACCTCAAGGAAGAATTGGTTGTTCAATAAATGGCTTCAAAGACATAAAGG

ATCACCCATTTTTCTCAAACTTTAATTGGGATAAATTGGCTGGTCGTTTGCTTGATCCGCCTTTAGTATC

AAAAAGTGAAACTTATGCAGAAGATATTGATATTAAACAAATAGAGGAGGAGGATGCTGAGGATGATGAG

GAACCATTGAACGATGAAGACAACTGGGACATAGATTTTTAA

Full Sequence: 1-853 amino acids (SEQ ID NO: 76)

MEEDDNLKKGNERNKKKAIFSNDDFTGEDSLMEDHLELREKLSEDIDMIKTSLKNNLVCSTLNDNEILTL

SNYMQFFVFKSGNLVIKQGEKGSYFFIINSGKFDVYVNDKKVKTMGKGSSFGEAALIHNTQRSATIIAET

DGTLWGVQRSTFRATLKQLSNRNFNENRTFIDSVSVFDMLTEAQKNMITNACVIQNFKSGETIVKQGDYG

DVLYILKEGKATVYINDEEIRVLEKGSYFGERALLYDEPRSATITAKEPTACASICRKLLNIVLGNLQVV

LFRNIMTEALQQSEIFKQFSGDQLNDLADTAIVRDYPANYNILHKDKVKSVKYIIVLEGKVELFLDDTSI

GILSRGMSFGDQYVLNQKQPFKHTIKSLEVCKIALITETCLADCLGNNNIDASIDYNNKKSIIKKMYIFR

YLTDKQCNLLIEAFRTTRYEEGDYIIQEGEVGSRFYIIKNGEVEIVKNKKRLRTLGKNDYFGERALLYDE

PRTASVISKVNNVECWFVDKSVFLQIIQGPMLAHLEERIKMQDTKVEMDELETERIIGRGTFGTVKLVHH

KPTKIRYALKCVSKRSIINLNQQNNIKLEREITAENDHPFIIRLVRTFKDSKYFYFLTELVTGGELYDAI

RKLGLLSKSQAQFYLGSIILAIEYLHERNIVYRDLKPENILLDKQGYVKLIDFGCAKKVQGRAYTLVGTP

HYMAPEVILGKGYGCTVDIWALGICLYEFICGPLPFGNDEEDQLEIFRDILTGQLTFPDYVTDTDSINLM

KRLLCRLPQGRIGCSINGFKDIKDHPFFSNFNWDKLAGRLLDPPLVSKSETYAEDIDIKQIEEEDAEDDE

EPLNDEDNWDIDF

Underlined amino acid sequences and cDNA nucleic acid sequences correspond to immunorelevant regions of the gene products and nucleic acids encoding them. The antigenic fragments (polypeptides) were identified by virtue of binding of antibodies from patients that are resistant to malaria.

The invention encompasses "fragments" and "peptides" of SEQ ID NOs: 2, 3, 6, 7, 10, 11, 14, 15, 18, 19, 22, 23, 26, 27, 30, 31, 34, 35, 38, 39, 42, or 43, 47, 67, 70, 74, or 76 preferably, the clone 2 polypeptide or the PF10_0212a polypeptide (a.k.a., PfSEP-1A; SEQ ID NO:2) described herein. Such peptides represent portions of the polypeptide that have, for example, specific immunogenic or binding properties. A fragment can be between 3-10 amino acids, 10-20 amino acids, 20-40 amino acids, 40-56 amino acids in length or even longer. Amino acid sequences having at least 70% amino acid identity, preferably at least 80% amino acid identity, more preferably at least 90% identity, and most preferably 95% identity to the fragments described herein are also included within the scope of the present invention.

Furthermore, the present invention encompasses fragments and derivatives of the nucleic acid sequences of the present invention, as well as fragments and portions of the amino acid sequences of the present invention.

A "polynucleotide" is a nucleic acid polymer of ribonucleic acid (RNA), deoxyribonucleic acid (DNA), modified RNA or DNA, or RNA or DNA mimetics (such as PNAs), and derivatives thereof, and homologues thereof. Thus, polynucleotides include polymers composed of naturally occurring nucleobases, sugars and covalent internucleoside (backbone) linkages as well as polymers having non-naturally-occurring portions that function similarly. Such modified or substituted nucleic acid polymers are well known in the art and for the purposes of the present invention, are referred to as "analogues." Oligonucleotides are generally short polynucleotides from about 10 to up to about 160 or 200 nucleotides.

A "variant polynucleotide" or a "variant nucleic acid sequence" means a polynucleotide having at least about 60% nucleic acid sequence identity, more preferably at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with the nucleic acid sequence of SEQ ID NOs: 1, 4, 5, 8, 9, 12, 13, 16, 17, 20, 21, 24, 25, 28, 29, 32, 33, 36, 37, 40, 41, 44, 45, or 48, preferably SEQ ID NO: 1. Variants do not encompass the native nucleotide sequence. Other variant polynucleotides include those that differ from SEQ ID NO: 1, but because of the redundancy of the genetic code, encode a polypeptide of SEQ ID No: 2, or amino acids 2-50 of SEQ ID No: 2, fragments of variants thereof.

Ordinarily, variant polynucleotides are at least about 8 nucleotides in length, often at least about 9, 10, 11, 12, 13, 14, 15, 16, 17, 18, 19, 20, 21, 22, 23, 24, 25, 26, 27, 28, 29 30, 35, 40, 45, 50, 55, 60 nucleotides in length, or even about 75-200 nucleotides in length, or more.

In general, a polypeptide variant preserves antigenic function and includes any variant in which residues at a particular position in the sequence have been substituted by other amino acids, and further includes the possibility of inserting an additional residue or residues between two residues of the parent polypeptide as well as the possibility of deleting one or more residues from the parent sequence. comprising "A polypeptide variant" means a polypeptide having at least about 70% amino acid sequence identity with an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2 or SEQ ID NO:3. For example, polypeptide variants include those wherein one or more amino acid residues are added or deleted at the N- or C-terminus of the full-length native amino acid sequence. A polypeptide variant will have at least about 71%-75% amino acid sequence identity; at least about 76%-79% amino acid sequence identity; at least about 80% amino acid sequence identity, at least about 81% amino acid sequence identity, at least about 82%, 83%, 84%, 85%, 86%, 87%, 88%, 89%, 90%, 91%, 92%, 93%, 94%, 95%, 96%, 97%, 98% amino acid sequence identity and at least about 99% amino acid sequence identity with a full-length sequence. Ordinarily, variant polypeptides are at least about 10 amino acids in length, often at least about 20 amino acids in length, more often at least about 30, 40, 50, 60, 70, 80, 90, 100, 150, 200, or 300 amino acids in length, or more.

Useful conservative substitutions are shown in Table 2 below. Conservative substitutions whereby an amino acid of one class is replaced with another amino acid of the same type fall within the scope of the subject invention so long as the substitution does not materially alter the biological activity of the compound.

TABLE 2

Exemplary substitutions

| Origional residue | Exemplary substitutions | Preferred substitutions |
|---|---|---|
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |

TABLE 2-continued

Exemplary substitutions

| Origional residue | Exemplary substitutions | Preferred substitutions |
|---|---|---|
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

The polypeptides of the invention can be either synthesized in vitro or expressed recombinantly from the polynucleotide sequences. Because of redundancy in the genetic code, the sequences need not be identical to practice the invention. Polynucleotide and polypeptide sequence identities can be from 70%-100%, such as 70%, 75%, 80%, 81%, 82%, 83%, 84%, 85%, 86%, 87%, 88%, 89%, 90%, 91%, 92%, 93%, 94%, 95%, 96%, 97%, 98%, 99% and of course, 100%.

The polypeptides of the invention can be readily synthesized in vitro using polypeptide chemistry. For example, polypeptide synthesis can be carried out in a stepwise manner on a solid phase support using an automated polypeptide synthesizer, such as a Rainin Symphony Peptide Synthesizer, Advanced Chemtech Peptide Synthesizer, Argonaut Parallel Synthesis System, or an Applied Biosystems Peptide Synthesizer. The peptide synthesizer instrument combines the Fmoc chemistry with HOBt/HBTU/DIEA activation to perform solid-phase peptide synthesis.

The side chains of many amino acids contain chemically reactive groups, such as amines, alcohols, or thiols. These side chains must be additionally protected to prevent undesired side-reactions during the coupling step. Side chain protecting groups that are base-stable, more preferably, both base-stabile and acid-labile are most useful.

"Percent (%) nucleic acid sequence identity" with respect to nucleic acid sequences is defined as the percentage of nucleotides in a candidate sequence that are identical with the nucleotides in the sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Consisting essentially of a polynucleotide having a % sequence identity" means that the polynucleotide does not substantially differ in length, but may differ substantially in sequence. Thus, a polynucleotide "A" consisting essentially of a polynucleotide having at least 80% sequence identity to a known sequence "B" of 100 nucleotides means that polynucleotide "A" is about 100 nts long, but up to 20 nts can vary from the "B" sequence. The polynucleotide sequence in question can be longer or shorter due to modification of the termini, such as, for example, the addition of 1-15 nucleotides to produce specific types of probes, primers and other molecular tools, etc., such as the case of when substantially non-identical sequences are added to create intended secondary structures. Such non-identical nucleotides are not considered in the calculation of sequence identity when the sequence is modified by "consisting essentially of."

Vaccine Compositions

The present invention is further directed to an immunogenic composition, e.g., a vaccine composition capable of blocking *P. falciparum* infection, for example a peptide vaccine or a DNA vaccine capable of blocking Schizont rupture at blood stage infection. The vaccine composition comprises one or more of the polypeptides, the nucleic acid sequences, or antigens thereof, as described herein.

A person skilled in the art will be able to select preferred peptides, polypeptides, nucleic acid sequences or combination of therof by testing, e.g., the blocking of the Schizont rupture or parasite egress from RBCs in vitro. Peptide(s) with the desired activity are then combined as a vaccine. A suitable vaccine will preferably contain between 1 and 20 peptides, more preferably 2, 3, 4, 5, 6, 7, 8, 9, 10, 11, 12, 13, 14, 15, 16, 17, 18, 19, or 20 different peptides, further preferred 6, 7, 8, 9, 10 11, 12, 13, or 14 different peptides, and most preferably 12, 13 or 14 different peptides. Alternatively, a suitable vaccine will preferably contain between 1 and 20 nucleic acid sequences, more preferably 2, 3, 4, 5, 6, 7, 8, 9, 10, 11, 12, 13, 14, 15, 16, 17, 18, 19, or 20 different nucleic acid sequences, further preferred 6, 7, 8, 9, 10 11, 12, 13, or 14 different nucleic acid sequences, and most preferably 12, 13 or 14 different nucleic acid sequences.

Such a vaccine is used for active immunization of a mammal, for example, a human who risks being exposed to one or more *Plasmodium* antigens (for example, due to travel within a region in which malaria is prevalent). For example, the vaccine can contain at least one antigen selected from the group consisting of: 1) a *P. falciparum* antigen comprising a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3; 2) a *P. falciparum* antigen comprising a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3, or fragment thereof; 3) a *P. falciparum* antigen comprising a polypeptide consisting essentially of the amino acid sequences of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3; 4) a *P. falciparum* antigen consisting of the amino acid sequences of SEQ ID NOs: 2, 3, 6, 7, 10, 11, 14, 15, 18, 19, 22, 23, 26, 27, 30, 31, 34, 35, 28, 39, 42, 43, 46, 47, 66, 67, 70, 72, 74, and/or 76, preferably SEQ ID NO:2, SEQ ID NO:3, or amino acid residues 811-1083 of SEQ ID NO:3; 5) a nucleic acid sequence having at least 70% sequence identity with a nucleic acid sequence encoding any one of the peptides listed above, preferably SEQ ID NO: 1 or SEQ ID NO: 4; 6) a nucleic acid sequence having at least 70% to 99%, such as 80%, 85%, 90%, 91%, 92%, 93%, 94%, 95%, 96%, 97%, 98% and 99% sequence identity to a nucleic acid sequence encoding the listed polypeptides, preferably SEQ ID NO: 1 or SEQ ID NO: 4; 7) a nucleic acid sequence consisting essentially of the nucleic acid sequence sequences described above. and 8) a nucleic acid sequence described above, preferably SEQ ID NO: 1 or SEQ ID NO: 4. A fragment of these polypeptides can be approximately 8-56 amino acid residues, such as 8, 9, 10, 20, 30, 40, 50, 51, 52, 53, 54, 55, and 56 residues. A fragment of these nucleic acid sequences can be approximately 10-300 nucleotides, such as 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nucleotides.

Alternatively, if passive immunization is desired, one can administer one or more antibodies to the following antigens (as a vaccination): 1) a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47 preferably SEQ ID NO:2, SEQ ID NO:3, or amino acid residues 811-1083 of SEQ ID NO:3; 2) a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, and amino acid residues 811-1083 of SEQ ID NO:3, or fragment thereof; 3) a polypeptide consisting essentially of the amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3; and 4) an amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3. A fragment of these polypeptides can be approximately 8-56 amino acid residues, such as 8, 9, 10, 20, 30, 40, 50, 51, 52, 53, 54, 55, and 56 residues.

The vaccine composition can further comprise an adjuvant and/or a carrier. Examples of useful adjuvants and carriers are given herein below. The peptides and/or polypeptides in the composition can be associated with a carrier such as e.g. a protein or an antigen-presenting cell such as e.g. a dendritic cell (DC) capable of presenting the peptide to a T-cell.

Adjuvants are any substance whose admixture into the vaccine composition increases or otherwise modifies the immune response to the mutant peptide. Carriers are scaffold structures, for example a polypeptide or a polysaccharide, to which the neoantigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to aluminium salts, Montanide ISA 206, Montanide ISA 50V, Montanide ISA 50, Montanide ISA-51, Montanide ISA-720, 1018 ISS, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, Lipo- Vac, MF59, monophosphoryl lipid A, Montanide IMS 1312, OK-432, OM-174, OM-197-MP-EC, ONTAK, PepTel® vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are preferred. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11). Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

Other examples of useful immunostimulatory agents include, but are not limited to, Toll-like Receptor (TLR) agonists such as chemically modified CpGs (e.g. CpR, Idera), Poly(I:C)(e.g. polyi:CI2U), non-CpG bacterial DNA or RNA as well as immunoactive small molecules, such as cyclophosphamide, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim). The vaccine may also contain a blocker of PD-L1 (CD274) binding to its receptor (PD-1) or to CD80 to prevent/inhibit the development of T regulatory cells (Treg) and thereby reducing the development of tolerance to the vaccine antigen. And exemplary PD-1 inhibitor is Bristol Meyers Squibb's BMS-936558 (also known as MDX-1106 and ONO-4538).

A vaccine composition according to the present invention may comprise more than one different adjuvants. Furthermore, the invention encompasses a therapeutic composition comprising any adjuvant substance including any of the above or combinations thereof. It is also contemplated that the peptide or polypeptide, and the adjuvant can be administered separately in any appropriate sequence.

A carrier may be present independently of an adjuvant. The function of a carrier can for example be to increase the molecular weight of in particular mutant in order to increase their activity or immunogenicity, to confer stability, to increase the biological activity, or to increase serum half-life. Furthermore, a carrier may aid presenting peptides to T-cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diptheria toxoid are suitable carriers in one embodiment of the invention. Alternatively, the carrier may be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments the vaccine composition according to the present invention additionally contains at least one antigen presenting cell.

In the case of a DNA vaccine, a nucleic acid comprising the sequence of SEQ ID NOs: 1, 4, 5, 8, 9, 12, 13, 16, 17, 20, 21, 24, 25, 28, 29, 32, 33, 36, 37, 40, 41, 44, 45, or 48, preferably SEQ ID NO: 1 or SEQ ID NO: 4 formulated in a eukaryotic vector for use as a vaccine that is administered to human subjects. The nucleotides encoding the antigen are operably linked promoter and other regulatory sequences in the vector. Such eukaryotic, e.g., mammalian vectors, are known in the art [e.g., pcDNA (Invitrogen) and vectors available from Vical Inc. (San Diego, Calif.)]. Other exemplary vectors, e.g., pNGVL4a, and derivatives thereof, are described in Moorty et al., 2003, Vaccine 21:1995-2002; Cebere et al., 2006, Vaccine 24:41-425; or Trimble et al., 2009, Clin. Cancer Res. 15:364-367; hereby incorporated by reference).

Recombinant Expression Vectors and Host Cells

The antigen of the present invention can be made by any recombinant method that provides the epitope of interest. Accordingly, another aspect of the invention pertains to vectors, preferably expression vectors, containing a nucleic acid encoding any clones of Table 1, such as a PF10_0212a or clone 2 protein, or derivatives, fragments, analogs or homologs thereof. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PF10_0212a or clone 2 proteins, mutant forms of PF10_0212a or clone 2 (e.g., PfSEP-1A, SEQ ID NO:2), fusion proteins, etc.).

The recombinant expression vectors of the invention can be designed for expression of any of the polypeptides or polynucleotide sequences of the present invention in prokaryotic or eukaryotic cells. For example, any of the polypeptides or polynucleotide sequences of the present invention can be expressed in bacterial cells such as *E. coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31 40), pMAL (New England Biolabs, Beverly, Mass.) and pRIT5 (Pharmacia, Piscataway, N.J.) that fuse glutathione S transferase (GST), maltose E binding protein, or protein A, respectively, to the target recombinant protein. Examples of suitable inducible non fusion *E. coli* expression vectors include pTrc (Amrann et al., (1988) Gene 69:301 315) and pET 11d (Studier et al., GENE EXPRESSION TECHNOLOGY: METHODS IN ENZYMOLOGY 185, Academic Press, San Diego, Calif. (1990) 60 89).

One strategy to maximize recombinant protein expression in *E. coli* is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119 128. Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111 2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari, et al., (1987) EMBO J 6:229 234), pMFa (Kurjan and Herskowitz, (1982) Cell 30:933 943), pJRY88 (Schultz et al., (1987) Gene 54:113 123), pYES2 (Invitrogen Corporation, San Diego, Calif.), and picZ (InVitrogen Corp, San Diego, Calif.).

Alternatively, any of the polypeptides or polynucleotide sequences of the present invention can be expressed in insect cells using baculovirus expression vectors. Baculovirus vectors available for expression of proteins in cultured insect cells (e.g., SF9 cells) include the pAc series (Smith et al. (1983) Mol Cell Biol 3:2156 2165) and the pVL series (Lucklow and Summers (1989) Virology 170:31 39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufinan et al. (1987) EMBO J 6: 187 195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue specific regulatory elements are used to express the nucleic acid). Tissue specific regulatory elements are known in the art. Non limiting examples of suitable tissue specific promoters include the albumin promoter (liver specific; Pinkert et al. (1987) Genes Dev 1:268 277), lymphoid specific promoters (Calame and Eaton (1988) Adv Immunol 43:235 275), in particular promoters of T cell receptors (Winoto and Baltimore (1989) EMBO J 8:729 733) and immunoglobulins (Banerji et al. (1983) Cell 33:729 740; Queen and Baltimore (1983) Cell 33:741 748), neuron specific promoters (e.g., the neurofilament promoter; Byrne and Ruddle (1989) PNAS 86:5473 5477), pancreas specific promoters (Edlund et al. (1985) Science 230:912 916), and mammary gland specific promoters (e.g., milk whey promoter; U.S. Pat. No. 4,873,316 and European Application Publication No. 264,166). Developmentally regulated promoters are also encompassed, e.g., the murine hox promoters (Kessel and Gruss (1990) Science 249:374 379) and the α-fetoprotein promoter (Campes and Tilghman (1989) Genes Dev 3:537 546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to mRNA of any of the polynucleotide sequences of the present invention. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, any of the polypeptides or polynucleotide sequences of the present invention can be expressed in bacterial cells such as *E. coli*, insect cells, yeast or mammalian cells (such as Chinese hamster ovary cells (CHO) or COS cells). Alternatively, a host cell can be a premature mammalian cell, i.e., pluripotent stem cell. A host cell can also be derived from other human tissue. Other suitable host cells are known to those skilled in the art.

Vector DNA can be introduced into prokaryotic or eukaryotic cells via conventional transformation, transduction, infection or transfection techniques. As used herein, the terms "transformation" "transduction", "infection" and "transfection" are intended to refer to a variety of art recognized techniques for introducing foreign nucleic acid (e.g., DNA) into a host cell, including calcium phosphate or calcium chloride co precipitation, DEAE dextran mediated transfection, lipofection, or electroporation. In addition transfection can be mediated by a transfection agent. By "transfection agent" is meant to include any compound that mediates incorporation of DNA in the host cell, e.g., liposome. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. Transfection may be "stable" (i.e. integration of the foreign DNA into the host genome) or "transient" (i.e., DNA is episomally expressed in the host cells).

For stable transfection of mammalian cells, it is known that, depending upon the expression vector and transfection technique used, only a small fraction of cells may integrate the foreign DNA into their genome the remainder of the DNA remains episomal. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding any of the polypeptides or polynucleotide sequences of the present invention can be introduced on a separate vector. Cells stably transfected with the introduced nucleic acid can be identified by drug selection (e.g., cells that have incorporated the selectable marker gene will survive, while the other cells die). In a specific embodiment, the promoter is the insulin promoter driving the expression of green fluorescent protein (GFP).

In one embodiment nucleic acid of any of the polypeptides or polynucleotide sequences of the present invention is present in a viral vector. In another embodiment the nucleic acid is encapsulated in a virus. In some embodiments the virus preferably infects pluripotent cells of various tissue types, e.g. hematopoietic stem, cells, neuronal stem cells, hepatic stem cells or embryonic stem cells, preferably the virus is hepatropic. By "hepatotropic" it is meant that the virus has the capacity to preferably target the cells of the liver either specifically or non-specifically. In further embodiments the virus is a modulated hepatitis virus, SV-40, or Epstein-Bar virus. In yet another embodiment, the virus is an adenovirus.

"Recombinant" refers to an artificial combination of two otherwise separated segments of sequence, e.g., by chemical synthesis or by the manipulation of isolated segments of nucleic acids by genetic engineering techniques.

A transgenic mammal can also be used in order to express the protein of interest encoded by one or both of the above-described nucleic acid sequences. More specifically, once the above-described construct is created, it can be inserted into the pronucleus of an embryo. The embryo can then be implanted into a recipient female. Alternatively, a nuclear transfer method could also be utilized (Schnieke et al., 1997). Gestation and birth are then permitted to occur (see, e.g., U.S. Pat. Nos. 5,750,176 and 5,700,671), and milk, tissue or other fluid samples from the offspring should then contain the protein of interest. The mammal utilized as the host can be selected from the group consisting of, for example, a mouse, a rat, a rabbit, a pig, a goat, a sheep, a horse and a cow. However, any mammal can be used provided it has the ability to incorporate DNA encoding the protein of interest into its genome.

Therapeutic Methods

The invention further provides a method of inducing a *P. falciparum* specific immune response in a subject, vaccinating against malaria, treating and or alleviating a symptom of malaria in a subject by administering the subject a peptide or vaccine composition of the invention.

The subject has been diagnosed with malaria or is at risk of developing malaria. The subject has resistant malaria. The subject is a human, dog, cat, horse or any animal in which a *P. falciparum* specific immune response is desired. Preferably, the subject is a child under 5 years old of age. More preferably, the subject is at least about 6-8 weeks old of age.

The peptide or composition of the invention is administered in an amount sufficient to induce an immune response.

The invention provides methods of treating or prevention malaria by administering to a subject one or more peptides of the instant invention. The antigen peptide, polypeptide, nucleic acid sequences or vaccine composition of the invention can be administered alone or in combination with one or more therapeutic agents. The therapeutic agent is, for example, one, two, three, four, or more additional vaccines, an antimalarials artemisinin-combination therapy, or an immunotherapy. Any suitable therapeutic treatment for malaria may be administered. The additional vaccine may comprise an inhibitor of parasite liver invasion or an inhibitor of parasite RBC invasion. Such additional vaccines include, but are not limited to, anti-RBC invasion vaccines (MSP-1), RTS,S (Mosquirix), NYVAC-Pf7, CSP, and [NANP]19-5.1. The antigen peptide, polypeptide, nucleic acid sequences, or vaccine composition of the invention can be administered prior to, concurrently, or after other therapeutic agents.

The optimum amount of each peptide to be included in the vaccine composition and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. For example, doses of between 1 and 500 mg 50 μg and 1.5 mg, preferably 125 μg to 500 μg, of peptide or DNA may be given and will depend from the respective peptide or DNA. Doses of this range were successfully used in previous trials (Brunsvig P F, et al., Cancer Immunol Immunother. 2006; 55(12):1553-1564; M. Staehler, et al., ASCO meeting 2007; Abstract No 3017). Other methods of administration of the vaccine composition are known to those skilled in the art.

Pharmaceutical compositions comprising the peptide of the invention may be administered to an individual already suffering from malaria. In therapeutic applications, compositions are administered to a patient in an amount sufficient to elicit an effective immune response to the present antigen and to cure or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 μg to about 50,000 μg of peptide for a 70 kg patient, followed by boosting dosages or from about 1.0 μg to about 10,000 μg of peptide pursuant to a boosting regimen over weeks to months depending upon the patient's response and condition by measuring specific immune activity in the patient's blood.

The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. Preferably, the vaccine is administered intramuscularly. The invention provides compositions for parenteral administration which comprise a solution of the peptides and vaccine compositions are dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptide of the invention may also be administered via liposomes, which target the peptides to a particular cells tissue, such as lymphoid tissue. Liposomes are also useful in increasing the half-life of the peptides. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional or nanoparticle nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included as desired, as with, e.g., lecithin for intranasal delivery.

For therapeutic or immunization purposes, nucleic acids encoding the peptide of the invention and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles.

The nucleic acids can also be delivered complexed to cationic compounds, such as cationic lipids. Lipid-mediated gene delivery methods are described, for instance, in 9618372 WOAWO 96/18372; 9324640 WOAWO 93/24640; Mannino & Gould-Fogerite, BioTechniques 6(7): 682-691 (1988); 5279833USARose U.S. Pat. No. 5,279,833; 9106309WOAWO 91/06309; and Felgner et al., Proc. Natl. Acad. Sci. USA 84: 7413-7414 (1987).

The peptides and polypeptides of the invention can also be expressed by attenuated viral hosts, such as vaccinia or fowlpox. This approach involves the use of vaccinia virus as a vector to express nucleotide sequences that encode the peptide of the invention. Upon introduction into an acutely or chronically infected host or into a noninfected host, the recombinant vaccinia virus expresses the immunogenic peptide, and thereby elicits a host CTL response. Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vectors useful for therapeutic administration or immunization of the peptides of the invention, e.g., *Salmonella typhi* vectors and the like, will be apparent to those skilled in the art from the description herein.

A preferred means of administering nucleic acids encoding the peptide of the invention uses minigene constructs encoding multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes may be improved by including synthetic (e.g. poly-alanine) or naturally-occurring flanking sequences adjacent to the CTL epitopes.

The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The vaccine of the present invention can be administered intramuscularly once every two weeks for 1, 2, 3, 4, 5, or more times, alone or in combination with 1, 2, 3, 4, or more additional vaccines in a subject, preferably a human subject.

Antibodies

"Antibody" (Ab) comprises single Abs directed against a target antigen (an anti-target antigen Ab), anti-target antigen Ab compositions with poly-epitope specificity, single chain anti-target antigen Abs, and fragments of anti-target antigen Abs. A "monoclonal antibody" (mAb) is obtained from a population of substantially homogeneous Abs, i.e., the individual Abs comprising the population are identical except for possible naturally-occurring mutations that can be present in minor amounts. Exemplary Abs include polyclonal (pAb), monoclonal (mAb), humanized, bi-specific (bsAb), and heteroconjugate Abs. The invention encompasses not only an intact monoclonal antibody, but also an immunologically-active antibody fragment, e. g., a Fab or (Fab)2 fragment; an engineered single chain Fv molecule; or a chimeric molecule, e.g., an antibody which contains the binding specificity of one antibody, e.g., of murine origin, and the remaining portions of another antibody, e.g., of human origin.

Also provided herein are antibodies to the following antigens (as a vaccination): 1) a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3; 2) a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3, or fragment thereof; 3) a polypeptide consisting essentially of the amino acid sequences of SEQ ID NOs: 2, 3, 6, 7, 10, 11, 14, 15, 18, 19, 22, 23, 26, 27, 30, 31, 34, 35, 38, 39, 42, 43, 6, or 47, preferably SEQ ID NO:2, SEQ ID NO:3, or amino acid residues 811-1083 of SEQ ID NO:3; and 4) an amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3. A fragment of these polypeptides can be approximately 8-56 amino acid residues, such as 8, 9, 10, 20, 30, 40, 50, 51, 52, 53, 54, 55, and 56 residues.

Polyclonal Abs can be raised in a mammalian host by one or more injections of an immunogen and, if desired, an adjuvant. Monoclonal antibodies of the invention can be produced by any hybridoma liable to be formed according to classical methods from splenic or lymph node cells of an animal, particularly from a mouse or rat, immunized against the clone 2 polypeptides or peptides according to the invention.

The antigen and antibody of the present invention can be attached to a signal generating compound or "label". This signal generating compound or label is in itself detectable or can be reacted with one or more additional compounds to generate a detectable product. Examples of such signal generating compounds include chromogens, radioisotopes (e.g., $^{125}I$, $^{131}I$, $^{32}P$, $^{3}H$, $^{35}S$, and $^{14}C$), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, β-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

Also provided herein is a method of treating *P. falciparum* malaria in a subject in need of by administering a therapeutically effective amount of an antibody described herewith to the subject. Preferably, the antibody is a purified monoclonal antibody, e.g., one that has been raised to and is specific for the protein of SEQ ID NO: 2. For example, the monoclonal antibody is a humanized antibody. The treatment can be initiated at an early stage after the appearance of recrudescent parasites. The symptoms of the subject may be mild or absent and parasitemia is low but increasing, for example from range 4,000-10,000/ul. Alternative, the subject may have fever <38.5° C. without any other accompanying symptom. The subject can be a child under 10 years of age. The subject can also be an elder child or an adult. In one example, the subject is characterized as suffering from acute *P. falciparum* malaria but has not responded to treatment with anti-malarial drugs. In this passive immunity approach, the purified humanized monoclonal antibody that binds specifically to the protein of clones of Table 1, preferably SEQ ID NO: 2 is administered to the subject to kill the infective agent and/or inhibit RBC invasion.

The antibody can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. Preferably, the antibody is administered intravenously or intramuscularly. For example, the antibody is administered in 1-2 gram amounts, 1, 2, 3, or 4 times. The dosing regimen that can be used in the methods of the invention includes, but is not limited to, daily, three times weekly (intermittent), two times weekly, weekly, or every 14 days. Alternatively, dosing regimen includes, but is not limited to, monthly dosing or dosing every 6-8 weeks. The antibody of the present invention can be administered intravenously once, twice or three times alone or in combination with 1, 2, 3, 4, or more additional therapeutic agents in a subject, preferably a human subject. The additional therapeutic agent is, for example, one, two, three, four, or more additional vaccines or antibodies, an antimalarials artemisinin-combination therapy, or an immunotherapy. Any suitable therapeutic treatment for malaria may be administered. The additional vaccine may comprise an inhibitor of parasite liver invasion or an inhibitor of parasite RBC invasion. Such additional vaccines include, but are not limited to, anti-RBC invasion vaccines (MSP-1), RTS,S (Mosquirix), NYVAC-Pf7, CSP, and [NANP]19-5.1. The antibody of the invention can be administered prior to, concurrently, or after other therapeutic agents.

Amounts effective for this use will depend on, e.g., the antibody composition, the manner of administration, the stage and severity of *P. falciparum* malaria being treated, the weight and general state of health of the patient, and the judgment of the prescribing physician, but generally range for the treatment from about 10 mg/kg (weight of a subject) to 300 mg/kg, preferably 20 mg/kg-200 mg/kg.

Kits

Kits are also included within the scope of the present invention. The present invention includes kits for determining the presence of antibodies to *P. falciparum* in a test sample. A kit can comprise: (a) a *P. falciparum* antigen comprising a polypeptide having at least 70% sequence identity with an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3; and (b) a conjugate comprising an antibody attached to a signal-generating compound capable of generating a detectable signal. The kit can also contain a control or calibrator which comprises a reagent which binds to the antigen. The *P. falciparum* antigen can comprise a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NOs: 2, 3, 6, 7, 10, 11, 14, 15, 18, 19, 22, 23, 26, 27, 30, 31, 34, 35, 38, 39, 42, 43, 46, or 47 preferably SEQ ID NO:2, SEQ ID NO:3, and amino acid residues 811-1083 of SEQ ID NO:3, or fragment thereof. A fragment of these polypeptides can be approximately 8-56 amino acid residues, such as 8, 9, 10, 20, 30, 40, 50, 51, 52, 53, 54, 55, and 56 residues. The antigen can comprise a polypeptide consisting essentially of the amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3. Finally, the antigen can consist of the amino acid sequences of SEQ ID NOs: 2, 3, 6, 7, 10, 11, 14, 15, 18, 19, 22, 23, 26, 27, 30, 31, 34, 35, 38, 39, 42, 43, 46, or 47, preferably SEQ ID NO:2, SEQ ID NO:3, or amino acid residues 811-1083 of SEQ ID NO:3.

The present invention also provides a pharmaceutical pack or kit comprising one or more containers filled with the vaccine in a form suitable for intramuscular administration or other routes of administration. The kits of the present invention may also contain one or more antibodies described herewith. Optionally the kit may contain disposable items, such as biodegradable items. The kit may also contain a sample collection means, including, but not limited to a needle for collecting blood, storage means for storing the collected sample, and for shipment. Alternatively, any kits of the present invention may contain an instruction for use to diagnose malaria or a receptacle for receiving subject derived bodily fluid or tissue.

The kit further comprises instructions for use or a CD, or CD-ROM with instructions on how to collect sample, ship sample, and means to interpret test results. The kit may also contain a control sample either positive or negative or a standard and/or an algorithmic device for assessing the results and additional reagents and components.

A "biological sample" is any bodily fluid or tissue sample obtained from a subject, including, but is not limited to, blood, blood serum, urine, and saliva.

The kit may further comprise one or more additional compounds to generate a detectable product. Examples of such signal generating compounds include chromogens, radioisotopes (e.g., $^{125}I$, $^{131}I$, $^{32}P$, $^{3}H$, $^{35}S$, and $^{14}C$), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, β-galactosidase, and ribonuclease).

By way of example, and not of limitation, examples of the present invention shall now be given.

Example 1: Antibodies to PfSEP-1Block Parasite Egress from RBCs and Protect Subjects from Severe Malaria

*P. falciparum* malaria is a leading cause of morbidity and mortality in developing countries, infecting hundreds of millions of individuals and killing over one million children in sub-Saharan Africa each year. Recent estimates indicate that even these staggering figures significantly underestimate the actual disease burden. Children suffer the greatest morbidity and mortality from malaria-yet this age group has not been targeted at the identification stage of vaccine development. Of the about 100 vaccine candidates currently under investigation, more than 60% are based on only four parasite antigens. New antigen candidates are urgently needed, but strategies to identify novel antigens are limited and many focus on rodent malarias.

Human residents of endemic areas develop protective immunity that limits parasitemia and disease, and naturally acquired human immunity provides an attractive model for vaccine antigen identification. Plasma from some chronically exposed individuals contains antibodies which limit parasite growth ex vivo and following adoptive transfer, a finding which confirms the protective efficacy of anti-parasite antibodies. One approach to identify and characterize new malarial vaccine candidate antigens is to identify malarial proteins that are uniquely recognized by antibodies in the plasma of chronically exposed, yet resistant individuals. Because of logistic difficulties in characterizing naturally acquired resistance in endemic populations, this approach has not been widely exploited.

Studies were carried out to identify vaccine candidates for pediatric *falciparum* malaria by identifying the parasite targets of naturally acquired protective human antibodies. A differential, whole proteome screening method using plasma and epidemiologic data from a birth cohort of children living in Tanzania was used to identify *P. falciparum* antigens associated with resistance in two-year old children. Schizont Egress Protein-1 (PfSEP-1), a 244-kDa parasite antigen, which localizes to the schizont/parasitophorous vacuole membrane, Maurer's clefts and the inner leaflet of the RBC membrane was identified in schizont infected RBCs. Antibodies to PfSEP-1 decrease parasite replication by 60% by arresting schizont rupture. Active vaccination with rPbSEP-1 resulted in a 4.5 fold reduction in parasitemia after challenge with *P. berghei* ANKA parasites. Children in the cohort experienced a dramatically increased incidence of severe malaria during periods with undetectable anti-PfSEP-1 antibody levels (45 cases/23,806 child weeks) compared to periods with detectable antibody levels (0 cases/1,688 child weeks). By blocking schizont egress, PfSEP-1 synergizes with vaccines targeting hepatocyte and red cell invasion.

Identification and In Vitro Evaluation of Vaccine Candidates

Figure 6:
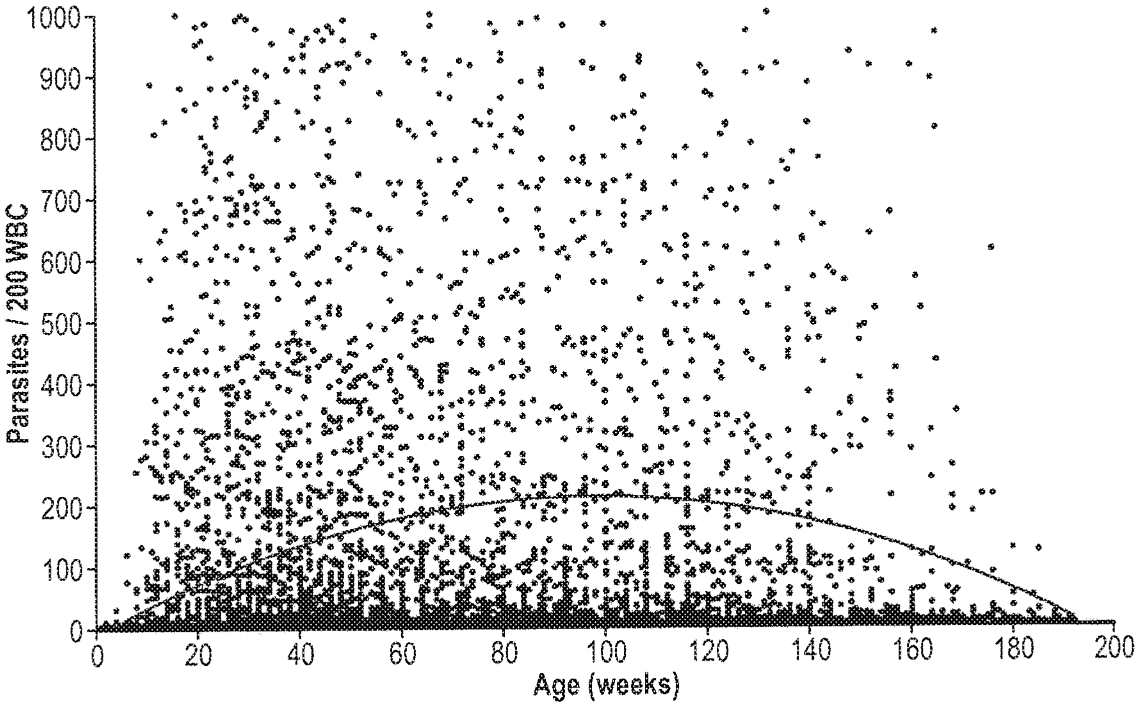
FIG. 6 is a dot plot showing the relationship between parasitemia and age for all available blood smears (n=34,038). In multivariate regression analysis, both age (P<0.001) and age2 (P <0.001) were related to parsitemia. Second degree (age and age2) polynomial regression line is depicted in red. Vertical axis is truncated at 1000 parasites/200 WBC for clarity.
Figure 7:
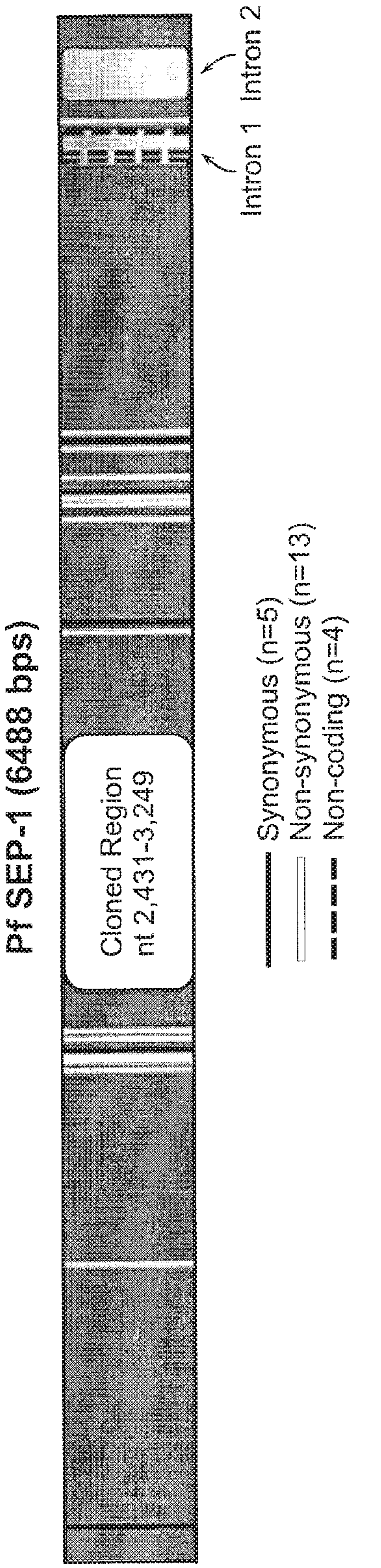
FIG. 7 is a diagram showing the location of SNPs in PfSEP-1. Data obtained from Plasmodb.org represent sequencing of fifteen lab and field isolates. No SNPs are reported in the region identified in the differential screening (nt 2,431-3,249).

Using a differential screening method, the *P. falciparum* blood stage proteome with plasma from resistant and susceptible two yr old children was interrogated to identify parasite proteins that are the targets of protective antibody responses. We focused on 2 yr old children because in our cohort, resistance to parasitemia is first detected at this age (FIG. 6). We selected twelve resistant and eleven susceptible 2 year old children with careful matching for potential non-immunologic factors, which may be related to resistance (see Table below and FIG. 16). Resistance was determined based on the geometric mean parasite density on all blood films collected between ages 2 and 3.5 yrs. We pooled plasma collected at age 2 yrs (+1-2 weeks) from the resistant individuals (RP) and susceptible individuals (SP) and performed differential screening experiments on a *P. falciparum* 3D7 strain blood stage cDNA library. We screened $1.25\times10^6$ clones and identified three clones that were uniquely recognized by RP, but not SP. The sequences of these clones were compared to the published *falciparum* genome (PlasmoDB.org) and found to encode nt 2,431-3,249 of PF3D7_1021800—a gene on chromosome 10, nt 3,490-5,412 of PF3D7 1134300—a gene on chromosome 11, and nt 201-1,052 of PF3D7 1335100—which encodes merozoite surface protein-7 (MSP-7)-a protein involved in RBC invasion which is currently under study as a potential vaccine candidate.

In silico analysis (PlasmoDB.org) predicts that PF3D7_1021800 contains a 6225 bp gene that encodes a 244-kDa acidic phospho-protein (SEQ ID NO:2), contains two introns near its 3' end, and has syntenic orthologs in all rodent and human malarias evaluated. Based on in vitro experiments, we designate the protein product of PF3D7_1021800 as *Plasmodium falciparum* Schizont Egress Protein 1 (PfSEP-1). PF3D7_1021800 mRNA expression increases throughout blood stage schizogeny and the gene displays minimal sequence variation, with no SNPs in the cloned region (nt 2,431-3,249), across fifteen field and laboratory isolates (FIG. 16). A recently reported deep sequencing effort on 227 field samples identified 3 non-synonymous and 1 synonymous SNPs in the cloned region. We have sequenced nt 2,431-3,249 of PF3D7_1021800 in 6 field isolates obtained from children in our cohort and found one isolate with a six bp insertion (encoding Asp-Gly-Asp-Gly instead of the canonical Asp-Gly) as well as one synonymous SNP. These data indicate that there is little or no sequence variability among parasite strains.

Figure 8A:
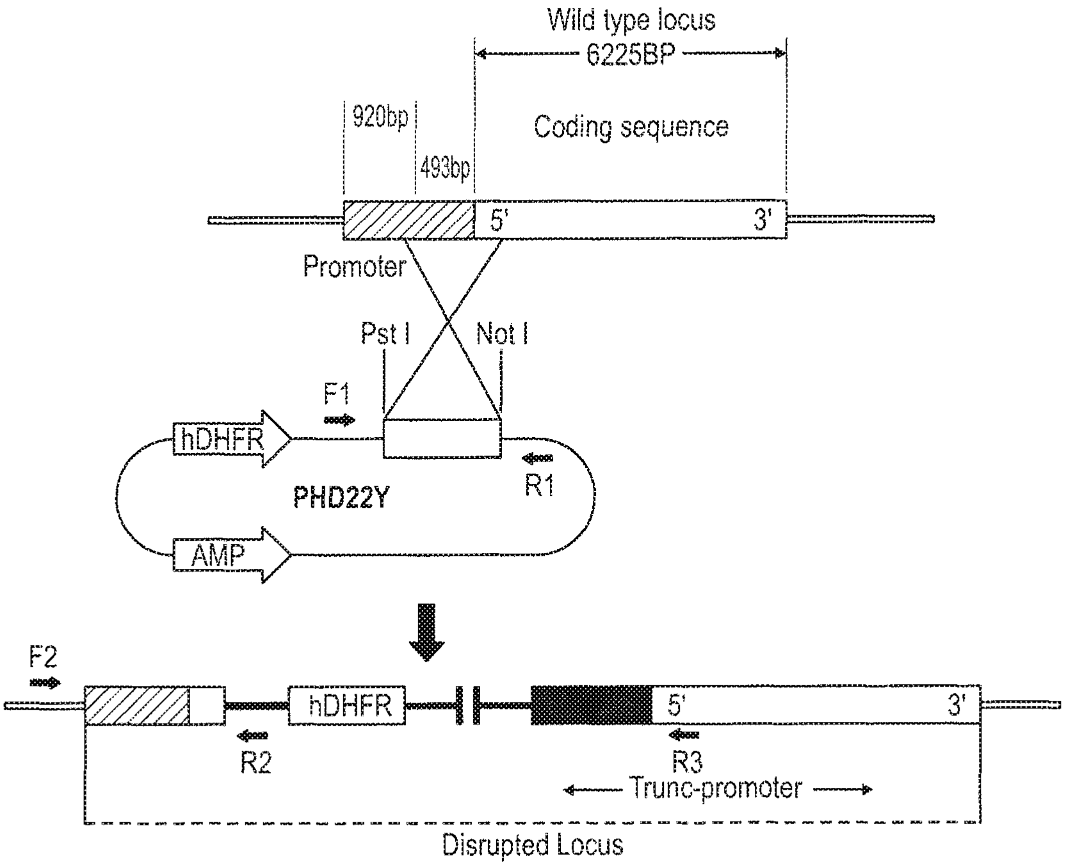
FIG. 8A-B are diagrams and FIG. 8C is a photograph of an electrophoretic gel. These figures show the knockdown and knockout strategy for PfSEP-1. A) targeting vector for knock down strategy designed to disrupt the promotor region, B) targeting vector for knock out strategy designed to disrupt protein coding region, C) Evaluation of drug resistant parasites for gene disruption. PCR amplification of drug selected parasites was carried out using: lane 1) F1 and R1 primers, lane 2) F2 and R2 primers and, lane 3) F2 and R3 primers. Only F1 and R1 primers amplified successfully indicating the presence of episomal, but not integrated vector.
Figure 8B:
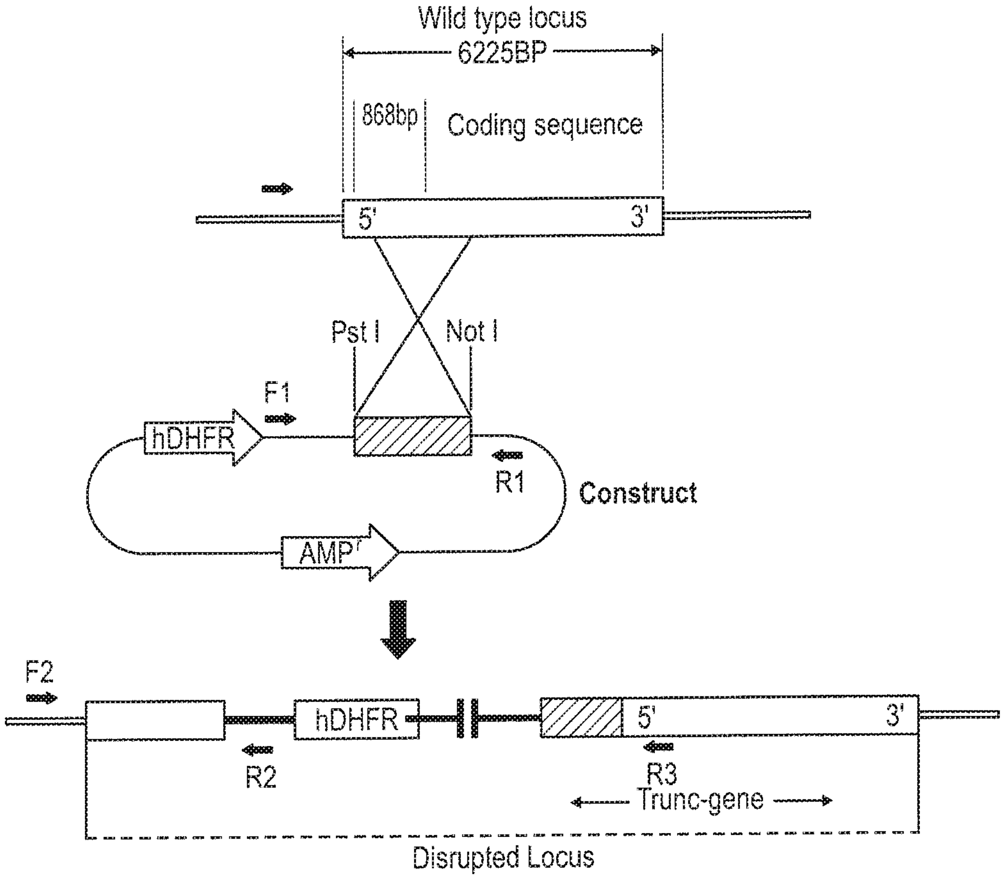
Figure 8C:
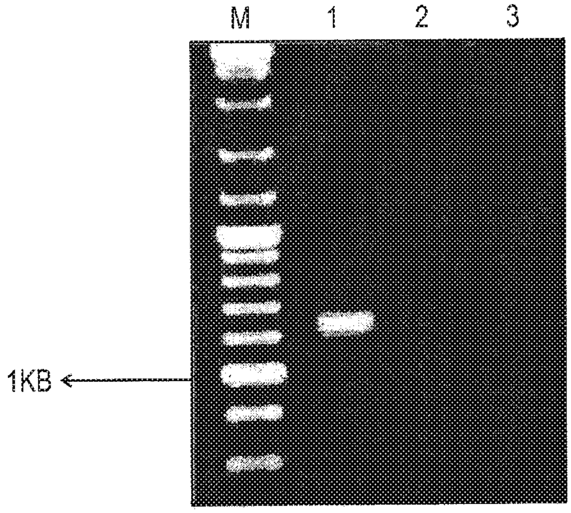

PfSEP-1 has no significant homology to proteins of known function. To explore the function of PfSEP-1, we have constructed vectors designed to disrupt the coding and promoter regions of the gene through the well described process of homologous recombination[9]. We have obtained episomal carriage of both targeting vectors, but have not recovered homologous integrants with either vector, suggesting that expression of PF3D7_1021800 is essential for blood stage replication (FIGS. 8A-C).

Figure 9:
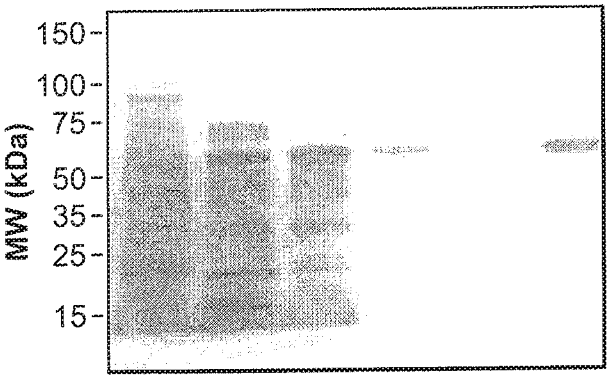
FIG. 9 is a photograph of an electrophoretic gel showing the results of chromatographic purification of rPfSEP-1A. Recombinant protein containing fractions were resolved on an 8-15% SDS PAGE-gel and stained with Gel-Code Blue. Lane 1) induced lysate, lane 2) nickel chelate chromatography of lane 1, lane 3) hydrophobic interaction chromatography of lane 2, lane 4) anion exchange chromatography of lane 3, lane 5) hydroxyappatite chromatography of lane 4, and lane 6) rPfSEP-1A post-tangential flow filtration, lyophilization and reconstitution.
Figure 10:
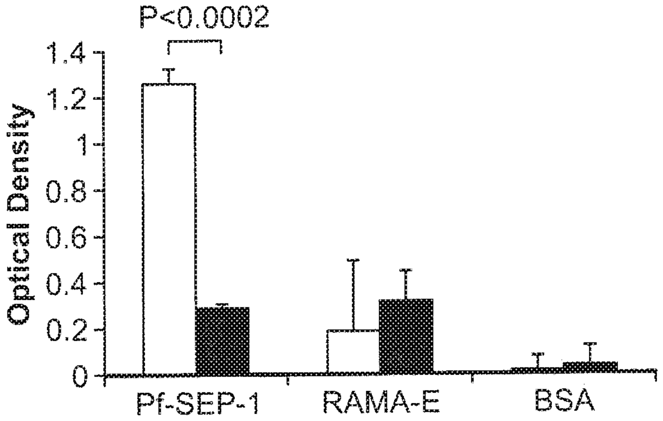
FIG. 10 is a bar graph showing differential recognition of rPfSEP-1A by IgG antibodies in plasma from resistant versus susceptible individuals. Antigen coated microtiter wells were probed with plasma pooled from resistant individuals (clear bars, n=11) or susceptible individuals (black bars, n=14, table S1) and bound antibody was detected with alkaline phosphatase conjugated goat anti-mouse IgG. RAMA-E is a *P. falciparum* merozoite protein, BSA is bovine serum albumin. Bars represent mean of 4 replicate wells. Error bars represent SEM. Recognition of rPfSEP-1A by antibodies in resistant plasma, as assessed by optical density, was 4.4 fold higher than by antibodies in susceptible plasma (Student's t-test, P<0.0002).

We have expressed and purified the polypeptide encoded by nt 2,431-3,249 of PF3D7_1021800 (aa 810-1083) in *E. coli* and designated this recombinant protein rPfSEP-1A (FIG. 9). Using an independent selection of resistant and susceptible individuals (see Table below), we confirmed and generalized the differential recognition of rPfSEP-1A (SEQ ID NO:2) in an ELISA based assay. IgG antibody recognition of rSEP-1A was 4.4 fold higher in RP (n=11) than in SP (n=14, P<0.0002, FIG. 10), yet did not differ for other malarial proteins or controls.

| Variable | Resistant | Susceptible | P value[a] |
|---|---|---|---|
| Number of Subjects | 12 | 11 | — |
| Hemoglobin phenotype (% AS) | 16.6 | 0 | 0.47 |
| Sex (% female) | 41.6 | 45.4 | 1 |
| Weeks of follow-up (median [IQR]) | 140.5 [44.5] | 152 [44] | 0.31 |
| # of Blood smears from age 2-3.5 yrs (median [IQR]) | 16.5 [21.5] | 21 [24] | 0.31 |
| # of Positive Blood smears from age 2-3.5 yrs (median [IQR]) | 0 [1] | 4 [10] | 0.04 |
| # of anti-malarial treatments before age 2 yrs (median [IQR]) | 2 [1.75] | 8 [8] | 0.01 |
| Pregnancy malaria (%) | 16.6 | 9 | 1 |

-continued

| Variable | Resistant | Susceptible | P value[a] |
|---|---|---|---|
| Maternal age (yrs, median [IQR]) | 22.5 [9.5] | 28 [10] | 0.35 |
| Birth Season (% in High Season) | 25 | 9 | 0.59 |
| Children using Bed Net (%) | 33.3 | 0 | 0.09 |
| # of Previous Pregnancies (median [IQR]) | 0 [2] | 1 [2] | 0.19 |
| Parasite density (parasites/ 200 WBCs) at 2 yr blood draw (median [IQR]) | 0 [0] | 0 [0] | 1 |
| Parasite density (parasites/ 200 WBCs) from a 2-3.5 yrs (median [IQR]) | 0 [25.6] | 3203 [944.1] | 0.05 |

[a]Comparisons of catagorical variables by 2 tailed Fisher's exact test.
Comparisons of continuous variables by Mann-Whitney U test

| Variable | Resistant | Susceptible | P value[a] |
|---|---|---|---|
| Number of Subjects | 11 | 14 | 1 |
| Hemoglobin phenotype (% AS) | 36 | 21 | 0.66 |
| Sex (% female) | 45 | 43 | 1 |
| Weeks of follow-up (median [IQR]) | 154 [14] | 165 [19] | 0.34 |
| # of Blood smears from age 2-3.5 yrs (median [IQR]) | 14 [5.8] | 20.5 [9.5] | 0.02 |
| # of Positive Blood smears from age 2-3.5 yrs (median [IQR]) | 0 | 7.8 [6] | <0.001 |
| # of anti-malarial treatments before age 2 yrs (median [IQR]) | 2.6 [2.9] | 6.3 [3.1] | 0.008 |
| Pregnancy malaria (%) | 9 | 14 | 1 |
| Maternal age (yrs, median [IQR]) | 27 [8] | 27 [7] | 0.85 |
| Birth Season (% in High Season) | 73 | 50 | 0.41 |
| Children using Bed Net (%) | 0 | 0 | 1 |
| # of Previous Pregnancies (median [IQR]) | 1 [3.0] | 1 [3.0] | 0.89 |
| Parasite density (parasites/ 200 WBCs) at 2 yr blood draw (median [IQR]) | 0 [0] | 0 [0] | 1 |
| Parasite density (parasites/ 200 WBCs) from a 2-3.5 yrs (median [IQR]) | 0 [0] | 2106.9 [2700] | <0.001 |

Figure 11A:
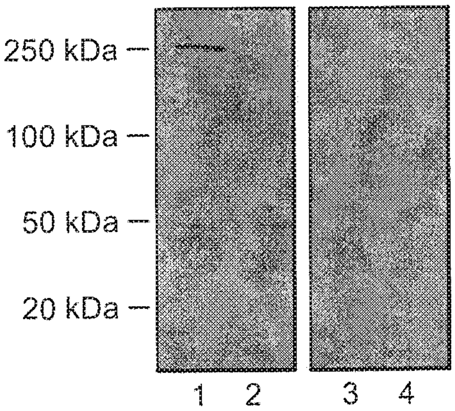
FIGS. 11A-B are photographs of electrophoretic gels showing that anti-Pf SEP-1 antibodies recognize a 244 kDa protein in *P. falciparum* extracts. Mixed stage 3D7 infected RBCs, uninfected RBCs and rPf SEP-1A were analyzed by western blot. A) lanes 1 and 3-3D7 infected RBC extracts, lanes 2 and 4-uninfected RBC extracts. Lanes 1 and 2-probed with anti-PfSEP-1 antisera (1:500), lanes 3 and 4-probed with pre-immune mouse sera (1:500). B) lanes 1 and 2-0.05 ug of rPfSEP-1A, lane 1-probed with anti-Pf SEP-1 mouse sera (1:2000), lane 2-probed with pre-immune mouse sera (1:2000).
Figure 11B:
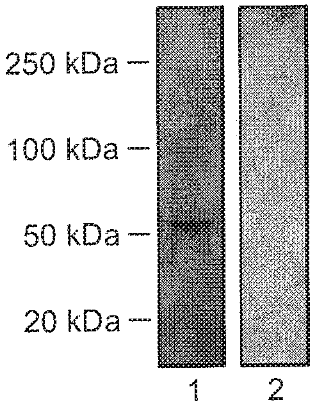
Figure 12A:
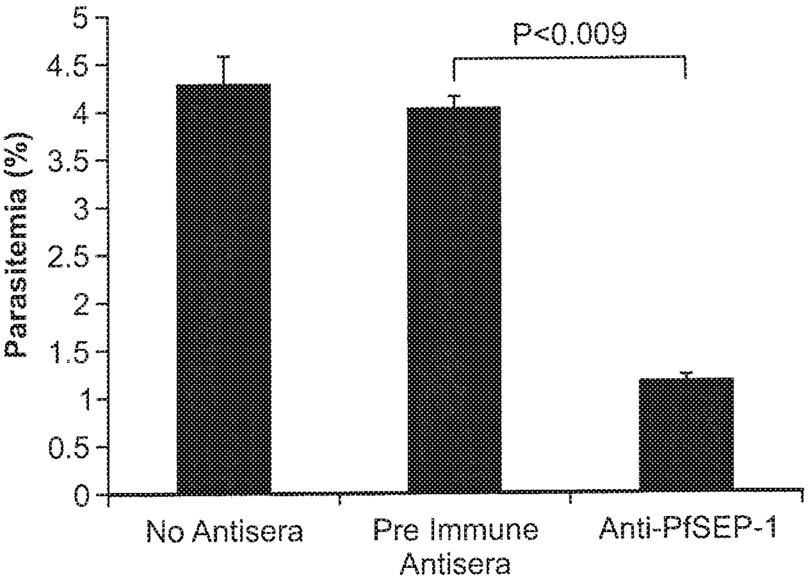
FIGS. 12A-B are bar graphs showing that anti-rPfSEP-1A antibodies generated by protein immunization inhibit parasite growth/invasion by 72-74% across 2 parasite strains in vitro. Ring stage 3D7 (A), and W2 (B) parasites were synchronized three times using sorbitol, plated at 0.3-0.4% parasitemia, and cultured to obtain mature trophozoites. Mature trophozoites were cultured in the presence of anti-rPfSEP-1A mouse sera (1:10 dilution). Negative controls included no mouse sera and pre-immune mouse sera (1:10 dilution). Sera was heat inactivated and dialyzed prior to use. Parasites were cultured for 24 hrs and ring stage parasites were enumerated by microscopic examination. Bars represent the mean of 5 independent replicates with each replicate performed in triplicate. Error bars represent SEMs. P<0.009 for comparison between pre and post immune mouse sera by non-parametric Mann-Whitney U test.
Figure 12B:
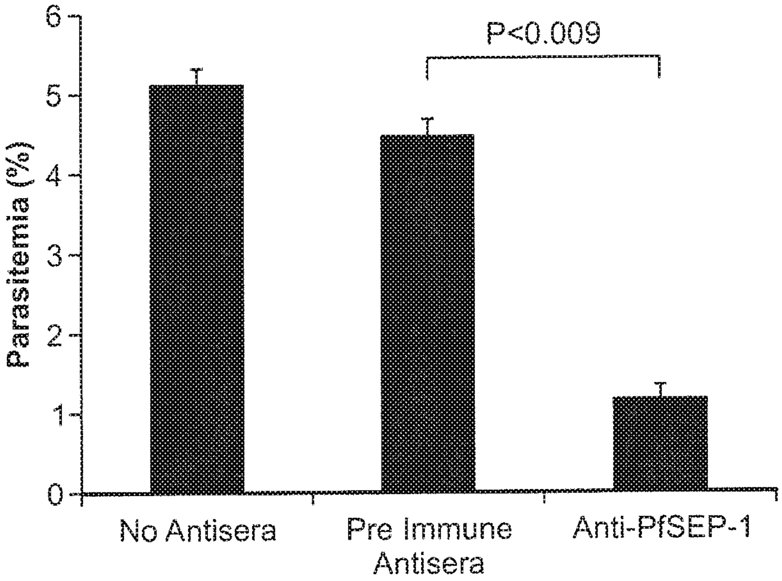

[a]Comparisons of catagorical variables by 2 tailed Fisher's exact test.
Comparisons of continuous variables by Mann-Whitney U test We have cloned this sequence into a eukaryotic expression plasmid (VR2001), immunized mice and generated anti-rPfSEP-1A anti-sera. To confirm that PF3D7_1021800 encodes a parasite protein, we probed *P. falciparum* 3D7 infected and uninfected RBCs with both pre-immune and post-immune sera. Anti-rPfSEP-1A recognized a 244-kDa protein in infected but not uninfected RBC (FIGS. 11A-B).

We performed growth inhibition assays using anti-rPfSEP-1A antisera prepared by both DNA vaccination and recombinant protein immunization. Parasites were synchronized to the ring stage, cultured to obtain mature trophozoites and then incubated with anti-rPfSEP-1A antisera or controls for 24 hr followed by enumeration of newly invaded ring stage parasites. Anti-rPfSEP-1A generated by both DNA plasmid and recombinant protein based immunization inhibited parasite growth by 58-75% across three parasite strains compared to controls (all P<0.009). Antisera prepared by DNA vaccination against an irrelevant *falciparum* protein (phosphatidylglycerophosphate synthase, PF3D7_0820200) showed no growth inhibition.

Figure 19:
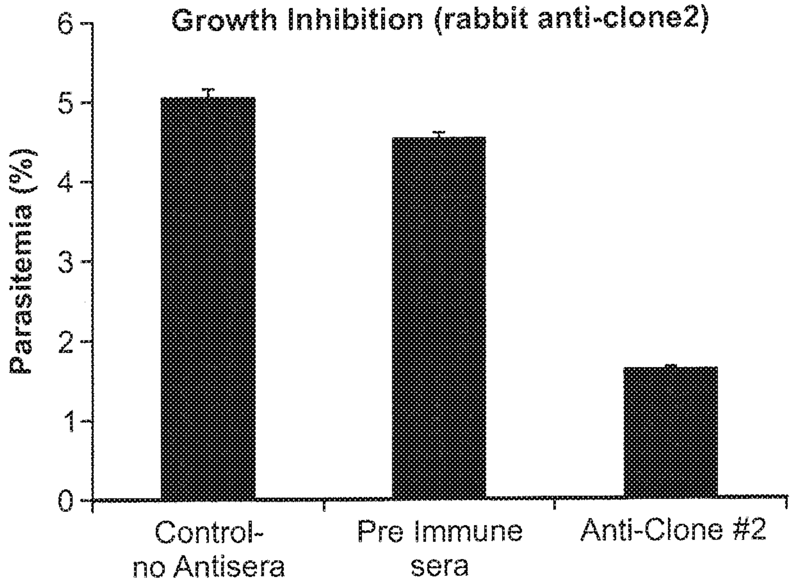
FIG. 19 is a bar graph showing growth inhibition assay. Rabbit anti-PfSEP-1 inhibits parasite growth/invasion by 68% in vitro.

As shown in FIG. 19, rabbit anti-PfSEP-1 inhibits parasite growth/invasion by 68% in vitro. Ring stage 3D7 parasites were synchronized twice using sorbitol plated at 1% parasitemia, allowed to mature to trophozoites (24 hrs), followed by addition of anti-clone 2 rabbit sera (1:10 dilution). Negative controls included no rabbit sera and pre-immune rabbit sera (1:10 dilution). Parasites were cultured for 24 hrs and ring stage parasites were enumerated by microscopic examination. Bars represent the mean of 3 independent replicates. Error bars represent SEMs. P <0.0001 for comparison between pre and post immune rabbit sera by non-parametric Mann-Whitney U test.

Figure 2A:
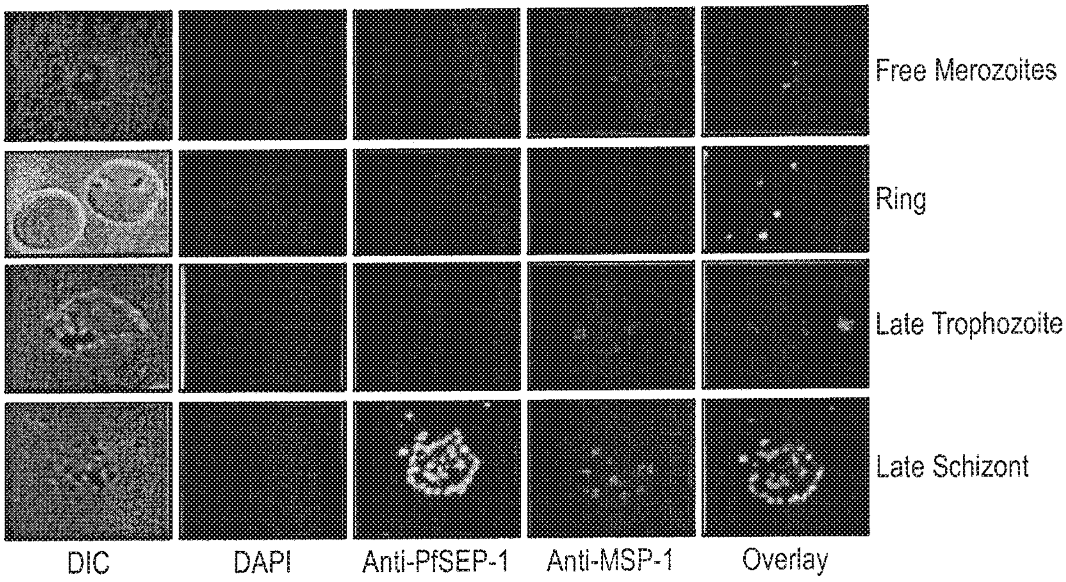
FIGS. 2A-D are photomicrographs showing immunolocalization of PfSEP-1. A) methanol fixed infected RBC were probed with mouse anti-PfSEP-1 (green) and rabbit anti-MSP-1 (red) and counterstained with DAPI to label parasite nuclei. PfSEP-1 is detected only in schizont infected RBCs, B) methanol fixed schizont infected RBCs do not label when probed with pre-immune mouse sera, C) non-permeabilized, non-fixed schizont infected RBCs were probed with mouse anti-PfSEP-1 (red) and rabbit anti-glycophorin A (green) and counterstained with DAPI to label parasite nuclei. PfSEP-1 co-localized with glycophorin A to the surface of schizont infected RBCs, D) non-permeabilized, non-fixed schizont infected RBCs were probed with mouse anti-PfSEP-1 (5 nm gold particles) and rabbit anti-glycophorin A (10 nm gold particles) and counterstained with uranyl acetate to enhance membrane contrast. PfSEP-1 localized to the schizont/parasitophorous vacuole membrane (black arrow), Maurer's clefts (yellow arrow) and the inner leaflet of the RBC membrane (grey arrow) while glycophorin A was confined to the outer leaflet of the RBC membrane (white arrow). Similar results were obtained when PfSEP-1 was detected with 18 nm gold particles.
Figure 2B:
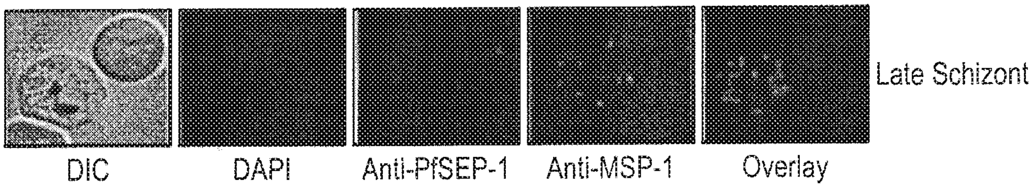
Figure 2C:
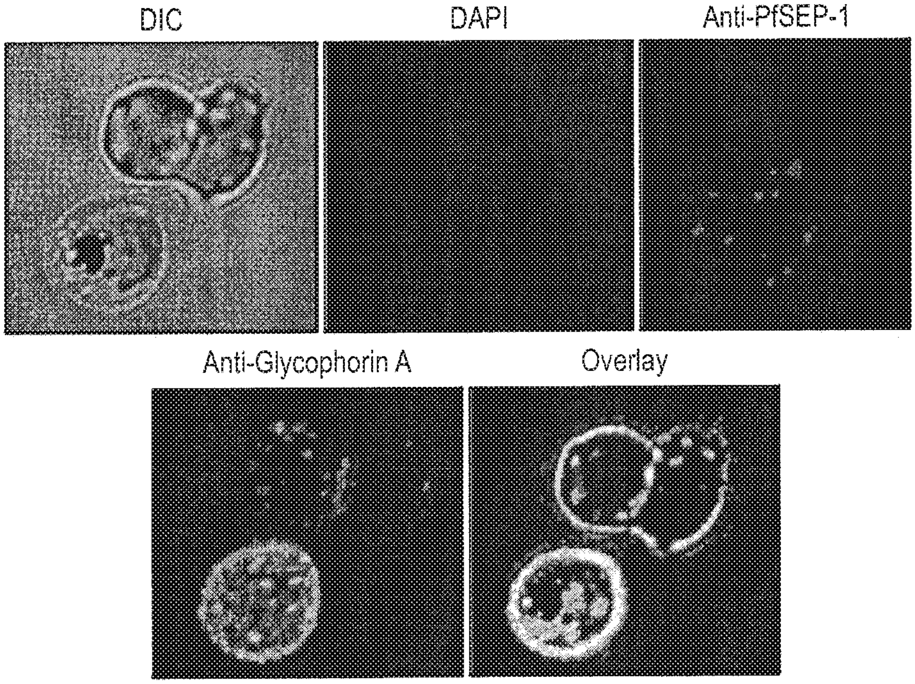
Figure 2D:
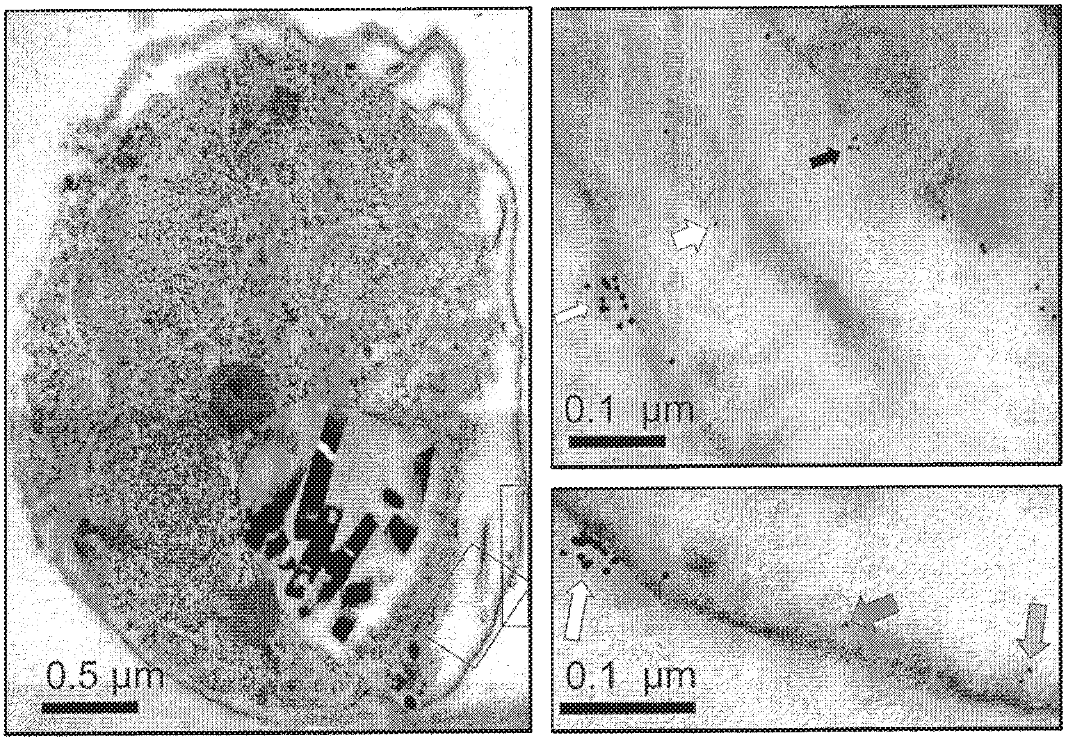
Figure 13A:
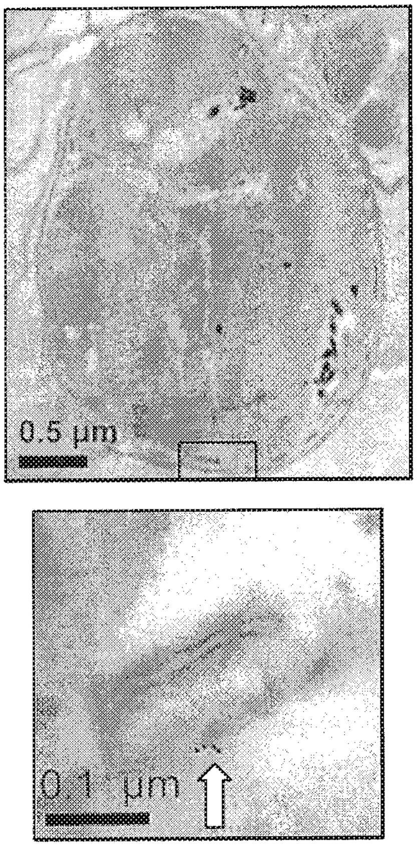
FIGS. 13A-B are photomicrographs showing that PfSEP-1 is not detected in trophozoite infected RBCs or non-infected RBCs. Non-permeabilized, non-fixed trophozoite infected RBCs (A) or uninfected RBCs (B) were probed with mouse anti-PfSEP-1 (5 nm gold particles) and rabbit anti-glycophorin A (10 nm gold particles) and counterstained with uranyl acetate to enhance membrane contrast. PfSEP-1 was not detected in trophozoite infected RBC or uninfected RBCs, while glycophorin A was confined to the outer leaflet of the RBC membrane (white arrow).
Figure 13B:
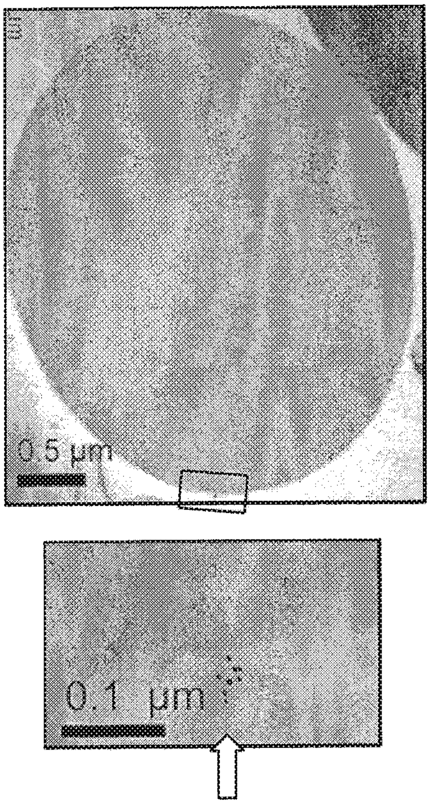

We immunolocalized PfSEP-1 by both immunofluorescence confocal microscopy and immunogold transmission electron microscopy (FIGS. 2A-C). Anti-PfSEP-1 did not bind to free merozoites, rings or late trophozoite stage parasites, but did specifically recognize an antigen expressed by late schizont infected RBC (FIGS. 2A-B). In non-permeabilized, non-fixed schizont infected RBCs, PfSEP-1 co-localized with glycophorin A (FIG. 2C). This localization was further evaluated by immunoelectron microscopy (FIG. 2D). In non-permeabilized, non-fixed schizont infected RBCs, PfSEP-1 localized to the schizont/parasitophorous vacuole membrane, Maurer's clefts and the inner leaflet of the RBC membrane while glycophorin A was confined to the outer leaflet of the RBC membrane. This pattern of staining was observed in essentially all of the late schizont infected RBCs examined. No staining for PfSEP-1 was observed in uninfected RBC or ring/trophozoite infected RBCs (FIGS. 13A-B). The close juxtaposition of these structures in late schizont infected RBCs with the RBC outer membrane explains the apparent co-localization of PfSEP-1 with glycophorin A observed by confocal microscopy. The accessibility of antibodies to PfSEP-1 in non-permeabilized, non-fixed schizont infected RBCs is consistent with the known permeability of parasitized RBCs at the later stages of schizogony.

Figure 3A:
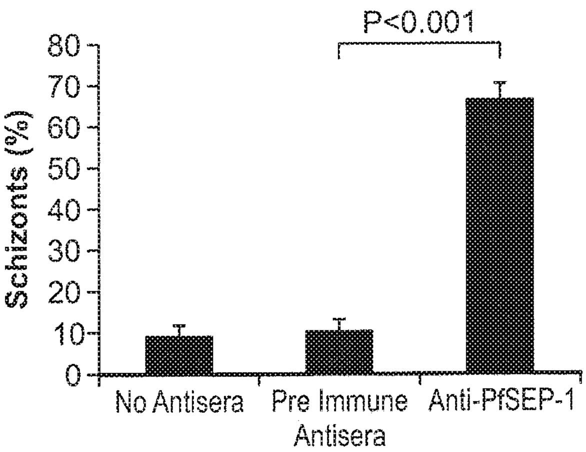
FIGS. 3A-C are bar graphs showing that anti-PfSEP-1 antibodies generated by DNA vaccination inhibit schizont egress across 3 parasite strains in vitro. Ring stage 3D7 (A), W2 (B) and D10 (C) parasites were synchronized three times using sorbitol, plated at 3.5% parasitemia, and cultured to obtain early schizonts. Parasites were incubated in in the presence of of anti-PfSEP-1 mouse sera (1:10 dilution). Negative controls included no mouse sera and pre-immune mouse sera (1:10 dilution). Sera was heat inactivated and dialyzed prior to use. Schizonts were enumerated at 12 hrs post-treatment. Bars represent the mean of 5 independent replicates with each replicate performed in triplicate. Error bars represent SEMs. P<0.001 for comparison between pre and post immune mouse sera by non-parametric Mann-Whitney U test. Schizontemia was 5.3-6.8 fold higher in post versus pre-immune sera treated cultures.
Figure 3B:
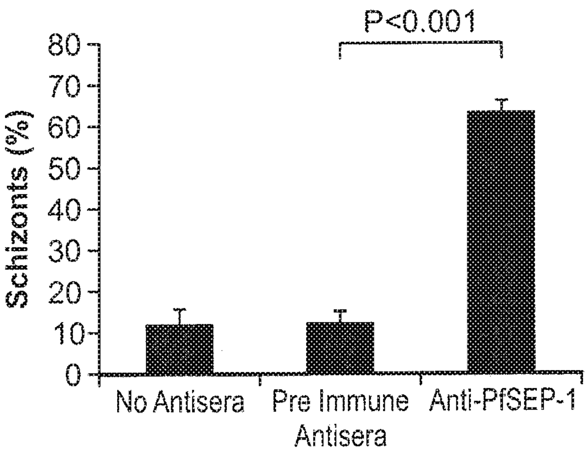
Figure 3C:
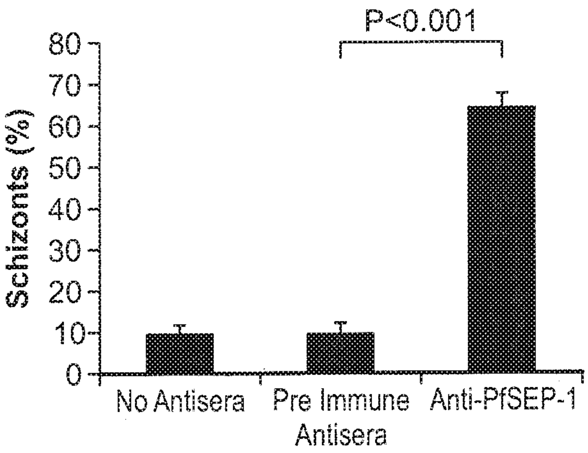

The localization of PfSEP-1 was not consistent with a role in RBC invasion, rather it suggested a role in parasite egress from infected RBCs. To determine the mechanism of growth inhibition we performed schizont arrest assays using anti-rPfSEP-1A antisera prepared by both DNA vaccination (FIGS. 3A-C) and recombinant protein immunization (FIGS. 14A-B). Parasites were synchronized to the ring stage at high (3.5%) parasite density, cultured to obtain early schizonts and then incubated with anti-rPfSEP-1A antisera or controls for 12 hr followed by enumeration of remaining schizont stage parasites. Under these conditions, the majority of schizont infected RBCs should rupture, releasing merozoites, which would invade new RBCs and develop into ring stage parasites. Anti-rPfSEP-1A generated by both DNA plasmid and recombinant protein based immunization dramatically inhibited schizont egress resulting in 4.3-6.8 fold higher proportion of schizonts across three parasite strains compared to controls (all P<0.009).

Active Vaccination with SEP-1 Protects Mice from *P. berghei* Challenge

Figure 4A:
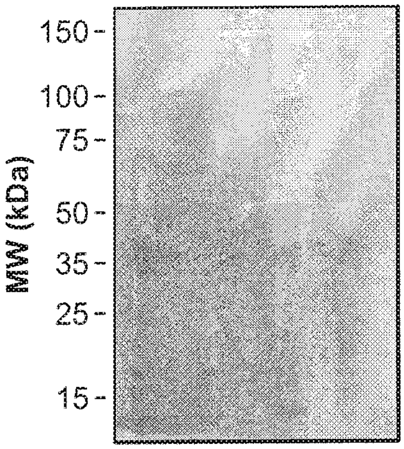
FIG. 4A is a photograph of an electrophoretic gel, FIG. 4 B is a bar graph showing antibody responses of mice vaccinated with rPbSEP-1A.
Figure 4B:
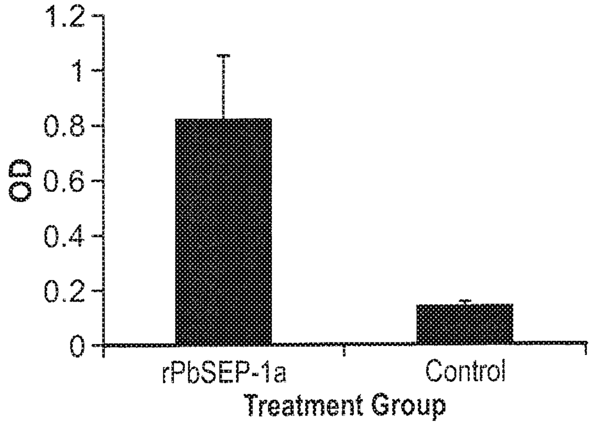
Figure 4C:
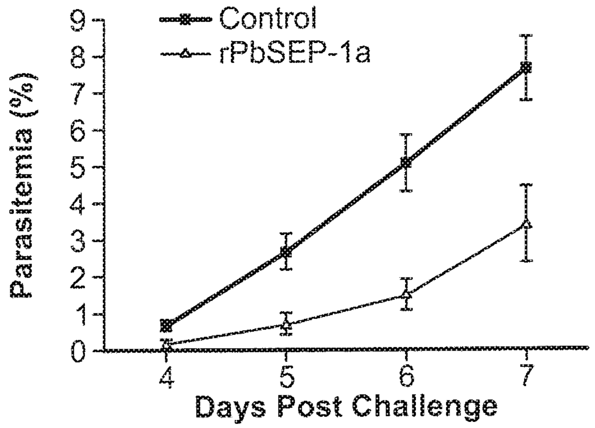
FIG. 4C is a line graph showing parasite burden.

To evaluate the protective efficacy of active vaccination with SEP-1 in vivo, we cloned the *P. berghei* ANKA strain ortholog of PfSEP-1 (nt 2173-3000) into the expression plasmid pET30 and expressed and purified rPbSEP-1A (aa 725-1000) from (FIG. 4A). We vaccinated Balb/C mice (n=11) with rPbSEP-1A in TiterMax Gold adjuvant or adjuvant alone (n=11), measured their antibody responses to rPbSEP-1A (FIG. 4B), and challenged them with $10^6$ *P. berghei* ANKA parasite infected red blood cells intraperitoneally. Mice vaccinated with rPbSEP-1A had 4.5 fold decreased parasitemia on day 7 post challenge compared to controls treated with adjuvant alone (FIG. 4C).

Human Antibody Responses to PfSEP-1

To evaluate the impact of naturally acquired anti-PfSEP-1 antibodies on clinical malaria, we measured anti-PfSEP-1 IgG antibody levels using a fluorescent, bead-based assay in our birth cohort and related these levels to subsequent malaria outcomes. We measured anti-PfSEP-1 IgG antibody levels in available plasma obtained at scheduled, non-sick visits between 2 and 3.5 yrs of life (total of 156 antibody measures on 155 children). Anti-PfSEP-1 antibodies were detectable in 3.2% of these samples and children were followed for a total of 6,350 child-weeks of observation (201 weeks with detectable anti-PfSEP-1 and 6,149 weeks with undetectable levels). We related the presence of detectable anti-PfSEP-1 antibodies to malarial outcomes, including parasite density, mild malaria, severe malaria, all cause and malaria attributed mortality. For each antibody measurement, the time interval examined for malaria outcomes extended from the time of the antibody measurement until the child had a subsequent antibody determination or completed the study.

We used generalized estimating equations (GEE) based longitudinal regression models to evaluate the relationship between time varying anti-PfSEP-1 antibody responses and dichotomous malaria endpoints. Similar GEE based linear regression models were used for the continuous endpoints of parasite density on all available blood smears and parasite density on positive blood smears. These models adjust for both potential confounders and the lack of independence (correlation) among observations taken from the same subject over time. Potential confounders included hemoglobin phenotype, age, and average prior parasitemia on all blood smears.

Figure 15A:
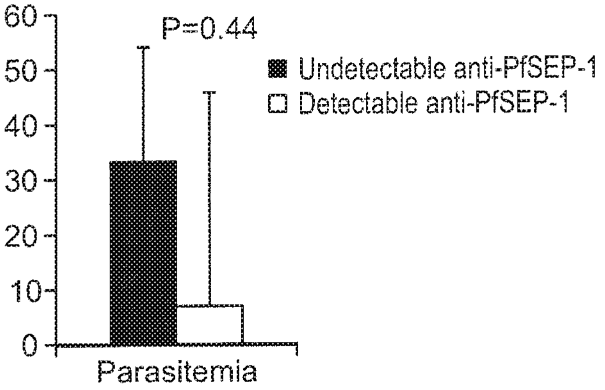
FIGS. 15A-C are bar graphs. Parasite density on A) all blood smears and B) positive blood smears in children aged 2-3.5 yrs during intervals with detectable and undetectable anti-PfSEP-1 antibodies, after adjusting for hemoglobin phenotype, age, average prior parasitemia on all blood smears, and repeated measures. Error bars represent SEM. C) Incidence of mild malaria in children aged 2-3.5 yrs of age during intervals with detectable and undetectable anti-PfSEP-1 antibodies after adjusting for hemoglobin phenotype, age, average prior parasitemia on all blood smears, and repeated measures. Error bars represent 95% CI.
Figure 15B:
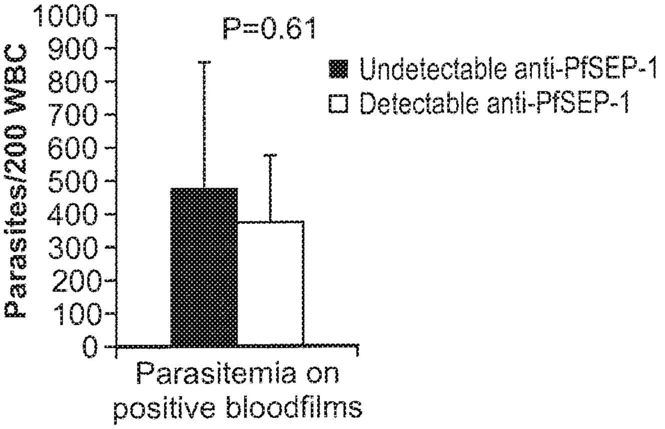
Figure 15C:
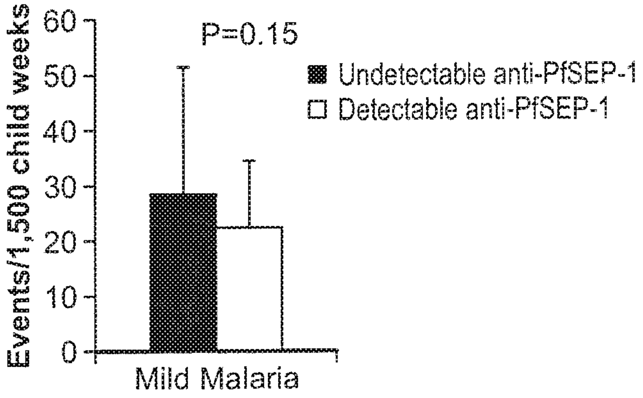

Children without detectable anti-PfSEP-1 IgG antibody had higher parasite densities on all available blood smears, higher parasite densities on positive blood smears, and increased incidence of mild malaria. (FIGS. 15A-C).

Figure 5:
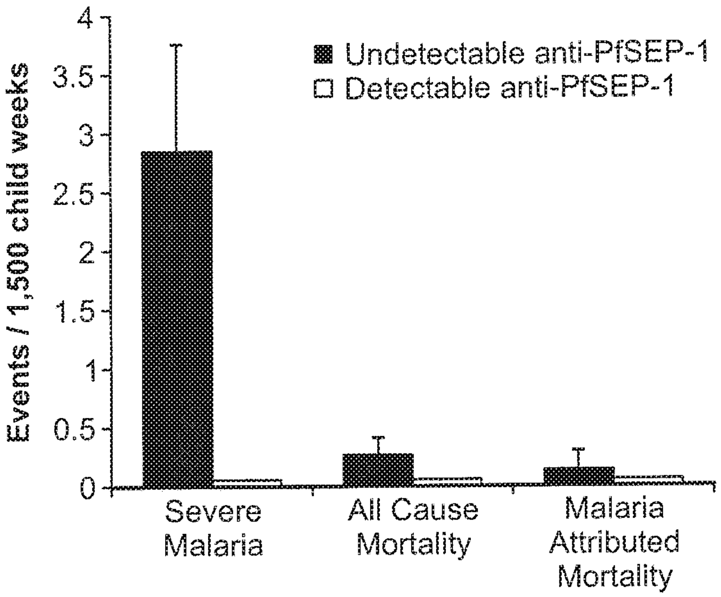
FIG. 5 is a line graph showing the incidence of severe malaria and death in children aged 1.5-3.5 yrs of age during intervals with detectable and undetectable anti-PfSEP-1 antibodies (1,688 and 23,806 weeks respectively). No cases of severe malaria or death occurred during intervals with detectable anti-PfSEP-1 antibodies. Error bars represent 95% CI adjusted for repeated measures.

Severe malaria did not occur during periods when children had detectable anti-PfSEP-1 antibody levels (0 cases/201 child weeks with detectable anti-PfSEP-1 antibody vs. 6 cases/6,149 child weeks with undetectable anti-PfSEP-1 antibody), however the small number of total cases precluded meaningful analysis. In our cohort, severe malaria is strongly age dependent with the majority of cases occurring before 2 yrs of age. To increase the number of severe malaria cases for analysis, we extended the age range examined to 1.5-3.5 yrs of life encompassing 687 antibody measures on 453 children. Anti-PfSEP-1 antibodies were detectable in 6.0% of these samples and children were followed for a total of 25,494 child-weeks of observation (1,688 child weeks with detectable anti-PfSEP-1 and 23,806 child weeks with undetectable levels). Strikingly, severe malaria did not occur during periods when children had detectable anti-PfSEP-1 antibody levels (0 cases/1,688 child weeks with detectable anti-PfSEP-1 antibody vs. 45 cases/23,806 child weeks with undetectable anti-PfSEP-1 antibody, FIG. 5).

Individuals without detectable anti-PfSEP-1 IgG antibody had significantly increased risk of developing severe clinical malaria (adjusted OR 4.4; Type III fixed effects P<0.01) compared to individuals with detectable anti-PfSEP-1 IgG antibody levels even after adjusting for potential confounders. There was no significant difference in the risk for all-cause mortality or malaria-associated mortality, though the event rates for mortality were low. These results represent the first demonstration that antibodies that specifically block schizont egress can protect against severe malaria in humans.

Blocking Parasite Egress Protects Against Malaria

*Falciparum* malaria remains a leading cause of childhood mortality and vaccines are urgently needed to attenuate this public health threat. We report the rational identification of vaccine candidates by identifying parasite proteins uniquely recognized by antibodies expressed by resistant, but not susceptible children. Using a differential screen, we identified two genes encoding useful vaccine antigens as well as MSP-7, a known vaccine candidate. We have extensively characterized PfSEP-1, the protein product of PF3D7 1021800. PfSEP-1 localizes to the schizont/parasitophorous vacuole membrane, Maurer's clefts and the inner leaflet of the RBC membrane in schizont infected RBCs. PfSEP-1 is accessible to antibodies during late schizogeny, and displays minimal sequence variation, particularly in the region identified by our differential screening experiments (aa 810-1083; SEQ ID NO:2). Antibodies to PfSEP-1 significantly attenuate parasite growth via a unique mechanism; arresting schizont egress from infected RBCs without causing schizont agglutination.

Schizont egress is a complex tightly regulated process involving calcium dependent phosphorylation of parasite target proteins followed by proteolytic remodeling of parasite, as well as RBC cytoskeletal proteins. One of these proteolytic events involves SERA-5, the target of antibodies that agglutinate merozoites and schizonts and mediate schizont killing in cooperation with complement. Unlike SERA 5 and other proteins involved in schizont egress, PfSEP-1 was not identified in global profiles of proteolysis during schizont egress, and we did not observe any evidence of cleavage events within PfSEP-1 at any blood stage of development. The localization of PfSEP-1 to the inner RBC leaflet is consistent with a role in remodeling the RBC cytoskeleton prior to rupture.

In active vaccination experiments, rPbSEP-1A conferred marked protection against *P. berghei* ANKA challenge as evidenced by a 4.5 fold reduction in parasitemia seven days post-challenge. In addition, vaccination with rPbSEP-1A resulted in self-cure in one out of eleven vaccinated mice. These data constitute the first report of protection in *P. berghei* by vaccines targeting schizont egress and offer a pathway forward for advancing these vaccines toward non-human primate models.

In our longitudinal birth cohort, anti-PfSEP-1 antibodies were associated with significant protection from severe malaria, with no cases occurring while children had detectable anti-PfSEP-1 antibodies. This represents the first time that antibodies that specifically block schizont egress have been associated with protection from severe malaria. Under conditions of natural exposure, only 6% of 1.5 to 3.5 yr old children in our cohort had detectable anti-PfSEP-1 antibodies. This low natural prevalence suggests that adjuvanted vaccination with PfSEP-1 could have a marked impact on reducing severe malaria in young children.

The data validate the field-to-lab-to-field based strategy for the rational identification of vaccine candidates and indicate that PfSEP-1 is useful as a vaccine for pediatric *falciparum* malaria. By blocking schizont egress, PfSEP-1 synergizes with vaccines targeting hepatocyte and red cell invasion such as MSP-4, MSP-7, and/or RTSS.

The following materials and methods were used to generate the data described herein.

Study Population

Subjects participated in the Mother Offspring Malaria Studies (MOMS) project, which is based at Muheza Designated District Hospital (DDH), in north eastern Tanzania. Mothers presenting at Muheza DDH for delivery were enrolled and provided signed, informed consent prior to participation of themselves and their newborns in the study. Details of the MOMS study design, enrolment methods, and exclusion criteria have been described (Mutabingwa et al., PLoS Med 2, e407 (2005), and Kabyemela et al., J. Infect. Dis. 198, 163-166 (2008))

Inclusion Criteria and Clinical Monitoring

We monitored N=785 children for *P. falciparum* infection from birth up to 3.5 years of age. Children were evaluated at routine, well-child visits by a clinician every two weeks from birth to one year of age, and monthly thereafter, including blood smear analysis. Routine blood samples were collected once every 6 months from 1.5 to 3.5 years of life. Blood smears and blood samples were also collected any time the child became sick. Sick children were examined by a medical officer upon presentation to the hospital or mobile clinic. Treatment outside the study was minimized by active, weekly surveillance by our mobile clinics.

Clinical malaria was defined as asexual *P. falciparum* parasitemia by blood smear coupled with symptoms suggestive of malaria such as temperature >37.5° C., nausea or vomiting, irritability, and poor feeding. Prompt treatment was provided to sick children according to the guidelines of the Tanzanian Ministry of Health, and study participants were instructed to obtain all medications including antimalarials through the project staff.

Sample Collection and Processing

Venous blood was collected and stored at 4° C. until processing. Following centrifugation, plasma was stored at −80° C. *P. falciparum* parasitemia was determined by Giemsa-stained thick blood smears prepared from capillary or venous blood. Parasite density was expressed as the number of asexual stage parasites/200 white blood cells in the thick smear. Sickle cell trait was determined by electrophoresis (Helena Laboratories, Beaumont, Tex. USA). Hemograms were obtained on an impedance-based analyzer (Abbott Cell Dyne® 1200).

Case Definitions

Mild malaria was defined as a positive bloodsmear and one or more of the following: 1) anemia defined by Hgb <6 g/dL; 2) vomiting; 3) diarrheal disease or gastroenteritis; 4) lower respiratory infection; or 5) oral temperature >=38 deg C.

Severe malaria was defined as a positive bloodsmear and one or more of the following: 1) respiratory distress defined by respiratory rate of >40/min for children older than two months of age or a respiratory rate of >50/min for children less than two months of age; 2) a history of one or more convulsions in the twenty-four hours prior to or during hospitalization; 3) prostration defined by inability to sit unaided; 4) hypoglycemia defined by glucose <2.2 mmol/L; 5) severe anemia defined by Hgb <6 g/dL; or 6) oral temperature >40 deg C.

Malaria-associated mortality was defined as death with a positive blood film obtained during the terminal illness. One child who died of bacterial meningitis, but had a positive blood film was adjudicated as a non-malarial death.

Selection of Resistant and Susceptible Individuals

We excluded individuals with less than 9 of the total n=18 scheduled monthly blood smears collected between the ages of 2-3.5 yrs, individuals with less than 200 ul of plasma available from the plasma sample obtained at age 2 (+/−2 weeks), and individuals who were parasitemic at the time the 2 yrs (+/−2 weeks) plasma sample was obtained. We then rank ordered individuals based on the geometric mean parasite density on all blood films collected between ages 2 and 3.5 yrs. This mean parasite density included the scheduled monthly blood smears as well as positive blood smears obtained during sick visits. Ten individuals from the high and low extremes of this distribution were chosen to comprise the Resistant and Susceptible groups. Selections were made with matching based on village of residence, # of malaria-associated clinic visits, sex, and # of doses of anti-malarials. Potential confounders examined included: Hgb phenotype, presence of placental malaria, maternal age, birth season, use of bed nets, and # of previous pregnancies. A second, independent selection of resistant and susceptible individuals (table S2) was chosen for ELISA-based confirmatory assays.

Whole Proteome Differential Screening

We obtained a *P. falciparum* blood-stage cDNA expression library in Lambda Zap (MRA-299) from MR4. We plated this library at 25,000 clones/plate on 150 mm NZY plates in XL-1 Blue strain of *E. coli*. Duplicate IPTG-soaked nitrocellulose filters were prepared from each of 50 plates. Filters were blocked in 5% milk, TBS pH 7.4 (MTBS). Resistant plasma (RP) and susceptible plasma (SP) were diluted 1:100 in MTBS. Duplicate filters were probed with either RP or SP for 3 hr at 37 deg Celsius. Filters were washed 3×5 min in 0.05% Tween 20, TBS pH 7.4 (TTBS) and probed with alkaline phosphatase conjugated anti-human IgG diluted 1:5000 in MTBS for 1 hr at 37 deg Celsius. Filters were washed 3×5 min in TTBS. Filters were developed in BCIP/NBT. Clones which reacted with RP but not SP were cored out of their corresponding plate, eluted in SM buffer, re-plated and re-screened. Three rounds of plaque purification typically resulted in homogeneous clones which are reactive with RP but not reactive with SP. cDNA inserts uniquely reactive with RP were recovered by PCR amplification using vector specific primers and sequenced.

PfSEP-1A Expression and Purification

We subcloned the ORF encoding as 810-1083 of PfSEP-1 into pET30 (Novagen) and transformed the resulting plasmid into the expression host *E. coli* BL21(DE3) (Novagen). Transformants were grown in Terrific broth supplemented with 100 tig/mL kanamycin, at 37 deg C. in a 10 L fermenter with oxygen sparging (10 L/min) until OD600=8.0. Isopropyl-b-D-thiogalactopyranoside was added to a final concentration of 1 mmol/L, and the culture was fed continuously with 0.3 g/ml glucose, 0.09 g/ml yeast extract at 50 ml/hr for 12 h. Cultures were harvested by centrifugation and 750 gr of wet cell paste was resuspended in 10 L of 10 mmol/L potassium phosphate, 150 mmol/L NaCl, and 10 mmol/L imidazole (pH 8.0) and lysed by high pressure disruption at 20, 000 PSI (Microfluidics, Model 110-T). The lysate was clarified by tangential flow microfiltration (filter area 1 m2, pore size 1 um, Milipore) and 8 L of clarified lysate was recovered.

Protein purification was achieved by a 4-step process on BioPilot chromatography equipment (Pharmacia). Briefly, clarified lysate was applied to a FineLine Pilot 35 (GE Healthcare) column containing 90 mL of Ni-NTA Superflow Resin (Novagen). The protein of interest was eluted with a stepped gradient containing increasing concentrations of imidazole. Fractions containing the protein of interest were pooled, adjusted to 400 mmol/L ammonium sulfate, 10 mmol/L DTT and further purified, by hydrophobic-interaction chromatography on a FineLine Pilot 35 (GE Healthcare) column containing 150 ml of Source 15PHE (GE Healthcare). Recombinant proteins were eluted with a linear gradient of elution buffer (10 mmol/L Tris, 1 mmole/L DTT, 1 mmol/L EDTA [pH 8.0]). Fractions containing the protein of interest were pooled, and further purified, by anion exchange chromatography on a FineLine Pilot 35 (GE Healthcare)

column containing 130 ml of MacroPrep High Q (BioRad). Recombinant proteins were eluted with a linear gradient of elution buffer (10 mmol/L Tris, 1 mole/L NaCl, 1 mmole/L DTT, 1 mmol/L EDTA [pH 8.0]). Final purification was achieved by ceramic hydroxyapatite chromatography on a FineLine Pilot 35 (GE Healthcare) column containing 70 ml of CHT type 1 (BioRad). Recombinant proteins were eluted with a linear gradient of elution buffer (500 mmole/L potassium phosphate, and 1 mmole/L DTT, pH 7.4)

Purified rPfSEP-1A was buffer exchanged into 10 mmol/L sodium phosphate, 0.05% Tween 20, 3% sucrose and concentrated to 500 μg/ml by tangential flow ultrafiltration (filter area 50 cm2, pore size 5 kDa, Pall). rPFSEP-1A was lyophilized at 500 μg/vial and stoppered under nitrogen. Endotoxin levels were less than 2 EU/mg protein as determined by an FDA cleared assay (Lonza). Typical yields are >50 mg rPfSEP-1A per 750 gr of wet cell paste.

PbSEP-1A Expression and Purification

We subcloned the ORF encoding as 725-1000 of PbSEP-1 into pET30 (Novagen) and transformed the resulting plasmid into the expression host *E. coli* BL21(DE3) (Novagen). Transformants were grown in Terrific broth supplemented with 100 μg/mL kanamycin, at 37 deg C. in a 10 L fermenter with oxygen sparging (10 L/min) until OD600=8.0. Isopropyl-b-D-thiogalactopyranoside was added to a final concentration of 1 mmol/L, and the culture was fed continuously with 0.3 g/ml glucose, 0.09 g/ml yeast extract at 50 ml/hr for 12 h. Cultures were harvested by centrifugation and 750 gr of wet cell paste was resuspended in 10 L of 10 mmol/L potassium phosphate, 150 mmol/L NaCl, and 10 mmol/L imidazole (pH 8.0) and lysed by high pressure disruption at 20, 000 PSI (Microfluidics, Model 110-T). The lysate was clarified by tangential flow microfiltration (filter area 1 m2, pore size 1 um, Milipore) and 8 L of clarified lysate was recovered.

Protein purification was achieved by a 3-step process on BioPilot chromatography equipment (Pharmacia). Briefly, clarified lysate was applied to a FineLine Pilot 35 (GE Healthcare) column containing 90 mL of Ni-NTA Superflow Resin (Novagen). The protein of interest was eluted with a stepped gradient containing increasing concentrations of imidazole. Fractions containing the protein of interest were pooled, adjusted to 400 mmol/L ammonium sulfate, 10 mmol/L DTT and further purified, by hydrophobic-interaction chromatography on a FineLine Pilot 35 (GE Healthcare) column containing 150 ml of Source 15PHE (GE Healthcare). Recombinant proteins were eluted with a linear gradient of elution buffer (10 mmol/L Tris, 1 mmole/L DTT, 1 mmol/L EDTA [pH 8.0]). Fractions containing the protein of interest were pooled, and further purified, by anion exchange chromatography on a FineLine Pilot 35 (GE Healthcare) column containing 130 ml of MacroPrep High Q (BioRad). Recombinant proteins were eluted with a linear gradient of elution buffer (10 mmol/L Tris, 1 mole/L NaCl, 1 mmole/L DTT, 1 mmol/L EDTA [pH 8.0]).

Purified rPbSEP-1A was buffer exchanged into 10 mmol/L sodium phosphate, 0.05% Tween 20, 3% sucrose and concentrated to 125 μg/ml by tangential flow ultrafiltration (filter area 50 cm2, pore size 5 kDa, Pall). rPFSEP-1A was lyophilized at 125 μg/vial and stoppered under nitrogen. Endotoxin levels were less than 2 EU/mg protein as determined by an FDA cleared assay (Lonza). Typical yields are >50 mg rPbSEP-1A per 750 gr of wet cell paste.

Parasite Strains and Culture

*P. falciparum* strains (3D7, D10, and W2) were obtained from MR4. The parasites were cultured in vitro according to the methods of Trager and Jensen with minor modifications 29. Briefly, parasites were maintained in RPMI 1640 medium containing 25 mm HEPES, 5% human 0+ erythrocytes, 0.5% Albumax II (Invitrogen) or 10% heat inactivated human AB+ serum, 24 mm sodium bicarbonate, and 10 μg/ml gentamycin at 37° C. with 5% CO2, 1% 02, and 94% N2.

*P. berghei* ANKA was obtained from MR4 as a stabilite and was expanded in Balb/C mice prior to challenge studies.

Anti-PfSEP-1 Antisera Production

Mouse anti-PfSEP-1 antisera was produced by either DNA or recombinant protein immunization. For DNA immunization, we subcloned the ORF encoding as 810-1083 of PfSEP-1 into VR2001, transformed into the host *E. coli* NovaBlue (Novagen), and purified endotoxin free plasmid (Endofree Giga, Qiagen). Balb/C mice were immunized with 180 μg of plasmid (50 ug intramuscular injection in each hind leg and 80 μg intradermal injection at base of tail) followed by 80 μg intradermal injections at base of tail every two weeks for a total of four doses. For protein immunization, we emulsified rPfSEP-1 in an equal volume of TiterMax adjuvant (CytRx Corporation) and injected 50 μg of rPfSEP-1 intraperitoneally at two week intervals for a total of four doses.

Western Blot

Parasite pellets were prepared by treatment of parasitized RBCs with 0.15% saponin in phosphate buffered saline (PBS), pH 7.4 on ice for 10 min followed by centrifugation (3,000×g, 5 min), and resuspension in cold PBS, and centrifugation (3,000×g, 5 min). Parasite pellets or rPfSEP-1A were dissolved in SDS sample loading buffer (Bio-Rad), heated to 95 deg C. for 10 min, and proteins were separated in 4-11% gradient SDS-PAGE gels. Separated proteins were transferred to nitrocellulose membranes which were blocked in 5% milk PBS (pH 7.4) and 0.05% Tween 20 for 1 h. Membranes were probed with polyclonal anti-PfSEP-1A or pre-immune mouse sera, detected by use of anti-mouse IgG antibody conjugated to alkaline phosphatase, and developed with 5-bromo-4-chloro-3-indolyl phosphate/nitro blue tetrazolium (Sigma).

SNP Detection in Field Isolates

We extracted DNA from filter paper containing dried blood spots obtained from six parasitemic children in our cohort (QIAmp DNA Blood Mini Kit, Qiagen). We amplified nt 2,431-3,249 of PF3D7_1021800 from extracted DNA using a nested PCR based approach. First round primers were: F1 5'-GAAGATGTTTGTCATAATAATAACGTGGAAGACC-3' (SEQ ID NO: 49), R1 5'-TCCTACAACATCTATTTCTCCTGTGTAAGG-3'. (SEQ ID NO: 50) Second round primers were: F2 5'-GAATAAAAAAATGGATGAGATGAAAG-3'(SEQ ID NO: 51), R2 5'-CTATTACTATCCTCATTTGCATCTGTATATTTATCC-3'(SEQ ID NO: 52). First round PCR conditions were: 10 min initial denature at 94 deg C. followed by 40 cycles of 45 sec at 94 deg C., 60 sec at 55 deg C., 90 sec at 70 deg C., extension at 70 deg C. for 10 min. Second round PCR conditions were: 10 min initial denature at 94 deg C. followed by 35 cycles of 45 sec at 94 deg C., 60 sec at 55 deg C., 60 sec at 70 deg C., extension at 70 deg C. for 10 min. DNA fragments were purified with Quickclean II PCR Kit (GenScript), cloned into pDrive (Qiagen) and sequenced.

PfSEP-1 Knock Out/Down Strategy

We constructed vectors designed to disrupt the promoter region (knockdown) and the coding region (knock-out) of the gene encoding PfSEP-1. For the knock-down construct, we amplified a 749 bp segment (−493-257 bp) from 3D7 genomic DNA using PCR forward primers 5'-GCACTGCAGAGCACTGAATAAATGAAATG-3'(SEQ ID NO: 53) and reverse primer 5'-GCAGCGGCCGCGTG-GATGCACCATCATCGAG-3' (SEQ ID NO: 54). For the knockout construct, we amplified a 868 bp segment (232-1099 bp) from 3D7 genomic DNA using PCR forward primers 5'-GCACTGCAGGAGTTATCTCGATGATGGTG-3' (SEQ ID NO: 55) and reverse primer 5'-GCAGCGGCCGCGATCCATGATATTAACATGGCTC-3'(SEQ ID NO: 56).

Amplified DNA fragments were digested with the restriction enzymes Pstl and Notl and cloned into plasmid pHD22Y 30. The DNA sequences and location of all inserts were confirmed by using vector specific primers in the sequencing reaction which spanned the cloning region of the vector.

Asexual stages of W2 and 3D7 parasites were cultured as described above. The parasites were synchronized using 5% d-sorbitol, and schizont stages at 10% parasitemia were purified using a Percoll-sorbitol separation method 31. Uninfected RBCs were electroporated with 200 lag of supercoiled pHD22Y containing DNA inserts as described 9'32. Following transformation, purified schizonts were added to electroporated RBCs and were maintained in culture for 48 h before the addition of drug WR99210 (Sigma) to a final concentration of 5 nmole/L. Drug-resistant parasites appeared three to four weeks after transfection. Episomal carriage of plasmids in the drug resistant parasites was confirmed by PCR for both constructs using genomic DNA obtained from the drug resistant parasites and vector specific primers F 1 5'-CATGTTTTGTAATTTATGGGA-TAGCG-3'(SEQ ID NO: 57) and R1 5'-CGC-CAAGCTCGAAATTAACCCTCAC-3'(SEQ ID NO: 58). Six to eight weeks after transfection, we tested for chromosomal integration for both constructs by PCR using genomic DNA obtained from the drug resistant parasites and chromosomal and vector specific primers F2 5'-GCCA-CATATAATTCTTGTACTTGTC-3' (SEQ ID NO: 59) and R2 5'-CGAAATTAACCCTCACTAAAGG-3' (SEQ ID NO: 60) or R3 5'-GACAAGTACAAGAATTATATGTGGC-3' (SEQ ID NO: 61) for knockdown constructs, or F2 5'-GTAT-GATGGAAAATAAATACCCAAATG-3'(SEQ ID NO: 62) and R2 CGAAATTAACCCTCACTAAAGG-3' (SEQ ID NO: 63) or R3 5'-GACAAGTACAAGAATTATATGTGGC-3'(SEQ ID NO: 64) for knockout constructs (FIGS. 16A-C).

Anti-PfSEP-1 Antibody Assays

Initial, confirmatory antibody assays were performed with rPfSEP-1A coated ELISA plates according to known methods (FIG. 18).

To measure IgG anti-rPfSEP-1A antibody levels in the entire cohort, a bead-based assay was used. 100 μg of rPfSEP-1A or 100 ug of BSA was conjugated to $1.25\times10^7$ microspheres (Luminex) and conjugated rPfSEP-1 and BSA beads were pooled and lyophilized in single use aliquots. Reconstituted beads were incubated for 30 min at 37 deg C. with human plasma samples at 1:80 dilution in Assay Buffer E (ABE, PBS pH 7.4 containing 0.1% BSA, 0.05% Tween-20, and 0.05% sodium azide) in microtiter filter bottom plates (Millipore). Beads were washed three times in ABE by vacuum filtration and incubated for 30 min at 37 deg C. with biotinylated anti-human IgG (Pharmingen) diluted 1:1000 in ABE. Beads were washed three times in ABE by vacuum filtration and incubated for 10 min at 37 deg C. with phycoerythrin conjugated streptavidin (Pharmingen) diluted 1:500 in ABE. Beads were washed three times in ABE by vacuum filtration, resuspended in ABE and analyzed on a BioPlex 200 multi-analyte analyzer. Fluorescence values for BSA beads were subtracted from rPfSEP-1A beads. The cut-off for detectable anti-PfSEP-1 antibody levels was defined as fluorescence values greater than the mean+2SD fluorescence level of 95 healthy North American children.

Growth Inhibition Assays

Growth inhibition assays (GIA) were carried out with anti-PfSEP-1 mouse sera or controls. Sera were dialyzed overnight in PBS, pH7.4, heat inactivated at 56° C. for 30 min and pre-incubated with human RBC for 1 hour before use in GIA assays. GIA assays were carried out using W2, 3D7 and D10 strains of *P. falciparum*. Parasites were synchronized to the ring stage by treatment with 5% sorbitol 34 for three successive replication cycles and cultured to the mature trophozoite stage. Parasites at 0.3-0.4% parasitemia and 2% hematocrit were incubated with anti-sera at a final concentration of 10% in a final volume of 100 μl in microtiter wells. Cultures were performed in triplicate with five replicates (comprising a total of 15 individual wells) prepared for each treatment condition. After 24 hr, blood films were prepared from each replicate, stained with Giemsa, ring stage parasites were enumerated, and the results from the three wells were averaged.

Schizont Arrest Assays

Schizont arrest assay (SAA) were carried out with anti-PfSEP-1 mouse sera or controls. Sera were dialyzed overnight in PBS, pH7.4, heat inactivated at 56° C. for 30 min and pre-incubated with human RBC for 1 hour before use in SAA assays. SAA assays were carried out using W2 and 3D7 strains of *P. falciparum*. Parasites were synchronized to the ring stage by treatment with 5% sorbitol 34 for three successive replication cycles and cultured to the early-schizont stage. Parasites at 3.5% parasitemia and 2% hematocrit, consisting mainly of early schizonts were incubated with anti-sera at a final concentration of 10% in a final volume of 100 pl in microtiter wells. Cultures were performed in triplicate with five replicates (comprising a total of 15 individual wells) prepared for each treatment condition. After 12 hr, blood films were prepared from each replicate, stained with Giemsa, schizont stage parasites were enumerated, and the results from the three wells were averaged.

Immunofluorescence Assays

Blood smears of asynchronous 3D7 strain parasite cultures were prepared, fixed in cold methanol for 15 minutes, and probed with anti-PfSEP-1 prepared by DNA vaccination, pre-immune sera, or rabbit anti-PfMSP-1 (MR4) diluted 1:200 in PBS, 5% BSA, pH 7.4. Blood smears were incubated with primary antibodies for 1 hr at 25 deg C., washed three times in PBS, 0.05% Tween-20 and incubated with goat anti-mouse IgG conjugated with Alexa fluor 488 (Molecular Probes) and goat anti-rabbit IgG conjugated with Alexa Fluor 594 (Molecular Probes). Blood smears were incubated for 10 minute in 1 lig/ml of 4',6'-diamino-2-phenylindole (DAPI, Sigma) to label nuclei and cover slipped with ProLong Gold anti-fade reagent (Invitrogen). Blood smears were imaged using a confocal microscope (Leica SP2, Leica Microsystems, Exton, Pa.) equipped with a 100× oil immersion objective and sequential Z-sections of the infected RBC were collected.

For localization of PfSEP-1 in late stage schizonts, we performed live cell staining and imaging. Briefly, 3D7 strain parasites were synchronized to the ring stage by treatment with 5% sorbitol 34 for three successive replication cycles and cultured to the early-schizont stage. Anti-PfSEP-1 prepared by DNA vaccination (1:200) and rabbit anti-human glycophorin A (1:200) were incubated with live schizont infected RBCs in PBS, 5% BSA pH 7.4 for one hr at 25 deg C. Samples were washed three times in PBS and incubated with goat anti-mouse IgG conjugated with Alexa Fluor 594

(Molecular Probes) and goat anti-rabbit IgG conjugated with Alexa Fluor 488 (Molecular Probes). Samples were washed 3 times with PBS and incubated for 10 minute in 1 μg/ml of 4', 6'-diamino-2-phenylindole (DAPI, Sigma) to label nuclei. Blood smears were prepared and cover slipped with ProLong Gold anti-fade reagent (Invitrogen). Blood smears were imaged using a confocal microscope (Leica SP2, Leica Microsystems, Exton, Pa.) equipped with a 100× oil immersion objective and sequential Z-sections of the infected RBC were collected.

Immunoelectron Microscopy

3D7 strain parasites were synchronized to the ring stage by treatment with 5% sorbitol 34 for three successive replication cycles and cultured to the early-schizont stage. Samples were blocked for 1 hour at 25 deg C. in I×PBS containing 2% BSA. Samples were incubated with anti-PfSEP-1 prepared by DNA vaccination (diluted 1:50 in PBS) and rabbit anti-human glycophorin-A polyclonal sera (diluted 1:50 in PBS) for 3 hr at 25 deg C. Pre-immune mouse sera was used as a negative control. Samples were washed three times in 1×PBS, and incubated for 1 h at 25 deg C. with 5 or 18-nm gold-conjugated goat anti-mouse IgG (Invitrogen) and 10-nm gold-conjugated goat anti-rabbit IgG (Invitrogen). Samples were washed three times in I×PBS, and were fixed for 30 min at 4° C. with 2% glutaraldehyde, 1% paraformaldehyde in 0.1 M sodium cacodyldate buffer. Samples were dehydrated, embedded in Epon (EMS), sectioned on an ultra-microtome, counter stained for 10 min in 5% aqueous uranyl acetate and examined on a Philips CM10 electron microscope.

PbSEP-1A Antibody and Vaccination Studies

Antibody assays were performed with rPbSEP-1A coated ELISA plates according to our published methods 14 using anHRP conjugated anti-Mouse IgG antibody (Sigma) for detection of bound anti-PbSEP-1A antibodies.

We immunized Balb/C mice (n=11) with 40 ug of rPbSEP-1A emulsified in 100 ul of TiterMax Gold adjuvant or adjuvant alone (n=11). Mice were immunized IP on days 0, 14, 28, and 42 and SC on day 56. On day 63, mice were challenged IP with 106 *P. berghei* ANKA parasite infected red blood cells. Mice were monitored daily from day 4 post-challenge with blood films to quantify parasitemia. Mice with parasitemias greater than 20% or exhibiting signs of illness (hunching, immobility, decreased food intake, etc.) were euthanized.

Statistical Analyses

To assess the relationship between anti-PfSEP-1 antibody responses and resistance to clinical malaria outcomes, we developed repeated measures models using SAS version 9.3 (Cary, N.C.). Generalized estimating equations using quasi-likelihood estimation were employed for these correlated (repeated measures) binary outcome data (Zeger, S. L. & Liang, K. Y. Longitudinal data analysis for discrete and continuous outcomes. Biometrics 42, 121-130 (1986)). Proc Genmod with a binomial distribution and logit link function were specified with separate models for each of the dichotomous clinical malaria outcomes. Due to the lack of independence of the repeated measures on children over time, we utilized longitudinal (repeated measures) modeling techniques in Proc Genmod to adjust for the correlation of responses within individuals. An autoregressive correlation structure was chosen given the expectation that the correlation of responses will decline over time. The fit of the model with different correlation structures was evaluated with the Quasi-Akaike Information Criterion (QIC). Similar GEE based linear regression models were used for the continuous endpoints of parasite density on all available blood smears and parasite density on positive blood smears. For some dichotomous malaria outcomes, including severe malaria, sampling zeros (i.e. no cases of severe malaria) occurred among children with detectable anti-PfSEP-1 antibody responses. This leads to "infinite bias" whereby odds ratios are skewed far above the true odds ratio. To address this, we used the Laplace correction, adding one adverse event to the group with detectable anti-PfSEP-1 antibody levels and a proportional number of events to the group with undetectable anti-PfSEP-1 antibody levels to restore the discordant pair ratios (Greenland, S., Schwartzbaum, J. A. & Finkle, W. D. Problems due to small samples and sparse data in conditional logistic regression analysis. Am J Epidemiol 151, 531-539 (2000)).

The data from these studies indicate that resistant individuals had 4 fold higher antibody levels to recombinant Pf SEP-1 compared to susceptible individuals, anti-Pf SEP-1 detects a 244 kDa antigen in *P. falciparum* infected, but not uninfected RBCs, Pf SEP-1 localizes to the schizont/parasitophorous vacuole membrane, Mauer's clefts and the inner leaflet of the RBC membrane in schizont infected RBCs, anti-Pf SEP-1 inhibits parasite growth by 48-74%. In schizont arrest assays, anti-Pf SEP-1 inhibits schizont rupture by 4-7 fold, and PfSEP-1 is a useful vaccine antigen to target schizont rupture and thereby reduce the severity of malaria.

Example 2: Role of Phosphorylation and Protein-Protein Interaction in Schizont Egress PfSEP-1 is involved in the process of schizont egress from *P. falciparum* infected RBCs. As was described above, PfSEP-1, a 244-kDa parasite antigen, localizes to the schizont/parasitophorous vacuole membrane, Maurer's clefts and the inner leaflet of the RBC membrane in schizont infected RBCs. Antibodies to a central, highly conserved 274 aa region of PfSEP-1 (rPfSEP-1A, aa 810-1083) decrease parasite replication by 58-75% (all p<0.009) by blocking schizont rupture. Active vaccination with rPbSEP-1A results in a 2.25 fold reduction in parasitemia after in vivo challenge with *P. berghei*. In human cohort studies, children experienced a dramatically increased incidence of severe malaria during periods with undetectable anti-PfSEP-1 antibody levels (45 cases/23,806 child weeks) compared to periods with detectable antibody levels (0 cases/1,688 child weeks; adjusted OR 4.4; Type III fixed effects p<0.01). These results demonstrate that PfSEP-1 is critical for parasite egress and that antibodies against this protein are protective in vivo against severe malaria.

Schizont egress is a complex and tightly regulated process that requires both calcium-signaling and activation of a protease cascade which processes both parasite and host RBC proteins. Central events include activation of PfPKG, release of PfSUB1 into the parasitophorous vacuole, and proteolytic processing/activation of PfSERA5 by PfSUB1. Conditional knockdown of the calcium dependent kinase PfCDPK5 also results in arrest of schizont egress. Vaccination with PfSERA5 reduces and blocks schizont egress as well as parasite invasion. An in vivo phosphorylation substrate(s) of PfCDPK-5 is PfSEP-1.

Figure 20:
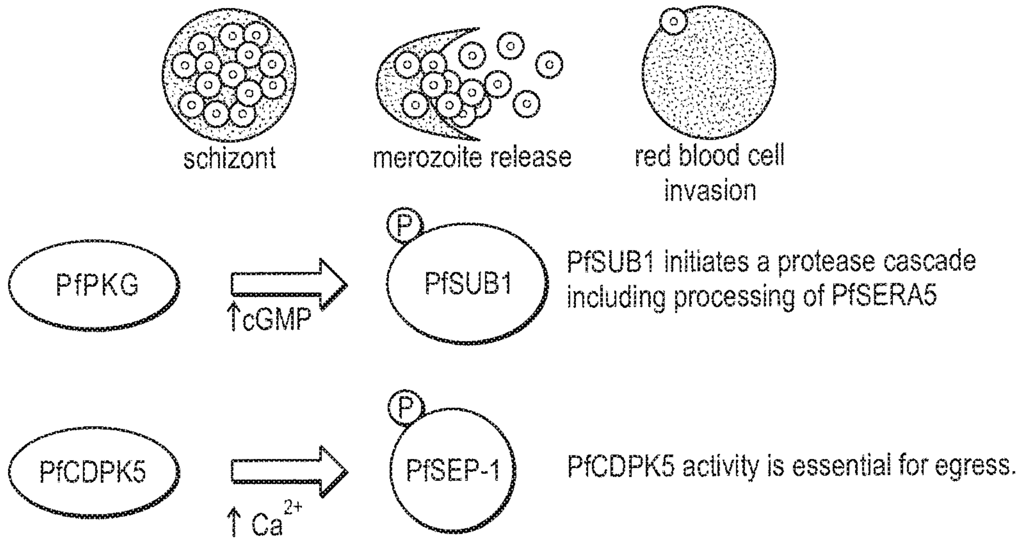
FIG. 20 is a diagram showing mechanisms of schizont egress and protein-protein interactions involved in the process.
Figure 21A:
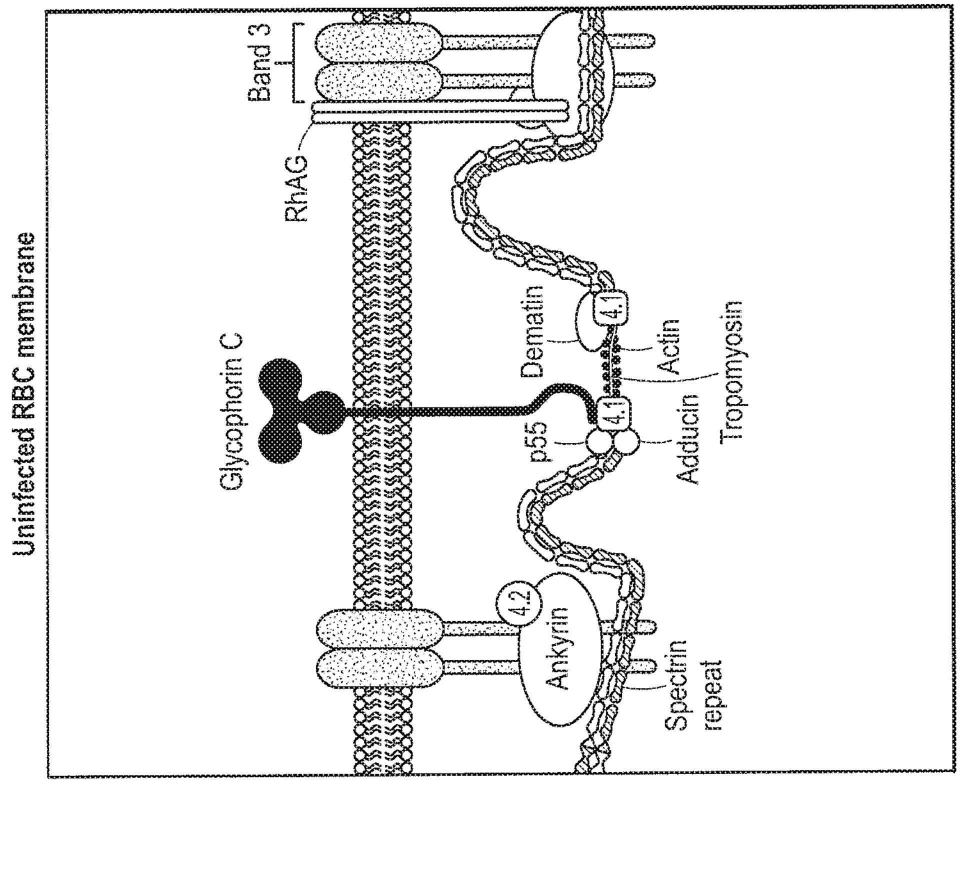
FIG. 21A-B are diagrams showing intracellular proteins and their interactions in uninfected RBCs (A) compared to parasite infected RBCs (B).
Figure 21B:
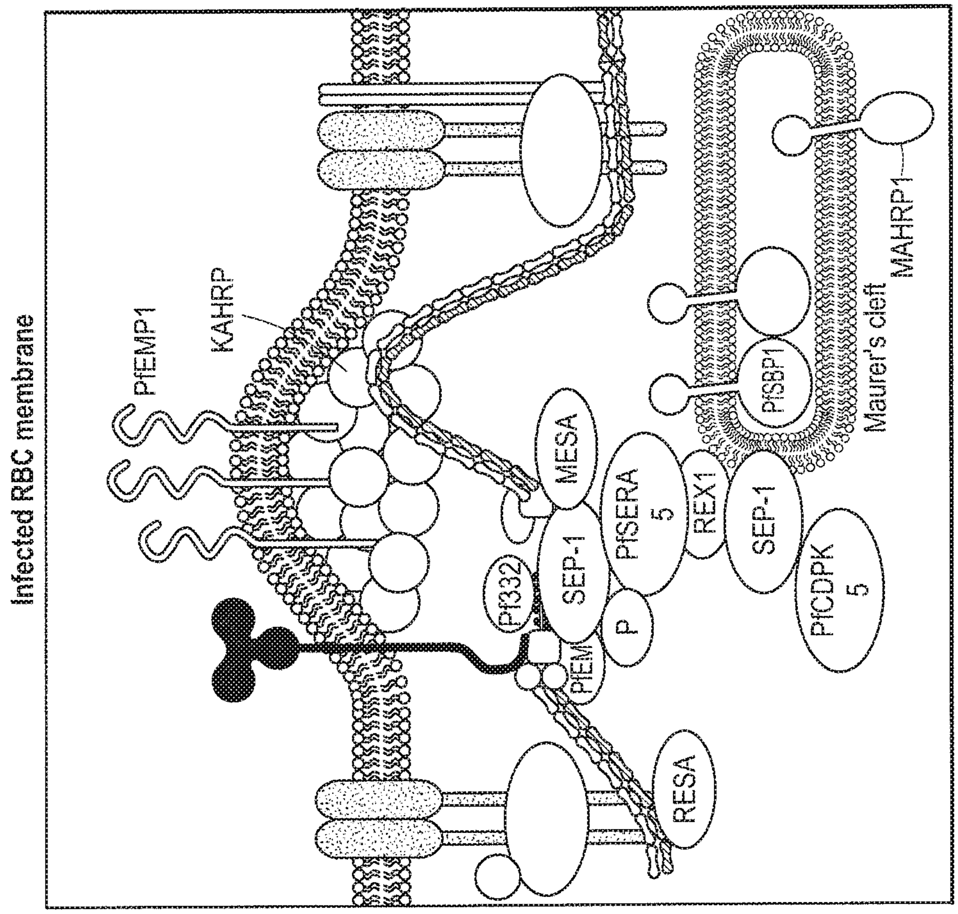

Protein-protein interactions of PfSEP-1 were studied using yeast two-hybrid (Y2H) and focusing on the rPfSEP-1A region (aa 810-1083; SEQ ID NO:2) and confirmed by immunoprecipitation of schizont extracts with anti-PfSEP-1 and sequencing (FIG. 20). PfSEP-1 was cloned into a "bait" plasmid as fusion with truncated transcription factor; malaria cDNAs were cloned into target plasmid as fusion with truncated transcription factor; screening was carried out in yeast for complementation of transcription factor via reporter gene assay; and PfSERA5 was identified as binding partner for PfSEP-1. The analysis also identified PfMESA as binding partner. These screens have identified 26 potential interacting proteins including PfSERA5, PfEMP2 (MESA), RAP-1, and RhopH3, which have also been identified as substrates for the egress critical protease PfSUB1. An immune response against SERA5 and SUB 1 sequences inhibit schizont egresss. SERA5 was identified in yeast-2-hybrid screen using PfSEP-1A as bait. rPfCDPK-5 was found to phosphorylate rPfSEP-1A (see FIGS. 20-21).

Phosphorylation-mediated regulation of PfSEP-1 and binding of this protein to both parasite and RBC proteins is essential for parasite egress. Parasite and RBC proteins which interact with, or phosphorylate PfSEP-1, are useful as vaccine antigens alone or together with PfSEP-1 (e.g., PfSEP-1A peptide) for immunization against malaria. Thus, plasmodial kinases (e.g., Pf CDPK5) and PfSEP-1-interacting proteins (e.g., PfSERA5, PfEMP2 (MESA), RAP-1, RhopH3) are used alone or as components of an PfSEP-1 based vaccine composition to generate an antibody or cellular immune response, which leads to a synergistic reduction in parasite growth, schizont egress, and (as a result) reduction in severity of malaria.

Example 3: Transmission Blocking and Reduction of Mosquito Invasion

Gametocytes, a form of blood stage parasite, are picked up by a female *Anopheles* mosquito during a blood meal. PfSEP-1 is expressed in male and female gametocytes—the sexual stage of the parasite's development that forms within host red blood cells. After being taken up by the mosquito with a blood meal, gametocytes must rupture from their encasing red blood cell in a process analogous to schizont rupture. This process takes place within the gut of the mosquito. Male and female gametocytes that fail to rupture from their red blood cell cannot join to make an ookinete and thus cannot infect the mosquito.

Several transmission blocking vaccine candidates attempt to target ookinete development in the mosquito (Kaslow et al., Infect Immun 1994; 62:5576-80; Bustamante et al., Parasite Immunol 2000; 22:373-80). Because PfSEP-1 is expressed in gametocytes (FIGS. 18 E-G), antibodies to PfSEP-1 taken up with the blood meal prevent gametocyte rupture from host red blood cells within the mosquito, thus affording a transmission blocking effect. Thus a vaccine that elicits an antibody immune response against PfSEP-1 (e.g., antibodies that specifically bind to PfSEP-1A) also leads to blocking of gametocyte egress out of RBCs. Antibodies made as a result of the vaccination regimen described herein readily gain access to the RBC, because the membrane permeability of infected RBCs. Thus, these data indicate that the vaccine is also useful to prevent or reduce invasion of mosquitos from a human blood meal.

Example 4: Vaccination of Mothers and Adolescents

Maternal transmission of anti-PfSEP-1 antibodies from a mother to a fetus, e.g., across the maternal-fetal interface via the placenta, was found to reduce malaria in infants. We have identified PfSEP-1 antibodies in the sera of pregnant women whose children were protected from severe malaria during infancy (first yr of life), but do not detect anti-PfSEP-1 antibodies in pregnant women whose children do have severe malaria during infancy. Because neonates (first 28 days of life) have poorly developed immune systems, they often do not make robust immune responses to vaccines. The vaccine described herein is therefore also useful to protect infants. Pregnant women and/or women of child bearing age are immunized with a vaccine containing PfSEP-1 peptide(s). Anti-PfSEP-1 antibodies produced as a result of the immunization cross the placenta and protect the newborn from malarial infection, morbidity and mortality. Females are immunized starting at age 9, e.g., 3 doses over 6 months. Immunization of females prior to pregnancy or early in pregnancy is useful to prevent, slow, or inhibit infection and the development of malaria in fetuses and newborns.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank, NCBI, and Plasmodb submissions indicated by accession number cited herein are hereby incorporated by reference. Plasmdb.org sequence version is the version as of Nov. 30, 2012. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A vaccine for reducing the severity of malaria or immunizing against malaria comprising a composition, wherein said composition comprises a purified PF3D7 polypeptide antigen comprising the amino acid sequence of SEQ ID NO: 47, or a fragment thereof, said fragment thereof comprising the amino acid sequence of DYTEFLAACLDHSIFQQDVICRNAFNVFDLDGDGVITKDELFKILSFSAVQVSFSKEIIENLIKEVDSNN DGFIDYDEFYKMMTGVKE (SEQ ID NO:77), and further comprising a purified anti-PF3D7 antibody or antigen binding fragment thereof and an adjuvant.

2. The vaccine of claim 1, wherein said composition comprises a purified polypeptide comprising the amino acid sequence of DYTEFLAACLDHSIFQQDVICRNAFNVFDLDGDGVITKDELFKILSFSAVQVSFSKEIIENLIKEVDSNN DGFIDYDEFYKMMTGVKE (SEQ ID NO:77).

3. A vaccine for reducing the severity of malaria or immunizing against malaria comprising a composition, wherein said composition comprises a purified PF3D7 polypeptide antigen comprising the amino acid sequence of (SEQ ID NO: 47) or a fragment thereof, said fragment thereof comprising the amino acid sequence of DYTEFLAACLDHSIFQQDVICRNAFNVFDLDGDGVITKDELFKILSFSAVQVSFSKEIIENLIKEVDSNNDGFIDYD EFYKMMTGVKE (SEQ ID NO: 77), wherein said composition further comprises an adjuvant and a purified polypeptide comprising the amino acid sequence of SERA5 (SEQ ID NO: 70, 72), PfSUB1 (SEQ ID NO: 74), PfSEP1 (SEQ ID NO: 2), PfSEP1 (SEQ ID NO: 3), PfGARP (SEQ ID NO: 26), PfGARP (SEQ ID NO: 27), or PfPKG (SEQ ID NO: 76).

4. The vaccine of claim 1, wherein said composition comprises a purified polypeptide that elicits an antibody immune response against PF3D7.

5. The vaccine of claim 4, wherein said antibody immune response produces antibodies that bind to an antigen comprising a polypeptide having at least 70% identity with an amino acid sequence of SEQ ID NO: 47 or a fragment thereof.

6. A vaccine for reducing the severity of malaria or immunizing against malaria comprising a composition, wherein said composition comprises a purified PF3D7 polypeptide antigen comprising the amino acid sequence of (SEQ ID NO: 47) or a fragment thereof, said fragment thereof comprising the amino acid sequence of DYTEFLAACLDHSIFQQDVICRNAFNVFDLDGDGVITKDELFKILSFSAVQVSFSKEIIENLIKEVDSNNDGFIDYD EFYKMMTGVKE (SEQ ID NO: 77), wherein said composition further comprises an adjuvant and a purified polypeptide comprising an amino acid sequence selected from the group consisting of SEQ ID NO: 10, 14, 18, 22, 30, 34, 38, 42, 46, 66 and 72.

7. A vaccine for reducing the severity of malaria or immunizing against malaria comprising a composition, wherein said composition comprises a purified PF3D7 polypeptide antigen comprising the amino acid sequence of (SEQ ID NO: 47) or a fragment thereof, said fragment thereof comprising the amino acid sequence of DYTEFLAACLDHSIFQQDVICRNAFNVFDLDGDGVITKDELFKILSFSAVQVSFSKEIIENLIKEVDSNNDGFIDYD EFYKMMTGVKE (SEQ ID NO: 77), wherein said composition further an adjuvant and comprises a purified polypeptide comprising an amino acid sequence selected from the group consisting of SEQ ID NO: 8, 11, 15, 19, 22, 31, 35, 39, 43, 67, 70, 74, and 76 or fragments thereof.

8. A vaccine for reducing the severity of malaria or immunizing against malaria comprising a composition, wherein said composition comprises a purified PF3D7 polypeptide antigen comprising the amino acid sequence of (SEQ ID NO: 47) or a fragment thereof, said fragment thereof comprising the amino acid sequence of DYTEFLAACLDHSIFQQDVICRNAFNVFDLDGDGVITKDELFKILSFSAVQVSFSKEIIENLIKEVDSNNDGFIDYD EFYKMMTGVKE (SEQ ID NO: 77), wherein said composition further comprises an adjuvant and a purified polypeptide consisting of an amino acid sequence selected from the group consisting of SEQ ID NO: 6, 7, 10, 11, 14, 15, 18, 19, 22, 23, 30, 31, 34, 35, 38, 39, 42, 43, 46, 66, 67, 70, 72, 74, and 76 or an immunogenic fragment thereof.

9. A vaccine for reducing the severity of malaria or immunizing against malaria comprising a composition, wherein said composition comprises a purified PF3D7 polypeptide antigen comprising the amino acid sequence of (SEQ ID NO: 47) or a fragment thereof, said fragment thereof comprising the amino acid sequence of DYTEFLAACLDHSIFQQDVICRNAFNVFDLDGDGVITKDELFKILSFSAVQVSFSKEIIENLIKEVDSNNDGFIDYD EFYKMMTGVKE (SEQ ID NO: 77), wherein said composition further comprises an adjuvant and a purified polypeptide comprising an amino acid sequence of 6, 7, 10, 11, 14, 15, 18, 19, 22, 23, 30, 31, 34, 35, 38, 39, 42, 43, 46, 66, 67, 70, 72, 74, and/or 76.

10. The vaccine of claim 1, wherein said antigen comprises a polypeptide encoded by a polynucleotide having at least 70% identity with the nucleic acid sequence of SEQ ID NO: 48.

11. The vaccine of claim 10, wherein said polypeptide is encoded by a polynucleotide having the nucleic acid sequence of SEQ ID NO: 48.

12. A method for reducing the severity of malaria or immunizing against malaria comprising a composition, wherein said composition comprises a purified PF3D7 polypeptide antigen comprising the amino acid sequence of (SEQ ID NO: 47) or a fragment thereof, said fragment thereof comprising the amino acid sequence of DYTEFLAACLDHSIFQQDVICRNAFNVFDLDGDGVITKDELFKILSFSAVQVSFSKEIIENLIKEVDSNN DGFIDYDEFYKMMTGVKE (SEQ ID NO:77), and further comprising a purified anti-PF3D7 antibody or antigen binding fragment thereof and an adjuvant.

* * * * *